US010316294B2

(12) United States Patent
Mueller et al.

(10) Patent No.: US 10,316,294 B2
(45) Date of Patent: Jun. 11, 2019

(54) ATTENUATED INFLUENZA VIRUSES AND VACCINES

(71) Applicant: THE RESEARCH FOUNDATION FOR THE STATE UNIVERSITY OF NEW YORK, Albany, NY (US)

(72) Inventors: Steffen Mueller, Great Neck, NY (US); Eckard Wimmer, East Setauket, NY (US); Bruce Futcher, Stony Brook, NY (US); Steven Skiena, Setauket, NY (US); Chen Yang, Forest Hills, NY (US)

(73) Assignee: The Research Foundation for The State University of New York, Albany, NY (US)

( * ) Notice: Subject to any disclaimer, the term of this patent is extended or adjusted under 35 U.S.C. 154(b) by 0 days.

(21) Appl. No.: 14/777,204

(22) PCT Filed: Mar. 15, 2014

(86) PCT No.: PCT/US2014/030027
§ 371 (c)(1),
(2) Date: Sep. 15, 2015

(87) PCT Pub. No.: WO2014/145290
PCT Pub. Date: Sep. 18, 2014

(65) Prior Publication Data
US 2016/0024477 A1   Jan. 28, 2016

Related U.S. Application Data

(60) Provisional application No. 61/794,617, filed on Mar. 15, 2013.

(51) Int. Cl.
*C12N 7/00* (2006.01)
*A61K 39/145* (2006.01)

(52) U.S. Cl.
CPC .............. *C12N 7/00* (2013.01); *A61K 39/145* (2013.01); *C12N 2760/16034* (2013.01); *C12N 2760/16061* (2013.01); *C12N 2760/16134* (2013.01); *C12N 2760/16162* (2013.01)

(58) Field of Classification Search
None
See application file for complete search history.

(56) References Cited

U.S. PATENT DOCUMENTS 9,476,032 B2 * 10/2016 Wimmer ................. C12N 7/00
2012/0269849 A1   10/2012 Wimmer et al.

FOREIGN PATENT DOCUMENTS

| WO | 2006/042156 A9 | 4/2006 |
| WO | 2008/121992 A2 | 9/2008 |
| WO | 2011/044561 A1 | 4/2011 |

OTHER PUBLICATIONS

Mueller et al. Nature Biotechnology 2010, vol. 28, pp. 723-726.*
Ueda et al. 2008, vol. 136, pp. 91-97.*
Tamura, S. et al., "Mechanisms of brand cross-protection provided by influenza virus infection and their application to vaccines", Jpn J. Infec. Dis. (2005), vol. 58:4, pp. 195-207.
Yang, C. et al., "Deliberate reduction of hemagglutinin and neuraminidase expression of influenza virus leads to an untraprotective live vaccine in mice", PNAS (2013), vol. 110:23, pp. 9481-9486.
Belshe, R.B. et al., "Live Attenuated Versus Inactivated Influenza Vaccine in Infants and Young Children" N. Engl. J. Med (2007); vol. 356(7); pp. 685-696.
Bouvier, N.M. et al., "The Biology of Influenza Viruses"; Vaccine (2008); 26(Suppl. 4); pp. D49-D53.
Cello, J. et al., "Chemical Synthesis of Poliovirus cDNA: Generation of Infectious Virus in the Absence of Natural Template"; Science (2002); vol. 297(5583); pp. 1016-1018.
Coleman, J.R., et al., "Virus Attenuation by Genome-Scale Changes in Codon Pair Bias"; Science (2008) vol. 320 (5884); pp. 1784-1787.
De Jong, J.C. et al., "Haemagglutination-Inhibiting Antibody to Influenza Virus"; Dev Biol (Basel) (2003); vol. 115; pp. 63-73.
Doma, M.K. et al., "Endonucleolytic Cleavage of Eukaryotic mRNAs with Stalls in Translation Elongation"; Nature (2006); vol. 440(7083); pp. 561-564.
Dove, B.K., et al., "A Quantitative Proteomic Analysis of Lung Epithelial (A549) Cells Infected with 2009 Pandemic Influenza A Virus Using Stable Isotope Labelling with Amino Acids in Cell Culture"; Proteomics (2012); vol. 12(9); pp. 1431-1436.
Federov, A. et al., "Regularities of Context-Dependent Condon Bias in Eukaroytic Genes", NAR (2002); vol. 30:5; pp. 1192-1197.
Gutman, G.A. et al., "Nonrandom Utilization of Codon Pairs in *Escherichia Coli*"; Proc. Natl. Acad. Sci U. S. A. (1989); vol. 86(10); pp. 3699-3703.
Moura, G. et al., "Large Scale Comparative Codon-Pair Context Analysis Unveils General Rules that Fine-Tune Evolution of mRNA Primary Structure"; PLoS One (2007); vol. 2(9); p. e847 (10 pgs).
Simonsen, L., et al. "Impact of Influenza Vaccination on Seasonal Mortality in the U.S. Elderly Population"; Arch. Intern. Med (2005); vol. 165(3); pp. 265-272.
Smith, D.J., et al., "Mapping the Antigenic and Genetic Evolution of Influenza Virus"; Science (2004); vol. 305(5682); pp. 371-376.
Sutejo, R., et al., "Activation of Type I and III Interferon Signalling Pathways Occurs in Lung Epithelial Cells Infected with Low Pathogenic Avian Influenza Viruses"; PLoS One (2012); vol. 7(3); p. e33732 (15 pgs.).

(Continued)

Primary Examiner — Shanon A. Foley
Assistant Examiner — Myron G Hill
(74) Attorney, Agent, or Firm — Fox Rothschild LLP

(57) ABSTRACT

This invention provides highly attenuated influenza viruses and vaccines. The attenuated viruses and vaccines proliferate well and have high safety factors. The attenuated viruses providing protective immunity from challenge by virus of the same subtype, as well as cross protection against heterologous viruses.

13 Claims, 29 Drawing Sheets
Specification includes a Sequence Listing.

(56) References Cited

OTHER PUBLICATIONS

Thompson, W.W. et al. "Epidemiology of Seasonal Influenza: Use of Surveillance Data and Statistical Models to Estimate the Burden of Disease"; J. Infect. Dis. (2006); 194 (Suppl 2); pp. S82-S91.
Wang, F.P. et al., "Codon-Pair Usage and Genome Evolution" Gene (2009); vol. 433(1-2); pp. 8-15.
Wang, Z. et al., "Live attenuated or Inactivated Influenza Vaccines and Medical Encounters for Respiratory Illnesses Among US Military Personnel"; JAMA (2009); vol. 301(9); pp. 945-953.
World Health Organzation , WHO Manual on Animal Influenza Diagnosis and Surveillance (2002); www.who.int/vaccine_research/diseases/influenza/WHO_manual_on_animaldiagnosis_and_surveillance 2002 5.pdf (105 pgs.).

\* cited by examiner

| Virus | Mutations/Length (nt) |
|---|---|
| HA$^{Min}$ | 353/1775 |
| NA$^{Min}$ | 265/1413 |
| (NA+HA)$^{Min}$ | 618/3188 |

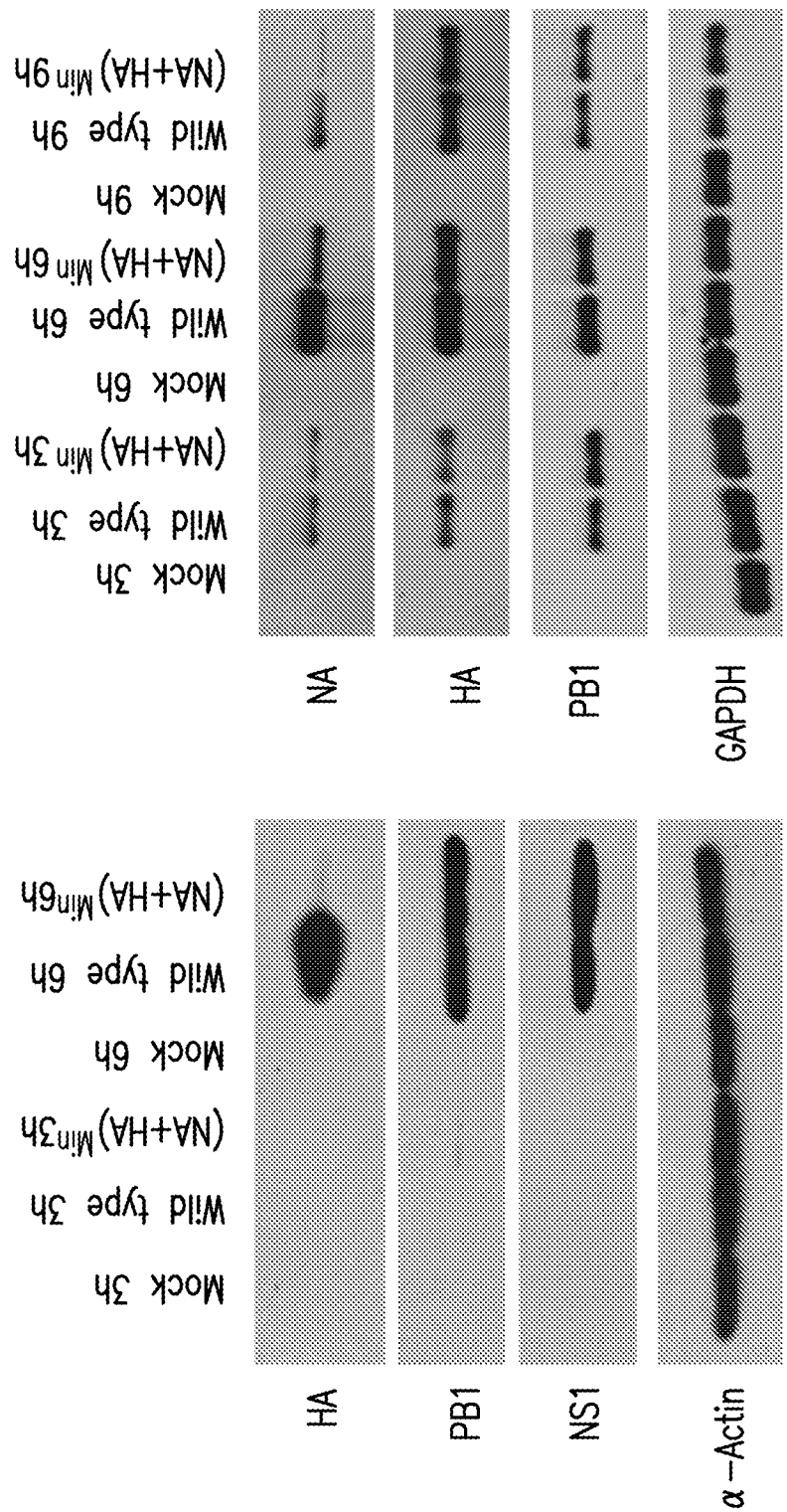

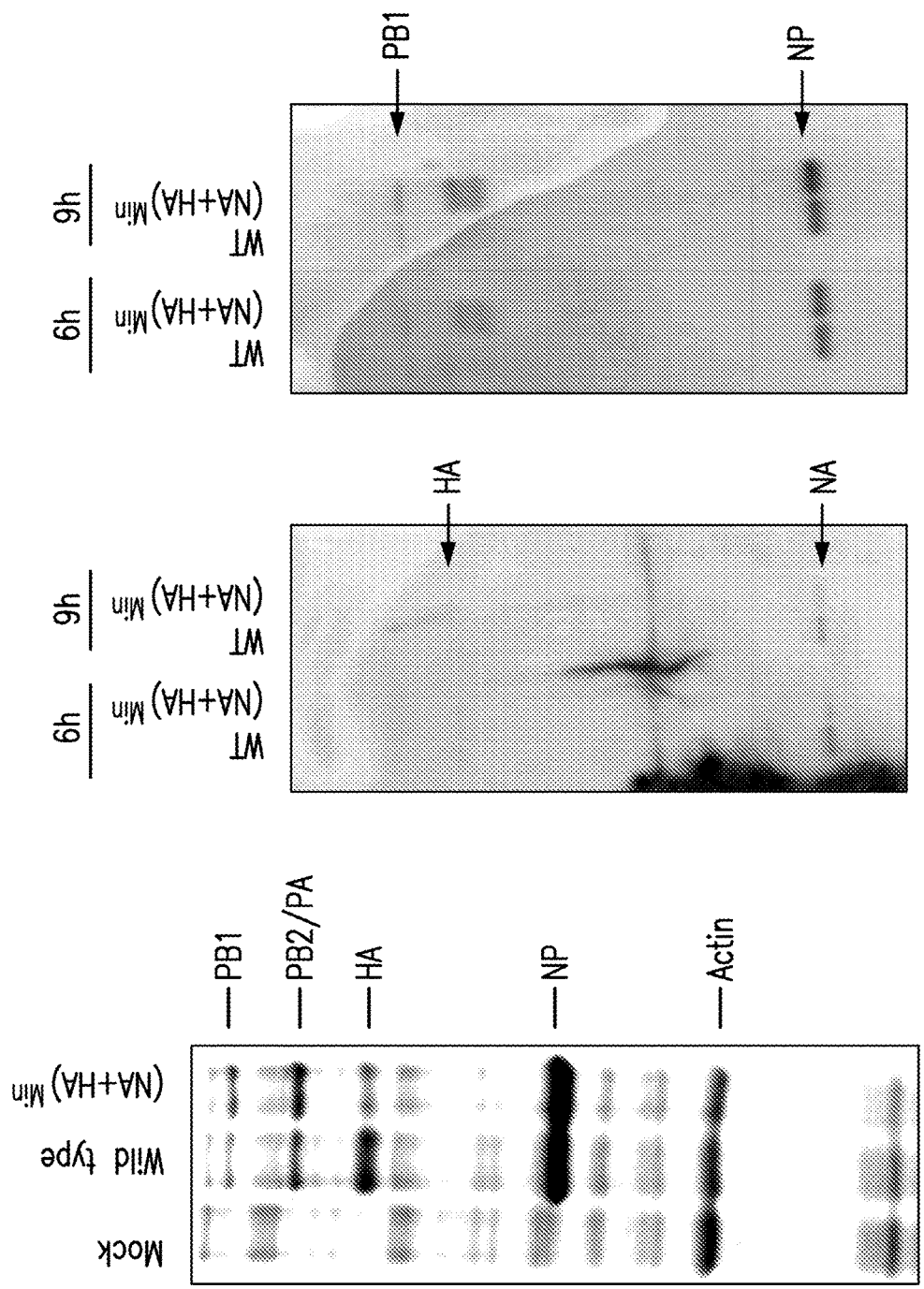

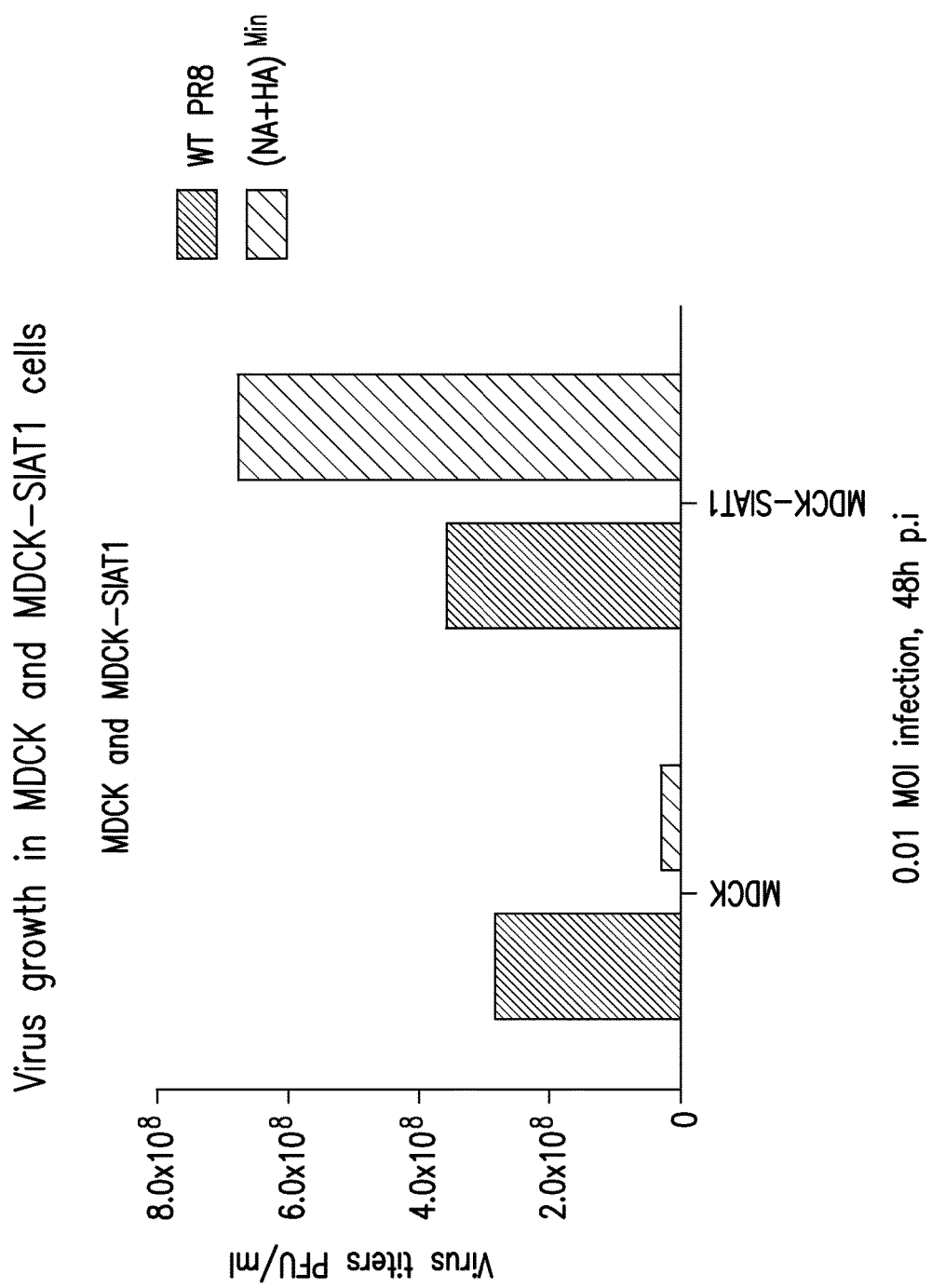

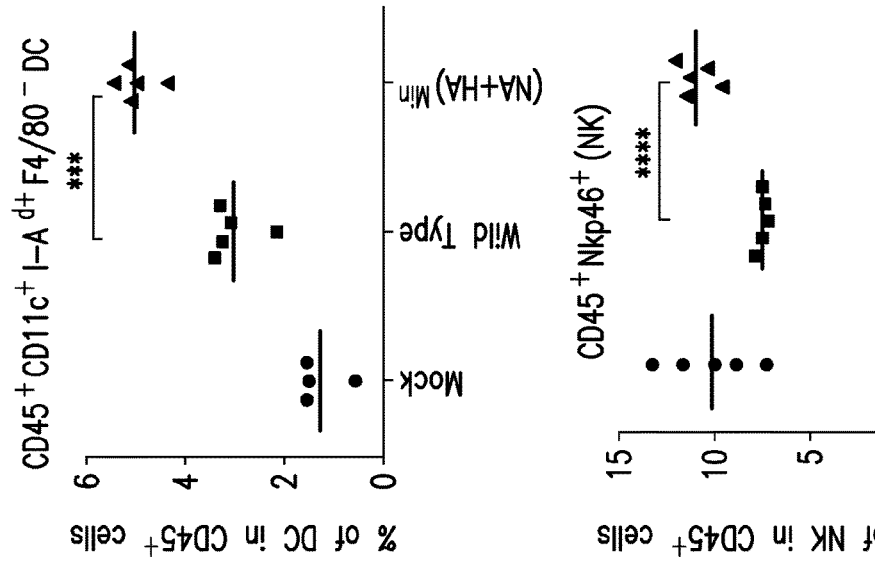
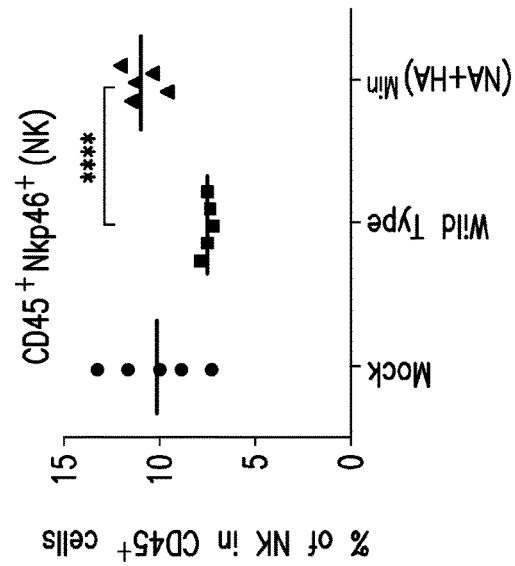
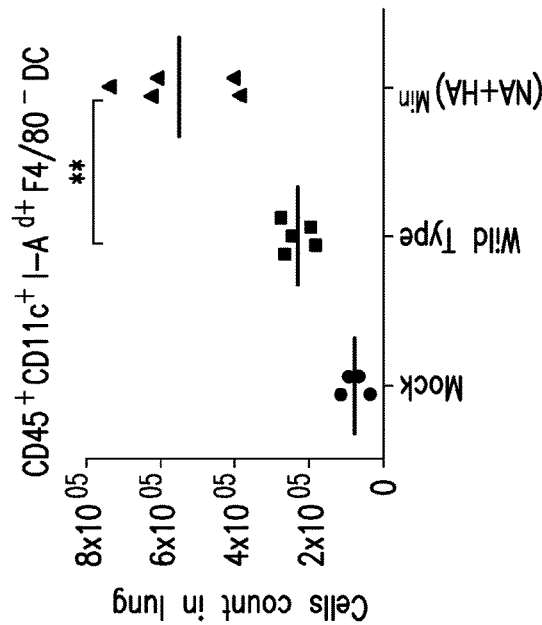
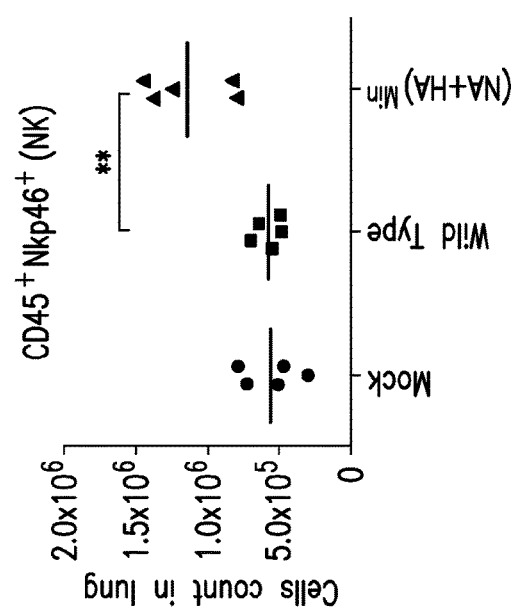
FIG. 19C
FIG. 19D

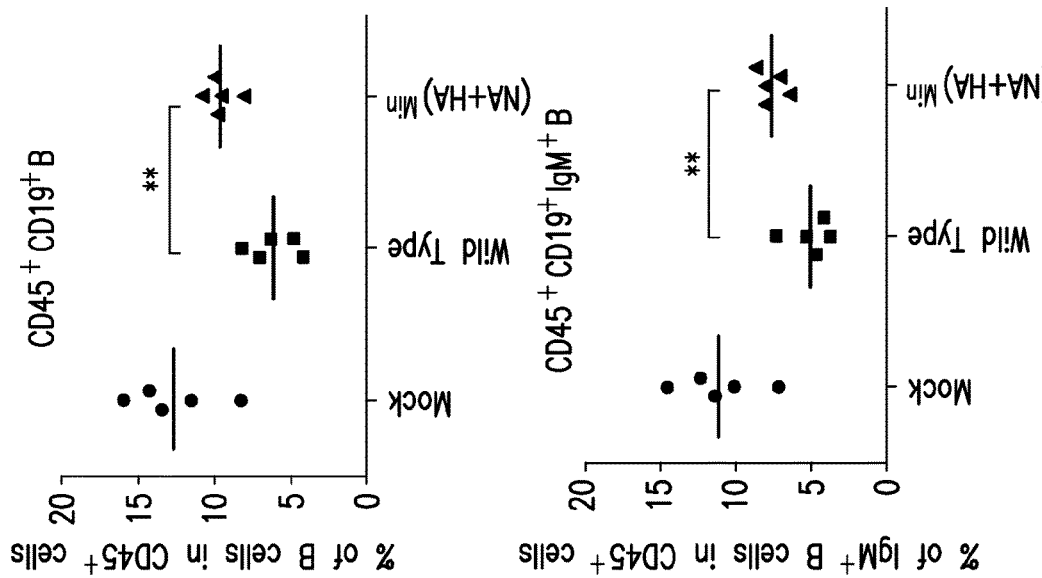
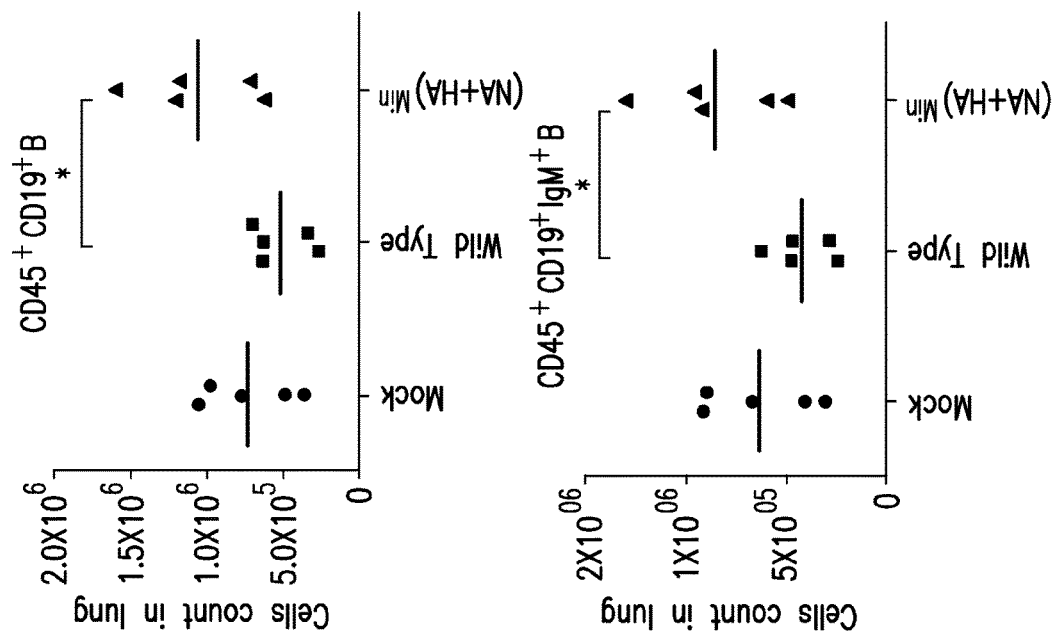
FIG. 19H
FIG. 19I

ATTENUATED INFLUENZA VIRUSES AND VACCINES

CROSS-REFERENCE TO RELATED APPLICATIONS

This application is the national phase of international patent application number PCT/US2014/030027, filed Mar. 15, 2014, which claims the benefit of priority to U.S. Application No. 61/794,617, filed Mar. 15, 2013, which are incorporated herein by reference in their entirety.

FEDERAL FUNDING

This invention was made with government support under grant numbers AI015122 and AI075219 awarded by the National Institutes of Health. The government has certain rights in the invention.

FIELD OF THE INVENTION

This invention provides highly attenuated influenza viruses and vaccines. The attenuated viruses and vaccines proliferate well and have high safety factors. The attenuated viruses providing protective immunity from challenge by virus of the same subtype, as well as cross protection against heterologous viruses.

BACKGROUND OF THE INVENTION

Influenza is a human disease that leads every year to >30,000 deaths in the US and several hundred thousand deaths globally (1). Major neutralization antigenic proteins, hemagglutinin (HA) and neuraminidase (NA) on the virion surface, provide protecting immunity, but undergo yearly genetic variation by point mutations (genetic drift). This renders the viruses resistant to population immunity and set the stage for seasonal epidemics. Further, influenza virus may acquire a new antigenic make-up (reassortment of heterologous genes, referred to as genetic shift) leading to pandemics. Because the flu is seasonal and variable, new vaccines must be produced every year. This is made more complex since more than one type or strain of influenza virus co-circulates in any flu season, a phenomenon demanding that more than one new vaccine may have to be developed every year.

Currently, only two major types of vaccines are licensed, the intramuscularly administered inactivated vaccines ("Flu shot"), and the live attenuated vaccine (LAIV), given intranasally ("FluMist®"). The efficacy of the two vaccines is suboptimal. The injectable inactivated vaccines that requires a large quantity of starting material (the equivalent of approximately $10^{10}$ plaque-forming units, PFU, per dose), are incapable of inducing significant cell-mediated immunity, which is being recognized as an important determinant of protection (4). Moreover, the overall efficacy of the inactivated vaccine in the U.S. adult population aged 18-65 years is only 59% (5). The LAIV "FluMist," on the other hand, induces both humoral and cellular immunity but it is restricted in use to people 2 to 49 yr of age (6, 7). Moreover, recurrent administration of LAIV, which always uses the same attenuating viral backbone, could result in tolerance in repeat recipients (8).

Influenza viruses that have been classified as type A, B, and C, are enveloped, negative-strand RNA viruses of Orthomyxoviridae of which subtypes of type A are the major culprit of human disease (3). The viruses transcribe and replicate their multipartite genome in the cell nucleus, each segment encoding one or two polypeptides. Of these the most important antigenic molecules are the glycoproteins hemagglutinin (HA) and neuraminidase (NA).

SUMMARY OF THE INVENTION

A long-held dogma posits that strong presentation to the immune system of the dominant influenza virus glycoprotein antigens hemagglutinin (HA) and neuraminidase (NA) is paramount for inducing protective immunity against influenza virus infection. It has now been discovered that attenuated viruses in which expression of the two dominant influenza virus glycoprotein antigens, HA and NA, is reduced, are highly effective in providing long lasting protective immunity against lethal wild type challenge and cross protection against diverse subtypes. Further, the viruses have exceptional safety profiles. Accordingly, the invention provides an attenuated influenza virus in which expression of hemagglutinin (HA) and neuraminidase (NA) is reduced. In certain embodiments, HA and NA are the only the only virus proteins having reduced expression. In other embodiments of the invention, the expression of one or more other virus proteins may also be reduced, such as, for example, PA, PB1, PB2, NP, NS, M1, or M2. In certain embodiments, when the expression of a virus proteins other than HA and NA is reduced, the reduction is small compared to the reduction of HA and NA. According to the invention, reduction in expression of virus proteins of the invention is accomplished by changes in protein encoding sequence, for example by lowering the codon pair bias of the protein-encoding sequence, substituting rare codons, modifying G+C content, modifying CG and/or TA (or UA) dinucleotide content, or combinations. Reduced expression can also be accomplished by modifications to the regulatory sequences of the proteins.

In one such embodiment, reducing the codon-pair bias comprises identifying a codon pair in the parent protein-encoding sequence having a codon-pair score that can be reduced, and reducing the codon-pair bias by substituting the codon pair with a codon pair that has a lower codon-pair score. In another such embodiment, reducing the codon-pair bias comprises rearranging the codons of a parent protein-encoding sequence. In certain embodiments, the reduced-expression HA protein-encoding sequence and the reduced-expression NA protein-encoding sequence individually have a codon pair bias less than −0.1, or less than −0.2, or less than −0.3, or less than −0.4. Codon pair bias of a protein-encoding sequence (i.e., an open reading frame) is calculated as described in Coleman et al., 2000 (ref 12) and herein.

In an embodiment of the invention, expression of one or both of the HA protein-encoding sequence and the NA protein-encoding sequence is reduced by replacing one or more codons with synonymous codons that are less frequent in the host.

The invention further provides an influenza vaccine composition for inducing a protective immune response in a subject, wherein the vaccine composition comprises virus in which expression of HA is reduced and expression of NA is reduced. In certain embodiments, only expression of HA and NA is reduced. In some embodiments, expression of another virus protein is also reduced.

The invention also provides a method of eliciting a protective immune response in a subject comprising administering to the subject a prophylactically or therapeutically effective dose of a vaccine composition comprising an attenuated influenza virus, wherein expression of HA is reduced and expression of NA is reduced. In certain embodiments, only expression of HA and NA is reduced. In some embodiments, expression of another virus protein is also reduced. In an embodiment of the invention, an immune response is elicited that is effective against influenza of the same subtype as the attenuated virus of the vaccine. In another embodiment, an immune response is elicited that is effective against a heterologous influenza virus.

The invention also provides a method of making an attenuated influenza virus genome comprising a) obtaining the nucleotide sequence encoding the hemagglutinin protein of an influenza virus and the nucleotide sequence encoding the neuraminidase protein of an influenza virus, b) recoding the hemagglutinin-encoding nucleotide sequence to reduce expression and recoding the neuraminidase-encoding nucleotide sequence to reduce expression, and substituting the recoded nucleotide sequences into an influenza virus genome to make an attenuated influenza virus genome. In certain embodiments, only expression of HA and NA is reduced. In some embodiments, expression of another virus protein is also reduced.

DESCRIPTION OF THE FIGURES

FIG. 2. Protein expression and mRNA levels in $(NA+HA)^{Min}$-infected in tissue culture cells. MDCK cells were infected with $(NA+HA)^{Min}$ or wt PR8 at a MOI of 5. (A) Western blot analyses were performed to determine the viral protein expression the infected cells at 3 h and 6 h p.i. (B) Northern blot analyses were performed to determine mRNA levels of HA, NA, PB1 and GAPDH in $(NA+HA)^{Min}$ or wt PR8-infected MDCK cells. At 3, 6, and 9 h p.i., cytoplasmic mRNA were collected and analyzed. For $HA^{Min}$ and $HA^{WT}$ transcript probes, the same 150 nt that recognized the common 3' end of the respective genes was used. Similarly, the probes for $NA^{Min}$ and $NA^{WT}$ have the same 150 nt sequence corresponding to the common 3' end of the NA genes.

FIG. 10. Expression of virus proteins and mRNAs in MDCK cells infected with WT influenza or $(NA+HA)^{Min}$.

(A) $^{35}$S labeled proteins in infected MDCK cells. (B) Northern analysis of viral mRNAs expressed in infected MDCK.

Figure 11:
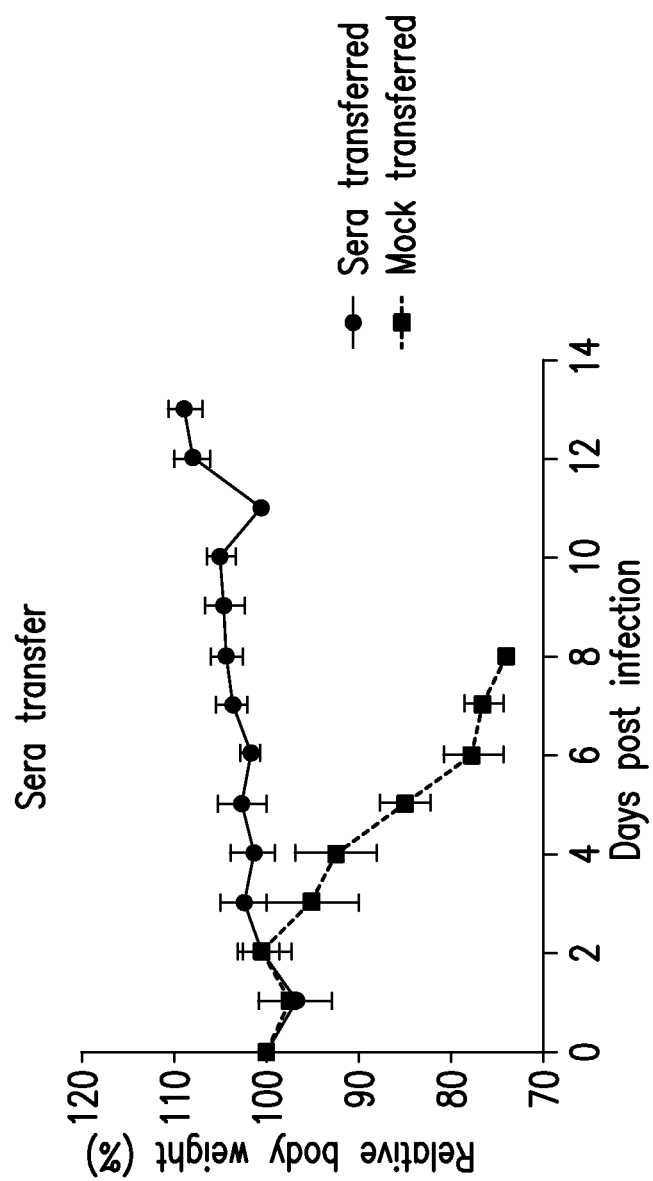

FIG. 11. Passive immunization with Serum from PR8-(NA+HA)$^{Min}$ vaccinated mice protects naïve mice from homologous WT PR8 challenge. FIG. 11 shows mice passively immunized with PR8-(NA+HA)$^{Min}$ sera survived and remained healthy upon challenge with WT virus.

Figure 12A:
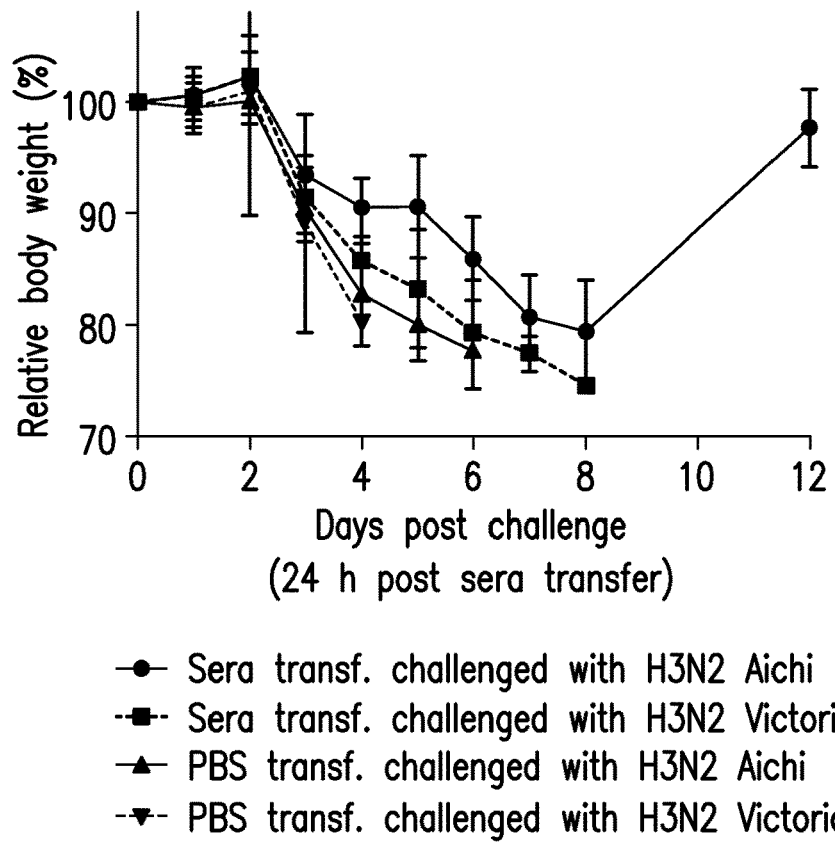
Figure 12B:
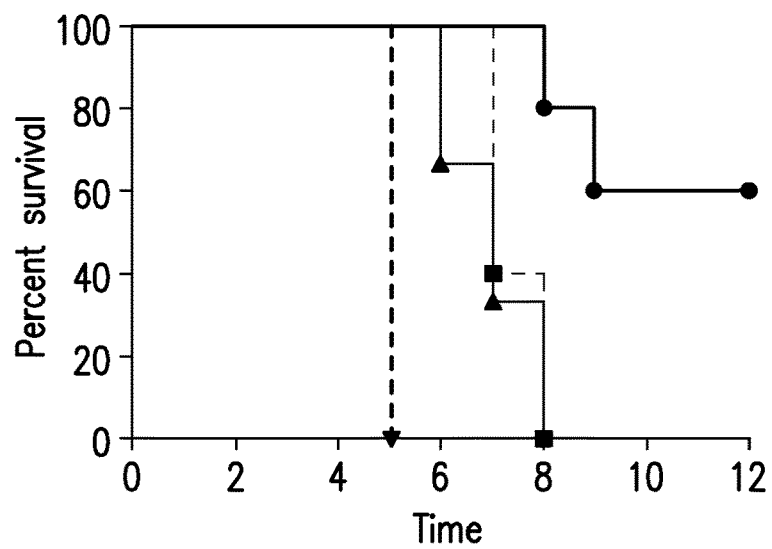

FIG. 12. Passive immunization with serum from PR8-(NA+HA)$^{Min}$ (H1N1) vaccinated mice protects naïve mice from heterologous challenge with an H3N2 virus. FIG. 11 shows mice passively immunized with PR8-(NA+HA)$^{Min}$ sera maintained weight (Panel A) and had improved survival (Panel B) when challenged with H3N2 virus.

Figure 13A:
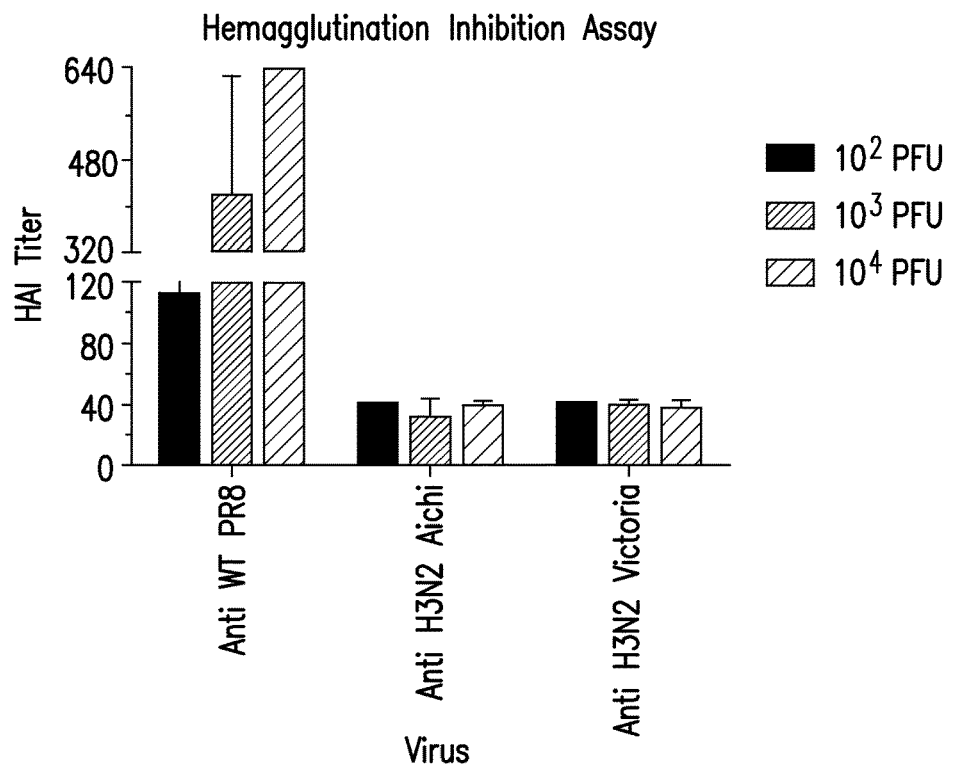
Figure 13B:
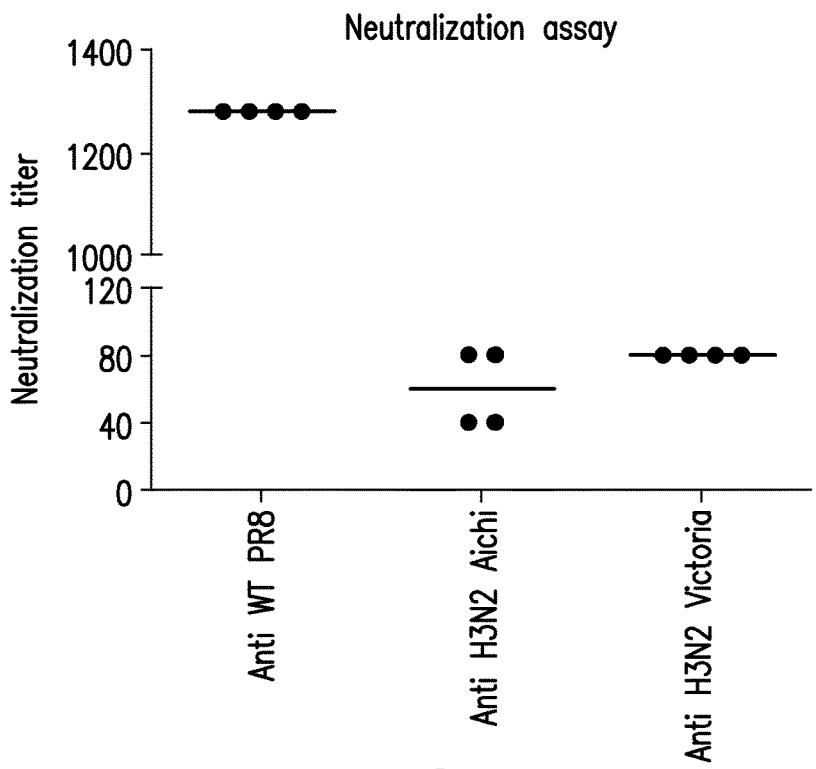

FIG. 13. Assessment of cross protection against H3N2 viruses conferred by immunization with PR8-(NA+HA)$^{Min}$. (A) Inhibition of hemagglutination by sera from PR8-(NA+HA)$^{Min}$ immunized mice. (B) Neutralization of virus infection of MDCK cells by sera from PR8-(NA+HA)$^{Min}$ immunized mice.

FIG. 14. Growth of WT and PR8-(NA+HA)$^{Min}$ virus in MDCK cells and MDCK cells transfected to express α-2,6-sialyltransferase.

Figure 15:
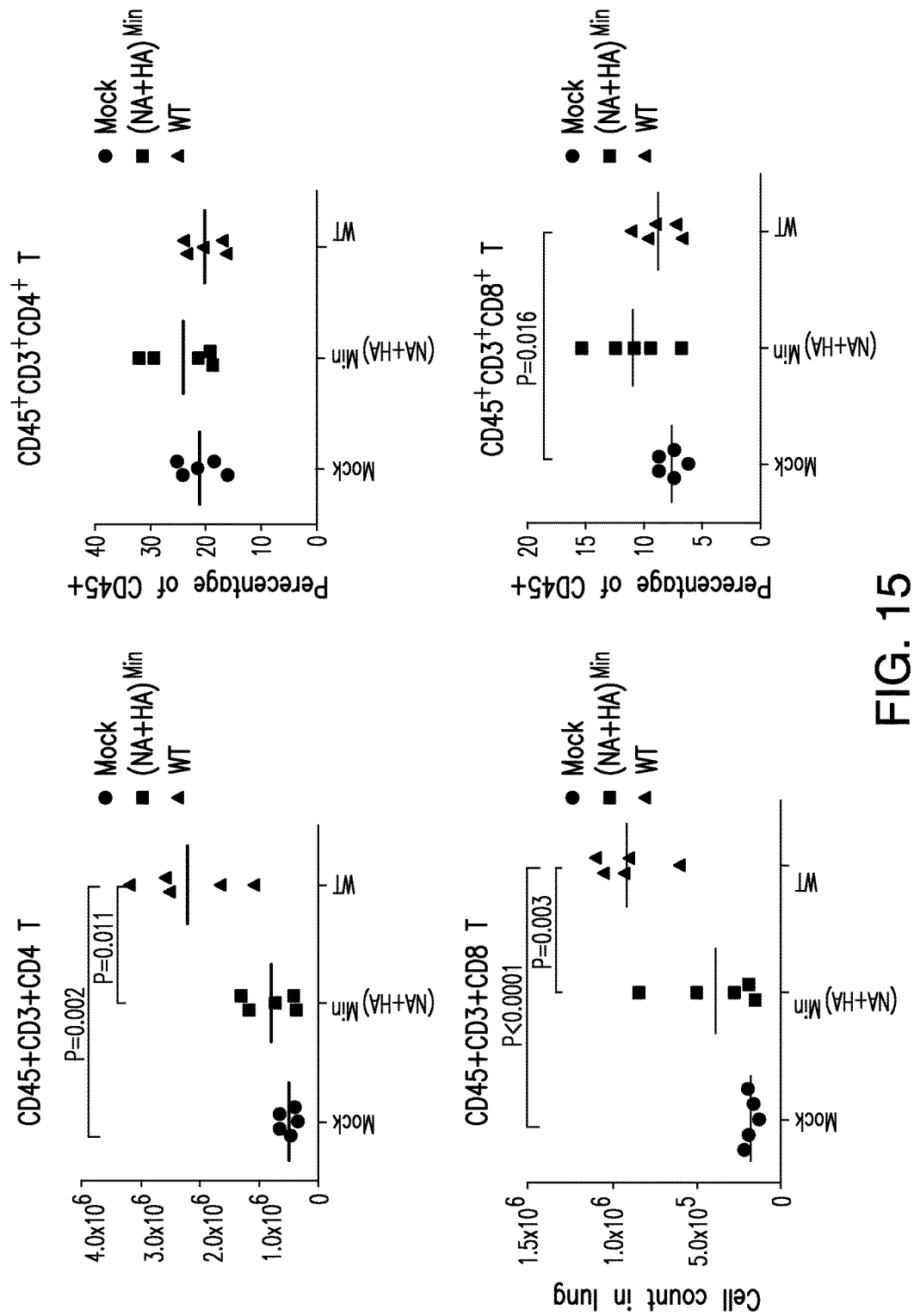
Figure 15:
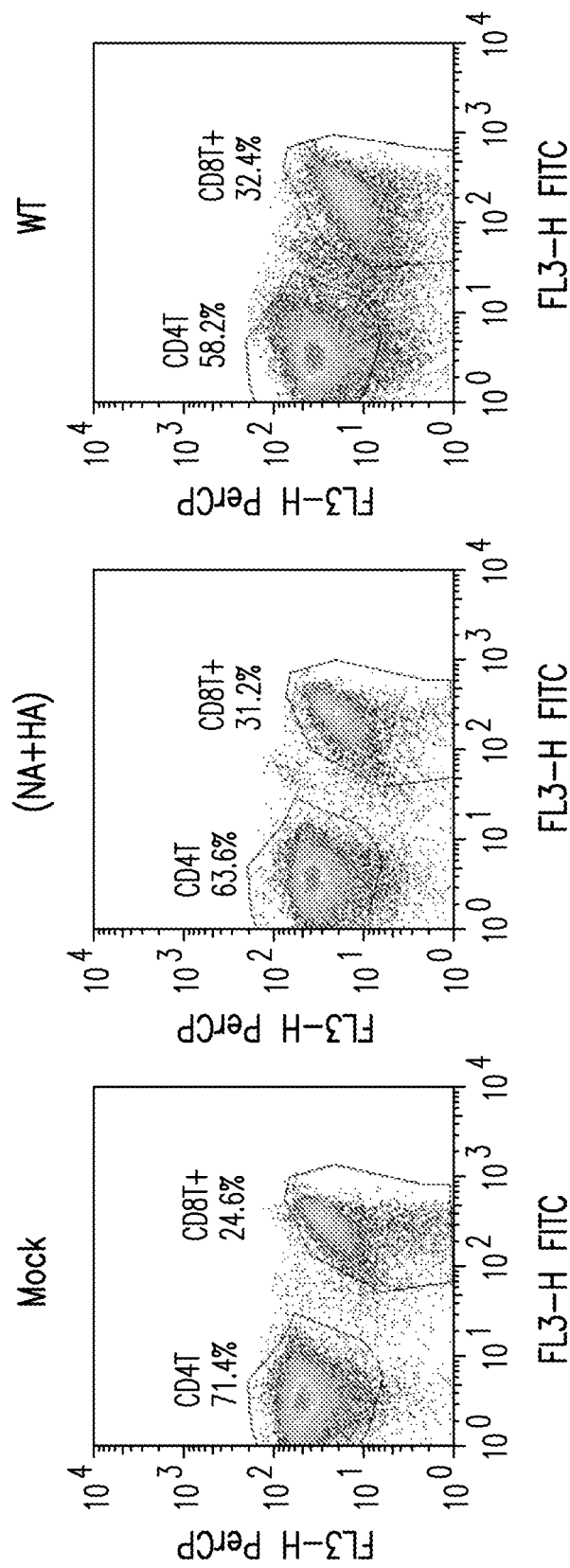

FIG. 15. T cell responses in lungs of Balb/C mice 7 days post-infection. Cell numbers are expressed as total cell count in lung (left panels) or percentage of CD45$^+$ cells (right panels).

Figure 16:
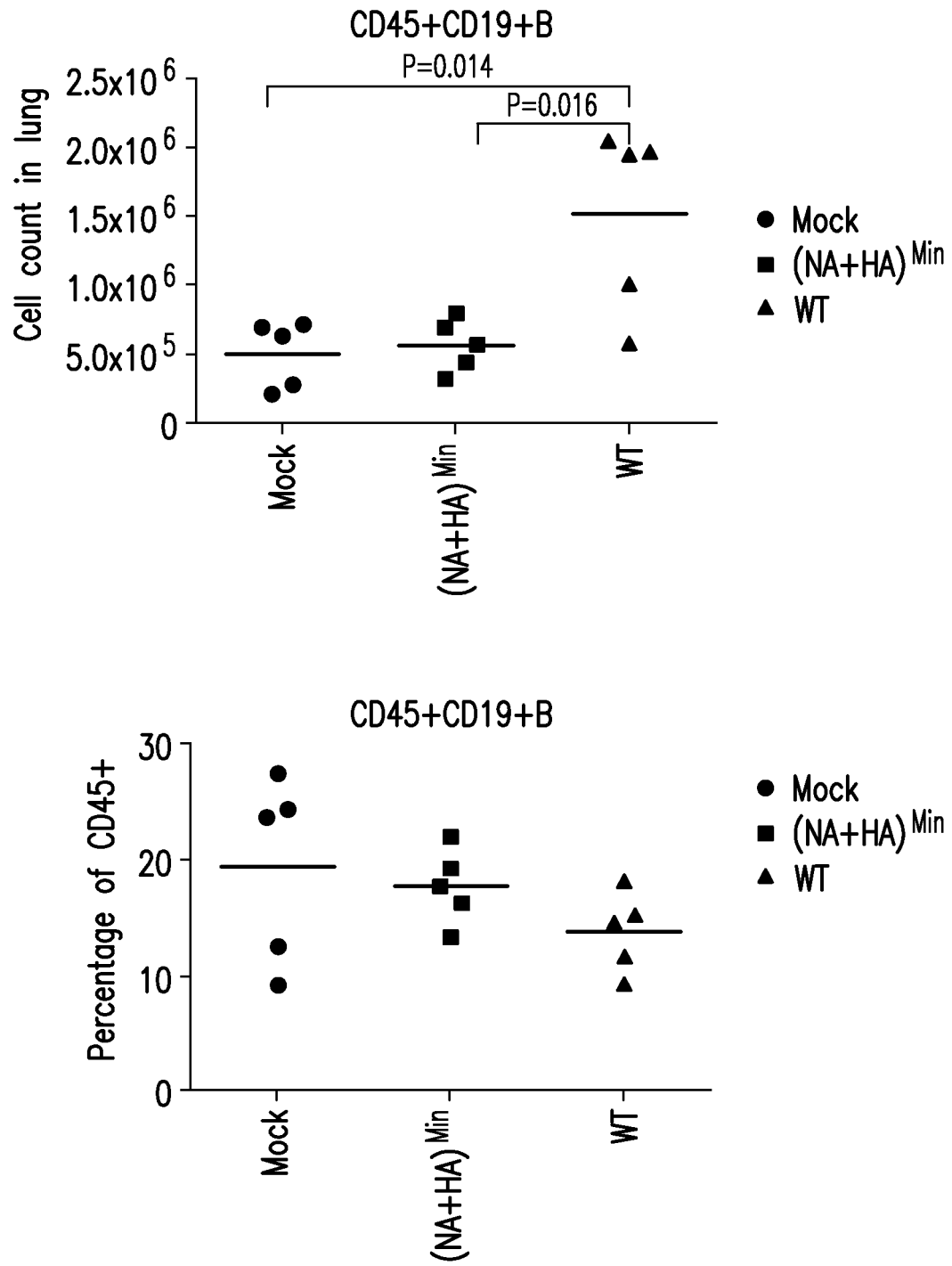

FIG. 16. B cell responses in lungs of Balb/C mice 7 days post-infection. Cell numbers are expressed as total cell count in lung (upper panel) or percentage of CD45$^+$ cells (lower panels).

Figure 17:
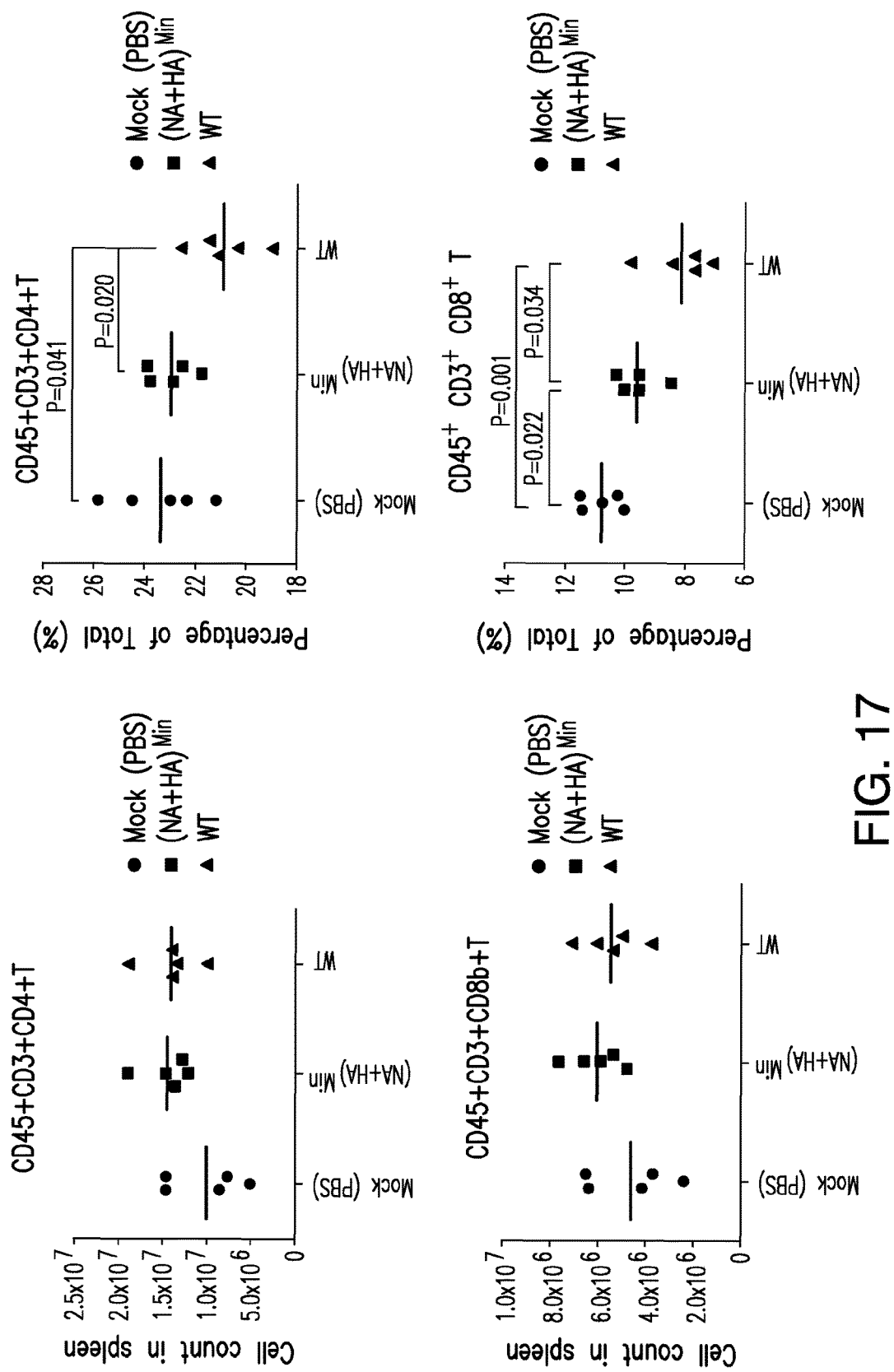
Figure 17:
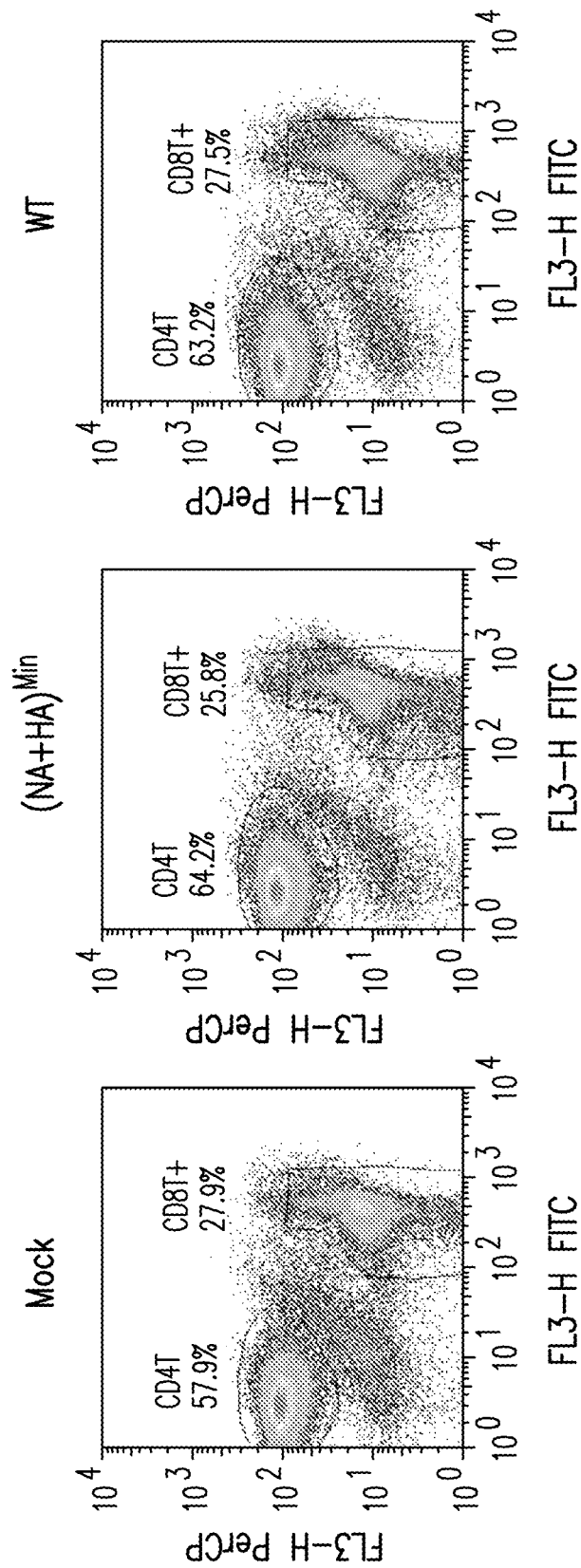

FIG. 17. T cell responses in spleens of Balb/C mice 7 days post-infection.

Figure 18:
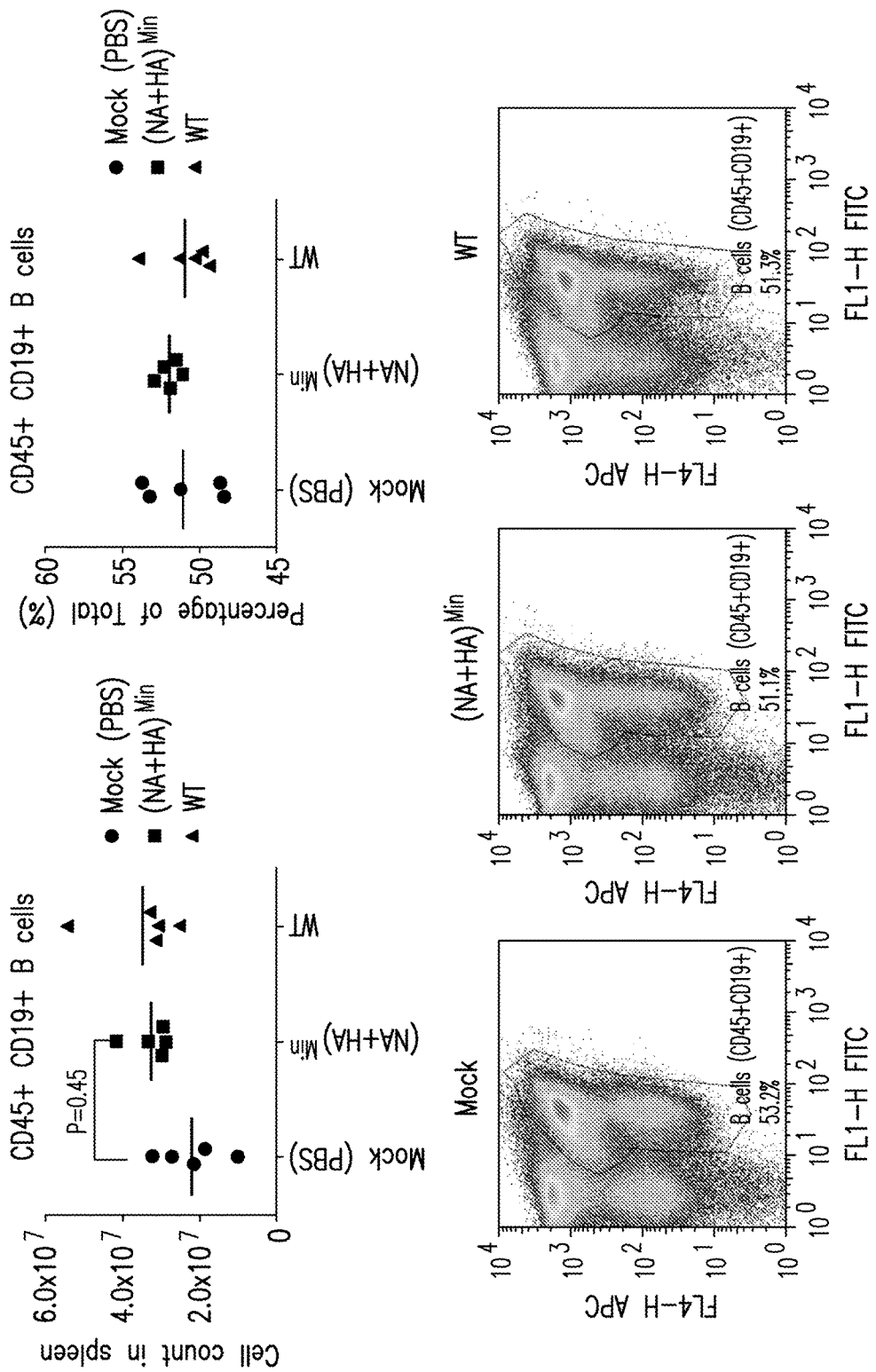
Figure 19A:
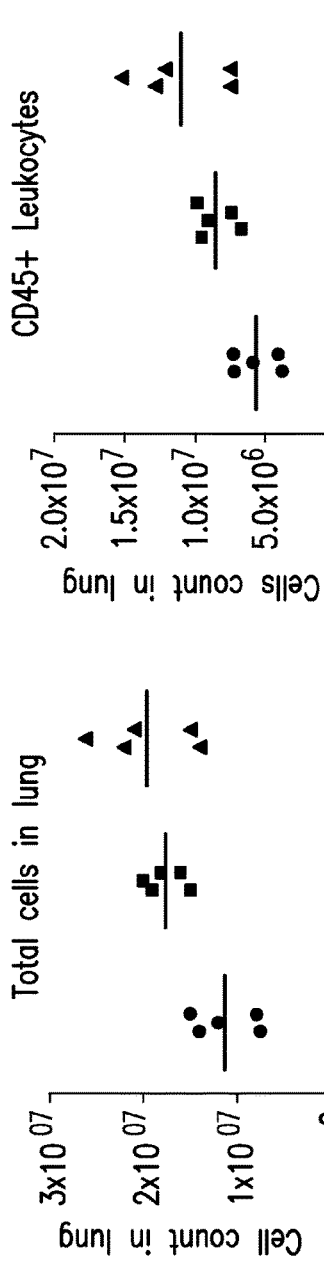
Figure 19B:
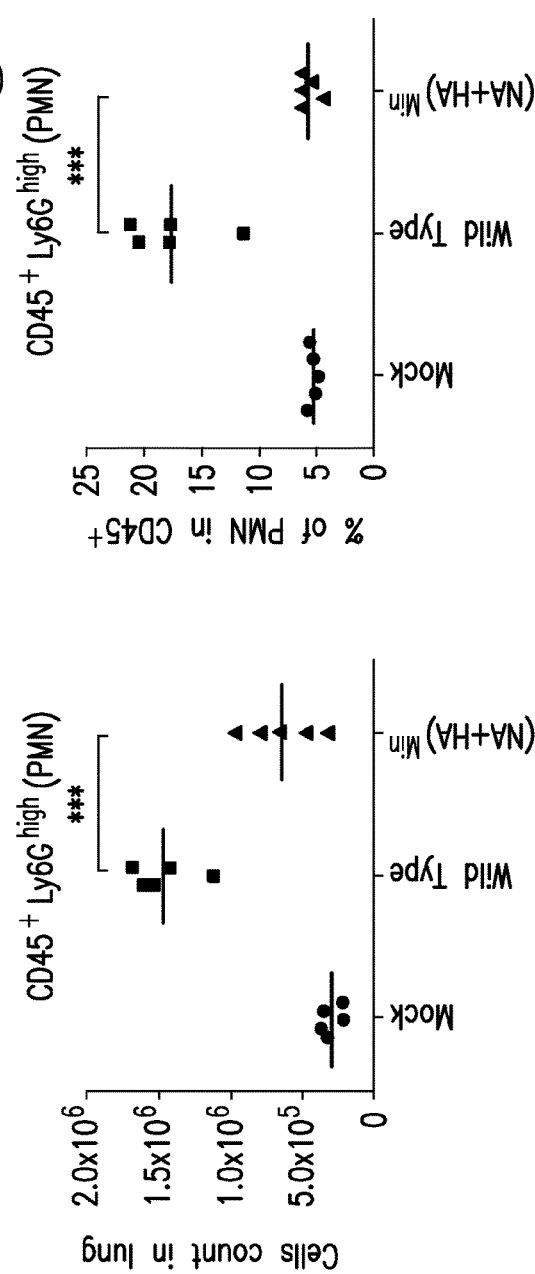
Figure 19E:
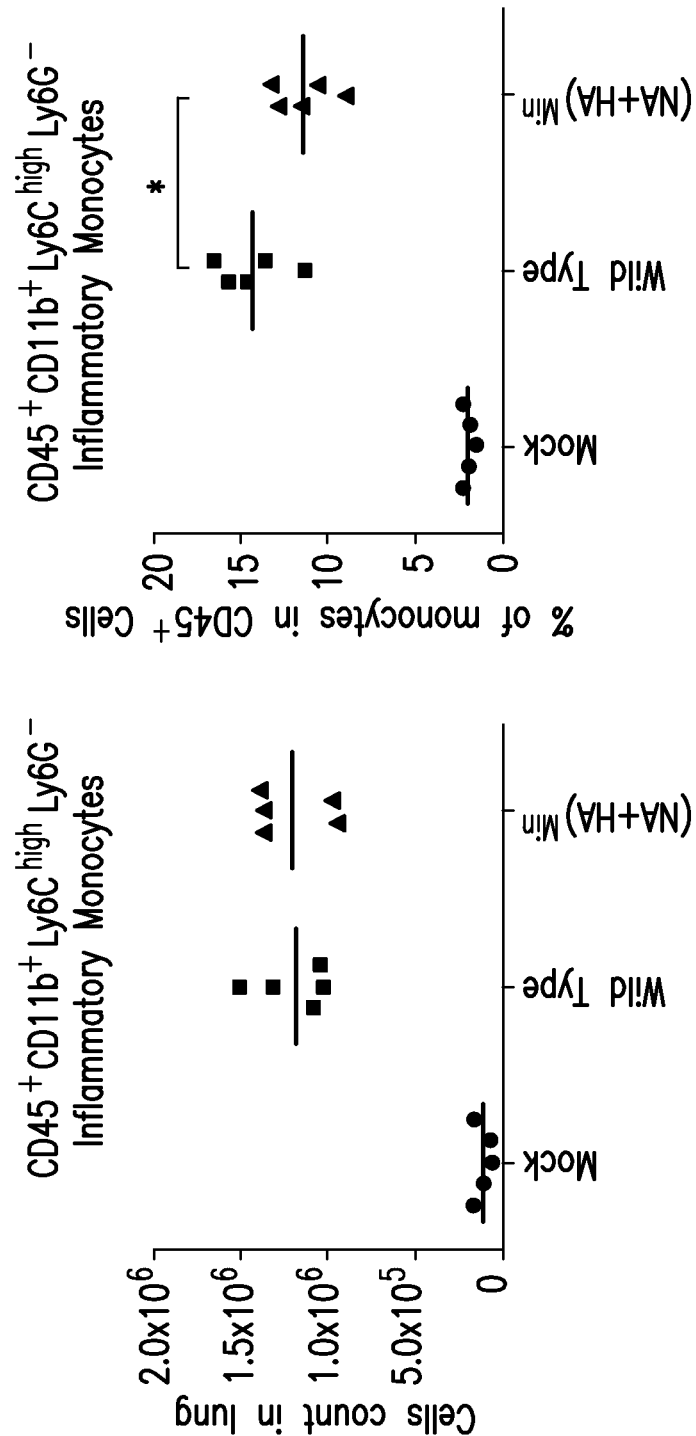
Figures 19F, 19G:
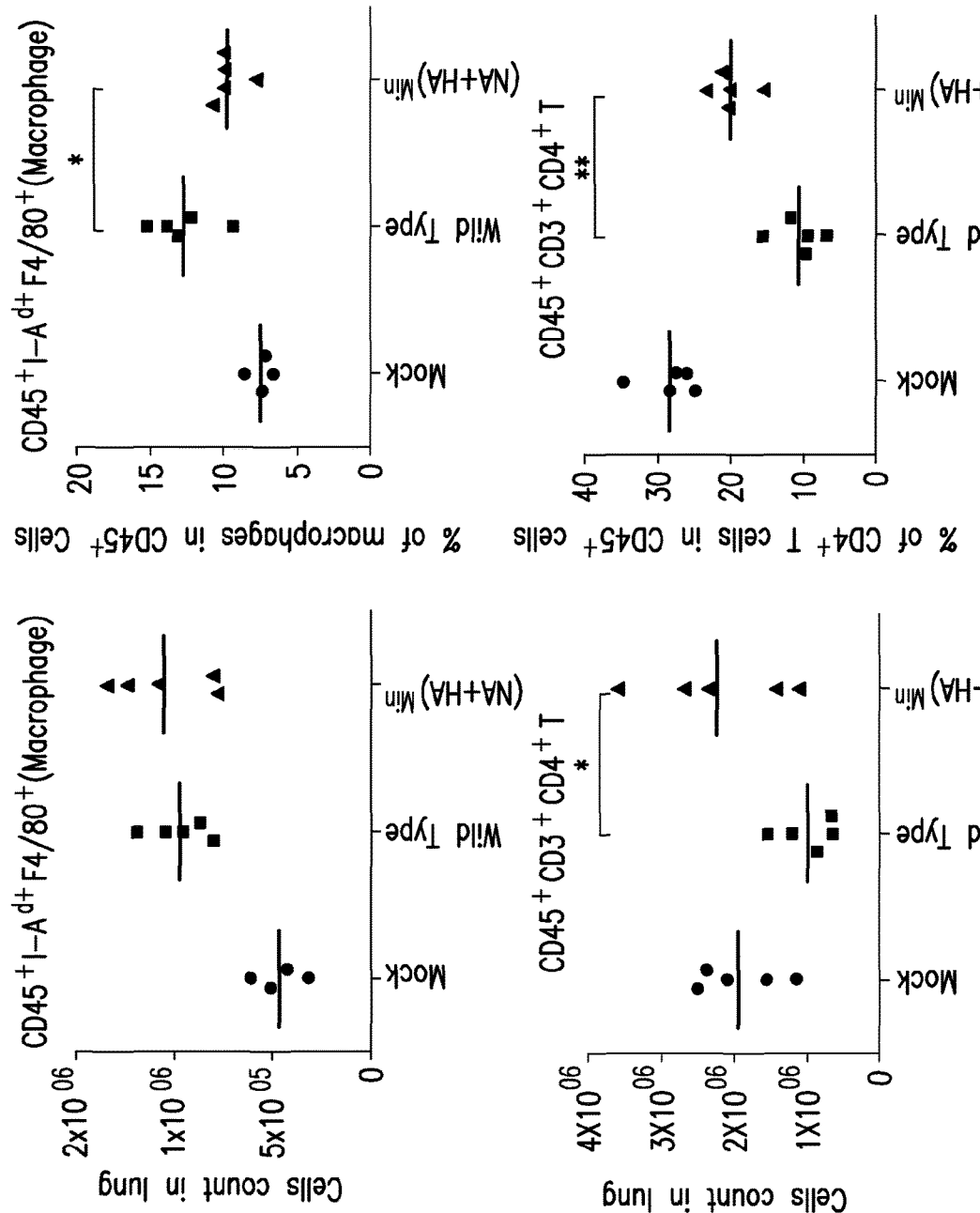

FIG. 18. T cell responses in spleens of Balb/C mice 7 days post-infection.

FIG. 19. Immune cell infiltration of lung tissue 3 days post-infection. (A) CD45$^+$ leukocytes, (B) CD45$^+$ Ly6G$^{high}$ polymorphonuclear leukocytes (PMN), (C) CD45$^+$CD11c$^+$ I-A$^{d+}$ F4/80$^-$ dendritic cells, (D) CD45$^+$ NKp46$^+$ natural killer cells, (E) CD45$^+$CD11 b$^+$Ly6C$^{high}$Ly6G$^-$ inflammatory monocytes, (F) CD45$^+$ I-A$^{d+}$ F4/80$^+$ macrophages, (G) CD45$^+$CD3$^+$CD4$^+$ T helper cells, (H) CD45$^+$ CD19$^+$ B cells, and (I) CD45$^+$CD19$^+$IgM$^+$ B cells.

DETAILED DESCRIPTION

The present invention relates to the production of attenuated influenza viruses that can be used to protect against viral infection and disease. A basic premise in flu vaccination is adequate delivery of HA and NA to vaccine recipients assuming that a very high dose ("Flu shot") or a dose corresponding to live viral infection ("FluMist") of these traditionally dominant antigenic polypeptides alone are sufficient for adequate vaccine efficacy. Those expectations aside, the present invention benefits from a contrary approach. The invention provides attenuated influenza viruses in which expression of HA and NA is reduced, which have excellent growth properties useful to vaccine production, yet possess an extraordinary safety profile and enhanced protective characteristics. The attenuated viruses proliferate nearly as well as wild type virus, have highly attenuated phenotypes, as revealed by LD$_{50}$ values, are unusually effective in providing protective immunity against challenge by influenza virus of the same subtype, and also provide protective immunity against challenge by influenza virus of other subtypes.

In certain attenuated viruses of the invention, the expression of one or more other virus proteins may also be reduced, such as, for example, PA, PB1, PB2, NP, NS, M1, or M2. In certain embodiments, when the expression of a virus proteins other than HA and NA is reduced, the reduction is small compared to the reduction of HA and NA.

In certain attenuated influenza viruses of the invention, expression of hemagglutinin (HA) and neuraminidase (NA) is reduced, and expression of other influenza proteins (i.e., NP, M (including M1 and M2), NS, PA, PB1, and PB2 protein is not substantially changed (i.e., substantially reduced or increased). In an embodiment of the invention, expression of NP, PA, PB1, and PB2 is not substantially reduced. That expression of the NP, M (including M1 and M2), NS, PA, PB1, and PB2 protein encoding sequences is not substantially reduced means that in embodiments where there is a small change in expression of one or more of those proteins (e.g., NP, PA, PB1, PB2, M, and or M), the change in expression of those proteins has little or no effect on attenuation. Little or no effect on attenuation includes one or both of the following: 1) Any reduced expression of NP, M (including M1 and M2), NS, PA, PB1, or PB2 does not reduce viral replication or viral infectivity more than 20% when the NP, M (including M1 and M2), NS, PA, PB1, or PB2 is expressed at the reduced level in a test influenza virus in which only the level of that protein is reduced; 2) The level of expression of NP, M (including M1 and M2), NS, PA, PB1, or PB2 is reduced by less than 20% in the attenuated virus in which expression of HA and NA is reduced.

In certain embodiments of the invention, the attenuated influenza viruses of the invention comprise a recoded hemagglutinin (HA) nucleic acid and a recoded neuraminidase (NA) nucleic acid. In certain of these embodiments, another virus protein, such as NP, M (including M1 and M2), NS, PA, PB1, or PB2, is recoded. In others of these embodiments, other protein encoding sequences (i.e., NP, M (including M1 and M2), NS, PA, PB1, and PB2 protein encoding sequences are not recoded. That the NP, M (including M1 and M2), NS, PA, PB1, and PB2 protein encoding sequences are not recoded does not exclude mutations and other variations in those sequences, but only means that any mutations or variations made in those sequences have little or no effect on attenuation. Little or no effect on attenuation includes one or both of the following: 1) The mutations or variations in the NP, M (including M1 and M2), NS, PA, PB1, or PB2 sequence do not reduce viral replication or viral infectivity more than 20% when the variant NP, M (including M1 and M2), NS, PA, PB1, or PB2 nucleic acid sequence is the only variant in a test influenza virus; 2) Mutations or variations in any of the NP, M (including M1 and M2), NS, PA, PB1, or PB2 nucleic acid represent fewer than 10% of the nucleotides in that coding sequence.

The viruses of the invention are highly attenuated. In embodiments of the invention, compared to wild type, the viruses are at least 5,000 fold attenuated, or at least 10,000 fold attenuated, or at least 20,000 fold attenuated, or at least 33,000 fold attenuated, or at least 50,000 fold attenuated, of at least 100,000 fold attenuated in the BALB/c mouse model compared to a wild type virus having proteins of the same sequence but encoded by a different nucleotide sequence.

The attenuated viruses are also highly protective against wild type virus of the same subtype. In embodiments of the invention, the protective dose (PD$_{50}$) of the viruses is less than 100 PFU, or less than 50 PFU, or less than 20 PFU, or less than 10 PFU, or less than 5 PFU, when measured by a mouse model, such as exemplified herein.

The attenuated viruses of the invention also exhibit a large margin of safety (i.e., the difference between LD$_{50}$ and PD$_{50}$), thus have high safety factors, defined herein as the ratio of LD$_{50}$/PD$_{50}$. In certain embodiments of the invention, the safety factor is at least $10^2$, or at least $10^3$, or at least $10^4$, or at least $10^5$, or at least $2\times10^5$, or at least $5\times10^5$, or at least $10^6$, or at least $2\times10^6$, or at least $5\times10^6$. In certain embodiments, the safety factor is from $10^2$ to $10^3$, or from $10^3$ to $10^4$, or from $10^4$ to $10^5$, or from $10^5$ to $10^6$.

The attenuated viruses of the invention are also highly protective against heterologous viruses. In certain embodiments of the invention, the protective dose (PD$_{50}$) of an attenuated virus of the invention is less than 1000 PFU, or less than 500 PFU, or less than 200 PFU, or less than 100 PFU, when measured by a mouse model, such as exemplified herein The recoding of HA and NA protein encoding sequences of the attenuated viruses of the invention can have been made utilizing any algorithm or procedure known in the art or newly devised for recoding a protein encoding sequence. According to the invention, nucleotide substitutions are engineered in multiple locations in the HA and NA coding sequences, wherein the substitutions introduce a plurality of synonymous codons into the genome. In certain embodiments, the synonymous codon substitutions alter codon bias, codon pair bias, the density of infrequent codons or infrequently occurring codon pairs, RNA secondary structure, CG and/or TA (or UA) dinucleotide content, C+G content, translation frameshift sites, translation pause sites, the presence or absence microRNA recognition sequences or any combination thereof, in the genome. The codon substitutions may be engineered in multiple locations distributed throughout the HA and NA coding sequences, or in the multiple locations restricted to a portion of the HA and NA coding sequences. Because of the large number of defects (i.e., nucleotide substitutions) involved, the invention provides a means of producing stably attenuated viruses and live vaccines.

As discussed further below, in some embodiments, a virus coding sequence is recoded by substituting one or more codon with synonymous codons used less frequently in the influenza host (e.g., humans, birds, pigs). In some embodiments, a virus coding sequence is recoded by substituting one or more codons with synonymous codons used less frequently in the influenza virus. In certain embodiments, the number of codons substituted with synonymous codons is at least 5. In some embodiments, at least 10, or at least 20 codons are substituted with synonymous codons.

In some embodiments, virus codon pairs are recoded to reduce (i.e., lower the value of) codon-pair bias. In certain embodiments, codon-pair bias is reduced by identifying a codon pair in an HA or NA coding sequence having a codon-pair score that can be reduced and reducing the codon-pair bias by substituting the codon pair with a codon pair that has a lower codon-pair score. In some embodiments, this substitution of codon pairs takes the form of rearranging existing codons of a sequence. In some such embodiments, a subset of codon pairs is substituted by rearranging a subset of synonymous codons. In other embodiments, codon pairs are substituted by maximizing the number of rearranged synonymous codons. It is noted that while rearrangement of codons leads to codon-pair bias that is reduced (made more negative) for the virus coding sequence overall, and the rearrangement results in a decreased CPS at many locations, there may accompanying CPS increases at other locations, but on average, the codon pair scores, and thus the CPB of the modified sequence, is reduced. In some embodiments, recoding of codons or codon-pairs can take into account altering the G+C content of the HA and NA coding sequences. In some embodiments, recoding of codons or codon-pairs can take into account altering the frequency of CG and/or TA dinucleotides in the HA and NA coding sequences.

In certain embodiments, the recoded (i.e., reduced-expression) HA protein-encoding sequence has a codon pair bias less than −0.1, or less than −0.2, or less than −0.3, or less than −0.4. In certain embodiments, the recoded (i.e., reduced-expression) NA protein-encoding sequence has a codon pair bias less than −0.1, or less than −0.2, or less than −0.3, or less than −0.4. In certain embodiments, the codon pair bias of the recoded HA protein encoding sequence is reduced by at least 0.1, or at least 0.2, or at least 0.3, or at least 0.4, compared to the parent HA protein encoding sequence from which it is derived. In certain embodiments, the codon pair bias of the recoded NA protein encoding sequence is reduced by at least 0.1, or at least 0.2, or at least 0.3, or at least 0.4, compared to the parent NA protein encoding sequence from which it is derived. In certain embodiments, rearrangement of synonymous codons of the HA protein-encoding sequence provides a codon-pair bias reduction of at least 0.1, or at least 0.2, or at least 0.3, or at least 0.4, parent HA parent encoding sequence from which it is derived. In certain embodiments, rearrangement of synonymous codons of the NA protein-encoding sequence provides a codon-pair bias reduction of at least 0.1, or at least 0.2, or at least 0.3, or at least 0.4, parent NA protein encoding sequence from which it is derived.

Usually, these substitutions and alterations are made and reduce expression of the encoded virus proteins without altering the amino acid sequence of the encoded protein. In certain embodiments, the invention also includes alterations in the HA and/or NA coding sequences that result in substitution of non-synonymous codons an amino acid substitutions in the encoded protein, which may or may not be conservative.

Most amino acids are encoded by more than one codon. See the genetic code in Table 1. For instance, alanine is encoded by GCU, GCC, GCA, and GCG. Three amino acids (Leu, Ser, and Arg) are encoded by six different codons, while only Trp and Met have unique codons. "Synonymous" codons are codons that encode the same amino acid. Thus, for example, CUU, CUC, CUA, CUG, UUA, and UUG are synonymous codons that code for Leu. Synonymous codons are not used with equal frequency. In general, the most frequently used codons in a particular organism are those for which the cognate tRNA is abundant, and the use of these codons enhances the rate and/or accuracy of protein translation. Conversely, tRNAs for the rarely used codons are found at relatively low levels, and the use of rare codons is thought to reduce translation rate and/or accuracy.

TABLE 1

Genetic Code$^a$

|   | U | C | A | G |   |
|---|---|---|---|---|---|
| U | Phe | Ser | Tyr | Cys | U |
|   | Phe | Ser | Tyr | Cys | C |
|   | Leu | Ser | STOP | STOP | A |
|   | Leu | Ser | STOP | Trp | G |
| C | Leu | Pro | His | Arg | U |
|   | Leu | Pro | His | Arg | C |
|   | Leu | Pro | Gln | Arg | A |
|   | Leu | Pro | Gln | Arg | G |
| A | Ile | Thr | Asn | Ser | U |
|   | Ile | Thr | Asn | Ser | C |

TABLE 1-continued

Genetic Code[a]

|   | U | C | A | G |   |
|---|---|---|---|---|---|
|   | Ile | Thr | Lys | Arg | A |
|   | Met | Thr | Lys | Arg | G |
| G | Val | Ala | Asp | Gly | U |
|   | Val | Ala | Asp | Gly | C |
|   | Val | Ala | Glu | Gly | A |
|   | Val | Ala | Glu | Gly | G |

[a]The first nucleotide in each codon encoding a particular amino acid is shown in the left-most column; the second nucleotide is shown in the top row; and the third nucleotide is shown in the right-most column.

Codon Bias

As used herein, a "rare" codon is one of at least two synonymous codons encoding a particular amino acid that is present in an mRNA at a significantly lower frequency than the most frequently used codon for that amino acid. Thus, the rare codon may be present at about a 2-fold lower frequency than the most frequently used codon. Preferably, the rare codon is present at least a 3-fold, more preferably at least a 5-fold, lower frequency than the most frequently used codon for the amino acid. Conversely, a "frequent" codon is one of at least two synonymous codons encoding a particular amino acid that is present in an mRNA at a significantly higher frequency than the least frequently used codon for that amino acid. The frequent codon may be present at about a 2-fold, preferably at least a 3-fold, more preferably at least a 5-fold, higher frequency than the least frequently used codon for the amino acid. For example, human genes use the leucine codon CTG 40% of the time, but use the synonymous CTA only 7% of the time (see Table 2). Thus, CTG is a frequent codon, whereas CTA is a rare codon. Roughly consistent with these frequencies of usage, there are 6 copies in the genome for the gene for the tRNA recognizing CTG, whereas there are only 2 copies of the gene for the tRNA recognizing CTA. Similarly, human genes use the frequent codons TCT and TCC for serine 18% and 22% of the time, respectively, but the rare codon TCG only 5% of the time. TCT and TCC are read, via wobble, by the same tRNA, which has 10 copies of its gene in the genome, while TCG is read by a tRNA with only 4 copies. It is well known that those mRNAs that are very actively translated are strongly biased to use only the most frequent codons. This includes genes for ribosomal proteins and glycolytic enzymes. On the other hand, mRNAs for relatively non-abundant proteins may use the rare codons.

TABLE 2

Codon usage in *Homo sapiens* (source: http://www.kazusa.or.jp/codon/)

| Amino Acid | Codon | Number | /1000 | Fraction |
|---|---|---|---|---|
| Gly | GGG | 636457.00 | 16.45 | 0.25 |
| Gly | GGA | 637120.00 | 16.47 | 0.25 |
| Gly | GGT | 416131.00 | 10.76 | 0.16 |
| Gly | GGC | 862557.00 | 22.29 | 0.34 |
| Glu | GAG | 1532589.00 | 39.61 | 0.58 |
| Glu | GAA | 1116000.00 | 28.84 | 0.42 |
| Asp | GAT | 842504.00 | 21.78 | 0.46 |
| Asp | GAC | 973377.00 | 25.16 | 0.54 |
| Val | GTG | 1091853.00 | 28.22 | 0.46 |
| Val | GTA | 273515.00 | 7.07 | 0.12 |
| Val | GTT | 426252.00 | 11.02 | 0.18 |
| Val | GTC | 562086.00 | 14.53 | 0.24 |
| Ala | GCG | 286975.00 | 7.42 | 0.11 |
| Ala | GCA | 614754.00 | 15.89 | 0.23 |
| Ala | GCT | 715079.00 | 18.48 | 0.27 |
| Ala | GCC | 1079491.00 | 27.90 | 0.40 |

TABLE 2-continued

Codon usage in *Homo sapiens* (source: http://www.kazusa.or.jp/codon/)

| Amino Acid | Codon | Number | /1000 | Fraction |
|---|---|---|---|---|
| Arg | AGG | 461676.00 | 11.93 | 0.21 |
| Arg | AGA | 466435.00 | 12.06 | 0.21 |
| Ser | AGT | 469641.00 | 12.14 | 0.15 |
| Ser | AGC | 753597.00 | 19.48 | 0.24 |
| Lys | AAG | 1236148.00 | 31.95 | 0.57 |
| Lys | AAA | 940312.00 | 24.30 | 0.43 |
| Asn | AAT | 653566.00 | 16.89 | 0.47 |
| Asn | AAC | 739007.00 | 19.10 | 0.53 |
| Met | ATG | 853648.00 | 22.06 | 1.00 |
| Ile | ATA | 288118.00 | 7.45 | 0.17 |
| Ile | ATT | 615699.00 | 15.91 | 0.36 |
| Ile | ATC | 808306.00 | 20.89 | 0.47 |
| Thr | ACG | 234532.00 | 6.06 | 0.11 |
| Thr | ACA | 580580.00 | 15.01 | 0.28 |
| Thr | ACT | 506277.00 | 13.09 | 0.25 |
| Thr | ACC | 732313.00 | 18.93 | 0.36 |
| Trp | TGG | 510256.00 | 13.19 | 1.00 |
| End | TGA | 59528.00 | 1.54 | 0.47 |
| Cys | TGT | 407020.00 | 10.52 | 0.45 |
| Cys | TGC | 487907.00 | 12.61 | 0.55 |
| End | TAG | 30104.00 | 0.78 | 0.24 |
| End | TAA | 38222.00 | 0.99 | 0.30 |
| Tyr | TAT | 470083.00 | 12.15 | 0.44 |
| Tyr | TAC | 592163.00 | 15.30 | 0.56 |
| Leu | TTG | 498920.00 | 12.89 | 0.13 |
| Leu | TTA | 294684.00 | 7.62 | 0.08 |
| Phe | TTT | 676381.00 | 17.48 | 0.46 |
| Phe | TTC | 789374.00 | 20.40 | 0.54 |
| Ser | TCG | 171428.00 | 4.43 | 0.05 |
| Ser | TCA | 471469.00 | 12.19 | 0.15 |
| Ser | TCT | 585967.00 | 15.14 | 0.19 |
| Ser | TCC | 684663.00 | 17.70 | 0.22 |
| Arg | CGG | 443753.00 | 11.47 | 0.20 |
| Arg | CGA | 239573.00 | 6.19 | 0.11 |
| Arg | CGT | 176691.00 | 4.57 | 0.08 |
| Arg | CGC | 405748.00 | 10.49 | 0.18 |
| Gln | CAG | 1323614.00 | 34.21 | 0.74 |
| Gln | CAA | 473648.00 | 12.24 | 0.26 |
| His | CAT | 419726.00 | 10.85 | 0.42 |
| His | CAC | 583620.00 | 15.08 | 0.58 |
| Leu | CTG | 1539118.00 | 39.78 | 0.40 |
| Leu | CTA | 276799.00 | 7.15 | 0.07 |
| Leu | CTT | 508151.00 | 13.13 | 0.13 |
| Leu | CTC | 759527.00 | 19.63 | 0.20 |
| Pro | CCG | 268884.00 | 6.95 | 0.11 |
| Pro | CCA | 653281.00 | 16.88 | 0.28 |
| Pro | CCT | 676401.00 | 17.48 | 0.29 |
| Pro | CCC | 767793.00 | 19.84 | 0.32 |

The propensity for highly expressed genes to use frequent codons is called "codon bias." A gene for a ribosomal protein might use only the 20 to 25 most frequent of the 61 codons, and have a high codon bias (a codon bias close to 1), while a poorly expressed gene might use all 61 codons, and have little or no codon bias (a codon bias close to 0). It is thought that the frequently used codons are codons where larger amounts of the cognate tRNA are expressed, and that use of these codons allows translation to proceed more rapidly, or more accurately, or both. The PV capsid protein, for example, is very actively translated, and has a high codon bias.

Codon Pair Bias

In addition, a given organism has a preference for the nearest codon neighbor of a given codon A, referred to a bias in codon pair utilization. A change of codon pair bias, without changing the existing codons, can influence the rate of protein synthesis and production of a protein.

Codon pair bias may be illustrated by considering the amino acid pair Ala-Glu, which can be encoded by 8 different codon pairs. If no factors other than the frequency of each individual codon (as shown in Table 2) are responsible for the frequency of the codon pair, the expected frequency of each of the 8 encodings can be calculated by multiplying the frequencies of the two relevant codons. For example, by this calculation the codon pair GCA-GAA would be expected to occur at a frequency of 0.097 out of all Ala-Glu coding pairs (0.23×0.42; based on the frequencies in Table 2). In order to relate the expected (hypothetical) frequency of each codon pair to the actually observed frequency in the human genome the Consensus CDS (CCDS) database of consistently annotated human coding regions, containing a total of 14,795 human genes, was used. This set of genes is the most comprehensive representation of human coding sequences. Using this set of genes the frequencies of codon usage were re-calculated by dividing the number of occurrences of a codon by the number of all synonymous codons coding for the same amino acid. As expected the frequencies correlated closely with previously published ones such as the ones given in Table 2. Slight frequency variations are possibly due to an oversampling effect in the data provided by the codon usage database at Kazusa DNA Research Institute (http://www.kazusa.or.jp/codon/codon.html) where 84949 human coding sequences were included in the calculation (far more than the actual number of human genes). The codon frequencies thus calculated were then used to calculate the expected codon-pair frequencies by first multiplying the frequencies of the two relevant codons with each other (see Table 3 expected frequency), and then multiplying this result with the observed frequency (in the entire CCDS data set) with which the amino acid pair encoded by the codon pair in question occurs. In the example of codon pair GCA-GAA, this second calculation gives an expected frequency of 0.098 (compared to 0.097 in the first calculation using the Kazusa dataset). Finally, the actual codon pair frequencies as observed in a set of 14,795 human genes was determined by counting the total number of occurrences of each codon pair in the set and dividing it by the number of all synonymous coding pairs in the set coding for the same amino acid pair (Table 3; observed frequency). Frequency and observed/expected values for the complete set of 3721 ($61^2$) codon pairs, based on the set of 14,795 human genes, are provided herewith as Supplemental Table 1.

TABLE 3

Codon Pair Scores Exemplified by the Amino Acid Pair Ala-Glu

| amino acid pair | codon pair | expected frequency | observed frequency | obs/exp ratio |
|---|---|---|---|---|
| AE | GCAGAA | 0.098 | 0.163 | 1.65 |
| AE | GCAGAG | 0.132 | 0.198 | 1.51 |
| AE | GCCGAA | 0.171 | 0.031 | 0.18 |
| AE | GCCGAG | 0.229 | 0.142 | 0.62 |
| AE | GCGGAA | 0.046 | 0.027 | 0.57 |
| AE | GCGGAG | 0.062 | 0.089 | 1.44 |
| AE | GCTGAA | 0.112 | 0.145 | 1.29 |
| AE | GCTGAG | 0.150 | 0.206 | 1.37 |
| Total | | 1.000 | 1.000 | |

If the ratio of observed frequency/expected frequency of the codon pair is greater than one the codon pair is said to be overrepresented. If the ratio is smaller than one, it is said to be underrepresented. In the example the codon pair GCA-GAA is overrepresented 1.65 fold while the coding pair GCC-GAA is more than 5-fold underrepresented.

Many other codon pairs show very strong bias; some pairs are under-represented, while other pairs are over-represented. For instance, the codon pairs GCCGAA (AlaGlu) and GATCTG (AspLeu) are three- to six-fold under-represented (the preferred pairs being GCAGAG and GACCTG, respectively), while the codon pairs GCCAAG (AlaLys) and AATGAA (AsnGlu) are about two-fold over-represented. It is noteworthy that codon pair bias has nothing to do with the frequency of pairs of amino acids, nor with the frequency of individual codons. For instance, the under-represented pair GATCTG (AspLeu) happens to use the most frequent Leu codon, (CTG).

As discussed more fully below, codon pair bias takes into account the score for each codon pair in a coding sequence averaged over the entire length of the coding sequence. According to the invention, codon pair bias is determined by $$CPB = \sum_{i=1}^{k} \frac{CPSi}{k-1}.$$

Accordingly, similar codon pair bias for a coding sequence can be obtained, for example, by minimized codon pair scores over a subsequence or moderately diminished codon pair scores over the full length of the coding sequence.

Calculation of Codon Pair Bias.

Every individual codon pair of the possible 3721 non-"STOP" containing codon pairs (e.g., GTT-GCT) carries an assigned "codon pair score," or "CPS" that is specific for a given "training set" of genes. The CPS of a given codon pair is defined as the log ratio of the observed number of occurrences over the number that would have been expected in this set of genes (in this example the human genome). Determining the actual number of occurrences of a particular codon pair (or in other words the likelihood of a particular amino acid pair being encoded by a particular codon pair) is simply a matter of counting the actual number of occurrences of a codon pair in a particular set of coding sequences. Determining the expected number, however, requires additional calculations. The expected number is calculated so as to be independent of both amino acid frequency and codon bias similarly to Gutman and Hatfield. That is, the expected frequency is calculated based on the relative proportion of the number of times an amino acid is encoded by a specific codon. A positive CPS value signifies that the given codon pair is statistically over-represented, and a negative CPS indicates the pair is statistically under-represented in the human genome.

To perform these calculations within the human context, the most recent Consensus CDS (CCDS) database of consistently annotated human coding regions, containing a total of 14,795 genes, was used. This data set provided codon and codon pair, and thus amino acid and amino-acid pair frequencies on a genomic scale.

The paradigm of Federov et al. (2002), was used to further enhanced the approach of Gutman and Hatfield (1989). This allowed calculation of the expected frequency of a given codon pair independent of codon frequency and non-random associations of neighboring codons encoding a particular amino acid pair.

$$S(P_{ij}) = \ln\left(\frac{N_O(P_{ij})}{N_E(P_{ij})}\right) = \ln\left(\frac{N_O(P_{ij})}{F(C_i)F(C_j)N_O(X_{ij})}\right)$$

In the calculation, $P_{ij}$ is a codon pair occurring with a frequency of $N_O(P_{ij})$ in its synonymous group. $C_i$ and $C_j$ are the two codons comprising $P_{ij}$, occurring with frequencies $F(C_i)$ and $F(C_j)$ in their synonymous groups respectively. More explicitly, $F(C_i)$ is the frequency that corresponding amino acid $X_i$ is coded by codon $C_i$ throughout all coding regions and $F(C_i)=N_O(C_i)/N_O(X_i)$, where $N_O(C_i)$ and $N_O(X_i)$ are the observed number of occurrences of codon $C_i$ and amino acid $X_i$ respectively. $F(C_j)$ is calculated accordingly. Further, $N_O(X_{ij})$ is the number of occurrences of amino acid pair $X_{ij}$ throughout all coding regions. The codon pair bias score $S(P_{ij})$ of $P_{ij}$ was calculated as the log-odds ratio of the observed frequency $N_o(P_{ij})$ over the expected number of occurrences of $N_e(P_{ij})$.

Using the formula above, it was then determined whether individual codon pairs in individual coding sequences are over- or under-represented when compared to the corresponding genomic $N_e(P_{ij})$ values that were calculated by using the entire human CCDS data set. This calculation resulted in positive $S(P_{ij})$ score values for over-represented and negative values for under-represented codon pairs in the human coding regions (FIG. 7).

The "combined" codon pair bias of an individual coding sequence was calculated by averaging all codon pair scores according to the following formula:

$$S(P_{ij}) = \sum_{i=1}^{k} \frac{S(Pij)l}{k-1}.$$

The codon pair bias of an entire coding region is thus calculated by adding all of the individual codon pair scores comprising the region and dividing this sum by the length of the coding sequence.

Calculation of Codon Pair Bias, Implementation of Algorithm to Alter Codon-Pair Bias.

An algorithm was developed to quantify codon pair bias. Every possible individual codon pair was given a "codon pair score", or "CPS". CPS is defined as the natural log of the ratio of the observed over the expected number of occurrences of each codon pair over all human coding regions, where humans represent the host species of the instant vaccine virus to be recoded.

$$CPS = \ln\left(\frac{F(AB)o}{\frac{F(A) \times F(B)}{F(X) \times F(Y)} \times F(XY)}\right)$$

Although the calculation of the observed occurrences of a particular codon pair is straightforward (the actual count within the gene set), the expected number of occurrences of a codon pair requires additional calculation. We calculate this expected number to be independent both of amino acid frequency and of codon bias, similar to Gutman and Hatfield. That is, the expected frequency is calculated based on the relative proportion of the number of times an amino acid is encoded by a specific codon. A positive CPS value signifies that the given codon pair is statistically over-represented, and a negative CPS indicates the pair is statistically under-represented in the human genome Using these calculated CPSs, any coding region can then be rated as using over- or under-represented codon pairs by taking the average of the codon pair scores, thus giving a Codon Pair Bias (CPB) for the entire gene.

$$CPB = \sum_{i=1}^{k} \frac{CPSi}{k-1}$$

The CPB has been calculated for all annotated human genes using the equations shown and plotted (FIG. 4). Each point in the graph corresponds to the CPB of a single human gene. The peak of the distribution has a positive codon pair bias of 0.07, which is the mean score for all annotated human genes. Also there are very few genes with a negative codon pair bias. Equations established to define and calculate CPB were then used to manipulate this bias.

Algorithm for Reducing Codon-Pair Bias.

Recoding of protein-encoding sequences may be performed with or without the aid of a computer, using, for example, a gradient descent, or simulated annealing, or other minimization routine. An example of the procedure that rearranges codons present in a starting sequence can be represented by the following steps:

1) Obtain wildtype viral genome sequence.
2) Select protein coding sequences to target for attenuated design.
3) Lock down known or conjectured DNA segments with non-coding functions.
4) Select desired codon distribution for remaining amino acids in redesigned proteins.
5) Perform random shuffle of at least two synonymous unlocked codon positions and calculate codon-pair score.
6) Further reduce (or increase) codon-pair score optionally employing a simulated annealing procedure.
7) Inspect resulting design for excessive secondary structure and unwanted restriction site:
   if yes→go to step (5) or correct the design by replacing problematic regions with wildtype sequences and go to step (8).
8. Synthesize DNA sequence corresponding to virus design.
9. Create viral construct and assess viral phenotype:
   if too attenuated, prepare subclone construct and go to 9;
   if insufficiently attenuated, go to 2.

Attenuation of viruses by reducing codon pair bias is disclosed in WO 2008/121992 and WO 2011/044561, which are incorporated by reference.

Attenuated Influenza Viruses

According to the invention, viral attenuation is accomplished by reducing expression of HA and NA coding sequences. One way to reduce expression of the coding sequences is by a reduction in codon pair bias, but other methods can also be used, alone or in combination. While codon bias may be changed, adjusting codon pair bias is particularly advantageous. For example, attenuating a virus through codon bias generally requires elimination of common codons, and so the complexity of the nucleotide sequence is reduced. In contrast, codon pair bias reduction or minimization can be accomplished while maintaining far greater sequence diversity, and consequently greater control over nucleic acid secondary structure, annealing temperature, and other physical and biochemical properties.

Codon pair bias of a protein-encoding sequence (i.e., an open reading frame) is calculated as set forth above and described in Coleman et al., 2000 (ref. 12).

Viral attenuation and induction or protective immune responses can be confirmed in ways that are well known to one of ordinary skill in the art, including but not limited to, the methods and assays disclosed herein. Non-limiting examples include plaque assays, growth measurements, reduced lethality in test animals, and protection against subsequent infection with a wild type virus.

In preferred embodiments, the invention provides viruses that are highly attenuated, and induce immunity against a plurality of influenza types and/or subtypes. Such flu varieties include viruses bearing all possible HA-NA combinations. Currently, there are 16 recognized hemagglutinins and nine neuraminidases, each of which has mutational variants. Examples of type A subtypes include, but are not limited to, H10N7, H10N1, H10N2, H10N3, H10N4, H10N5, H10N6, H10N7, H10N8, H10N9, H11N1, H11N2, H11N3, H11N4, H11N6, H11N8, H11N9, H12N1, H12N2, H12N4, H12N5, H12N6, H12N8, H12N9, H13N2, H13N3, H13N6, H13N9, H14N5, H14N6, H15N2, H15N8, H15N9, H16N3, H1N1, H1N2, H1N3, H1N5, H1N6, H1N8, H1N9, H2N1, H2N2, H2N3, H2N4, H2N5, H2N6, H2N7, H2N8, H2N9, H3N1, H3N2, H3N3, H3N4, H3N5, H3N6, H3N8, H3N9, H4N1, H4N2, H4N3, H4N4, H4N5, H4N6, H4N7, H4N8, H4N9, H5N1, H5N2, H5N3, H5N4, H5N6, H5N7, H5N8, H5N9, H6N1, H6N2, H6N3, H6N4, H6N5, H6N6, H6N7, H6N8, H6N9, H7N1, H7N2, H7N3, H7N4, H7N5, H7N7, H7N8, H7N9, H8N2, H8N4, H8N5, H9N1, H9N2, H9N3, H9N4, H9N5, H9N6, H9N7, H9N8, H9N9. Some subtypes of interest include, but are not limited to, H1N1 (one variant of which caused Spanish flu in 1918, another of which is pandemic in 2009), H2N2 (a variant of which caused Asian Flu in 1957), H3N2 (a variant of which caused Hong Kong Flu in 1968, H5N1 (a current pandemic threat), H7N7 (which has unusual zoonotic potential), and H1N2 (endemic in humans and pigs). Examples of attenuated influenza protein coding sequences are provided below.

TABLE 4

Reduced-Expression Influenza A Virus Genes

| | WT Coding Sequence | | | Recoded Coding Sequence | | |
|---|---|---|---|---|---|---|
| Gene | SEQ ID NO: | CDS | CPB | SEQ ID NO | Recoded Codons | CPB |
| H10N7 (A/northern shoveler/California/HKWF392sm/2007)(Avian) | | | | | | |
| HA | 1 | 1-1683 | 0.018 | 2 | 1-561 | −0.441 |
| NA | 3 | 1-1494 | 0.009 | 4 | 1-498 | −0.449 |
| H1N1 (A/New York/3568/2009)(Human) | | | | | | |
| HA | 5 | 1-1698 | 0.043 | 6 | 1-566 | −0.410 |
| NA | 7 | 1-1407 | 0.005 | 8 | 1-469 | −0.456 |
| H1N2 (A/New York/211/2003)(Human) | | | | | | |
| HA | 9 | 1-1695 | 0.036 | 10 | 1-565 | −0.421 |
| NA | 11 | 1-1407 | 0.034 | 12 | 1-469 | −0.476 |
| H2N2 (A/Albany/22/1957)(Human) | | | | | | |
| HA | 13 | 1-1686 | 0.040 | 14 | 1-562 | −0.422 |
| NA | 15 | 1-1407 | 0.008 | 16 | 1-469 | −0.453 |

TABLE 4-continued

Reduced-Expression Influenza A Virus Genes

| | WT Coding Sequence | | | Recoded Coding Sequence | | |
|---|---|---|---|---|---|---|
| Gene | SEQ ID NO: | CDS | CPB | SEQ ID NO | Recoded Codons | CPB |
| H3N2 (A/New York/933/2006)(Human) | | | | | | |
| HA | 17 | 1-1698 | 0.027 | 18 | 1-566 | −0.447 |
| NA | 19 | 1-1407 | 0.041 | 20 | 1-469 | −0.463 |
| H5N1 (A/Jiangsu/1/2007)(Human) | | | | | | |
| HA | 21 | 1-1701 | 0.017 | 22 | 1-567 | −0.435 |
| NA | 23 | 1-1347 | 0.009 | 24 | 1-449 | −0.407 |
| H7N2 (A/chicken/NJ/294508-12/2004)(Avian) | | | | | | |
| HA | 25 | 1-1656 | 0.036 | 26 | 1-552 | −0.377 |
| NA | 27 | 1-1359 | 0.013 | 28 | 1-453 | −0.491 |
| H7N3 (A/C anada/rv504/2004)(Human) | | | | | | |
| HA | 29 | 1-1701 | 0.029 | 30 | 1-567 | −0.405 |
| NA | 31 | 1-1407 | 0.042 | 32 | 1-469 | −0.413 |
| H7N7 (A/Netherlands/219/03)(Human) | | | | | | |
| HA | 33 | 1-1707 | 0.008 | 34 | 1-569 | −0.447 |
| NA | 35 | 1-1413 | −0.009 | 36 | 1-471 | −0.423 |
| H9N2 (A/Hong Kong/1073/99)(Human) | | | | | | |
| HA | 37 | 1-1680 | 0.021 | 38 | 1-560 | −0.440 |
| NA | 39 | 1-1401 | 0.020 | 40 | 1-467 | −0.453 |

Vaccine Compositions

The present invention provides a vaccine composition for inducing a protective immune response in a subject comprising any of the attenuated viruses described herein and a pharmaceutically acceptable carrier.

It should be understood that an attenuated virus of the invention, where used to elicit a protective immune response in a subject or to prevent a subject from becoming afflicted with a virus-associated disease, is administered to the subject in the form of a composition additionally comprising a pharmaceutically acceptable carrier. Pharmaceutically acceptable carriers are well known to those skilled in the art and include, but are not limited to, one or more of 0.01-0.1M and preferably 0.05M phosphate buffer, phosphate-buffered saline (PBS), or 0.9% saline. Such carriers also include aqueous or non-aqueous solutions, suspensions, and emulsions. Aqueous carriers include water, alcoholic/aqueous solutions, emulsions or suspensions, saline and buffered media. Examples of non-aqueous solvents are propylene glycol, polyethylene glycol, vegetable oils such as olive oil, and injectable organic esters such as ethyl oleate. Parenteral vehicles include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Solid compositions may comprise nontoxic solid carriers such as, for example, glucose, sucrose, mannitol, sorbitol, lactose, starch, magnesium stearate, cellulose or cellulose derivatives, sodium carbonate and magnesium carbonate. For administration in an aerosol, such as for pulmonary and/or intranasal delivery, an agent or composition is preferably formulated with a nontoxic surfactant, for example, esters or partial esters of C6 to C22 fatty acids or natural glycerides, and a propellant. Additional carriers such as lecithin may be included to facilitate intranasal delivery. Pharmaceutically acceptable carriers can further comprise minor amounts of auxiliary substances such as wetting or emulsifying agents, preservatives and other additives, such as, for example, antimicrobials, antioxidants and chelating agents, which enhance the shelf life and/or effectiveness of the active ingredients. The instant compositions can, as is well known in the art, be formulated so as to provide quick, sustained or delayed release of the active ingredient after administration to a subject.

In various embodiments of the instant vaccine composition, the attenuated virus (i) does not substantially alter the synthesis and processing of viral proteins in an infected cell; (ii) produces similar amounts of virions per infected cell as wt virus; and/or (iii) exhibits substantially lower virion-specific infectivity than wt virus. In further embodiments, the attenuated virus induces a substantially similar immune response in a host animal as the corresponding wt virus.

This invention also provides a modified host cell line specially isolated or engineered to be permissive for an attenuated virus that is inviable in a wild type host cell. Since the attenuated virus cannot grow in normal (wild type) host cells, it is absolutely dependent on the specific helper cell line for growth. This provides a very high level of safety for the generation of virus for vaccine production. Various embodiments of the instant modified cell line permit the growth of an attenuated virus, wherein the genome of said cell line has been altered to increase the number of genes encoding rare tRNAs.

In addition, the present invention provides a method for eliciting a protective immune response in a subject comprising administering to the subject a prophylactically or therapeutically effective dose of any of the vaccine compositions described herein. This invention also provides a method for preventing a subject from becoming afflicted with a virus-associated disease comprising administering to the subject a prophylactically effective dose of any of the instant vaccine compositions. In embodiments of the above methods, the subject has been exposed to a pathogenic virus. "Exposed" to a pathogenic virus means contact with the virus such that infection could result.

The invention further provides a method for delaying the onset, or slowing the rate of progression, of a virus-associated disease in a virus-infected subject comprising administering to the subject a therapeutically effective dose of any of the instant vaccine compositions.

As used herein, "administering" means delivering using any of the various methods and delivery systems known to those skilled in the art. Administering can be performed, for example, intranasally, intraperitoneally, intracerebrally, intravenously, orally, transmucosally, subcutaneously, transdermally, intradermally, intramuscularly, topically, parenterally, via implant, intrathecally, intralymphatically, intralesionally, pericardially, or epidurally. An agent or composition may also be administered in an aerosol, such as for pulmonary and/or intranasal delivery. Administering may be performed, for example, once, a plurality of times, and/or over one or more extended periods.

Eliciting a protective immune response in a subject can be accomplished, for example, by administering a primary dose of a vaccine to a subject, followed after a suitable period of time by one or more subsequent administrations of the vaccine. A suitable period of time between administrations of the vaccine may readily be determined by one skilled in the art, and is usually on the order of several weeks to months. The present invention is not limited, however, to any particular method, route or frequency of administration.

A "subject" means any animal or artificially modified animal. Animals include, but are not limited to, humans, non-human primates, cows, horses, sheep, pigs, dogs, cats, rabbits, ferrets, rodents such as mice, rats and guinea pigs, and birds. Artificially modified animals include, but are not limited to, SCID mice with human immune systems, and CD155tg transgenic mice expressing the human poliovirus receptor CD155. In a preferred embodiment, the subject is a human. Preferred embodiments of birds are domesticated poultry species, including, but not limited to, chickens, turkeys, ducks, and geese.

A "prophylactically effective dose" is any amount of a vaccine that, when administered to a subject prone to viral infection or prone to affliction with a virus-associated disorder, induces in the subject an immune response that protects the subject from becoming infected by the virus or afflicted with the disorder. "Protecting" the subject means either reducing the likelihood of the subject's becoming infected with the virus, or lessening the likelihood of the disorder's onset in the subject, by at least two-fold, preferably at least ten-fold. For example, if a subject has a 1% chance of becoming infected with a virus, a two-fold reduction in the likelihood of the subject becoming infected with the virus would result in the subject having a 0.5% chance of becoming infected with the virus. Most preferably, a "prophylactically effective dose" induces in the subject an immune response that completely prevents the subject from becoming infected by the virus or prevents the onset of the disorder in the subject entirely.

As used herein, a "therapeutically effective dose" is any amount of a vaccine that, when administered to a subject afflicted with a disorder against which the vaccine is effective, induces in the subject an immune response that causes the subject to experience a reduction, remission or regression of the disorder and/or its symptoms. In preferred embodiments, recurrence of the disorder and/or its symptoms is prevented. In other preferred embodiments, the subject is cured of the disorder and/or its symptoms.

Certain embodiments of any of the instant immunization and therapeutic methods further comprise administering to the subject at least one adjuvant. An "adjuvant" shall mean any agent suitable for enhancing the immunogenicity of an antigen and boosting an immune response in a subject. Numerous adjuvants, including particulate adjuvants, suitable for use with both protein- and nucleic acid-based vaccines, and methods of combining adjuvants with antigens, are well known to those skilled in the art. Suitable adjuvants for nucleic acid based vaccines include, but are not limited to, Quil A, imiquimod, resiquimod, and interleukin-12 delivered in purified protein or nucleic acid form. Adjuvants suitable for use with protein immunization include, but are not limited to, alum, Freund's incomplete adjuvant (FIA), saponin, Quil A, and QS-21.

The invention also provides a kit for immunization of a subject with an attenuated virus of the invention. The kit comprises the attenuated virus, a pharmaceutically acceptable carrier, an applicator, and an instructional material for the use thereof. In further embodiments, the attenuated virus may be one or more poliovirus, one or more rhinovirus, one or more influenza virus, etc. More than one virus may be preferred where it is desirable to immunize a host against a number of different isolates of a particular virus. The invention includes other embodiments of kits that are known to those skilled in the art. The instructions can provide any information that is useful for directing the administration of the attenuated viruses.

Throughout this application, various publications, reference texts, textbooks, technical manuals, patents, and patent applications have been referred to. The teachings and disclosures of these publications, patents, patent applications and other documents in their entireties are hereby incorporated by reference into this application to more fully describe the state of the art to which the present invention pertains. However, the citation of a reference herein should not be construed as an acknowledgement that such reference is prior art to the present invention.

It is to be understood and expected that variations in the principles of invention herein disclosed can be made by one skilled in the art and it is intended that such modifications are to be included within the scope of the present invention. The following Examples further illustrate the invention, but should not be construed to limit the scope of the invention in any way. Detailed descriptions of conventional methods, such as those employed in the construction of recombinant plasmids, transfection of host cells with viral constructs, polymerase chain reaction (PCR), and immunological techniques can be obtained from numerous publications, including Sambrook et al. (1989) and Coligan et al. (1994). All references mentioned herein are incorporated in their entirety by reference into this application. The contents of WO 2008/121992 and WO 2011/044561 are incorporated by reference.

EXAMPLES

Example 1—Construction and Characterization of an HA and NA Codon Pair-Bias Reduced Influenza Virus in Tissue Culture To achieve attenuation of influenza virus PR8, codon pair bias was reduced (introducing underrepresented codon pairs) in viral genes HA and NA according to computer algorithms (12, 13) and chemical synthesis (14), in order to reduce the expression level of the targeted viral genes.

Cells and viruses. MDCK, A549 and HEK293 T cell lines were maintained in DMEM supplemented with 10% FBS at 37° C. Influenza A/PR/8/34 (PR8) was cultured in MDCK cells.

Figure 1C:
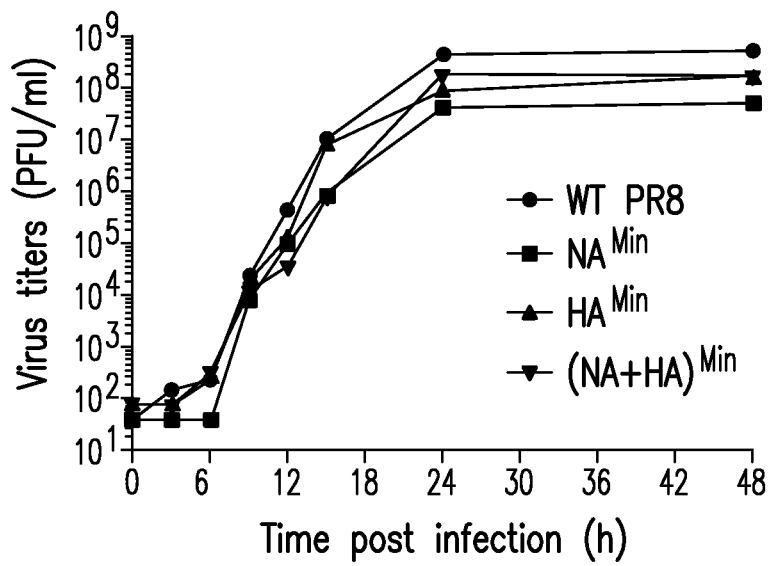
FIG. 1. Construction of variants having reduced codon pair bias and phenotypes in tissue cultures. (A) $NA^{Min}$ and $HA^{Min}$ were designed (leaving 120-200 nt long wt sequences at 5' and 3' ends) and constructed by chemical synthesis. They were then used to replace by reverse genetics (13) one or two corresponding genes of wt PR8. The number of synonymous mutations is shown. (B) Recovered viruses were analyzed for plaque size phenotypes on MDCK monolayers. (C) Growth kinetics of wt PR8 and reduced codon-pair bias variants were analyzed on MDCK cells after infections at an MOI of 0.01. Every three hours post-infection, cell supernatants were collected and analyzed for virus titers by plaque assays. (D) Growth kinetics of wt PR8 and $(NA+HA)^{Min}$ virus in A549 cells. Cells were infected at an MOI of 1.

Variant $(NA+HA)^{Min}$ (618/3188 nt changes), combining the $HA^{Min}$ (SEQ ID NO:53) and $NA^{Min}$ (SEQ ID NO:60) genes, expressed growth and plaque phenotypes in MDCK cells comparable to those of the individual $HA^{Min}$ and $NA^{Min}$ variants (FIG. 1B, C). Similarly, a variant with a codon-pair bias reduced NA gene ($NA^{Min}$, 265/1413 synonymous mutations; FIG. 1A) also replicated well in MDCK cells (FIG. 1C) and expressed an only slightly smaller plaque size phenotype (FIG. 1B) than wt PR8. In A549 cells the $(NA+HA)^{Min}$ variant was highly attenuated (FIG. 1D), growing to a final titer three to four orders of magnitudes lower than wt PR8. A549 cells retain a complex signaling network that is related to the innate host response (15, 16).

Example 2—Levels of NA mRNA and HA Protein are Reduced in $(NA+HA)^{Min}$-Infected Cells The apparent yield of HA polypeptide was examined by western blotting in MDCK cells at 3 h and 6 h post infection (p.i.) with 5 MOI of wt virus or $(NA+HA)^{Min}$. Remarkably, at 6 h p.i., expression of HA protein was significantly reduced in $(NA+HA)^{Min}$-infected cells when compared to PR8-infected cells whereas PB1 and NS1 were synthesized to equal levels by viruses (FIG. 2A). Using the levels of PB1 and GAPDH mRNAs as control, the Northern blot analysis of mRNA levels in $(NA+HA)^{Min}$-infected cells indicated only a slight reduction of $HA^{Min}$ mRNA at 3 h and 6 h (FIG. 2B).

In contrast, Northern blot analyses indicated an extensive reduction of the recoded $NA^{Min}$ mRNA after 6 h and particularly after 9 h p.i. (FIG. 2B). Early in infection (3 h), the level of $NA^{Min}$ mRNA was slightly reduced.

Figure 3A:
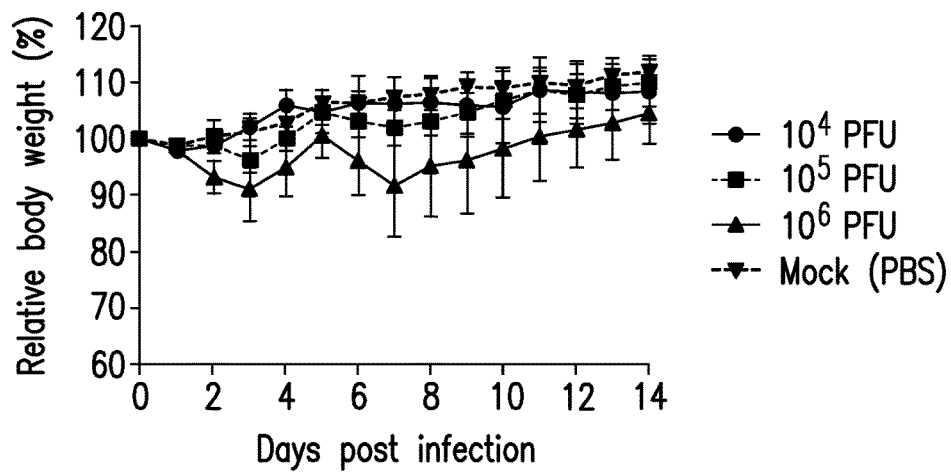
FIG. 3. Virus phenotypes in infected mice. (A and B) Measurement of the median lethal dose ($LD_{50}$). Groups of five male Balb/C mice were intranasally infected with the $(NA+HA)^{Min}$ variant at $10^4$, $10^5$, or $10^6$ PFU and the relative body weight and survival rate were monitored for 14 days p.i. Mice that lost 25% of their body weight were euthanized. $LD_{50}$ was calculated based on the method of Reed-Muench (24). (C and D) Measurement of the median protective dose ($PD_{50}$). Groups of five male Balb/C mice were vaccinated with $10^2$, $10^1$, or $10^0$ PFU of $(NA+HA)^{Min}$ on day 0. On day 28 post vaccination, all mice were challenged with $10^5$ PFU wt PR8 virus. The relative body weight and survival rate after challenge were monitored. $PD_{50}$ was calculated based on the method of Reed-Muench (24). (E and F) Safe and effective vaccine range of the $(NA+HA)^{Min}$ (open box) and wt PR8 virus (gray zone) were plotted. Any vaccine dose within this region warranted survival of the animals, and also completely protected them from lethal homogeneous challenge. Error bars represent SD.
Figure 3B:
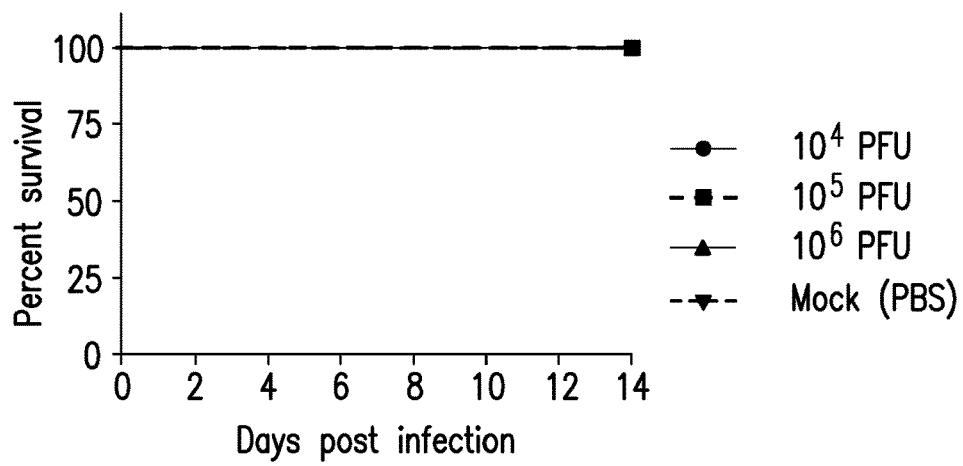

Example 3—Characterization of the Reduced Codon-Pair Bias Variants as Vaccine Candidates in Mice The growth phenotype and pathogenesis of the $(NA+HA)^{Min}$ variant was examined in an animal model. Groups of five BALB/c mice received $(NA+HA)^{Min}$ at doses of $10^4$, $10^5$ or $10^6$ PFU intra-nasally, and body weight and survival of the animals was monitored continuously for 14 days p.i. (FIG. 3A, B). Morbidity and mortality (weight loss, reduced activity, death) was monitored. The Lethal Dose 50 ($LD_{50}$) of the wildtype virus and the vaccine candidates was calculated by the method of Reed and Muench (Reed, L. J.; Muench, H., 1938, The American Journal of Hygiene 27: 493-497). Remarkably, the $(NA+HA)^{Min}$ variant did not induce apparent disease after a dose up to $10^5$ PFU. Even at $10^6$ PFU, mice only suffered transient weight loss, but all animals survived. Therefore, the theoretical LD50 of the $(NA+HA)^{Min}$ variant was calculated to be equal or greater than $3.16 \times 10^6$ PFU, which exceeds that of wt PR8 by a factor of at least 100,000 (Table 1).

Whereas the $(NA+HA)^{Min}$, $HA^{Min}$, and $NA^{Min}$ variants replicated with nearly equal efficiency and similar kinetics as wt PR8 in MDCK cells (FIG. 1C), the $LD_{50}$ of the variants were by orders of magnitude different: PR8=32 PFU, $HA^{Min}=1.7 \times 10^3$ PFU (13), $NA^{Min}=2.4 \times 10^5$ PFU (FIG. 7, Table 5), and $(NA+HA)^{Min} > 3.3 \times 10^6$. By itself, the $NA^{Min}$ gene is about 100-fold more attenuated than the $HA^{Min}$ gene, but reducing expression of NA and NP in the same virus significantly increases attenuation of the virus.

TABLE 5

| $LD_{50}$ and $PD_{50}$ of Attenuated Virus | | |
|---|---|---|
| | $LD_{50}$ | $PD_{50}$ |
| WT PR8 | $3.2 \times 10^1$ | ~1 |
| $NA^{Min}$ | $2.4 \times 10^5$ | <32 |
| $HA^{Min}$ | $1.7 \times 10^3$ | n.d. |
| $(NA + HA)^{Min}$ | $>3.3 \times 10^6$ | 2.4 |

Figure 3C:
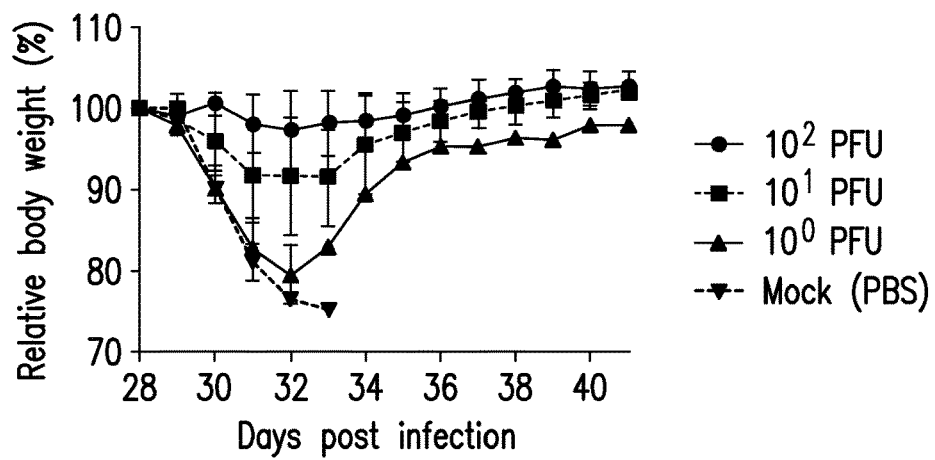
Figure 3D:
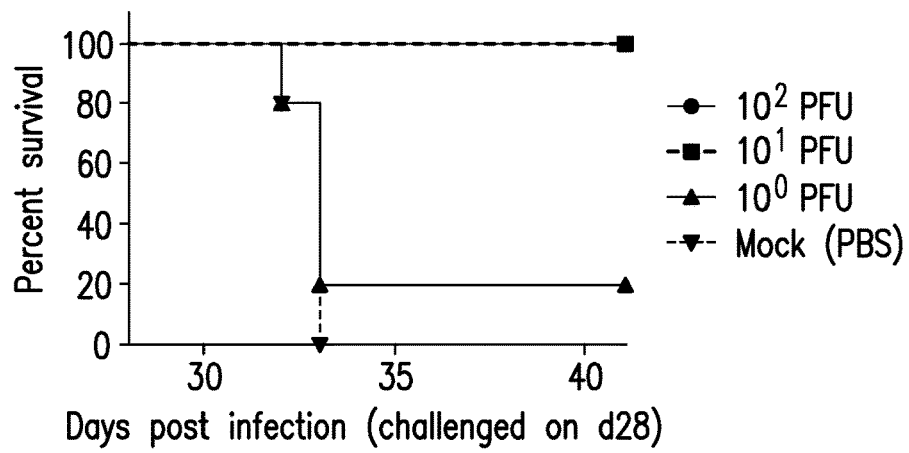

Vaccine candidates should be capable of providing, at low dose, long-term protection from challenge with a lethal dose of wt virus. The dose of $(NA+HA)^{Min}$ required to protect 50% of vaccinated animals from subsequent lethal wild type challenge (defined as "protective dose 50", $PD_{50}$) was determined. Groups of five Balb/c mice were vaccinated with a single dose of $10^0$, $10^1$, or $10^2$ PFU of $(NA+HA)^{Min}$. 28 days after vaccination, the animals were challenged with $10^5$ PFU ($3000 \times LD_{50}$) of wt PR8 virus. As with the original infections, we monitored body weight and survival of the animals 14 days after challenge. Remarkably, although $(NA+HA)^{Min}$ was highly attenuated in mice, it was also highly proficient at protecting against lethal challenge with wt virus. As little as 10 PFU of $(NA+HA)^{Min}$ protected all five mice from lethal challenge (FIG. 3C, 3D). The $PD_{50}$ value calculated by the method of Reed-Muench was only 2.4 PFU. (Table 5) To our knowledge this is the lowest reported protective dose of an experimental vaccine in a mouse model.

Figure 3E:
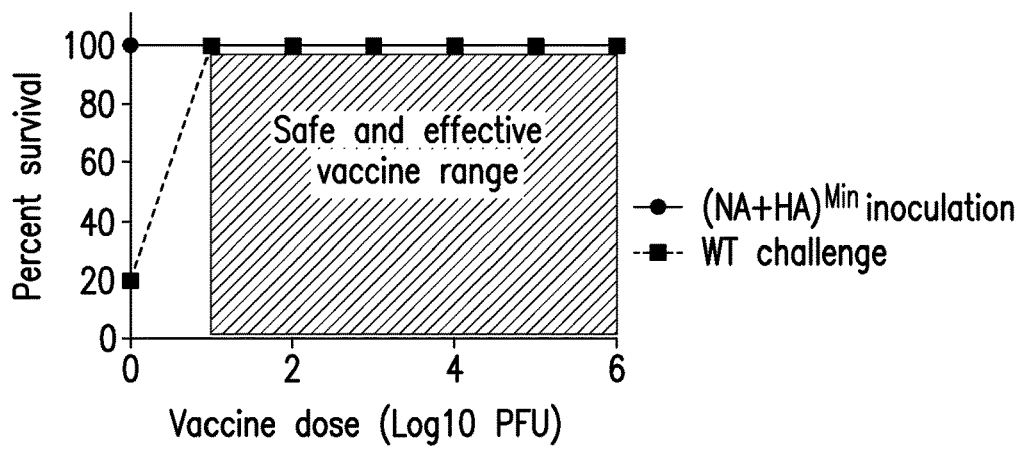
Figure 3F:
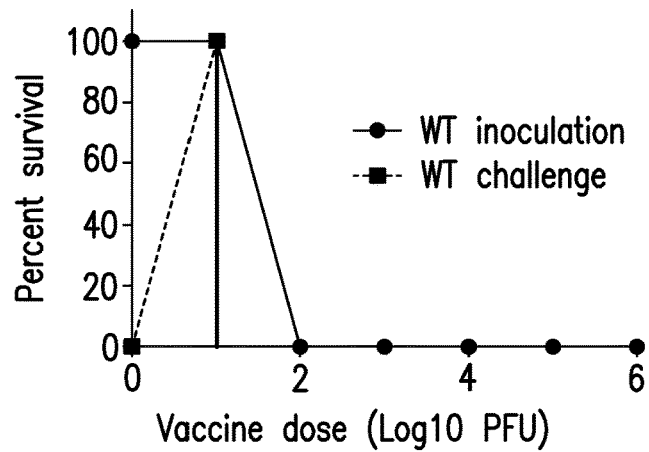

Vaccine safety and protective range was evaluated with various doses of either $(NA+HA)^{Min}$ variant or wt PR8. As shown in FIG. 3E, a zone of five orders of magnitude (from 10 PFU to $10^6$ PFU) can be considered the "region of safety"

of (NA+HA)$^{Min}$ vaccination since all mice receiving increasing doses of "vaccine" within this region were protected from lethal challenge with wt virus. In contrast, the safe and effective region for wt PR8 was extremely limited (FIG. 3F).

Figure 1D:
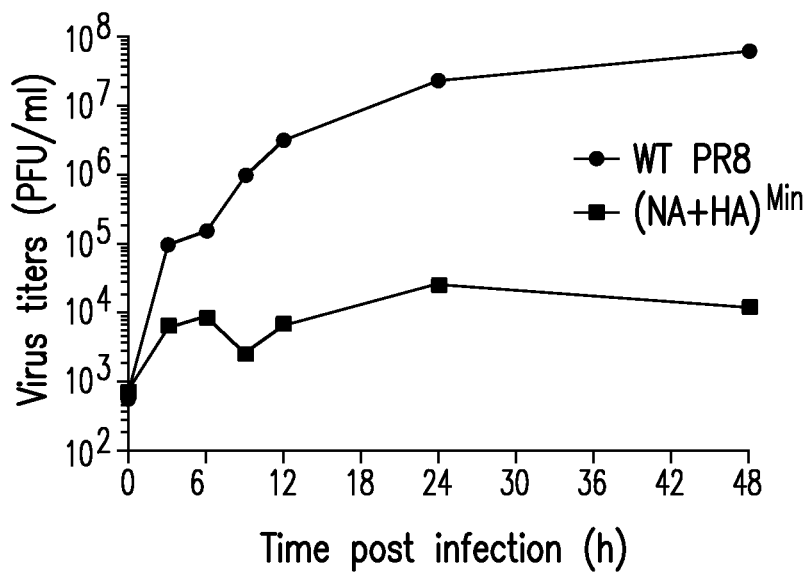
Figure 4A:
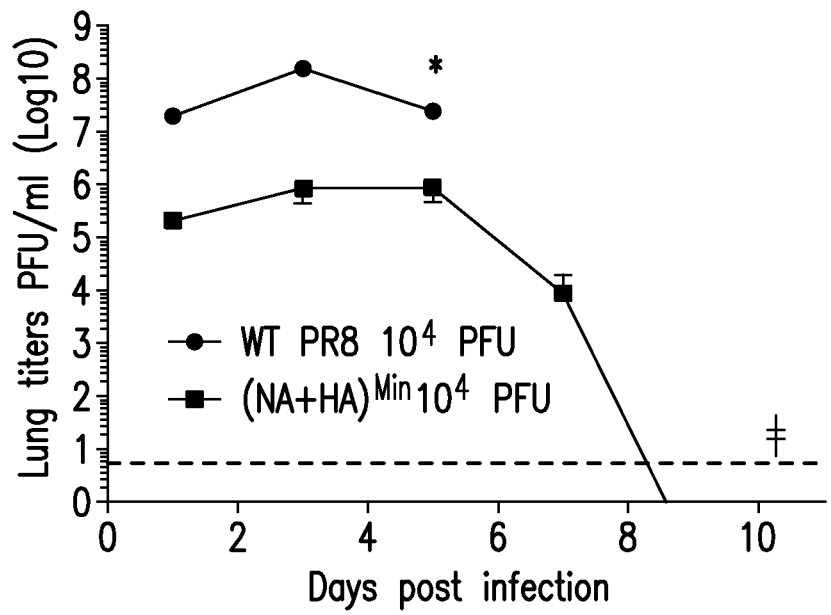
FIG. 4. Virus titers in lungs of infected mice. (A) Groups of three male Balb/C mice were infected with $10^4$ PFU of wt PR8 or $(NA+HA)^{Min}$. On day 1, 3, 5, 7, 9 and 11p.i., the mice were euthanized and their lungs harvested and homogenized. Viral titers in the homogenates were determined by plaque assays on MDCK cells. * All wt PR8-infected mice were dead on day 5. ǀ The virus titers in $(NA+HA)^{Min}$-infected mice after day 9 were undetectable (less than 4 PFU). (B) Comparison of virus titers in lungs of three mice each infected with wt PR8 or $(NA+HA)^{Min}$ at a dose from $10^1$ to $10^4$ PFU. The lungs of the animals were harvest on day 3, and plaque assays were performed to determine virus titers. Error bars represent SD.
Figure 4B:
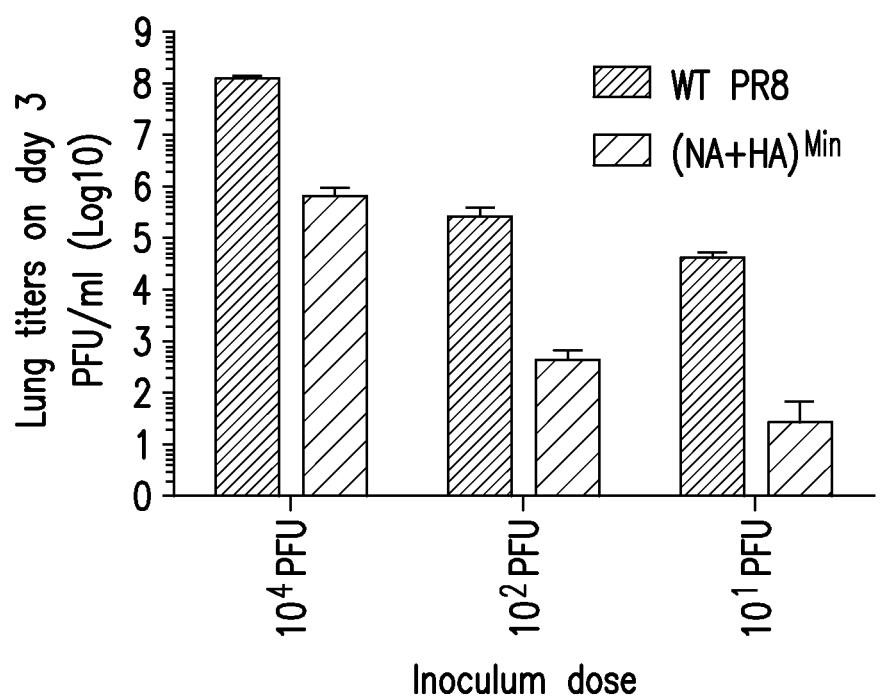

Example 4—The Growth of (NA+HA)Min is Greatly Reduced in the Lungs of Vaccinated Mice To determine parameters of the (NA+HA)$^{Min}$ pathogenicity in vivo, groups of BALB/c mice were infected with $10^4$ PFU of wt PR8 or (NA+HA)$^{Min}$. On day 1, 3, 5, 7, 9 and 11, three mice each from the wt and (NA+HA)$^{Min}$ groups were euthanized, their lungs were homogenized, and virus titers in the homogenates were determined by plaque assays. As expected, wt PR8 replicated well, but even (NA+HA)$^{Min}$ replicated noticeably in lungs of the vaccinated animals. Both PR8 and variant achieved maximum titers around day 3 (FIG. 4A) although there was a ~100 fold difference in the titers between the two viruses. All wt PR8-infected mice died on day 5, whereas all (NA+HA)$^{Min}$-infected mice remained healthy. (NA+HA)$^{Min}$ was eventually cleared at 8 to 9 days p.i. (FIG. 4A). When mice were inoculated at different doses, the (NA+HA)$^{Min}$ titers were always 100-1000 fold lower in lungs when compare to those of wt PR8 on day 3 p.i. (FIG. 4B). Strikingly, at a vaccination dose of 10 PFU when (NA+HA)$^{Min}$ barely replicated in the lungs of the animals, it nevertheless provided complete protection against wt PR8 challenge (FIGS. 4B and 3D). Interestingly, the attenuation of (NA+HA)$^{Min}$ in mice correlates with the attenuation of (NA+HA)$^{Min}$ in A549 cells (FIG. 1D).

Figure 5A:
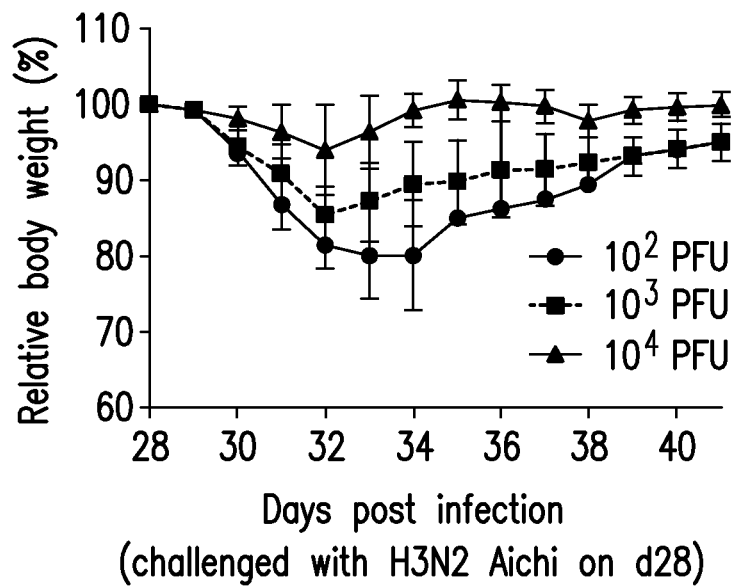
FIG. 5. Cross protection against H3N2 virus infections in $(NA+HA)^{Min}$(H1N1)-vaccinated mice. Groups of five Balb/c mice were vaccinated with $(NA+HA)^{Min}$ at different doses. On day 28 post vaccination, mice were challenged with (A and B) 100 $LD_{50}$ heterologous viruses A/Aichi/2/1968 (H3N2) virus (=$1.5 \times 10^4$ PFU). Survival rate and relative body weights were monitored for 14 days. All mice vaccinated with at least $10^3$ PFU of $(NA+HA)^{Min}$ (H1N1) survived the lethal challenge. The cross protection $PD_{50}$ against H3N2 Aichi virus calculated is 237 PFU. (C and D) Mice vaccinated with $(NA+HA)^{Min}$ virus were also challenged with 100 $LD_{50}$ A/Victoria/3/75 (H3N2) virus (=$3.2 \times 10^4$ PFU). Survival rate and relative body weights were monitored for 14 days. All mice vaccinated with at least $10^3$ PFU of $(NA+HA)^{Min}$ (H1N1) survived the lethal challenge. The cross protection $PD_{50}$ against H3N2 Victoria virus calculated is 147 PFU based on the method of Reed-Muench (24). Error bars represent SD.
Figure 5B:
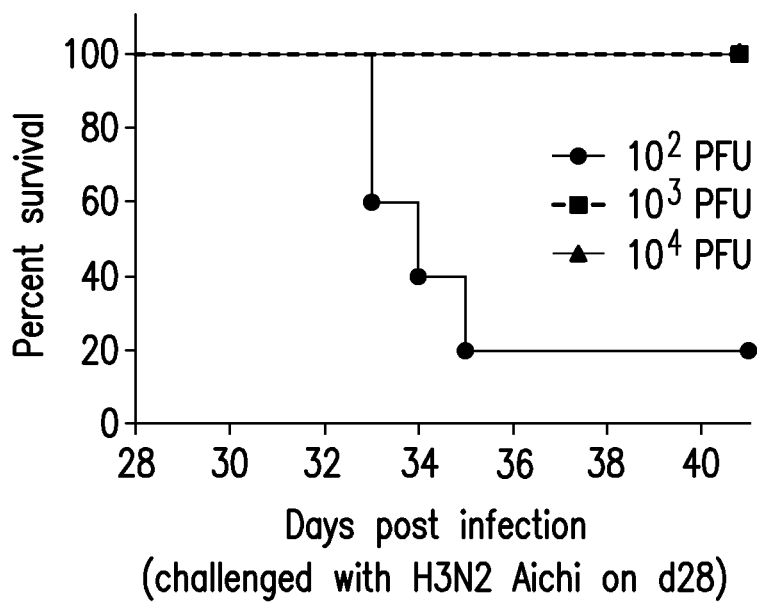
Figure 5C:
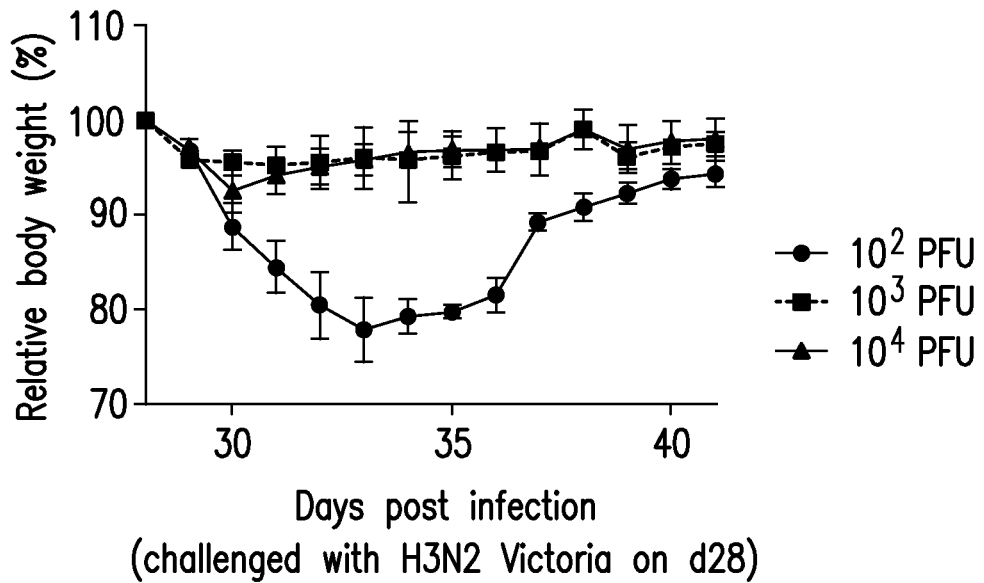
Figure 5D:
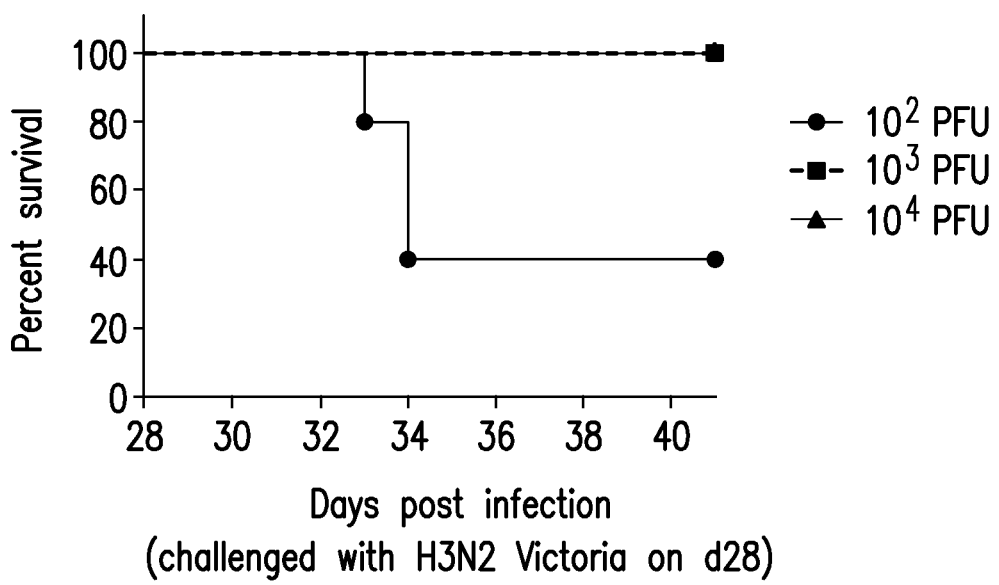

Example 5—Cross Protection and Long Term Protection Induced by the (NA+HA)$^{Min}$ Variant The (NA+HA)$^{Min}$ variant of PR8, which belongs to the influenza H1N1 subtype, was further tested for its capacity to cross protect animals against infections with a heterologous influenza virus strain, such as a mouse adapted H3N2 strain (A/Aichi/2/1968) (21). Groups of five BALB/c mice were vaccinated with (NA+HA)$^{Min}$ virus at doses ranging from $10^2$ to $10^4$ PFU and challenged 28 days post vaccination with 100×LD$_{50}$ doses of A/Aichi/2/1968 (H3N2) virus (1.5×$10^4$ PFU). Remarkably, 1000 PFU of (NA+HA)$^{Min}$ were sufficient to protect mice from the heterologous lethal challenge, corresponding to a PD$_{50}$ value of only 237 PFU (FIG. 5A, 5B). A similar result was obtained when the vaccinated (NA+HA)$^{Min}$ mice were challenged with a different strain of mouse adapted H3N2, A/Victoria/3/75. Again, as little as 1000 PFU of the H1N1 PR8-(NA+HA)$^{Min}$ variant protected all mice from lethal challenge with 100× LD$_{50}$ dose (3.2×$10^4$ PFU) of A/Victoria/3/75. The PD$_{50}$ of (NA+HA)$^{Min}$ protecting against A/Victoria/3/75 (H3N2) was only 147 PFU (FIG. 5C, 5D). Both results indicate that (NA+HA)$^{Min}$ of H1N1 PR8 can induce a robust cross protective immune response in mice against H3N2 subtypes.

Figure 8A:
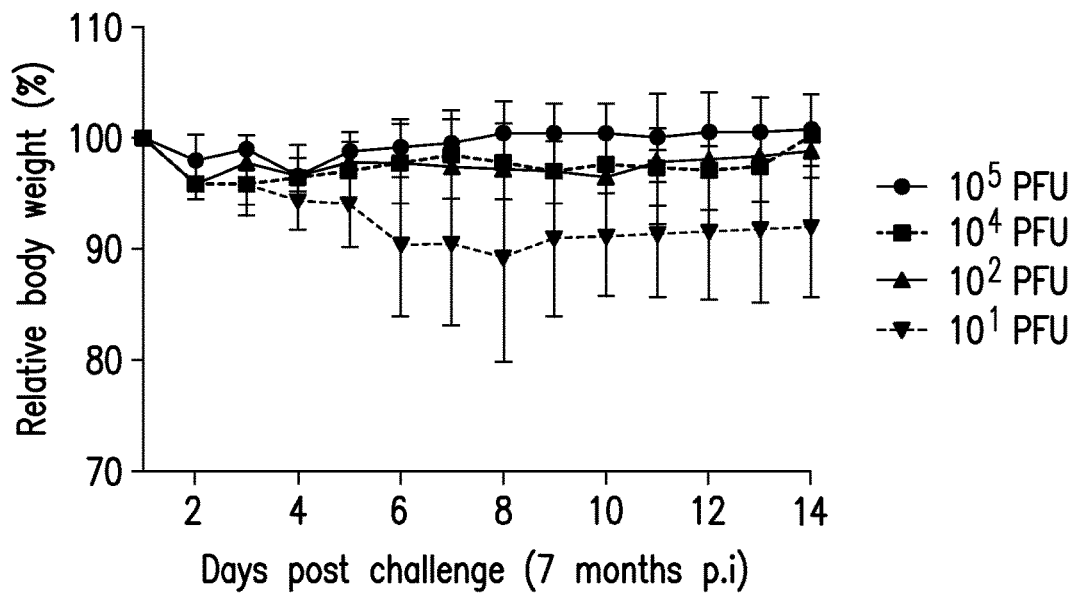
FIG. 8. Long term protection of $(NA+HA)^{Min}$-vaccinated mice. Groups of five Balb/c mice (5-6 weeks) were infected intranasally with $(NA+HA)^{Min}$ at different doses. After seven months, mice were challenged with $10^5$ PFU wt PR8. Their body weight and survival rate were monitored for 14 days. Error bars represent SD.
Figure 8B:
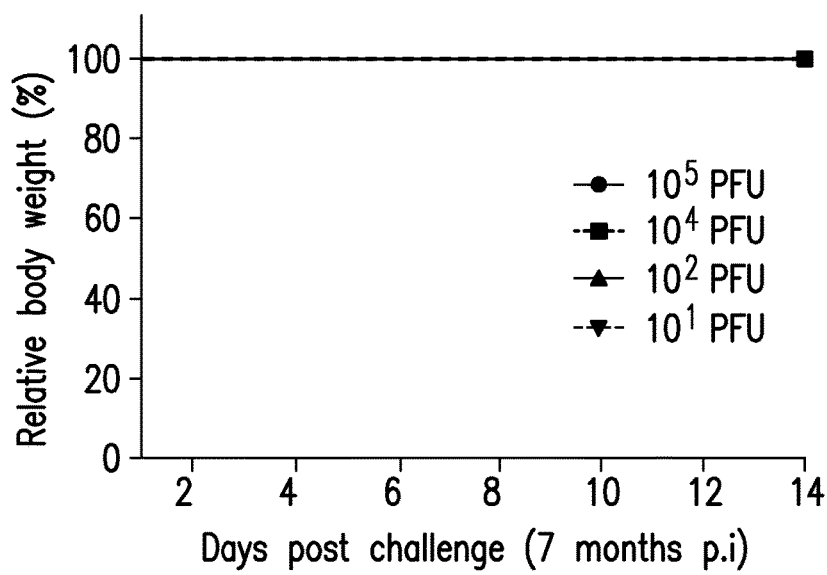

(NA+HA)$^{Min}$-vaccinated animals were tested to determine whether they were protected against challenge after an extended period of time. Groups of five mice were vaccinated with different doses ($10^1$ to $10^5$ PFU) of (NA+HA)$^{Min}$ and the animals were challenged seven months later with $10^5$ PFU of wt PR8. All vaccinated animals were completely protected without signs of disease (FIG. 8).

Example 6—The (NA+HA)$^{Min}$ Variant Induces a Robust Antibody Response

Figure 6:
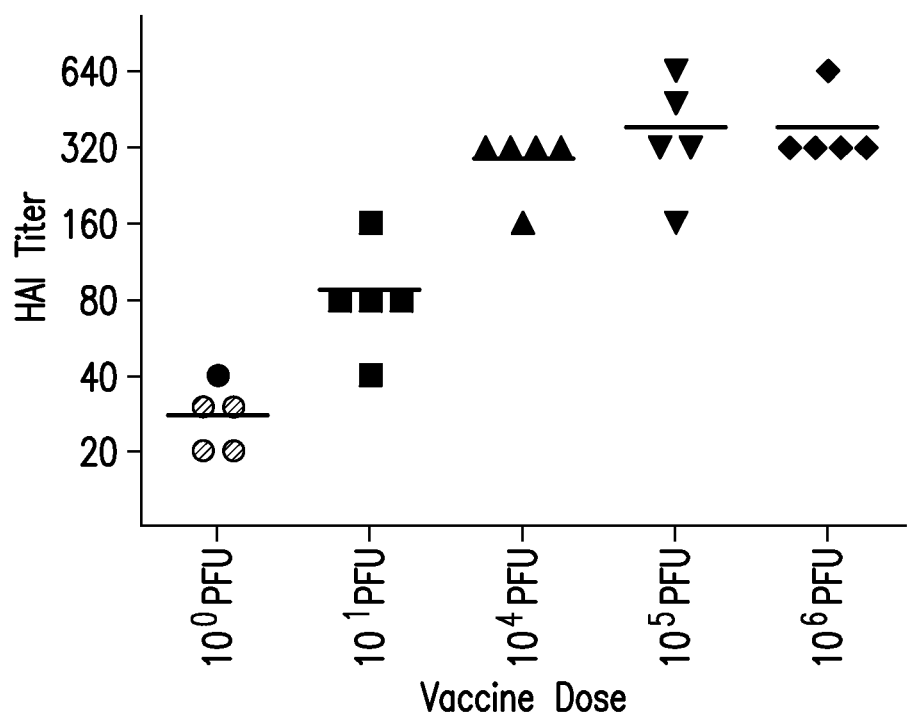
FIG. 6. Hemagglutination inhibition (HAI) assay with serum of vaccinated mice. Mice were infected at different doses with PR8 or $(NA+HA)^{Min}$. Serum was collected on day 28 p.i. and antibody titers were determined by hemagglutination inhibition assays, as described in Material and Methods. Mice were then challenged with $10^5$ PFU wt PR8 and survival rates were monitored. Gray labeled dots indicated mice that did not survive.
Figure 7A:
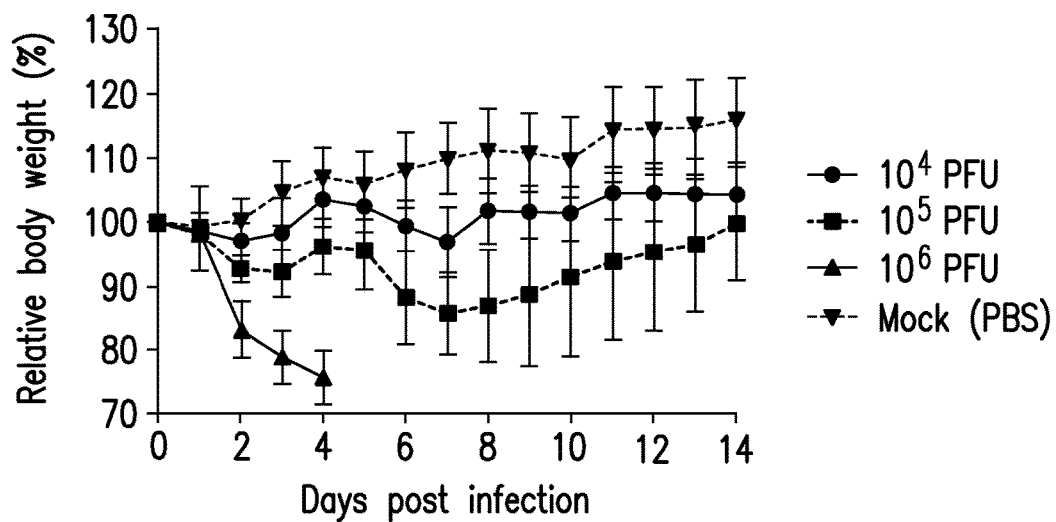
FIG. 7. $LD_{50}$ and $PD_{50}$ values of $NA^{Min}$ in mice. (A and B) Groups of five male Balb/c mice were infected intranasally with different doses of $NA^{Min}$ variant. The relative body weight and survival rate were monitored for 14 days. The $LD_{50}$ calculated was $2.4 \times 10^5$ PFU. (C and D) Groups of five males were vaccinated with different dose of $NA^{Min}$ variant, 28 days p.i., mice were challenged with $10^5$ PFU wt influenza A/PR/8/34 (PR8). The relative body weight and survival rate were monitored for 14 days. Error bars represent SD.
Figure 7B:
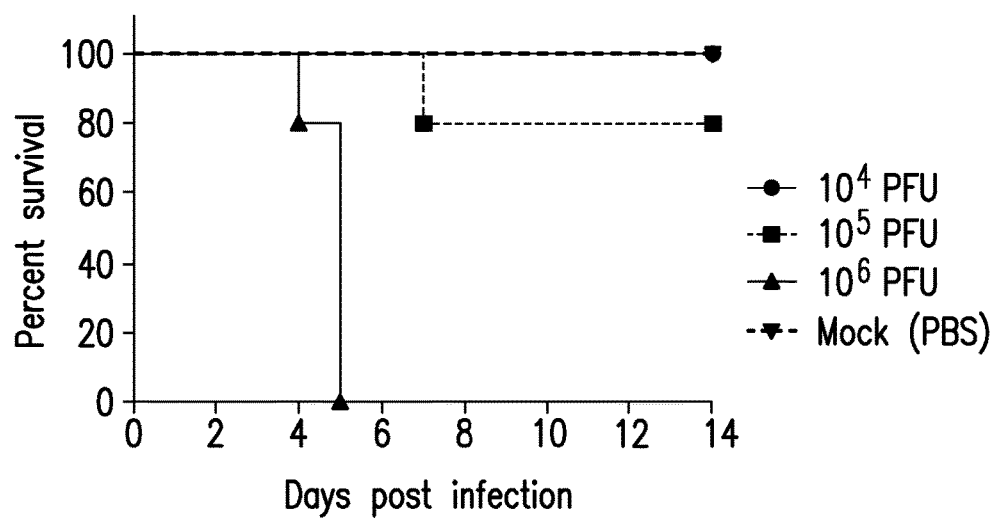
Figure 7C:
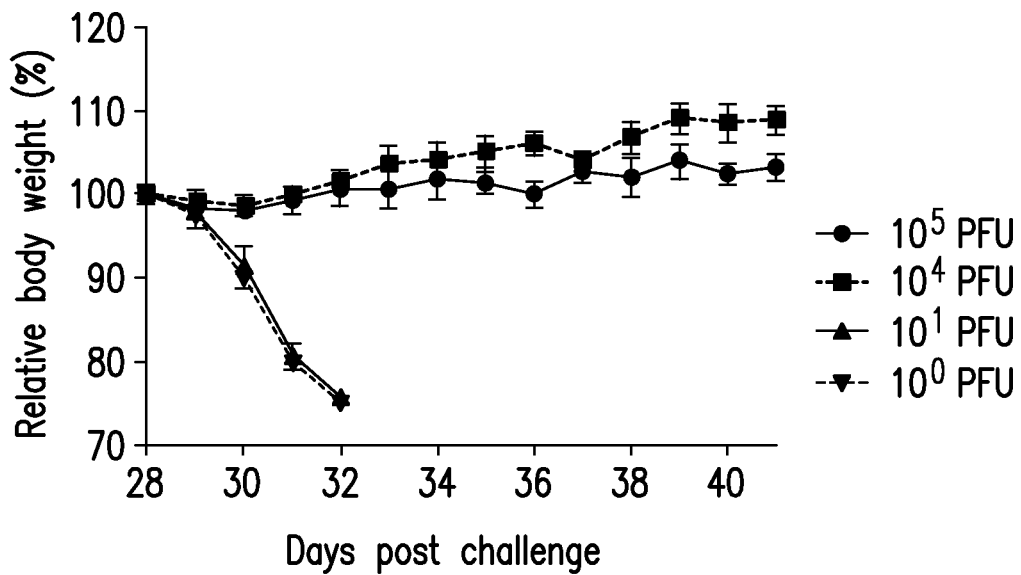
Figure 7D:
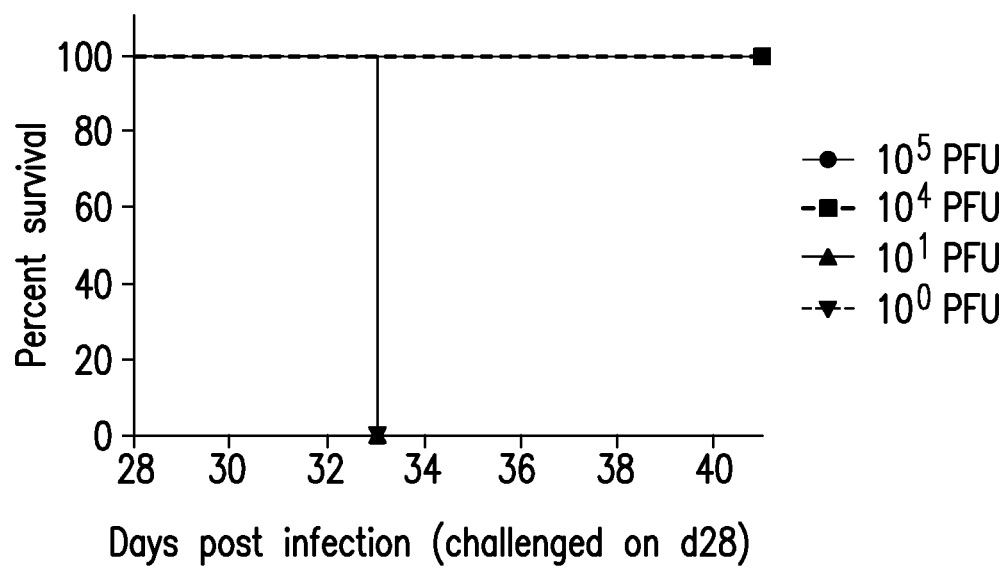

The host response to (NA+HA)$^{Min}$ inoculation suggested a strong host response, including adaptive immunity. Groups of five Balb/c mice were vaccinated with varying doses of (NA+HA)$^{Min}$ or wt PR8 (see FIG. 6). Sera were collected on day 28 p.i., and antibody responses were determined by hemagglutination inhibition (HAI) assays performed according to the protocol in the WHO Manual on Animal Influenza Diagnosis and Surveillance (23). The mice were challenged with a lethal dose of PR8 ($10^5$ PFU). An HAI titer of 40 or more in the serum is generally considered to be protective (22). This level was reached with just $10^1$ PFU of (NA+HA)$^{Min}$ (FIG. 6) and protected vaccinated mice from challenge with $10^5$ PFU wt PR8 virus (FIG. 6).

Example 7—Virus Composition

Both WT and (NA+HA)$^{Min}$ virus were purified by sucrose gradient. 5×$10^7$ PFU of both viruses were loaded onto SDS gels followed by Commassie blue stain (0.1% Coomassie blue R250 for 45 min.) (FIG. 9A) or silver stain (Bio-Rad silver stain kit) (FIGS. 9B and C) to detect virion protein composition. At the same PFU, WT virions contain more HA1 molecules than the (NA+HA)$^{Min}$ virus, while the latter contains more M1 proteins.

Figure 9D:
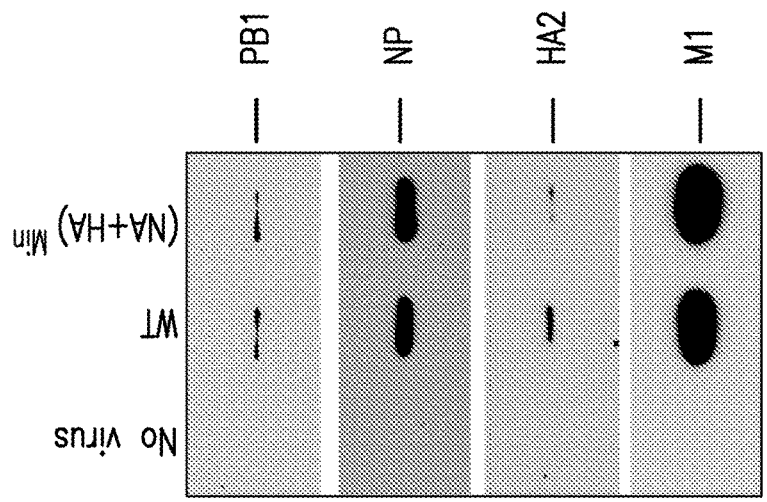
FIG. 9. Composition of $(NA+HA)^{Min}$ virus. WT and $(NA+HA)^{Min}$ virus were purified by sucrose gradient. Equivalent amounts of PFUs were compared to determine the relative amounts of the indicated virus proteins. (A) Commassie stain. (B and C) silver stain. (D) Western blot.
Figure 9C:
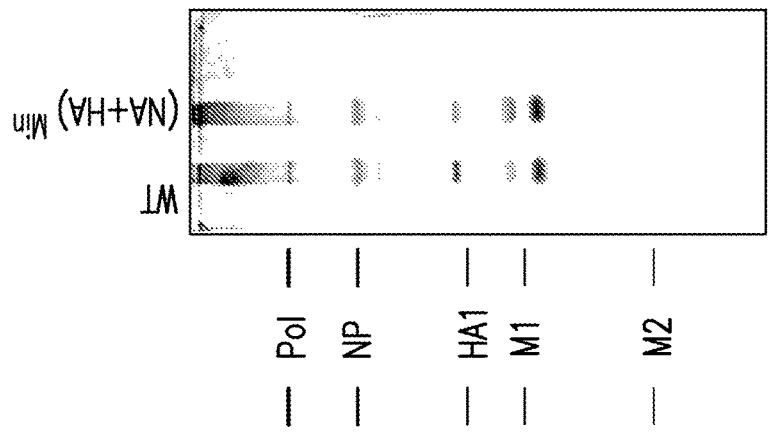
Figure 9B:
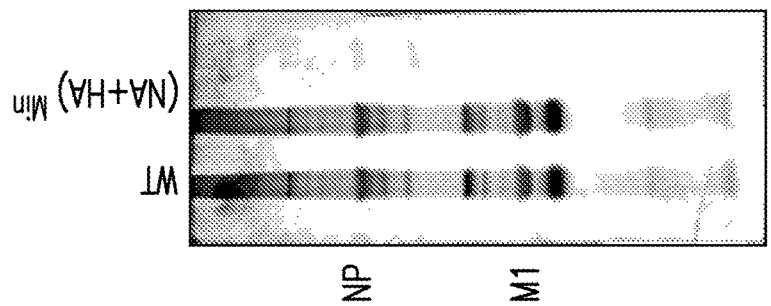
Figure 9A:
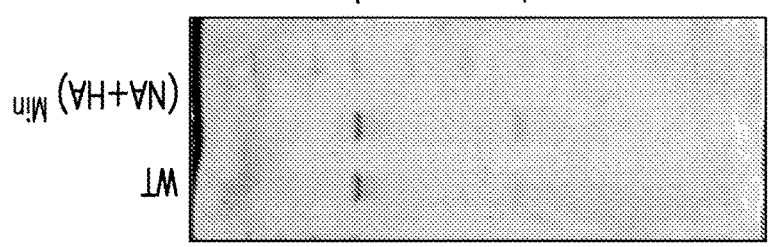

WT and (NA+HA)$^{Min}$ virus were also analyzed by Western blot. 2×$10^7$ PFU of WT and (NA+HA)$^{Min}$ viruses were loaded onto SDS-PAGE gels and analyzed for content of PB1, NP, HA2, and M1. At the same PFU of purified virions, the virus preparations have similar amounts of NP and PB1 protein. Purified WT virions, however, have more HA2 protein, while purified (NA+HA)$^{Min}$ virions have more M1 protein. (FIG. 9D).

Example 8—Expression of Virus Proteins and mRNAs in Infected MDCK Cells

HA protein expression was measured by $^{35}$S methionine incorporation. MDCK cells were infected with 10 MOI wild type PR8, or (NA+HA)$^{Min}$ virus. At 3 h post infection, cells were starved for 45 min, and then labeled for 30 min. Following cell lysis, equal amounts of cell lysates were resolved by SDS PAGE and labeled proteins were visualized by autoradiography. Expression of the HA protein is notably reduced relative to other viral proteins in (NA+HA)$^{Min}$ virus-infected cells. (FIG. 10A).

Viral mRNA in virus infected MDCK cells nucleus was analyzed by Northern blot. MDCK cells were infected with both WT and (NA+HA)$^{Min}$ viruses at an MOI of 1. At 6 h, and 9 h post infection, cells were lysed using Life Technologies PARIS Kit. Nucleus and cytoplasmic portions were separated and mRNA were extracted from both portions. Northern blotting was performed using isolated mRNAs. The nuclear NP mRNA signals were relatively similar between WT and (NA+HA)$^{Min}$ virus infected cells at all time points. Yet, WT virus infected cells, compared to (NA+HA)$^{Min}$ viruses infected cells, contained more nuclear HA and NA mRNA, and less nuclear PB1 mRNA. (FIG. 10B)

Example 9—Passive Immunization by Serum Transfer from PR8-(NA+HA)$^{Min}$ Vaccinated Mice Protects Naïve Mice from Homologous WT PR8 Challenge Groups of five Balb/C mice were vaccinated with $10^4$ PFU (NA+HA)$^{Min}$ virus or PBS. 28 days after vaccination mouse sera were collected, and transferred to five naïve Balb/C mice in a volume of 250 ul. 24 h post transfer, mice were challenged with $10^5$ PFU of WT PR8, corresponding to 3000×LD$_{50}$. All passively immunized mice survived and remained healthy upon challenge, while mock transferred mice died in 8 days. These results suggest that antibodies are the major mediator of immune protection induced by (NA+HA)$^{Min}$ virus vaccination. (FIG. 11).

Example 10—Passive Immunization by Serum Transfer from PR8-(NA+HA)$^{Min}$ Vaccinated Mice Protects Naïve Mice from Heterologous H3N2 Challenge Groups of five Balb/C mice were infected with 3×10$^5$ PFU H1N1-(NA+HA)$^{Min}$ virus or PBS. On day 28, all mice were euthanized and their blood was collected. Sera were prepared on the same day and immediately transferred to groups of five naïve Balb/c mice (i.p injection with 250 µl of sera). 24 h post transfer, mice were challenged with 10×LD$_{50}$ of H1N1-WT PR8, H3N2 Aichi or H3N2 Victoria viruses. Their body weights (FIG. 12A) and survival rates (FIG. 12B) were monitored for 14 days post infection. 60% of sera transferred mice were protected from lethal H3N2 Aichi challenge, and survival times upon challenge of lethal H3N2 Victoria virus were extended.

Example 11—Cross Protection

Cross protection was investigated by assay of hemagglutination inhibition and neutralization. To determine inhibition of hemagglutination, groups of five Balb/C mice were vaccinated with $10^2$-$10^4$ PFU of H1N1-(NA+HA)$^{Min}$ virus. Sera were collected on day 28 p.i. Hemagglutination inhibition assays were performed by incubating the serum with H1N1 PR8, H3N2 Aichi or H3N2 Victoria viruses. (FIG. 13A). H1N1-(NA+HA)$^{Min}$ virus infected mice contain abundant anti-H1N1 HA antibodies with a HAI titer from 100-640. The sera, however, do not contain much of the anti-H3N2 HA antibodies, since the HAI titer are 40 regardless of the vaccine dose. This data suggests that survival of (NA+HA)$^{Min}$ virus-vaccinated mice from heterologous challenge (as illustrated in Example 5) is mainly due to immunity not correlated with antibodies, such as cellular immunity.

To test neutralization, MDCK cells were seeded onto 96 well plate on day 0. 2 fold dilutions of sera from vaccinated mice were incubated with 100 $TCID_{50}$ viruses for 1 h and then added to pre-seeded MDCK cells on day 1. Cells were stained with crystal violet on day 4 to determine neutralization titers.

Groups of five Balb/C mice were vaccinated with $10^5$ PFU of H1N1-(NA+HA)$^{Min}$ virus. Sera were collected on day 28 p.i. Neutralization assays were performed by incubating the sera with H1N1 PR8, H3N2 Aichi or H3N2 Victoria viruses. H1N1-(NA+HA)$^{Min}$ virus infected mice were capable of neutralizing H1N1 PR8 with a neutralization titers above 1200. The sera, interestingly, were also able to neutralize H3N2 viruses. (FIG. 13B).

Example 12—Neuraminidase Encoded by (NA+HA)$^{Min}$

Viral neuraminidase cleaves terminal sialic acid residues from glycan structures on the surface of an infected cell, which promotes the release of progeny viruses. MDCK cells and MDCK-SIAT1 cells which overexpress overexpressing the α-2,6-Sialyltransferase, were infected with WT or (NA+HA)$^{Min}$ viruses at MOI of 0.01. Virus titers were examined at 48 h p.i. In MDCK-SIAT1 cells, which overexpressed influenza receptor sialic acid, both WT and (NA+HA)$^{Min}$ viruses grew better than MDCK cell lines. (FIG. 14). This indicates that (NA+HA)$^{Min}$ virus comprises neuraminidase molecules encoded by NA$^{Min}$ that cleave sialic acid residues normally.

Example 13—T and B Cell Responses in Lungs and Spleen

T cell responses in lungs. Groups of five Balb/C mice were with 10 PFU of WT (a dose close the LD50 of this virus) or 10 PFU (NA+HA)$^{Min}$ (a dose over 300,000-fold below the LD50 for this virus). On day 7 post infection, mice were euthanized and their lungs were collected for flow cytometry. (NA+HA)$^{Min}$ infected mice showed lower numbers of CD4+T and CD8+T cells than WT-infected mice, since (NA+HA)$^{Min}$ infection is cleared by 7 days, while WT infection is still ongoing. (FIG. 15).

B cell responses in lungs. Groups of five Balb/C mice were infected with 10 PFU of WT or (NA+HA)$^{Min}$ viruses. On day 7 post infection, mice were euthanized and their lungs were collected for flow cytometry. WT infected mice showed higher numbers of B cells than both the (NA+HA)$^{Min}$ viruses and the mock group, indicating the WT viruses were much harder to clear than the other two. Yet, the percentage of $CD45^+$ B cells in (NA+HA)$^{Min}$ virus infected mice were similar, or slightly higher, than the WT PR8 infected mice, which indicates they share similar ability in inducing long term protective antibodies. (FIG. 16)

T cell responses in spleen. Groups of five Balb/C mice were infected with 10 PFU of WT or (NA+HA)$^{Min}$ viruses. On day 7 post infection, mice were euthanized and their spleens were collected for flow cytometry. Both WT and (NA+HA)$^{Min}$ virus infected mice showed higher number of CD4+T and CD8+T cells than the mock group, indicating a strong adaptive immune responses triggered by both viruses. (FIG. 17).

B cell responses in spleen. Groups of five Balb/C mice were infected with 10 PFU of WT or (NA+HA)$^{Min}$ viruses. On day 7 post infection, mice were euthanized and their spleens were collected for flow cytometry. (NA+HA)$^{Min}$ infected mice showed significantly higher numbers of B cells than mock group, indicating (NA+HA)$^{Min}$ virus is highly efficient in inducing protective antibodies. (FIG. 18).

In summary, at 7 days post infection, the response to WT virus in lung tissue involved greater numbers of CD4+T, CD8+T and B cells to clear the viruses than the response to (NA+HA)$^{Min}$. In spleen, (NA+HA)$^{Min}$ and WT infected mice both showed elevated T and B cells, indicating strong adaptive immune responses. Also, the T cell proportion of cells in spleen responding to infection by (NA+HA)$^{Min}$ was higher than the proportion responding to infection by WT virus. (FIG. 17).

Example 14—Flow Cytometry Analyses of Immune Cells Infiltrating Lung Tissue

Groups of five male Balb/C mice received $10^4$ PFU wild type PR8 (a lethal dose equal to 300-fold the $LD_{50}$ for this virus), $10^4$ PFU (NA+HA)$^{Min}$ (a safe dose at least 300-fold below the $LD_{50}$ for this virus), or PBS. Note: A the chosen dose of $10^4$ PFU wild type PR8-infected mice invariably sucumb to the infection between 4 and 9 days. On day 3 post infection, lungs were collected and flow cytometry analyses were performed. FIG. 19 shows the results for various immune cells as follows: (A) $CD45^+$ leukocytes, (B) $CD45^+$ $Ly6G^{high}$ polymorphonuclear leukocytes (PMN), (C) $CD45^+$ $CD11c^+$ I-$A^{d+}$ $F4/80^-$ dendritic cells, (D) $CD45^+$ $NKp46^+$ natural killer cells, (E) CD45⁺CD11b⁺Ly6C$^{high}$Ly6G⁻ inflammatory monocytes, (F) CD45⁺ I-A$^{d+}$ F4/80⁺ macrophages, (G) CD45⁺CD3⁺CD4⁺ T helper cells, (H) CD45⁺CD19⁺ B cells, and (I) CD45⁺CD19⁺IgM⁺ B cells were monitored. Most notably (NA+HA)$^{Min}$ infection induced a significantly higher amount of natural killer cells, implicated in viral clearance, as well as a reduced infiltration of PMN, which are known to be associated with immune induced lung damage following natural influenza virus infection. Thus the marked lack of PMN infiltration during (NA+HA)$^{Min}$ infection may explain the high degree of attenuation (i.e the absence of virus induced disease and pathology) of (NA+HA)$^{Min}$.

REFERENCES

1. Thompson, W. W., Comanor, L., & Shay, D. K. (2006) Epidemiology of seasonal influenza: use of surveillance data and statistical models to estimate the burden of disease. *J. Infect. Dis.* 194 Suppl 2:S82-91.
2. Smith, D. J., et al. (2004) Mapping the antigenic and genetic evolution of influenza virus. *Science* 305(5682):371-376.
3. Bouvier, N. M. & Palese, P. (2008) The biology of influenza viruses. *Vaccine* 26 Suppl. 4:D49-53.
4. Simonsen, L., et al. (2005) Impact of influenza vaccination on seasonal mortality in the U.S. elderly population. *Arch. Intern. Med.* 165(3):265-272.
5. Osterholm, M. T., Kelley, N. S., Sommer, A., & Belongia, E. A. (2012) Efficacy and effectiveness of influenza vaccines: a systematic review and meta-analysis. *Lancet Infect. Dis.* 12(1):36-44.
6. Belshe, R. B., et al. (2007) Live attenuated versus inactivated influenza vaccine in infants and young children. *N. Engl. J. Med.* 356(7):685-696.
7. Hussain, A. I., Cordeiro, M., Sevilla, E., & Liu, J. (2010) Comparison of egg and high yielding MDCK cell-derived live attenuated influenza virus for commercial production of trivalent influenza vaccine: in vitro cell susceptibility and influenza virus replication kinetics in permissive and semi-permissive cells. *Vaccine* 28(22):3848-3855
8. Wang, Z., Tobler, S., Roayaei, J., & Eick, A. (2009) Live attenuated or inactivated influenza vaccines and medical encounters for respiratory illnesses among US military personnel. *JAMA* 301(9):945-953.
9. Gutman, G. A. & Hatfield, G. W. (1989) Nonrandom utilization of codon pairs in *Escherichia coli*. *Proc. Natl. Acad. Sci U.S.A.* 86(10):3699-3703.
10. Moura, G., et al. (2007) Large scale comparative codon-pair context analysis unveils general rules that fine-tune evolution of mRNA primary structure. *PLoS One* 2(9): e847.
11. Wang, F. P. & Li, H. (2009) Codon-pair usage and genome evolution. *Gene* 433(1-2):8-15.
12. Coleman, J. R., et al. (2008) Virus attenuation by genome-scale changes in codon pair bias. *Science* 320 (5884): 1784-1787.
13. Mueller, S., et al. (2010) Live attenuated influenza virus vaccines by computer-aided rational design. *Nat Biotechnol* 28(7):723-726.
14. Cello, J., Paul, A. V., & Wimmer, E. (2002) Chemical synthesis of poliovirus cDNA: generation of infectious virus in the absence of natural template. *Science* 297 (5583):1016-1018.
15. Sutejo, R., et al. (2012) Activation of type I and III interferon signalling pathways occurs in lung epithelial cells infected with low pathogenic avian influenza viruses. *PLoS One* 7(3):e33732.
16. Dove, B. K., et al. (2012) A quantitative proteomic analysis of lung epithelial (A549) cells infected with 2009 pandemic influenza A virus using stable isotope labelling with amino acids in cell culture. *Proteomics* 12(9):1431-1436.
17. Doma, M. K. & Parker, R. (2006) Endonucleolytic cleavage of eukaryotic mRNAs with stalls in translation elongation. *Nature* 440(7083):561-564.
18. Liu, C., Eichelberger, M. C., Compans, R. W., & Air, G. M. (1995) Influenza type A virus neuraminidase does not play a role in viral entry, replication, assembly, or budding. *J. Vivol.* 69(2):1099-1106.
19. Palese, P., Tobita, K., Ueda, M., & Compans, R. W. (1974) Characterization of temperature sensitive influenza virus mutants defective in neuraminidase. *Virology* 61(2):397-410.
20. Muster, T., et al. (1995) Mucosal model of immunization against human immunodeficiency virus type 1 with a chimeric influenza virus. *J. Vivol.* 69(11):6678-6686.
21. Koutsonanos, D. G., et al. (2009) Transdermal influenza immunization with vaccine-coated microneedle arrays. *PLoS One* 4(3):e4773.
22. de Jong, J. C., et al. (2003) Haemagglutination-inhibiting antibody to influenza virus. *Dev Biol (Basel)* 115:63-73.
23. WHO (2002) WHO Manual on Animal Influenza Diagnosis and Surveillance. www.who.int/vaccine_research/diseases/influenza/WHO_manual_on_animahllagnosis_and_surveillance_2002_5.pdf
24. Reed, L., Muench, M. (1938) A simple method for estimating fifty percent endpoints. *Am J. Hyg* 27(3):493-497.

| | Supplemental Table 1 | | | | |
|---|---|---|---|---|---|
| Expected and Observed Codon Pair Frequencies and Codon Pair Scores for 14,795 Human Genes | | | | | |
| amino acid pair | codon pair | expected | observed | observed/ expected | CPS |
| AA | GCGGCG | 630.04 | 2870 | 4.555 | 1.516 |
| AA | GCGGCC | 2330.20 | 4032 | 1.730 | 0.548 |
| AA | GCTGCT | 3727.41 | 5562 | 1.492 | 0.400 |
| AA | GCAGCA | 2856.40 | 4196 | 1.469 | 0.385 |
| AA | GCAGCT | 3262.97 | 4711 | 1.444 | 0.367 |
| AA | GCTGCA | 3262.97 | 4357 | 1.335 | 0.289 |
| AA | GCTGCC | 5667.77 | 7014 | 1.238 | 0.213 |
| AA | GCAGCC | 4961.56 | 6033 | 1.216 | 0.196 |
| AA | GCAGCG | 1341.51 | 1420 | 1.059 | 0.057 |
| AA | GCTGCG | 1532.46 | 1533 | 1.000 | 0.000 |
| AA | GCGGCT | 1532.46 | 1472 | 0.961 | -0.040 |
| AA | GCCGCG | 2330.20 | 2042 | 0.876 | -0.132 |
| AA | GCGGCA | 1341.51 | 1142 | 0.851 | -0.161 |
| AA | GCCGCC | 8618.21 | 5141 | 0.597 | -0.517 |
| AA | GCCGCT | 5667.77 | 1378 | 0.243 | -1.414 |

Supplemental Table 1

Expected and Observed Codon Pair Frequencies and Codon Pair Scores for 14,795 Human Genes

| amino acid pair | codon pair | expected | observed | observed/expected | CPS |
|---|---|---|---|---|---|
| AA | GCCGCA | 4961.56 | 1122 | 0.226 | −1.487 |
| AC | GCCTGC | 2333.61 | 3975 | 1.703 | 0.533 |
| AC | GCCTGT | 1965.56 | 2436 | 1.239 | 0.215 |
| AC | GCGTGC | 630.96 | 560 | 0.888 | −0.119 |
| AC | GCTTGT | 1292.65 | 1142 | 0.883 | −0.124 |
| AC | GCATGT | 1131.59 | 881 | 0.779 | −0.250 |
| AC | GCGTGT | 531.45 | 322 | 0.606 | −0.501 |
| AC | GCTTGC | 1534.70 | 894 | 0.583 | −0.540 |
| AC | GCATGC | 1343.47 | 554 | 0.412 | −0.886 |
| AD | GCAGAT | 2373.33 | 4215 | 1.776 | 0.574 |
| AD | GCTGAT | 2711.15 | 3887 | 1.434 | 0.360 |
| AD | GCTGAC | 3062.55 | 4374 | 1.428 | 0.356 |
| AD | GCGGAC | 1259.11 | 1625 | 1.291 | 0.255 |
| AD | GCAGAC | 2680.95 | 3395 | 1.266 | 0.236 |
| AD | GCGGAT | 1114.64 | 839 | 0.753 | −0.284 |
| AD | GCCGAC | 4656.80 | 2726 | 0.585 | −0.535 |
| AD | GCCGAT | 4122.47 | 920 | 0.223 | −1.500 |
| AE | GCAGAA | 3517.48 | 5814 | 1.653 | 0.503 |
| AE | GCAGAG | 4703.98 | 7094 | 1.508 | 0.411 |
| AE | GCGGAG | 2209.23 | 3171 | 1.435 | 0.361 |
| AE | GCTGAG | 5373.53 | 7362 | 1.370 | 0.315 |
| AE | GCTGAA | 4018.14 | 5186 | 1.291 | 0.255 |
| AE | GCCGAG | 8170.80 | 5082 | 0.622 | −0.475 |
| AE | GCGGAA | 1651.99 | 949 | 0.574 | −0.554 |
| AE | GCCGAA | 6109.85 | 1097 | 0.180 | −1.717 |
| AF | GCCTTC | 4447.90 | 7382 | 1.660 | 0.507 |
| AF | GCATTT | 2237.22 | 2332 | 1.042 | 0.041 |
| AF | GCTTTT | 2555.66 | 2580 | 1.010 | 0.009 |
| AF | GCCTTT | 3886.04 | 3842 | 0.989 | −0.011 |
| AF | GCTTTC | 2925.16 | 2315 | 0.791 | −0.234 |
| AF | GCGTTC | 1202.63 | 636 | 0.529 | −0.637 |
| AF | GCGTTT | 1050.71 | 518 | 0.493 | −0.707 |
| AF | GCATTC | 2560.68 | 1261 | 0.492 | −0.708 |
| AG | GCGGGC | 1369.64 | 2638 | 1.926 | 0.655 |
| AG | GCGGGG | 986.17 | 1738 | 1.762 | 0.567 |
| AG | GCTGGG | 2398.67 | 3855 | 1.607 | 0.474 |
| AG | GCTGGT | 1590.73 | 2524 | 1.587 | 0.462 |
| AG | GCTGGA | 2457.02 | 3783 | 1.540 | 0.432 |
| AG | GCAGGA | 2150.87 | 3074 | 1.429 | 0.357 |
| AG | GCAGGG | 2099.79 | 2782 | 1.325 | 0.281 |
| AG | GCAGGT | 1392.52 | 1748 | 1.255 | 0.227 |
| AG | GCTGGC | 3331.38 | 3961 | 1.189 | 0.173 |
| AG | GCAGGC | 2916.28 | 3119 | 1.070 | 0.067 |
| AG | GCGGGT | 654.00 | 617 | 0.943 | −0.058 |
| AG | GCGGGA | 1010.16 | 793 | 0.785 | −0.242 |
| AG | GCCGGG | 3647.33 | 2240 | 0.614 | −0.488 |
| AG | GCCGGC | 5065.58 | 2977 | 0.588 | −0.532 |
| AG | GCCGGT | 2418.80 | 581 | 0.240 | −1.426 |
| AG | GCCGGA | 3736.06 | 795 | 0.213 | −1.547 |
| AH | GCGCAC | 748.29 | 983 | 1.314 | 0.273 |
| AH | GCCCAC | 2767.53 | 3465 | 1.252 | 0.225 |
| AH | GCTCAT | 1319.86 | 1471 | 1.115 | 0.108 |
| AH | GCACAT | 1155.40 | 1122 | 0.971 | −0.029 |
| AH | GCCCAT | 2006.93 | 1827 | 0.910 | −0.094 |
| AH | GCTCAC | 1820.07 | 1526 | 0.838 | −0.176 |
| AH | GCACAC | 1593.29 | 1312 | 0.823 | −0.194 |
| AH | GCGCAT | 542.64 | 248 | 0.457 | −0.783 |
| AI | GCCATC | 3894.51 | 7798 | 2.002 | 0.694 |
| AI | GCCATT | 3079.73 | 3761 | 1.221 | 0.200 |
| AI | GCAATA | 815.43 | 924 | 1.133 | 0.125 |
| AI | GCAATT | 1773.02 | 1684 | 0.950 | −0.052 |
| AI | GCCATA | 1416.41 | 1257 | 0.887 | −0.119 |
| AI | GCTATT | 2025.39 | 1709 | 0.844 | −0.170 |
| AI | GCTATA | 931.50 | 771 | 0.828 | −0.189 |
| AI | GCTATC | 2561.23 | 1194 | 0.466 | −0.763 |
| AI | GCGATT | 832.70 | 373 | 0.448 | −0.803 |
| AI | GCAATC | 2242.09 | 984 | 0.439 | −0.824 |
| AI | GCGATA | 382.97 | 149 | 0.389 | −0.944 |
| AI | GCGATC | 1053.00 | 404 | 0.384 | −0.958 |
| AK | GCCAAG | 5767.01 | 9818 | 1.702 | 0.532 |

Supplemental Table 1

Expected and Observed Codon Pair Frequencies and Codon Pair Scores for 14,795 Human Genes

| amino acid pair | codon pair | expected | observed | observed/expected | CPS |
|---|---|---|---|---|---|
| AK | GCAAAA | 2563.57 | 3011 | 1.175 | 0.161 |
| AK | GCCAAA | 4452.91 | 4794 | 1.077 | 0.074 |
| AK | GCAAAG | 3320.10 | 3044 | 0.917 | -0.087 |
| AK | GCTAAA | 2928.46 | 2022 | 0.690 | -0.370 |
| AK | GCGAAG | 1559.29 | 765 | 0.491 | -0.712 |
| AK | GCTAAG | 3792.68 | 1725 | 0.455 | -0.788 |
| AK | GCGAAA | 1203.98 | 409 | 0.340 | -1.080 |
| AL | GCGCTG | 2369.16 | 4619 | 1.950 | 0.668 |
| AL | GCGCTC | 1140.05 | 1765 | 1.548 | 0.437 |
| AL | GCTTTG | 1873.51 | 2601 | 1.388 | 0.328 |
| AL | GCCCTG | 8762.30 | 11409 | 1.302 | 0.264 |
| AL | GCCTTG | 2848.79 | 3695 | 1.297 | 0.260 |
| AL | GCTTTA | 1115.24 | 1385 | 1.242 | 0.217 |
| AL | GCCCTC | 4216.45 | 4499 | 1.067 | 0.065 |
| AL | GCTCTT | 1912.07 | 2038 | 1.066 | 0.064 |
| AL | GCATTA | 976.28 | 986 | 1.010 | 0.010 |
| AL | GCTCTA | 1031.16 | 940 | 0.912 | -0.093 |
| AL | GCACTT | 1673.82 | 1444 | 0.863 | -0.148 |
| AL | GCATTG | 1640.07 | 1364 | 0.832 | -0.184 |
| AL | GCACTA | 902.68 | 747 | 0.828 | -0.189 |
| AL | GCGCTA | 423.94 | 342 | 0.807 | -0.215 |
| AL | GCCCTA | 1567.95 | 1228 | 0.783 | -0.244 |
| AL | GCTCTG | 5762.53 | 4505 | 0.782 | -0.246 |
| AL | GCCCTT | 2907.42 | 2230 | 0.767 | -0.265 |
| AL | GCTCTC | 2772.95 | 2036 | 0.734 | -0.309 |
| AL | GCCTTA | 1695.80 | 1205 | 0.711 | -0.342 |
| AL | GCACTG | 5044.51 | 3522 | 0.698 | -0.359 |
| AL | GCGTTG | 770.26 | 476 | 0.618 | -0.481 |
| AL | GCGCTT | 786.11 | 459 | 0.584 | -0.538 |
| AL | GCACTC | 2427.43 | 1415 | 0.583 | -0.540 |
| AL | GCGTTA | 458.51 | 169 | 0.369 | -0.998 |
| AM | GCCATG | 4236.47 | 6521 | 1.539 | 0.431 |
| AM | GCAATG | 2438.96 | 1900 | 0.779 | -0.250 |
| AM | GCTATG | 2786.11 | 1561 | 0.560 | -0.579 |
| AM | GCGATG | 1145.46 | 625 | 0.546 | -0.606 |
| AN | GCCAAC | 3190.28 | 5452 | 1.709 | 0.536 |
| AN | GCAAAT | 1667.60 | 2282 | 1.368 | 0.314 |
| AN | GCCAAT | 2896.62 | 3122 | 1.078 | 0.075 |
| AN | GCAAAC | 1836.66 | 1512 | 0.823 | -0.195 |
| AN | GCTAAT | 1904.97 | 1356 | 0.712 | -0.340 |
| AN | GCTAAC | 2098.09 | 925 | 0.441 | -0.819 |
| AN | GCGAAC | 862.59 | 331 | 0.384 | -0.958 |
| AN | GCGAAT | 783.19 | 260 | 0.332 | -1.103 |
| AP | GCGCCG | 406.74 | 1172 | 2.881 | 1.058 |
| AP | GCGCCC | 1122.56 | 2271 | 2.023 | 0.705 |
| AP | GCCCCG | 1504.34 | 2335 | 1.552 | 0.440 |
| AP | GCTCCA | 2360.19 | 2463 | 1.044 | 0.043 |
| AP | GCTCCT | 2445.47 | 2548 | 1.042 | 0.041 |
| AP | GCCCCC | 4151.78 | 3957 | 0.953 | -0.048 |
| AP | GCACCT | 2140.76 | 2028 | 0.947 | -0.054 |
| AP | GCCCCA | 3588.82 | 3371 | 0.939 | -0.063 |
| AP | GCACCA | 2066.10 | 1831 | 0.886 | -0.121 |
| AP | GCACCC | 2390.20 | 2111 | 0.883 | -0.124 |
| AP | GCCCCT | 3718.49 | 3269 | 0.879 | -0.129 |
| AP | GCTCCC | 2730.42 | 2384 | 0.873 | -0.136 |
| AP | GCTCCG | 989.33 | 773 | 0.781 | -0.247 |
| AP | GCGCCT | 1005.41 | 778 | 0.774 | -0.256 |
| AP | GCACCG | 866.06 | 571 | 0.659 | -0.417 |
| AP | GCGCCA | 970.35 | 595 | 0.613 | -0.489 |
| AQ | GCCCAG | 7143.67 | 9550 | 1.337 | 0.290 |
| AQ | GCGCAG | 1931.51 | 2101 | 1.088 | 0.084 |
| AQ | GCACAA | 1472.79 | 1416 | 0.961 | -0.039 |
| AQ | GCTCAA | 1682.42 | 1522 | 0.905 | -0.100 |
| AQ | GCTCAG | 4698.04 | 4141 | 0.881 | -0.126 |
| AQ | GCACAG | 4112.65 | 3374 | 0.820 | -0.198 |
| AQ | GCCCAA | 2558.23 | 1943 | 0.760 | -0.275 |
| AQ | GCGCAA | 691.70 | 244 | 0.353 | -1.042 |
| AR | GCGCGC | 580.17 | 1255 | 2.163 | 0.772 |
| AR | GCGCGG | 634.54 | 1175 | 1.852 | 0.616 |
| AR | GCCCGG | 2346.82 | 3946 | 1.681 | 0.520 |

Supplemental Table 1

Expected and Observed Codon Pair Frequencies and Codon Pair Scores for 14,795 Human Genes

| amino acid pair | codon pair | expected | observed | observed/expected | CPS |
|---|---|---|---|---|---|
| AR | GCCCGC | 2145.76 | 3135 | 1.461 | 0.379 |
| AR | GCCAGG | 2323.57 | 3242 | 1.395 | 0.333 |
| AR | GCAAGA | 1362.59 | 1559 | 1.144 | 0.135 |
| AR | GCTCGA | 836.64 | 943 | 1.127 | 0.120 |
| AR | GCCCGA | 1272.16 | 1418 | 1.115 | 0.109 |
| AR | GCCCGT | 918.67 | 935 | 1.018 | 0.018 |
| AR | GCTCGT | 604.17 | 595 | 0.985 | -0.015 |
| AR | GCCAGA | 2366.81 | 2219 | 0.938 | -0.064 |
| AR | GCTCGG | 1543.39 | 1295 | 0.839 | -0.175 |
| AR | GCGCGT | 248.39 | 205 | 0.825 | -0.192 |
| AR | GCAAGG | 1337.69 | 1089 | 0.814 | -0.206 |
| AR | GCGAGG | 628.25 | 486 | 0.774 | -0.257 |
| AR | GCACGA | 732.39 | 533 | 0.728 | -0.318 |
| AR | GCTCGC | 1411.16 | 941 | 0.667 | -0.405 |
| AR | GCGCGA | 343.97 | 226 | 0.657 | -0.420 |
| AR | GCACGT | 528.89 | 338 | 0.639 | -0.448 |
| AR | GCACGG | 1351.08 | 859 | 0.636 | -0.453 |
| AR | GCACGC | 1235.33 | 619 | 0.501 | -0.691 |
| AR | GCTAGA | 1556.53 | 714 | 0.459 | -0.779 |
| AR | GCGAGA | 639.94 | 263 | 0.411 | -0.889 |
| AR | GCTAGG | 1528.10 | 487 | 0.319 | -1.144 |
| AS | GCCTCG | 963.41 | 1977 | 2.052 | 0.719 |
| AS | GCGTCG | 260.49 | 465 | 1.785 | 0.579 |
| AS | GCCAGC | 4127.58 | 6466 | 1.567 | 0.449 |
| AS | GCCTCC | 3643.21 | 5443 | 1.494 | 0.401 |
| AS | GCTTCT | 2084.25 | 2488 | 1.194 | 0.177 |
| AS | GCCAGT | 2604.12 | 3085 | 1.185 | 0.169 |
| AS | GCATCT | 1824.55 | 2154 | 1.181 | 0.166 |
| AS | GCTTCA | 1684.99 | 1932 | 1.147 | 0.137 |
| AS | GCGTCC | 985.05 | 1079 | 1.095 | 0.091 |
| AS | GCATCA | 1475.04 | 1531 | 1.038 | 0.037 |
| AS | GCCTCT | 3169.23 | 3235 | 1.021 | 0.021 |
| AS | GCCTCA | 2562.14 | 2514 | 0.981 | -0.019 |
| AS | GCTTCC | 2395.96 | 2295 | 0.958 | -0.043 |
| AS | GCAAGT | 1499.21 | 1307 | 0.872 | -0.137 |
| AS | GCTTCG | 633.59 | 516 | 0.814 | -0.205 |
| AS | GCATCC | 2097.42 | 1658 | 0.790 | -0.235 |
| AS | GCATCG | 554.64 | 403 | 0.727 | -0.319 |
| AS | GCGTCT | 856.90 | 521 | 0.608 | -0.498 |
| AS | GCGAGC | 1116.02 | 595 | 0.533 | -0.629 |
| AS | GCGTCA | 692.75 | 319 | 0.460 | -0.775 |
| AS | GCAAGC | 2376.27 | 1080 | 0.454 | -0.789 |
| AS | GCTAGT | 1712.60 | 737 | 0.430 | -0.843 |
| AS | GCGAGT | 704.10 | 265 | 0.376 | -0.977 |
| AS | GCTAGC | 2714.51 | 673 | 0.248 | -1.395 |
| AT | GCCACG | 1262.40 | 2478 | 1.963 | 0.674 |
| AT | GCCACC | 3842.98 | 6598 | 1.717 | 0.541 |
| AT | GCCACA | 3111.04 | 4031 | 1.296 | 0.259 |
| AT | GCCACT | 2751.18 | 3205 | 1.165 | 0.153 |
| AT | GCAACA | 1791.05 | 1761 | 0.983 | -0.017 |
| AT | GCGACG | 341.33 | 329 | 0.964 | -0.037 |
| AT | GCAACT | 1583.87 | 1509 | 0.953 | -0.048 |
| AT | GCTACT | 1809.31 | 1395 | 0.771 | -0.260 |
| AT | GCTACA | 2045.98 | 1528 | 0.747 | -0.292 |
| AT | GCGACC | 1039.07 | 601 | 0.578 | -0.547 |
| AT | GCAACC | 2212.43 | 1259 | 0.569 | -0.564 |
| AT | GCTACC | 2527.34 | 1364 | 0.540 | -0.617 |
| AT | GCAACG | 726.77 | 384 | 0.528 | -0.638 |
| AT | GCTACG | 830.22 | 363 | 0.437 | -0.827 |
| AT | GCGACT | 743.87 | 308 | 0.414 | -0.882 |
| AT | GCGACA | 841.17 | 347 | 0.413 | -0.885 |
| AV | GCTGTT | 1736.99 | 3025 | 1.742 | 0.555 |
| AV | GCTGTG | 4399.56 | 7279 | 1.654 | 0.503 |
| AV | GCTGTA | 1127.89 | 1750 | 1.552 | 0.439 |
| AV | GCTGTC | 2223.90 | 3351 | 1.507 | 0.410 |
| AV | GCAGTA | 987.35 | 1401 | 1.419 | 0.350 |
| AV | GCGGTG | 1808.80 | 2487 | 1.375 | 0.318 |
| AV | GCAGTT | 1520.56 | 2087 | 1.373 | 0.317 |
| AV | GCAGTG | 3851.36 | 4349 | 1.129 | 0.122 |
| AV | GCGGTC | 914.32 | 883 | 0.966 | -0.035 |

Supplemental Table 1

Expected and Observed Codon Pair Frequencies and Codon Pair Scores for 14,795 Human Genes

| amino acid pair | codon pair | expected | observed | observed/expected | CPS |
|---|---|---|---|---|---|
| AV | GCAGTC | 1946.80 | 1806 | 0.928 | -0.075 |
| AV | GCCGTG | 6689.81 | 4322 | 0.646 | -0.437 |
| AV | GCGGTT | 714.13 | 423 | 0.592 | -0.524 |
| AV | GCGGTA | 463.71 | 270 | 0.582 | -0.541 |
| AV | GCCGTC | 3381.59 | 1798 | 0.532 | -0.632 |
| AV | GCCGTT | 2641.21 | 563 | 0.213 | -1.546 |
| AV | GCCGTA | 1715.03 | 329 | 0.192 | -1.651 |
| AW | GCCTGG | 2528.22 | 3848 | 1.522 | 0.420 |
| AW | GCGTGG | 683.58 | 558 | 0.816 | -0.203 |
| AW | GCTTGG | 1662.69 | 1066 | 0.641 | -0.445 |
| AW | GCATGG | 1455.51 | 858 | 0.589 | -0.529 |
| AY | GCCTAC | 2643.77 | 4073 | 1.541 | 0.432 |
| AY | GCCTAT | 2148.26 | 2457 | 1.144 | 0.134 |
| AY | GCTTAT | 1412.81 | 1478 | 1.046 | 0.045 |
| AY | GCATAT | 1236.77 | 1244 | 1.006 | 0.006 |
| AY | GCTTAC | 1738.68 | 1139 | 0.655 | -0.423 |
| AY | GCGTAC | 714.83 | 429 | 0.600 | -0.511 |
| AY | GCATAC | 1522.04 | 868 | 0.570 | -0.562 |
| AY | GCGTAT | 580.85 | 310 | 0.534 | -0.628 |
| CA | TGTGCT | 1164.04 | 2021 | 1.736 | 0.552 |
| CA | TGTGCC | 1769.99 | 2992 | 1.690 | 0.525 |
| CA | TGTGCA | 1019.00 | 1708 | 1.676 | 0.517 |
| CA | TGTGCG | 478.57 | 477 | 0.997 | -0.003 |
| CA | TGCGCG | 568.18 | 502 | 0.884 | -0.124 |
| CA | TGCGCC | 2101.42 | 1313 | 0.625 | -0.470 |
| CA | TGCGCT | 1382.00 | 368 | 0.266 | -1.323 |
| CA | TGCGCA | 1209.80 | 312 | 0.258 | -1.355 |
| CC | TGCTGC | 1534.17 | 2610 | 1.701 | 0.531 |
| CC | TGCTGT | 1292.21 | 1571 | 1.216 | 0.195 |
| CC | TGTTGT | 1088.41 | 529 | 0.486 | -0.721 |
| CC | TGTTGC | 1292.21 | 497 | 0.385 | -0.956 |
| CD | TGTGAC | 1920.20 | 3470 | 1.807 | 0.592 |
| CD | TGTGAT | 1699.87 | 2853 | 1.678 | 0.518 |
| CD | TGCGAC | 2279.75 | 1134 | 0.497 | -0.698 |
| CD | TGCGAT | 2018.17 | 461 | 0.228 | -1.477 |
| CE | TGTGAA | 1901.69 | 3636 | 1.912 | 0.648 |
| CE | TGTGAG | 2543.16 | 3935 | 1.547 | 0.437 |
| CE | TGCGAG | 3019.37 | 1709 | 0.566 | -0.569 |
| CE | TGCGAA | 2257.78 | 442 | 0.196 | -1.631 |
| CF | TGCTTC | 1891.74 | 2684 | 1.419 | 0.350 |
| CF | TGCTTT | 1652.78 | 1685 | 1.019 | 0.019 |
| CF | TGTTTT | 1392.11 | 1096 | 0.787 | -0.239 |
| CF | TGTTTC | 1593.38 | 1065 | 0.668 | -0.403 |
| CG | TGTGGG | 1594.78 | 3240 | 2.032 | 0.709 |
| CG | TGTGGA | 1633.57 | 2846 | 1.742 | 0.555 |
| CG | TGTGGT | 1057.61 | 1627 | 1.538 | 0.431 |
| CG | TGTGGC | 2214.90 | 3133 | 1.415 | 0.347 |
| CG | TGCGGG | 1893.40 | 1137 | 0.601 | -0.510 |
| CG | TGCGGC | 2629.63 | 1461 | 0.556 | -0.588 |
| CG | TGCGGT | 1255.64 | 344 | 0.274 | -1.295 |
| CG | TGCGGA | 1939.46 | 431 | 0.222 | -1.504 |
| CH | TGCCAC | 1618.50 | 2144 | 1.325 | 0.281 |
| CH | TGCCAT | 1173.68 | 1253 | 1.068 | 0.065 |
| CH | TGTCAT | 988.58 | 831 | 0.841 | -0.174 |
| CH | TGTCAC | 1363.24 | 916 | 0.672 | -0.398 |
| CI | TGCATC | 1821.04 | 2813 | 1.545 | 0.435 |
| CI | TGCATT | 1440.05 | 1579 | 1.096 | 0.092 |
| CI | TGCATA | 662.30 | 576 | 0.870 | -0.140 |
| CI | TGTATA | 557.84 | 474 | 0.850 | -0.163 |
| CI | TGTATT | 1212.94 | 927 | 0.764 | -0.269 |
| CI | TGTATC | 1533.83 | 859 | 0.560 | -0.580 |
| CK | TGCAAG | 2777.53 | 3348 | 1.205 | 0.187 |
| CK | TGCAAA | 2144.62 | 2441 | 1.138 | 0.129 |
| CK | TGTAAA | 1806.38 | 1770 | 0.980 | -0.020 |
| CK | TGTAAG | 2339.47 | 1509 | 0.645 | -0.438 |
| CL | TGCCTC | 1722.14 | 2468 | 1.433 | 0.360 |
| CL | TGCCTG | 3578.83 | 4525 | 1.264 | 0.235 |
| CL | TGTTTA | 583.38 | 704 | 1.207 | 0.188 |
| CL | TGCCTT | 1187.49 | 1384 | 1.165 | 0.153 |
| CL | TGTTTG | 980.04 | 1079 | 1.101 | 0.096 |

Supplemental Table 1

Expected and Observed Codon Pair Frequencies and Codon Pair Scores for 14,795 Human Genes

| amino acid pair | codon pair | expected | observed | observed/expected | CPS |
|---|---|---|---|---|---|
| CL | TGCTTG | 1163.55 | 1179 | 1.013 | 0.013 |
| CL | TGTCTT | 1000.21 | 940 | 0.940 | -0.062 |
| CL | TGCCTA | 640.41 | 585 | 0.913 | -0.090 |
| CL | TGTCTA | 539.40 | 481 | 0.892 | -0.115 |
| CL | TGCTTA | 692.62 | 565 | 0.816 | -0.204 |
| CL | TGTCTC | 1450.53 | 1010 | 0.696 | -0.362 |
| CL | TGTCTG | 3014.39 | 1633 | 0.542 | -0.613 |
| CM | TGCATG | 1518.22 | 1979 | 1.304 | 0.265 |
| CM | TGTATG | 1278.78 | 818 | 0.640 | -0.447 |
| CN | TGCAAC | 1825.04 | 2351 | 1.288 | 0.253 |
| CN | TGCAAT | 1657.05 | 1636 | 0.987 | -0.013 |
| CN | TGTAAT | 1395.71 | 1349 | 0.967 | -0.034 |
| CN | TGTAAC | 1537.20 | 1079 | 0.702 | -0.354 |
| CP | TGCCCG | 687.28 | 978 | 1.423 | 0.353 |
| CP | TGCCCC | 1896.80 | 2279 | 1.201 | 0.184 |
| CP | TGCCCA | 1639.61 | 1728 | 1.054 | 0.053 |
| CP | TGCCCT | 1698.85 | 1690 | 0.995 | -0.005 |
| CP | TGTCCT | 1430.91 | 1333 | 0.932 | -0.071 |
| CP | TGTCCA | 1381.01 | 1263 | 0.915 | -0.089 |
| CP | TGTCCC | 1597.65 | 1369 | 0.857 | -0.154 |
| CP | TGTCCG | 578.88 | 271 | 0.468 | -0.759 |
| CQ | TGCCAG | 3338.89 | 4321 | 1.294 | 0.258 |
| CQ | TGCCAA | 1195.69 | 1319 | 1.103 | 0.098 |
| CQ | TGTCAA | 1007.11 | 905 | 0.899 | -0.107 |
| CQ | TGTCAG | 2812.30 | 1809 | 0.643 | -0.441 |
| CR | TGCCGC | 1031.52 | 1860 | 1.803 | 0.590 |
| CR | TGCCGG | 1128.18 | 1543 | 1.368 | 0.313 |
| CR | TGCAGG | 1117.00 | 1450 | 1.298 | 0.261 |
| CR | TGCCGT | 441.63 | 541 | 1.225 | 0.203 |
| CR | TGCCGA | 611.56 | 742 | 1.213 | 0.193 |
| CR | TGCAGA | 1137.78 | 1252 | 1.100 | 0.096 |
| CR | TGTCGA | 515.11 | 458 | 0.889 | -0.118 |
| CR | TGTCGT | 371.98 | 308 | 0.828 | -0.189 |
| CR | TGTAGA | 958.34 | 570 | 0.595 | -0.520 |
| CR | TGTCGC | 868.83 | 497 | 0.572 | -0.559 |
| CR | TGTCGG | 950.24 | 463 | 0.487 | -0.719 |
| CR | TGTAGG | 940.83 | 389 | 0.413 | -0.883 |
| CS | TGCAGC | 1990.73 | 3150 | 1.582 | 0.459 |
| CS | TGCTCC | 1757.12 | 2397 | 1.364 | 0.311 |
| CS | TGCAGT | 1255.97 | 1701 | 1.354 | 0.303 |
| CS | TGCTCG | 464.65 | 571 | 1.229 | 0.206 |
| CS | TGTTCT | 1287.45 | 1184 | 0.920 | -0.084 |
| CS | TGCTCT | 1528.52 | 1393 | 0.911 | -0.093 |
| CS | TGTTCA | 1040.83 | 932 | 0.895 | -0.110 |
| CS | TGCTCA | 1235.72 | 1079 | 0.873 | -0.136 |
| CS | TGTTCC | 1479.99 | 1102 | 0.745 | -0.295 |
| CS | TGTAGT | 1057.88 | 699 | 0.661 | -0.414 |
| CS | TGTTCG | 391.37 | 192 | 0.491 | -0.712 |
| CS | TGTAGC | 1676.76 | 767 | 0.457 | -0.782 |
| CT | TGCACG | 535.88 | 829 | 1.547 | 0.436 |
| CT | TGCACC | 1631.31 | 2321 | 1.423 | 0.353 |
| CT | TGCACA | 1320.60 | 1508 | 1.142 | 0.133 |
| CT | TGCACT | 1167.85 | 1185 | 1.015 | 0.015 |
| CT | TGTACT | 983.66 | 802 | 0.815 | -0.204 |
| CT | TGTACA | 1112.32 | 830 | 0.746 | -0.293 |
| CT | TGTACC | 1374.02 | 942 | 0.686 | -0.377 |
| CT | TGTACG | 451.36 | 160 | 0.354 | -1.037 |
| CV | TGTGTC | 1064.94 | 1821 | 1.710 | 0.536 |
| CV | TGTGTT | 831.78 | 1383 | 1.663 | 0.508 |
| CV | TGTGTA | 540.10 | 866 | 1.603 | 0.472 |
| CV | TGTGTG | 2106.78 | 3241 | 1.538 | 0.431 |
| CV | TGCGTG | 2501.27 | 1537 | 0.614 | -0.487 |
| CV | TGCGTC | 1264.35 | 734 | 0.581 | -0.544 |
| CV | TGCGTT | 987.53 | 219 | 0.222 | -1.506 |
| CV | TGCGTA | 641.24 | 137 | 0.214 | -1.543 |
| CW | TGCTGG | 1275.05 | 1842 | 1.445 | 0.368 |
| CW | TGTTGG | 1073.95 | 507 | 0.472 | -0.751 |
| CY | TGCTAC | 1379.34 | 1995 | 1.446 | 0.369 |
| CY | TGCTAT | 1120.82 | 1170 | 1.044 | 0.043 |
| CY | TGTTCT | 944.05 | 653 | 0.692 | -0.369 |

Supplemental Table 1

Expected and Observed Codon Pair Frequencies and Codon Pair Scores for 14,795 Human Genes

| amino acid pair | codon pair | expected | observed | observed/expected | CPS |
|---|---|---|---|---|---|
| CY | TGTTCC | 1161.80 | 788 | 0.678 | -0.388 |
| DA | GATGCT | 2675.13 | 5292 | 1.978 | 0.682 |
| DA | GATGCA | 2341.80 | 3898 | 1.665 | 0.510 |
| DA | GATGCC | 4067.71 | 5983 | 1.471 | 0.386 |
| DA | GACGCG | 1242.39 | 1116 | 0.898 | -0.107 |
| DA | GATGCG | 1099.83 | 972 | 0.884 | -0.124 |
| DA | GACGCC | 4594.94 | 2668 | 0.581 | -0.544 |
| DA | GACGCA | 2645.34 | 852 | 0.322 | -1.133 |
| DA | GACGCT | 3021.87 | 908 | 0.300 | -1.202 |
| DC | GACTGC | 2386.86 | 3465 | 1.452 | 0.373 |
| DC | GACTGT | 2010.41 | 2804 | 1.395 | 0.333 |
| DC | GATTGT | 1779.74 | 1163 | 0.653 | -0.425 |
| DC | GATTGC | 2112.99 | 858 | 0.406 | -0.901 |
| DD | GATGAT | 4271.42 | 7846 | 1.837 | 0.608 |
| DD | GATGAC | 4825.06 | 7181 | 1.488 | 0.398 |
| DD | GACGAC | 5450.46 | 2965 | 0.544 | -0.609 |
| DD | GACGAT | 4825.06 | 1380 | 0.286 | -1.252 |
| DE | GATGAA | 5114.33 | 10045 | 1.964 | 0.675 |
| DE | GATGAG | 6839.48 | 9573 | 1.400 | 0.336 |
| DE | GACGAG | 7725.97 | 4498 | 0.582 | -0.541 |
| DE | GACGAA | 5777.22 | 1341 | 0.232 | -1.461 |
| DF | GACTTC | 4696.28 | 6094 | 1.298 | 0.261 |
| DF | GACTTT | 4103.05 | 4250 | 1.036 | 0.035 |
| DF | GATTTT | 3632.26 | 3485 | 0.959 | -0.041 |
| DF | GATTTC | 4157.42 | 2760 | 0.664 | -0.410 |
| DG | GATGGT | 1910.36 | 3443 | 1.802 | 0.589 |
| DG | GATGGA | 2950.72 | 5133 | 1.740 | 0.554 |
| DG | GATGGG | 2880.65 | 4437 | 1.540 | 0.432 |
| DG | GATGGC | 4000.77 | 5419 | 1.354 | 0.303 |
| DG | GACGGC | 4519.33 | 2987 | 0.661 | -0.414 |
| DG | GACGGG | 3254.02 | 1979 | 0.608 | -0.497 |
| DG | GACGGT | 2157.97 | 723 | 0.335 | -1.094 |
| DG | GACGGA | 3333.18 | 886 | 0.266 | -1.325 |
| DH | GACCAC | 2653.74 | 3480 | 1.311 | 0.271 |
| DH | GACCAT | 1924.41 | 2014 | 1.047 | 0.046 |
| DH | GATCAT | 1703.60 | 1623 | 0.953 | -0.048 |
| DH | GATCAC | 2349.25 | 1514 | 0.644 | -0.439 |
| DI | GACATC | 4715.94 | 6532 | 1.385 | 0.326 |
| DI | GACATT | 3729.31 | 4087 | 1.096 | 0.092 |
| DI | GATATT | 3301.40 | 3271 | 0.991 | -0.009 |
| DI | GATATA | 1518.36 | 1495 | 0.985 | -0.016 |
| DI | GACATA | 1715.16 | 1565 | 0.912 | -0.092 |
| DI | GATATC | 4174.83 | 2205 | 0.528 | -0.638 |
| DK | GACAAG | 5562.52 | 7324 | 1.317 | 0.275 |
| DK | GACAAA | 4295.02 | 4794 | 1.116 | 0.110 |
| DK | GATAAA | 3802.20 | 3855 | 1.014 | 0.014 |
| DK | GATAAG | 4924.27 | 2611 | 0.530 | -0.634 |
| DL | GACCTC | 3785.97 | 5029 | 1.328 | 0.284 |
| DL | GACTTG | 2557.95 | 3396 | 1.328 | 0.283 |
| DL | GATTTA | 1347.95 | 1740 | 1.291 | 0.255 |
| DL | GACCTG | 7867.71 | 9796 | 1.245 | 0.219 |
| DL | GATTTG | 2264.44 | 2687 | 1.187 | 0.171 |
| DL | GACCTT | 2610.58 | 2774 | 1.063 | 0.061 |
| DL | GATCTT | 2311.04 | 2416 | 1.045 | 0.044 |
| DL | GACCTA | 1407.87 | 1416 | 1.006 | 0.006 |
| DL | GACTTA | 1522.66 | 1403 | 0.921 | -0.082 |
| DL | GATCTA | 1246.33 | 1020 | 0.818 | -0.200 |
| DL | GATCTC | 3351.56 | 2214 | 0.661 | -0.415 |
| DL | GATCTG | 6964.95 | 3348 | 0.481 | -0.733 |
| DM | GACATG | 4089.63 | 5411 | 1.323 | 0.280 |
| DM | GATATG | 3620.37 | 2299 | 0.635 | -0.454 |
| DN | GACAAC | 3511.00 | 4849 | 1.381 | 0.323 |
| DN | GACAAT | 3187.82 | 3349 | 1.051 | 0.049 |
| DN | GATAAT | 2822.05 | 2549 | 0.903 | -0.102 |
| DN | GATAAC | 3108.14 | 1882 | 0.606 | -0.502 |
| DP | GACCCC | 3732.11 | 5119 | 1.372 | 0.316 |
| DP | GACCCG | 1352.28 | 1692 | 1.251 | 0.224 |
| DP | GACCCT | 3342.62 | 3700 | 1.107 | 0.102 |
| DP | GATCCT | 2959.08 | 3111 | 1.051 | 0.050 |
| DP | GACCCA | 3226.05 | 3205 | 0.993 | -0.007 |

Supplemental Table 1

Expected and Observed Codon Pair Frequencies and Codon Pair Scores for 14,795 Human Genes

| amino acid pair | codon pair | expected | observed | observed/expected | CPS |
|---|---|---|---|---|---|
| DP | GATCCA | 2855.89 | 2349 | 0.823 | -0.195 |
| DP | GATCCC | 3303.88 | 2338 | 0.708 | -0.346 |
| DP | GATCCG | 1197.11 | 455 | 0.380 | -0.967 |
| DQ | GACCAG | 5250.37 | 6524 | 1.243 | 0.217 |
| DQ | GACCAA | 1880.22 | 2169 | 1.154 | 0.143 |
| DQ | GATCAA | 1664.48 | 1808 | 1.086 | 0.083 |
| DQ | GATCAG | 4647.93 | 2942 | 0.633 | -0.457 |
| DR | GACCGC | 1807.77 | 2634 | 1.457 | 0.376 |
| DR | GACAGA | 1994.00 | 2869 | 1.439 | 0.364 |
| DR | GACAGG | 1957.57 | 2730 | 1.395 | 0.333 |
| DR | GACCGT | 773.97 | 1029 | 1.330 | 0.285 |
| DR | GACCGG | 1977.16 | 2568 | 1.299 | 0.261 |
| DR | GACCGA | 1071.78 | 1292 | 1.205 | 0.187 |
| DR | GATCGA | 948.80 | 923 | 0.973 | -0.028 |
| DR | GATCGT | 685.16 | 626 | 0.914 | -0.090 |
| DR | GATAGA | 1765.20 | 1123 | 0.636 | -0.452 |
| DR | GATCGG | 1750.30 | 859 | 0.491 | -0.712 |
| DR | GATCGC | 1600.34 | 754 | 0.471 | -0.753 |
| DR | GATAGG | 1732.96 | 658 | 0.380 | -0.968 |
| DS | GACTCG | 918.57 | 1527 | 1.662 | 0.508 |
| DS | GACAGC | 3935.48 | 6143 | 1.561 | 0.445 |
| DS | GACAGT | 2482.92 | 3657 | 1.473 | 0.387 |
| DS | GATTCT | 2675.01 | 2968 | 1.110 | 0.104 |
| DS | GACTCC | 3473.65 | 3800 | 1.094 | 0.090 |
| DS | GATTCA | 2162.59 | 2129 | 0.984 | -0.016 |
| DS | GACTCA | 2442.89 | 2382 | 0.975 | -0.025 |
| DS | GACTCT | 3021.73 | 2910 | 0.963 | -0.038 |
| DS | GATTCC | 3075.07 | 2186 | 0.711 | -0.341 |
| DS | GATAGT | 2198.02 | 1355 | 0.616 | -0.484 |
| DS | GATTCG | 813.17 | 414 | 0.509 | -0.675 |
| DS | GATAGC | 3483.91 | 1212 | 0.348 | -1.056 |
| DT | GACACG | 1110.58 | 1842 | 1.659 | 0.506 |
| DT | GACACC | 3380.79 | 4666 | 1.380 | 0.322 |
| DT | GACACA | 2736.88 | 3538 | 1.293 | 0.257 |
| DT | GACACT | 2420.30 | 2688 | 1.111 | 0.105 |
| DT | GATACT | 2142.59 | 1731 | 0.808 | -0.213 |
| DT | GATACA | 2422.85 | 1788 | 0.738 | -0.304 |
| DT | GATACC | 2992.87 | 1586 | 0.530 | -0.635 |
| DT | GATACG | 983.15 | 351 | 0.357 | -1.030 |
| DV | GATGTT | 1957.96 | 3699 | 1.889 | 0.636 |
| DV | GATGTA | 1271.37 | 2214 | 1.741 | 0.555 |
| DV | GATGTC | 2506.81 | 3869 | 1.543 | 0.434 |
| DV | GATGTG | 4959.23 | 6668 | 1.345 | 0.296 |
| DV | GACGTG | 5602.02 | 3616 | 0.645 | -0.438 |
| DV | GACGTC | 2831.73 | 1654 | 0.584 | -0.538 |
| DV | GACGTT | 2211.73 | 672 | 0.304 | -1.191 |
| DV | GACGTA | 1436.16 | 385 | 0.268 | -1.316 |
| DW | GACTGG | 2619.27 | 3853 | 1.471 | 0.386 |
| DW | GATTGG | 2318.73 | 1085 | 0.468 | -0.759 |
| DY | GACTAC | 3307.71 | 3930 | 1.188 | 0.172 |
| DY | GATTAT | 2379.36 | 2608 | 1.096 | 0.092 |
| DY | GACTAT | 2687.76 | 2853 | 1.061 | 0.060 |
| DY | GATTAC | 2928.18 | 1912 | 0.653 | -0.426 |
| EA | GAGGCG | 2437.29 | 3179 | 1.304 | 0.266 |
| EA | GAAGCA | 3880.59 | 4844 | 1.248 | 0.222 |
| EA | GAAGCT | 4432.94 | 5143 | 1.160 | 0.149 |
| EA | GAGGCC | 9014.27 | 9805 | 1.088 | 0.084 |
| EA | GAGGCT | 5928.25 | 5314 | 0.896 | -0.109 |
| EA | GAGGCA | 5189.57 | 4530 | 0.873 | -0.136 |
| EA | GAAGCC | 6740.57 | 5649 | 0.838 | -0.177 |
| EA | GAAGCG | 1822.52 | 982 | 0.539 | -0.618 |
| EC | GAATGT | 2182.58 | 3541 | 1.622 | 0.484 |
| EC | GAGTGT | 2918.80 | 2792 | 0.957 | -0.044 |
| EC | GAGTGC | 3465.35 | 2987 | 0.862 | -0.149 |
| EC | GAATGC | 2591.27 | 1838 | 0.709 | -0.343 |
| ED | GAAGAT | 6605.82 | 9691 | 1.467 | 0.383 |
| ED | GAGGAC | 9979.09 | 9684 | 0.970 | -0.030 |
| ED | GAAGAC | 7462.02 | 6820 | 0.914 | -0.090 |
| ED | GAGGAT | 8834.07 | 6686 | 0.757 | -0.279 |
| EE | GAAGAA | 10747.11 | 14461 | 1.346 | 0.297 |

Supplemental Table 1

Expected and Observed Codon Pair Frequencies and Codon Pair Scores for 14,795 Human Genes

| amino acid pair | codon pair | expected | observed | observed/expected | CPS |
|---|---|---|---|---|---|
| EE | GAGGAG | 19220.31 | 21731 | 1.131 | 0.123 |
| EE | GAAGAG | 14372.29 | 11875 | 0.826 | -0.191 |
| EE | GAGGAA | 14372.29 | 10645 | 0.741 | -0.300 |
| EF | GAATTT | 3136.91 | 4237 | 1.351 | 0.301 |
| EF | GAGTTC | 4801.58 | 4739 | 0.987 | -0.013 |
| EF | GAGTTT | 4195.05 | 4095 | 0.976 | -0.024 |
| EF | GAATTC | 3590.46 | 2653 | 0.739 | -0.303 |
| EG | GAAGGA | 3358.73 | 5032 | 1.498 | 0.404 |
| EG | GAAGGT | 2174.51 | 2839 | 1.306 | 0.267 |
| EG | GAAGGG | 3278.97 | 3559 | 1.085 | 0.082 |
| EG | GAGGGC | 6090.10 | 6505 | 1.068 | 0.066 |
| EG | GAAGGC | 4553.97 | 4340 | 0.953 | -0.048 |
| EG | GAGGGG | 4385.02 | 3795 | 0.865 | -0.145 |
| EG | GAGGGT | 2908.01 | 2378 | 0.818 | -0.201 |
| EG | GAGGGA | 4491.69 | 2793 | 0.622 | -0.475 |
| EH | GAACAT | 2017.28 | 2539 | 1.259 | 0.230 |
| EH | GAGCAC | 3720.16 | 4190 | 1.126 | 0.119 |
| EH | GAGCAT | 2697.74 | 2448 | 0.907 | -0.097 |
| EH | GAACAC | 2781.81 | 2040 | 0.733 | -0.310 |
| EI | GAAATA | 1687.78 | 3007 | 1.782 | 0.578 |
| EI | GAAATT | 3669.78 | 4788 | 1.305 | 0.266 |
| EI | GAGATC | 6206.03 | 6191 | 0.998 | -0.002 |
| EI | GAGATT | 4907.66 | 3978 | 0.811 | -0.210 |
| EI | GAGATA | 2257.09 | 1785 | 0.791 | -0.235 |
| EI | GAAATC | 4640.66 | 3620 | 0.780 | -0.248 |
| EK | GAGAAG | 12729.57 | 15133 | 1.189 | 0.173 |
| EK | GAAAAA | 7349.75 | 7522 | 1.023 | 0.023 |
| EK | GAGAAA | 9828.94 | 9127 | 0.929 | -0.074 |
| EK | GAAAAG | 9518.74 | 7645 | 0.803 | -0.219 |
| EL | GAGCTG | 10945.64 | 15625 | 1.428 | 0.356 |
| EL | GAATTA | 1584.03 | 2256 | 1.424 | 0.354 |
| EL | GAACTA | 1464.61 | 1830 | 1.249 | 0.223 |
| EL | GAACTT | 2715.79 | 3371 | 1.241 | 0.216 |
| EL | GAGCTC | 5267.08 | 5877 | 1.116 | 0.110 |
| EL | GAGCTA | 1958.64 | 2049 | 1.046 | 0.045 |
| EL | GAATTG | 2661.03 | 2335 | 0.877 | -0.131 |
| EL | GAGCTT | 3631.87 | 3084 | 0.849 | -0.164 |
| EL | GAGTTG | 3558.64 | 2719 | 0.764 | -0.269 |
| EL | GAACTC | 3938.54 | 2632 | 0.668 | -0.403 |
| EL | GAGTTA | 2118.35 | 1357 | 0.641 | -0.445 |
| EL | GAACTG | 8184.78 | 4894 | 0.598 | -0.514 |
| EM | GAAATG | 4983.92 | 5010 | 1.005 | 0.005 |
| EM | GAGATG | 6665.08 | 6639 | 0.996 | -0.004 |
| EN | GAAAAT | 4791.73 | 6977 | 1.456 | 0.376 |
| EN | GAGAAC | 7057.70 | 6756 | 0.957 | -0.044 |
| EN | GAAAAC | 5277.51 | 4930 | 0.934 | -0.068 |
| EN | GAGAAT | 6408.07 | 4872 | 0.760 | -0.274 |
| EP | GAGCCG | 1650.94 | 2438 | 1.477 | 0.390 |
| EP | GAGCCC | 4556.38 | 6270 | 1.376 | 0.319 |
| EP | GAGCCT | 4080.86 | 4236 | 1.038 | 0.037 |
| EP | GAGCCA | 3938.55 | 4067 | 1.033 | 0.032 |
| EP | GAACCA | 2945.12 | 2684 | 0.911 | -0.093 |
| EP | GAACCT | 3051.53 | 2547 | 0.835 | -0.181 |
| EP | GAACCC | 3407.10 | 2106 | 0.618 | -0.481 |
| EP | GAACCG | 1234.52 | 517 | 0.419 | -0.870 |
| EQ | GAACAA | 2579.50 | 3396 | 1.317 | 0.275 |
| EQ | GAGCAG | 9632.80 | 11185 | 1.161 | 0.149 |
| EQ | GAGCAA | 3449.61 | 3185 | 0.923 | -0.080 |
| EQ | GAACAG | 7203.08 | 5099 | 0.708 | -0.345 |
| ER | GAAAGA | 2650.27 | 3769 | 1.422 | 0.352 |
| ER | GAGAGG | 3479.50 | 4315 | 1.240 | 0.215 |
| ER | GAGCGG | 3514.32 | 4356 | 1.240 | 0.215 |
| ER | GAGCGC | 3213.23 | 3682 | 1.146 | 0.136 |
| ER | GAAAGG | 2601.85 | 2679 | 1.030 | 0.029 |
| ER | GAGAGA | 3544.25 | 3633 | 1.025 | 0.025 |
| ER | GAGCGT | 1375.70 | 1286 | 0.935 | -0.067 |
| ER | GAACGT | 1028.70 | 894 | 0.869 | -0.140 |
| ER | GAACGA | 1424.52 | 1188 | 0.834 | -0.182 |
| ER | GAGCGA | 1905.04 | 1562 | 0.820 | -0.199 |
| ER | GAACGG | 2627.88 | 1333 | 0.507 | -0.679 |

Supplemental Table 1

Expected and Observed Codon Pair Frequencies and Codon Pair Scores for 14,795 Human Genes

| amino acid pair | codon pair | expected | observed | observed/expected | CPS |
|---|---|---|---|---|---|
| ER | GAACGC | 2402.74 | 1071 | 0.446 | −0.808 |
| ES | GAAAGT | 2081.93 | 3138 | 1.507 | 0.410 |
| ES | GAGAGC | 4413.03 | 5786 | 1.311 | 0.271 |
| ES | GAGAGT | 2784.21 | 3237 | 1.163 | 0.151 |
| ES | GAGTCG | 1030.03 | 1174 | 1.140 | 0.131 |
| ES | GAATCT | 2533.73 | 2812 | 1.110 | 0.104 |
| ES | GAATCA | 2048.37 | 2131 | 1.040 | 0.040 |
| ES | GAAAGC | 3299.91 | 2880 | 0.873 | −0.136 |
| ES | GAGTCC | 3895.16 | 3392 | 0.871 | −0.138 |
| ES | GAGTCT | 3388.40 | 2799 | 0.826 | −0.191 |
| ES | GAGTCA | 2739.33 | 2198 | 0.802 | −0.220 |
| ES | GAATCC | 2912.67 | 1943 | 0.667 | −0.405 |
| ES | GAATCG | 770.22 | 407 | 0.528 | −0.638 |
| ET | GAGACG | 1658.42 | 2190 | 1.321 | 0.278 |
| ET | GAAACA | 3056.09 | 3851 | 1.260 | 0.231 |
| ET | GAAACT | 2702.59 | 3224 | 1.193 | 0.176 |
| ET | GAGACC | 5048.51 | 5514 | 1.092 | 0.088 |
| ET | GAGACA | 4086.97 | 3619 | 0.885 | −0.122 |
| ET | GAGACT | 3614.21 | 3028 | 0.838 | −0.177 |
| ET | GAAACC | 3775.11 | 2950 | 0.781 | −0.247 |
| ET | GAAACG | 1240.11 | 806 | 0.650 | −0.431 |
| EV | GAAGTA | 1580.16 | 2675 | 1.693 | 0.526 |
| EV | GAAGTT | 2433.50 | 3724 | 1.530 | 0.425 |
| EV | GAGGTG | 8242.83 | 9074 | 1.101 | 0.096 |
| EV | GAAGTC | 3115.66 | 2860 | 0.918 | −0.086 |
| EV | GAGGTC | 4166.62 | 3741 | 0.898 | −0.108 |
| EV | GAAGTG | 6163.71 | 5122 | 0.831 | −0.185 |
| EV | GAGGTT | 3254.36 | 2359 | 0.725 | −0.322 |
| EV | GAGGTA | 2113.17 | 1515 | 0.717 | −0.333 |
| EW | GAGTGG | 3085.08 | 3238 | 1.050 | 0.048 |
| EW | GAATGG | 2306.92 | 2154 | 0.934 | −0.069 |
| EY | GAATAT | 2307.55 | 3428 | 1.486 | 0.396 |
| EY | GAGTAC | 3797.72 | 3796 | 1.000 | 0.000 |
| EY | GAGTAT | 3085.93 | 2596 | 0.841 | −0.173 |
| EY | GAATAC | 2839.80 | 2211 | 0.779 | −0.250 |
| FA | TTTGCA | 1643.98 | 3299 | 2.007 | 0.696 |
| FA | TTTGCT | 1877.98 | 3746 | 1.995 | 0.690 |
| FA | TTTGCC | 2855.59 | 4348 | 1.523 | 0.420 |
| FA | TTTGCG | 772.10 | 622 | 0.806 | −0.216 |
| FA | TTCGCG | 883.73 | 598 | 0.677 | −0.391 |
| FA | TTCGCC | 3268.46 | 1802 | 0.551 | −0.595 |
| FA | TTCGCT | 2149.50 | 516 | 0.240 | −1.427 |
| FA | TTCGCA | 1881.67 | 402 | 0.214 | −1.543 |
| FC | TTCTGC | 2058.60 | 3045 | 1.479 | 0.391 |
| FC | TTCTGT | 1733.93 | 2055 | 1.185 | 0.170 |
| FC | TTTTGT | 1514.90 | 1159 | 0.765 | −0.268 |
| FC | TTTTGC | 1798.56 | 847 | 0.471 | −0.753 |
| FD | TTTGAT | 2786.65 | 5380 | 1.931 | 0.658 |
| FD | TTTGAC | 3147.84 | 4737 | 1.505 | 0.409 |
| FD | TTCGAC | 3602.96 | 1746 | 0.485 | −0.724 |
| FD | TTCGAT | 3189.55 | 864 | 0.271 | −1.306 |
| FE | TTTGAA | 3016.02 | 6247 | 2.071 | 0.728 |
| FE | TTTGAG | 4033.37 | 6066 | 1.504 | 0.408 |
| FE | TTCGAG | 4616.53 | 2165 | 0.469 | −0.757 |
| FE | TTCGAA | 3452.08 | 640 | 0.185 | −1.685 |
| FF | TTCTTC | 3429.53 | 5168 | 1.507 | 0.410 |
| FF | TTCTTT | 2996.32 | 2989 | 0.998 | −0.002 |
| FF | TTTTTT | 2617.83 | 1937 | 0.740 | −0.301 |
| FF | TTTTTC | 2996.32 | 1946 | 0.649 | −0.432 |
| FG | TTTGGA | 2068.21 | 4271 | 2.065 | 0.725 |
| FG | TTTGGT | 1339.00 | 2552 | 1.906 | 0.645 |
| FG | TTTGGG | 2019.09 | 3449 | 1.708 | 0.535 |
| FG | TTTGGC | 2804.20 | 3462 | 1.235 | 0.211 |
| FG | TTCGGG | 2311.02 | 1292 | 0.559 | −0.581 |
| FG | TTCGGC | 3209.64 | 1648 | 0.513 | −0.667 |
| FG | TTCGGT | 1532.60 | 419 | 0.273 | −1.297 |
| FG | TTCGGA | 2367.24 | 558 | 0.236 | −1.445 |
| FH | TTCCAC | 2463.48 | 3200 | 1.299 | 0.262 |
| FH | TTTCAT | 1560.78 | 1697 | 1.087 | 0.084 |
| FH | TTCCAT | 1786.44 | 1866 | 1.045 | 0.044 |

Supplemental Table 1

Expected and Observed Codon Pair Frequencies and Codon Pair Scores for 14,795 Human Genes

| amino acid pair | codon pair | expected | observed | observed/expected | CPS |
|---|---|---|---|---|---|
| FH | TTTCAC | 2152.30 | 1200 | 0.558 | -0.584 |
| FI | TTCATC | 3454.46 | 5156 | 1.493 | 0.400 |
| FI | TTCATT | 2731.75 | 2953 | 1.081 | 0.078 |
| FI | TTTATT | 2386.67 | 2296 | 0.962 | -0.039 |
| FI | TTTATA | 1097.66 | 950 | 0.865 | -0.144 |
| FI | TTCATA | 1256.36 | 1035 | 0.824 | -0.194 |
| FI | TTTATC | 3018.10 | 1555 | 0.515 | -0.663 |
| FK | TTCAAG | 4090.45 | 5137 | 1.256 | 0.228 |
| FK | TTCAAA | 3158.38 | 3245 | 1.027 | 0.027 |
| FK | TTTAAA | 2759.42 | 2762 | 1.001 | 0.001 |
| FK | TTTAAG | 3573.75 | 2438 | 0.682 | -0.382 |
| FL | TTCCTC | 3228.53 | 4426 | 1.371 | 0.315 |
| FL | TTCCTG | 6709.28 | 8734 | 1.302 | 0.264 |
| FL | TTTTTA | 1134.45 | 1334 | 1.176 | 0.162 |
| FL | TTTCTT | 1945.00 | 2267 | 1.166 | 0.153 |
| FL | TTCCTA | 1200.58 | 1280 | 1.066 | 0.064 |
| FL | TTTCTA | 1048.92 | 1087 | 1.036 | 0.036 |
| FL | TTCTTG | 2181.32 | 2239 | 1.026 | 0.026 |
| FL | TTCCTT | 2226.21 | 2150 | 0.966 | -0.035 |
| FL | TTTTTG | 1905.78 | 1799 | 0.944 | -0.058 |
| FL | TTCTTA | 1298.47 | 1144 | 0.881 | -0.127 |
| FL | TTTCTC | 2820.70 | 1904 | 0.675 | -0.393 |
| FL | TTTCTG | 5861.77 | 3197 | 0.545 | -0.606 |
| FM | TTCATG | 2804.11 | 3662 | 1.306 | 0.267 |
| FM | TTTATG | 2449.89 | 1592 | 0.650 | -0.431 |
| FN | TTCAAC | 2855.47 | 3919 | 1.372 | 0.317 |
| FN | TTTAAT | 2265.13 | 2185 | 0.965 | -0.036 |
| FN | TTCAAT | 2592.63 | 2456 | 0.947 | -0.054 |
| FN | TTTAAC | 2494.77 | 1648 | 0.661 | -0.415 |
| FP | TTCCCG | 961.40 | 1205 | 1.253 | 0.226 |
| FP | TTTCCT | 2076.25 | 2539 | 1.223 | 0.201 |
| FP | TTCCCC | 2653.35 | 3099 | 1.168 | 0.155 |
| FP | TTTCCA | 2003.85 | 2141 | 1.068 | 0.066 |
| FP | TTCCCA | 2293.57 | 2310 | 1.007 | 0.007 |
| FP | TTCCCT | 2376.44 | 2379 | 1.001 | 0.001 |
| FP | TTTCCC | 2318.18 | 1529 | 0.660 | -0.416 |
| FP | TTTCCG | 839.96 | 321 | 0.382 | -0.962 |
| FQ | TTCCAG | 5468.69 | 7069 | 1.293 | 0.257 |
| FQ | TTTCAA | 1711.02 | 1803 | 1.054 | 0.052 |
| FQ | TTCCAA | 1958.40 | 1980 | 1.011 | 0.011 |
| FQ | TTTCAG | 4777.89 | 3064 | 0.641 | -0.444 |
| FR | TTCCGC | 1531.47 | 2588 | 1.690 | 0.525 |
| FR | TTCCGA | 907.97 | 1410 | 1.553 | 0.440 |
| FR | TTCCGG | 1674.97 | 2451 | 1.463 | 0.381 |
| FR | TTCCGT | 655.68 | 893 | 1.362 | 0.309 |
| FR | TTCAGA | 1689.24 | 1852 | 1.096 | 0.092 |
| FR | TTCAGG | 1658.38 | 1810 | 1.091 | 0.087 |
| FR | TTTCGA | 793.28 | 850 | 1.072 | 0.069 |
| FR | TTTCGT | 572.85 | 490 | 0.855 | -0.156 |
| FR | TTTAGA | 1475.86 | 947 | 0.642 | -0.444 |
| FR | TTTAGG | 1448.90 | 691 | 0.477 | -0.740 |
| FR | TTTCGG | 1463.39 | 688 | 0.470 | -0.755 |
| FR | TTTCGC | 1338.02 | 540 | 0.404 | -0.907 |
| FS | TTCTCC | 2990.83 | 4507 | 1.507 | 0.410 |
| FS | TTCAGC | 3388.47 | 4577 | 1.351 | 0.301 |
| FS | TTCAGT | 2137.80 | 2692 | 1.259 | 0.231 |
| FS | TTCTCG | 790.89 | 910 | 1.151 | 0.140 |
| FS | TTTTCT | 2273.08 | 2536 | 1.116 | 0.109 |
| FS | TTCTCT | 2601.73 | 2741 | 1.054 | 0.052 |
| FS | TTTTCA | 1837.65 | 1903 | 1.036 | 0.035 |
| FS | TTCTCA | 2103.34 | 1997 | 0.949 | -0.052 |
| FS | TTTTCC | 2613.03 | 1872 | 0.716 | -0.334 |
| FS | TTTAGT | 1867.76 | 1201 | 0.643 | -0.442 |
| FS | TTTTCG | 690.99 | 258 | 0.373 | -0.985 |
| FS | TTTAGC | 2960.44 | 1062 | 0.359 | -1.025 |
| FT | TTCACC | 2909.29 | 4513 | 1.551 | 0.439 |
| FT | TTCACG | 955.69 | 1315 | 1.376 | 0.319 |
| FT | TTCACT | 2082.75 | 2494 | 1.197 | 0.180 |
| FT | TTCACA | 2355.18 | 2372 | 1.007 | 0.007 |
| FT | TTTACT | 1819.66 | 1622 | 0.891 | -0.115 |

Supplemental Table 1

Expected and Observed Codon Pair Frequencies and Codon Pair Scores for 14,795 Human Genes

| amino acid pair | codon pair | expected | observed | observed/expected | CPS |
|---|---|---|---|---|---|
| FT | TTTACA | 2057.68 | 1485 | 0.722 | -0.326 |
| FT | TTTACC | 2541.79 | 1495 | 0.588 | -0.531 |
| FT | TTTACG | 834.97 | 261 | 0.313 | -1.163 |
| FV | TTTGTA | 912.19 | 1711 | 1.876 | 0.629 |
| FV | TTTGTT | 1404.80 | 2620 | 1.865 | 0.623 |
| FV | TTTGTC | 1798.60 | 2635 | 1.465 | 0.382 |
| FV | TTTGTG | 3558.17 | 5206 | 1.463 | 0.381 |
| FV | TTCGTG | 4072.62 | 2589 | 0.636 | -0.453 |
| FV | TTCGTC | 2058.64 | 1086 | 0.528 | -0.640 |
| FV | TTCGTT | 1607.91 | 386 | 0.240 | -1.427 |
| FV | TTCGTA | 1044.07 | 224 | 0.215 | -1.539 |
| FW | TTCTGG | 2126.30 | 2834 | 1.333 | 0.287 |
| FW | TTTTGG | 1857.70 | 1150 | 0.619 | -0.480 |
| FY | TTCTAC | 2720.70 | 3710 | 1.364 | 0.310 |
| FY | TTTTAT | 1931.51 | 2003 | 1.037 | 0.036 |
| FY | TTCTAT | 2210.77 | 2145 | 0.970 | -0.030 |
| FY | TTTTAC | 2377.02 | 1382 | 0.581 | -0.542 |
| GA | GGTGCT | 1531.20 | 2505 | 1.636 | 0.492 |
| GA | GGGGCG | 949.27 | 1433 | 1.510 | 0.412 |
| GA | GGGGCC | 3510.85 | 5061 | 1.442 | 0.366 |
| GA | GGTGCC | 2328.29 | 3109 | 1.335 | 0.289 |
| GA | GGAGCA | 2070.38 | 2678 | 1.293 | 0.257 |
| GA | GGTGCA | 1340.41 | 1715 | 1.279 | 0.246 |
| GA | GGCGCG | 1318.38 | 1659 | 1.258 | 0.230 |
| GA | GGAGCT | 2365.08 | 2975 | 1.258 | 0.229 |
| GA | GGGGCT | 2308.91 | 2850 | 1.234 | 0.211 |
| GA | GGAGCC | 3596.25 | 3845 | 1.069 | 0.067 |
| GA | GGGGCA | 2021.22 | 2074 | 1.026 | 0.026 |
| GA | GGTGCG | 629.52 | 501 | 0.796 | -0.228 |
| GA | GGAGCG | 972.36 | 712 | 0.732 | -0.312 |
| GA | GGCGCC | 4876.02 | 3121 | 0.640 | -0.446 |
| GA | GGCGCT | 3206.72 | 906 | 0.283 | -1.264 |
| GA | GGCGCA | 2807.15 | 688 | 0.245 | -1.406 |
| GC | GGCTGC | 1888.96 | 4102 | 2.172 | 0.775 |
| GC | GGCTGT | 1591.04 | 2360 | 1.483 | 0.394 |
| GC | GGTTGT | 759.72 | 658 | 0.866 | -0.144 |
| GC | GGATGT | 1173.45 | 793 | 0.676 | -0.392 |
| GC | GGTTGC | 901.97 | 523 | 0.580 | -0.545 |
| GC | GGATGC | 1393.18 | 655 | 0.470 | -0.755 |
| GC | GGGTGC | 1360.09 | 628 | 0.462 | -0.773 |
| GC | GGGTGT | 1145.59 | 495 | 0.432 | -0.839 |
| GD | GGGGAC | 3126.50 | 4967 | 1.589 | 0.463 |
| GD | GGTGAT | 1835.49 | 2621 | 1.428 | 0.356 |
| GD | GGTGAC | 2073.40 | 2960 | 1.428 | 0.356 |
| GD | GGAGAT | 2835.09 | 3829 | 1.351 | 0.301 |
| GD | GGAGAC | 3202.56 | 4240 | 1.324 | 0.281 |
| GD | GGGGAT | 2767.76 | 2575 | 0.930 | -0.072 |
| GD | GGCGAC | 4342.22 | 1955 | 0.450 | -0.798 |
| GD | GGCGAT | 3843.98 | 880 | 0.229 | -1.474 |
| GE | GGAGAA | 3433.99 | 5903 | 1.719 | 0.542 |
| GE | GGGGAG | 4483.27 | 6552 | 1.461 | 0.379 |
| GE | GGTGAA | 2223.23 | 3248 | 1.461 | 0.379 |
| GE | GGAGAG | 4592.33 | 5961 | 1.298 | 0.261 |
| GE | GGTGAG | 2973.17 | 2988 | 1.005 | 0.005 |
| GE | GGGGAA | 3352.44 | 3041 | 0.907 | -0.098 |
| GE | GGCGAG | 6226.56 | 3530 | 0.567 | -0.568 |
| GE | GGCGAA | 4656.01 | 718 | 0.154 | -1.869 |
| GF | GGCTTC | 3466.22 | 6121 | 1.766 | 0.569 |
| GF | GGATTT | 2233.54 | 2666 | 1.194 | 0.177 |
| GF | GGTTTT | 1446.04 | 1665 | 1.151 | 0.141 |
| GF | GGCTTT | 3028.37 | 3201 | 1.057 | 0.055 |
| GF | GGTTTC | 1655.11 | 1548 | 0.935 | -0.067 |
| GF | GGATTC | 2556.47 | 1534 | 0.600 | -0.511 |
| GF | GGGTTT | 2180.50 | 1244 | 0.571 | -0.561 |
| GF | GGGTTC | 2495.76 | 1083 | 0.434 | -0.835 |
| GG | GGTGGT | 1061.28 | 2286 | 2.154 | 0.767 |
| GG | GGTGGC | 2222.59 | 3657 | 1.645 | 0.498 |
| GG | GGTGGA | 1639.25 | 2618 | 1.597 | 0.468 |
| GG | GGAGGA | 2531.97 | 3609 | 1.425 | 0.354 |
| GG | GGTGGG | 1600.32 | 2267 | 1.417 | 0.348 |

Supplemental Table 1

Expected and Observed Codon Pair Frequencies and Codon Pair Scores for 14,795 Human Genes

| amino acid pair | codon pair | expected | observed | observed/expected | CPS |
|---|---|---|---|---|---|
| GG | GGGGGC | 3351.47 | 4673 | 1.394 | 0.332 |
| GG | GGAGGT | 1639.25 | 2152 | 1.313 | 0.272 |
| GG | GGAGGC | 3433.00 | 3776 | 1.100 | 0.095 |
| GG | GGCGGC | 4654.67 | 4787 | 1.028 | 0.028 |
| GG | GGGGGT | 1600.32 | 1543 | 0.964 | -0.036 |
| GG | GGAGGG | 2471.84 | 2351 | 0.951 | -0.050 |
| GG | GGGGGA | 2471.84 | 1517 | 0.614 | -0.488 |
| GG | GGCGGG | 3351.47 | 2001 | 0.597 | -0.516 |
| GG | GGGGGG | 2413.14 | 1080 | 0.448 | -0.804 |
| GG | GGCGGT | 2222.59 | 936 | 0.421 | -0.865 |
| GG | GGCGGA | 3433.00 | 845 | 0.246 | -1.402 |
| GH | GGCCAC | 2540.15 | 3679 | 1.448 | 0.370 |
| GH | GGTCAT | 879.57 | 1022 | 1.162 | 0.150 |
| GH | GGACAT | 1358.57 | 1438 | 1.058 | 0.057 |
| GH | GGCCAT | 1842.04 | 1679 | 0.911 | -0.093 |
| GH | GGGCAC | 1828.97 | 1629 | 0.891 | -0.116 |
| GH | GGTCAC | 1212.92 | 1008 | 0.831 | -0.185 |
| GH | GGACAC | 1873.46 | 1479 | 0.789 | -0.236 |
| GH | GGGCAT | 1326.31 | 928 | 0.700 | -0.357 |
| GI | GGCATC | 3372.48 | 5474 | 1.623 | 0.484 |
| GI | GGAATA | 904.63 | 1338 | 1.479 | 0.391 |
| GI | GGAATT | 1966.96 | 2560 | 1.302 | 0.264 |
| GI | GGCATT | 2666.92 | 2670 | 1.001 | 0.001 |
| GI | GGTATT | 1273.45 | 1052 | 0.826 | -0.191 |
| GI | GGGATC | 2428.27 | 1958 | 0.806 | -0.215 |
| GI | GGTATA | 585.67 | 461 | 0.787 | -0.239 |
| GI | GGAATC | 2487.34 | 1910 | 0.768 | -0.264 |
| GI | GGGATA | 883.14 | 666 | 0.754 | -0.282 |
| GI | GGGATT | 1920.24 | 1421 | 0.740 | -0.301 |
| GI | GGCATA | 1226.55 | 885 | 0.722 | -0.326 |
| GI | GGTATC | 1610.35 | 931 | 0.578 | -0.548 |
| GK | GGAAAA | 3199.11 | 4553 | 1.423 | 0.353 |
| GK | GGGAAG | 4044.81 | 5674 | 1.403 | 0.338 |
| GK | GGGAAA | 3123.14 | 4119 | 1.319 | 0.277 |
| GK | GGCAAG | 5617.61 | 5712 | 1.017 | 0.017 |
| GK | GGAAAG | 4143.21 | 3706 | 0.894 | -0.112 |
| GK | GGCAAA | 4337.55 | 3581 | 0.826 | -0.192 |
| GK | GGTAAA | 2071.17 | 1334 | 0.644 | -0.440 |
| GK | GGTAAG | 2682.40 | 540 | 0.201 | -1.603 |
| GL | GGCCTC | 3017.19 | 4559 | 1.511 | 0.413 |
| GL | GGTTTA | 579.43 | 820 | 1.415 | 0.347 |
| GL | GGTTTG | 973.39 | 1294 | 1.329 | 0.285 |
| GL | GGGCTG | 4514.62 | 5878 | 1.302 | 0.264 |
| GL | GGTCTT | 993.42 | 1258 | 1.266 | 0.236 |
| GL | GGCCTG | 6270.10 | 7822 | 1.248 | 0.221 |
| GL | GGGCTC | 2172.45 | 2563 | 1.180 | 0.165 |
| GL | GGATTA | 894.98 | 991 | 1.107 | 0.102 |
| GL | GGACTT | 1534.44 | 1613 | 1.051 | 0.050 |
| GL | GGCTTG | 2038.53 | 2109 | 1.035 | 0.034 |
| GL | GGCCTT | 2080.48 | 2098 | 1.008 | 0.008 |
| GL | GGACTA | 827.51 | 799 | 0.966 | -0.035 |
| GL | GGGCTT | 1497.99 | 1445 | 0.965 | -0.036 |
| GL | GGTCTC | 1440.70 | 1365 | 0.947 | -0.054 |
| GL | GGTCTA | 535.75 | 487 | 0.909 | -0.095 |
| GL | GGGCTA | 807.86 | 726 | 0.899 | -0.107 |
| GL | GGCCTA | 1121.99 | 968 | 0.863 | -0.148 |
| GL | GGCTTA | 1213.47 | 935 | 0.771 | -0.261 |
| GL | GGACTC | 2225.29 | 1656 | 0.744 | -0.295 |
| GL | GGATTG | 1503.50 | 1062 | 0.706 | -0.348 |
| GL | GGTCTG | 2993.96 | 2034 | 0.679 | -0.387 |
| GL | GGGTTG | 1467.79 | 870 | 0.593 | -0.523 |
| GL | GGGTTA | 873.73 | 467 | 0.534 | -0.626 |
| GL | GGACTG | 4624.44 | 2384 | 0.516 | -0.663 |
| GM | GGCATG | 3177.11 | 3953 | 1.244 | 0.219 |
| GM | GGAATG | 2343.24 | 2482 | 1.059 | 0.058 |
| GM | GGGATG | 2287.59 | 2247 | 0.982 | -0.018 |
| GM | GGTATG | 1517.06 | 643 | 0.424 | -0.858 |
| GN | GGAAAT | 2150.19 | 3332 | 1.550 | 0.438 |
| GN | GGGAAC | 2311.93 | 2816 | 1.218 | 0.197 |
| GN | GGCAAC | 3210.92 | 3701 | 1.153 | 0.142 |

Supplemental Table 1

Expected and Observed Codon Pair Frequencies and Codon Pair Scores for 14,795 Human Genes

| amino acid pair | codon pair | expected | observed | observed/expected | CPS |
|---|---|---|---|---|---|
| GN | GGAAAC | 2368.18 | 2679 | 1.131 | 0.123 |
| GN | GGGAAT | 2099.13 | 1823 | 0.868 | -0.141 |
| GN | GGCAAT | 2915.36 | 2061 | 0.707 | -0.347 |
| GN | GGTAAT | 1392.08 | 784 | 0.563 | -0.574 |
| GN | GGTAAC | 1533.21 | 785 | 0.512 | -0.669 |
| GP | GGGCCC | 2634.22 | 3947 | 1.498 | 0.404 |
| GP | GGGCCG | 954.47 | 1417 | 1.485 | 0.395 |
| GP | GGCCCC | 3658.52 | 4576 | 1.251 | 0.224 |
| GP | GGCCCG | 1325.61 | 1623 | 1.224 | 0.202 |
| GP | GGTCCT | 1564.62 | 1910 | 1.221 | 0.199 |
| GP | GGGCCT | 2359.31 | 2542 | 1.077 | 0.075 |
| GP | GGTCCC | 1746.93 | 1827 | 1.046 | 0.045 |
| GP | GGCCCT | 3276.71 | 2994 | 0.914 | -0.090 |
| GP | GGGCCA | 2277.03 | 2003 | 0.880 | -0.128 |
| GP | GGTCCA | 1510.06 | 1264 | 0.837 | -0.178 |
| GP | GGACCC | 2698.30 | 2240 | 0.830 | -0.186 |
| GP | GGACCA | 2332.42 | 1908 | 0.818 | -0.201 |
| GP | GGACCT | 2416.70 | 1957 | 0.810 | -0.211 |
| GP | GGCCCA | 3162.44 | 2548 | 0.806 | -0.216 |
| GP | GGTCCG | 632.98 | 351 | 0.555 | -0.590 |
| GP | GGACCG | 977.69 | 421 | 0.431 | -0.843 |
| GQ | GGACAA | 1382.58 | 1677 | 1.213 | 0.193 |
| GQ | GGGCAG | 3769.06 | 4425 | 1.174 | 0.160 |
| GQ | GGCCAG | 5234.64 | 6081 | 1.162 | 0.150 |
| GQ | GGTCAA | 895.11 | 953 | 1.065 | 0.063 |
| GQ | GGCCAA | 1874.58 | 1593 | 0.850 | -0.163 |
| GQ | GGGCAA | 1349.74 | 1124 | 0.833 | -0.183 |
| GQ | GGACAG | 3860.75 | 3134 | 0.812 | -0.209 |
| GQ | GGTCAG | 2499.53 | 1879 | 0.752 | -0.285 |
| GR | GGCCGC | 1832.29 | 3615 | 1.973 | 0.680 |
| GR | GGAAGA | 1490.60 | 2294 | 1.539 | 0.431 |
| GR | GGCCGG | 2003.98 | 2892 | 1.443 | 0.367 |
| GR | GGCCGT | 784.47 | 1022 | 1.303 | 0.265 |
| GR | GGTCGT | 374.58 | 450 | 1.201 | 0.183 |
| GR | GGCCGA | 1086.32 | 1252 | 1.153 | 0.142 |
| GR | GGGCGC | 1319.29 | 1471 | 1.115 | 0.109 |
| GR | GGTCGA | 518.71 | 546 | 1.053 | 0.051 |
| GR | GGCAGG | 1984.13 | 2022 | 1.019 | 0.019 |
| GR | GGGAGG | 1428.62 | 1435 | 1.004 | 0.004 |
| GR | GGGCGG | 1442.91 | 1437 | 0.996 | -0.004 |
| GR | GGAAGG | 1463.37 | 1370 | 0.936 | -0.066 |
| GR | GGGAGA | 1455.20 | 1344 | 0.924 | -0.079 |
| GR | GGACGT | 578.58 | 514 | 0.888 | -0.118 |
| GR | GGACGA | 801.20 | 671 | 0.837 | -0.177 |
| GR | GGGCGT | 564.84 | 471 | 0.834 | -0.182 |
| GR | GGCAGA | 2021.05 | 1684 | 0.833 | -0.182 |
| GR | GGGCGA | 782.17 | 626 | 0.800 | -0.223 |
| GR | GGTCGC | 874.92 | 596 | 0.681 | -0.384 |
| GR | GGTCGG | 956.90 | 555 | 0.580 | -0.545 |
| GR | GGTAGA | 965.05 | 529 | 0.548 | -0.601 |
| GR | GGACGC | 1351.39 | 729 | 0.539 | -0.617 |
| GR | GGACGG | 1478.01 | 737 | 0.499 | -0.696 |
| GR | GGTAGG | 947.42 | 244 | 0.258 | -1.357 |
| GS | GGCAGC | 3581.32 | 6542 | 1.827 | 0.603 |
| GS | GGCTCC | 3161.05 | 5376 | 1.701 | 0.531 |
| GS | GGCTCG | 835.91 | 1323 | 1.583 | 0.459 |
| GS | GGCAGT | 2259.47 | 2875 | 1.272 | 0.241 |
| GS | GGAAGT | 1666.45 | 2085 | 1.251 | 0.224 |
| GS | GGTTCT | 1313.02 | 1563 | 1.190 | 0.174 |
| GS | GGCTCT | 2749.80 | 3087 | 1.123 | 0.116 |
| GS | GGGAGC | 2578.63 | 2566 | 0.995 | -0.005 |
| GS | GGTTCC | 1509.39 | 1428 | 0.946 | -0.055 |
| GS | GGCTCA | 2223.05 | 2101 | 0.945 | -0.056 |
| GS | GGTTCA | 1061.50 | 981 | 0.924 | -0.079 |
| GS | GGAAGC | 2641.36 | 2137 | 0.809 | -0.212 |
| GS | GGATCA | 1639.59 | 1281 | 0.781 | -0.247 |
| GS | GGGAGT | 1626.88 | 1267 | 0.779 | -0.250 |
| GS | GGATCT | 2028.08 | 1470 | 0.725 | -0.322 |
| GS | GGGTCC | 2276.03 | 1646 | 0.723 | -0.324 |
| GS | GGGTCT | 1979.92 | 1280 | 0.646 | -0.436 |

Supplemental Table 1

Expected and Observed Codon Pair Frequencies and Codon Pair Scores for 14,795 Human Genes

| amino acid pair | codon pair | expected | observed | observed/expected | CPS |
|---|---|---|---|---|---|
| GS | GGGTCG | 601.87 | 379 | 0.630 | −0.463 |
| GS | GGTAGT | 1078.89 | 646 | 0.599 | −0.513 |
| GS | GGATCT | 2331.40 | 1342 | 0.576 | −0.552 |
| GS | GGGTCA | 1600.65 | 887 | 0.554 | −0.590 |
| GS | GGTTCG | 399.14 | 209 | 0.524 | −0.647 |
| GS | GGATCG | 616.51 | 276 | 0.448 | −0.804 |
| GS | GGTAGC | 1710.07 | 723 | 0.423 | −0.861 |
| GT | GGCACT | 3271.07 | 4870 | 1.489 | 0.398 |
| GT | GGCACG | 1074.53 | 1368 | 1.273 | 0.241 |
| GT | GGGACC | 2355.25 | 2817 | 1.196 | 0.179 |
| GT | GGAACA | 1953.05 | 2290 | 1.173 | 0.159 |
| GT | GGAACT | 1727.13 | 1900 | 1.100 | 0.095 |
| GT | GGGACGG | 773.69 | 838 | 1.083 | 0.080 |
| GT | GGGACA | 1906.66 | 1903 | 0.998 | −0.002 |
| GT | GGCACT | 2341.75 | 2331 | 0.995 | −0.005 |
| GT | GGCACA | 2648.06 | 2499 | 0.944 | −0.058 |
| GT | GGGACT | 1686.11 | 1534 | 0.910 | −0.095 |
| GT | GGAACC | 2412.54 | 1841 | 0.763 | −0.270 |
| GT | GGTACT | 1118.18 | 840 | 0.751 | −0.286 |
| GT | GGTACC | 1561.93 | 994 | 0.636 | −0.452 |
| GT | GGTACA | 1264.44 | 780 | 0.617 | −0.483 |
| GT | GGAACG | 792.51 | 445 | 0.562 | −0.577 |
| GT | GGTACG | 513.09 | 150 | 0.292 | −1.230 |
| GV | GGTGTT | 816.93 | 1802 | 2.206 | 0.791 |
| GV | GGTGTC | 1045.94 | 2070 | 1.979 | 0.683 |
| GV | GGTGTA | 530.46 | 957 | 1.804 | 0.590 |
| GV | GGTGTG | 2069.18 | 3207 | 1.550 | 0.438 |
| GV | GGAGTA | 819.35 | 1225 | 1.495 | 0.402 |
| GV | GGAGTT | 1261.S3 | 1841 | 1.459 | 0.378 |
| GV | GGGGTC | 1577.18 | 2150 | 1.363 | 0.310 |
| GV | GGAGTC | 1615.55 | 1839 | 1.138 | 0.130 |
| GV | GGGGTT | 1231.86 | 1123 | 0.912 | −0.093 |
| GV | GGGGTG | 3120.14 | 2770 | 0.888 | −0.119 |
| GV | GGAGTG | 3196.04 | 2641 | 0.826 | −0.191 |
| GV | GGGGTA | 799.89 | 631 | 0.789 | −0.237 |
| GV | GGCGTC | 2190.46 | 1653 | 0.755 | −0.282 |
| GV | GGCGTG | 4333.39 | 2790 | 0.644 | −0.440 |
| GV | GGCGTT | 1710.87 | 499 | 0.292 | −1.232 |
| GV | GGCGTA | 1110.93 | 232 | 0.209 | −1.566 |
| GW | GGCTGG | 2102.85 | 3748 | 1.782 | 0.578 |
| GW | GGTTGG | 1004.11 | 690 | 0.687 | −0.375 |
| GW | GGATGG | 1550.94 | 1012 | 0.653 | −0.427 |
| GW | GGGTGG | 1514.10 | 722 | 0.477 | −0.741 |
| GY | GGCTAC | 2577.81 | 4581 | 1.777 | 0.575 |
| GY | GGTTAT | 1000.20 | 1309 | 1.309 | 0.269 |
| GY | GGCTAT | 2094.66 | 2528 | 1.207 | 0.188 |
| GY | GGATAT | 1544.90 | 1478 | 0.957 | −0.044 |
| GY | GGTTAC | 1230.90 | 1074 | 0.873 | −0.136 |
| GY | GGATAC | 1901.24 | 1052 | 0.553 | −0.592 |
| GY | GGGTAC | 1856.09 | 982 | 0.529 | −0.637 |
| GY | GGGTAT | 1508.21 | 710 | 0.471 | −0.753 |
| HA | CATGCT | 1101.90 | 1959 | 1.778 | 0.575 |
| HA | CATGCA | 964.61 | 1670 | 1.731 | 0.549 |
| HA | CATGCC | 1675.52 | 2408 | 1.437 | 0.363 |
| HA | CACGCG | 624.72 | 681 | 1.090 | 0.086 |
| HA | CATGCG | 453.03 | 447 | 0.987 | −0.013 |
| HA | CACGCC | 2310.52 | 1649 | 0.714 | −0.337 |
| HA | CACGCA | 1330.18 | 617 | 0.464 | −0.768 |
| HA | CACGCT | 1519.52 | 549 | 0.361 | −1.018 |
| HC | CACTGC | 1778.65 | 2629 | 1.478 | 0.391 |
| HC | CACTGT | 1498.13 | 1717 | 1.146 | 0.136 |
| HC | CATTGT | 1086.40 | 673 | 0.619 | −0.479 |
| HC | CATTGC | 1289.82 | 634 | 0.492 | −0.710 |
| HD | CATGAT | 1329.76 | 2349 | 1.766 | 0.569 |
| HD | CATGAC | 1502.11 | 2329 | 1.550 | 0.439 |
| HD | CACGAC | 2071.40 | 1343 | 0.648 | −0.433 |
| HD | CACGAT | 1833.73 | 716 | 0.390 | −0.940 |
| HE | CATGAA | 1769.46 | 3512 | 1.985 | 0.686 |
| HE | CATGAG | 2366.33 | 3307 | 1.398 | 0.335 |
| HE | CACGAG | 3263.15 | 2230 | 0.683 | −0.381 |

Supplemental Table 1

Expected and Observed Codon Pair Frequencies and Codon Pair Scores for 14,795 Human Genes

| amino acid pair | codon pair | expected | observed | observed/expected | CPS |
|---|---|---|---|---|---|
| HE | CACGAA | 2440.07 | 790 | 0.324 | -1.128 |
| HF | CACTTC | 2538.66 | 3116 | 1.227 | 0.205 |
| HF | CATTTT | 1608.41 | 1806 | 1.123 | 0.116 |
| HF | CACTTT | 2217.98 | 1884 | 0.849 | -0.163 |
| HF | CATTTC | 1840.95 | 1400 | 0.760 | -0.274 |
| HG | CATGGA | 1246.72 | 2238 | 1.795 | 0.585 |
| HG | CATGGT | 807.15 | 1426 | 1.767 | 0.569 |
| HG | CATGGG | 1217.11 | 1849 | 1.519 | 0.418 |
| HG | CATGGC | 1690.37 | 2320 | 1.372 | 0.317 |
| HG | CACGGC | 2331.01 | 1680 | 0.721 | -0.328 |
| HG | CACGGG | 1678.38 | 1184 | 0.705 | -0.349 |
| HG | CACGGT | 1113.05 | 468 | 0.420 | -0.866 |
| HG | CACGGA | 1719.21 | 638 | 0.371 | -0.991 |
| HH | CACCAC | 2269.33 | 2795 | 1.232 | 0.208 |
| HH | CATCAT | 1193.37 | 1250 | 1.047 | 0.046 |
| HH | CACCAT | 1645.65 | 1453 | 0.883 | -0.125 |
| HH | CATCAC | 1645.65 | 1256 | 0.763 | -0.270 |
| HI | CACATC | 2433.52 | 3538 | 1.454 | 0.374 |
| HI | CACATT | 1924.40 | 1924 | 1.000 | 0.000 |
| HI | CACATA | 885.05 | 867 | 0.980 | -0.021 |
| HI | CATATT | 1395.51 | 1260 | 0.903 | -0.102 |
| HI | CATATA | 641.81 | 552 | 0.860 | -0.151 |
| HI | CATATC | 1764.71 | 904 | 0.512 | -0.669 |
| HK | CACAAG | 3102.81 | 3928 | 1.266 | 0.236 |
| HK | CACAAA | 2395.79 | 2432 | 1.015 | 0.015 |
| HK | CATAAA | 1737.35 | 1690 | 0.973 | -0.028 |
| HK | CATAAG | 2250.06 | 1436 | 0.638 | -0.449 |
| HL | CATTTA | 707.71 | 1053 | 1.488 | 0.397 |
| HL | CATTTG | 1188.90 | 1485 | 1.249 | 0.222 |
| HL | CACCTG | 5042.69 | 6030 | 1.196 | 0.179 |
| HL | CACCTC | 2426.56 | 2850 | 1.175 | 0.161 |
| HL | CATCTT | 1213.36 | 1409 | 1.161 | 0.149 |
| HL | CACTTG | 1639.48 | 1700 | 1.037 | 0.036 |
| HL | CATCTA | 654.36 | 649 | 0.992 | -0.008 |
| HL | CACCTT | 1673.21 | 1499 | 0.896 | -0.110 |
| HL | CACCTA | 902.35 | 761 | 0.843 | -0.170 |
| HL | CATCTC | 1759.66 | 1422 | 0.808 | -0.213 |
| HL | CACTTA | 975.93 | 781 | 0.800 | -0.223 |
| HL | CATCTG | 3656.80 | 2202 | 0.602 | -0.507 |
| HM | CACATG | 2348.18 | 3023 | 1.287 | 0.253 |
| HM | CATATG | 1702.82 | 1028 | 0.604 | -0.505 |
| HN | CACAAC | 2031.88 | 2762 | 1.359 | 0.307 |
| HN | CACAAT | 1844.85 | 1832 | 0.993 | -0.007 |
| HN | CATAAT | 1337.83 | 1225 | 0.916 | -0.088 |
| HN | CATAAC | 1473.45 | 869 | 0.590 | -0.528 |
| HP | CACCCG | 846.94 | 1341 | 1.583 | 0.460 |
| HP | CATCCT | 1518.15 | 1770 | 1.166 | 0.153 |
| HP | CACCCC | 2337.46 | 2530 | 1.082 | 0.079 |
| HP | CATCCA | 1465.21 | 1577 | 1.076 | 0.074 |
| HP | CACCCA | 2020.51 | 1919 | 0.950 | -0.052 |
| HP | CACCCT | 2093.51 | 1859 | 0.888 | -0.119 |
| HP | CATCCC | 1695.05 | 1265 | 0.746 | -0.293 |
| HP | CATCCG | 614.18 | 330 | 0.537 | -0.621 |
| HQ | CATCAA | 1143.96 | 1358 | 1.187 | 0.172 |
| HQ | CACCAG | 4405.09 | 4761 | 1.081 | 0.078 |
| HQ | CATCAG | 3194.43 | 2957 | 0.926 | -0.077 |
| HQ | CACCAA | 1577.51 | 1245 | 0.789 | -0.237 |
| HR | CACAGG | 1447.19 | 1936 | 1.338 | 0.291 |
| HR | CACCGC | 1336.44 | 1772 | 1.326 | 0.282 |
| HR | CACAGA | 1474.12 | 1788 | 1.213 | 0.193 |
| HR | CACCGG | 1461.67 | 1772 | 1.212 | 0.193 |
| HR | CACCGT | 572.18 | 667 | 1.166 | 0.153 |
| HR | CATCGA | 574.58 | 627 | 1.091 | 0.087 |
| HR | CATCGT | 414.93 | 452 | 1.089 | 0.086 |
| HR | CACCGA | 792.34 | 855 | 1.079 | 0.076 |
| HR | CATCGG | 1059.96 | 729 | 0.688 | -0.374 |
| HR | CATAGA | 1068.98 | 635 | 0.594 | -0.521 |
| HR | CATCGC | 969.15 | 565 | 0.583 | -0.540 |
| HR | CATAGG | 1049.46 | 423 | 0.403 | -0.909 |
| HS | CACTCG | 551.81 | 880 | 1.595 | 0.467 |

Supplemental Table 1

Expected and Observed Codon Pair Frequencies and Codon Pair Scores for 14,795 Human Genes

| amino acid pair | codon pair | expected | observed | observed/expected | CPS |
|---|---|---|---|---|---|
| HS | CACAGC | 2364.16 | 3726 | 1.576 | 0.455 |
| HS | CACAGT | 1491.56 | 1957 | 1.312 | 0.272 |
| HS | CATTCA | 1064.20 | 1307 | 1.228 | 0.206 |
| HS | CATTCT | 1316.36 | 1517 | 1.152 | 0.142 |
| HS | CACTCC | 2086.72 | 1964 | 0.941 | -0.061 |
| HS | CACTCA | 1467.52 | 1318 | 0.898 | -0.107 |
| HS | CATTCC | 1513.23 | 1219 | 0.806 | -0.216 |
| HS | CACTCT | 1815.24 | 1231 | 0.678 | -0.388 |
| HS | CATAGT | 1081.63 | 710 | 0.656 | -0.421 |
| HS | CATTCG | 400.16 | 256 | 0.640 | -0.447 |
| HS | CATAGC | 1714.41 | 782 | 0.456 | -0.785 |
| HT | CACACG | 778.62 | 1526 | 1.960 | 0.673 |
| HT | CACACT | 1696.86 | 2036 | 1.200 | 0.182 |
| HT | CACACA | 1918.82 | 2255 | 1.175 | 0.161 |
| HT | CACACC | 2370.26 | 2537 | 1.070 | 0.068 |
| HT | CATACT | 1230.51 | 1306 | 1.061 | 0.060 |
| HT | CATACA | 1391.46 | 979 | 0.704 | -0.352 |
| HT | CATACC | 1718.84 | 806 | 0.469 | -0.757 |
| HT | CATACG | 564.63 | 225 | 0.398 | -0.920 |
| HV | CATGTT | 869.32 | 1563 | 1.798 | 0.587 |
| HV | CATGTA | 564.48 | 880 | 1.559 | 0.444 |
| HV | CATGTC | 1113.00 | 1607 | 1.444 | 0.367 |
| HV | CATGTG | 2201.86 | 2797 | 1.270 | 0.239 |
| HV | CACGTG | 3036.34 | 2579 | 0.849 | -0.163 |
| HV | CACGTC | 1534.82 | 1158 | 0.754 | -0.282 |
| HV | CACGTT | 1198.78 | 434 | 0.362 | -1.016 |
| HV | CACGTA | 778.41 | 279 | 0.358 | -1.026 |
| HW | CACTGG | 1602.74 | 2197 | 1.371 | 0.315 |
| HW | CATTGG | 1162.26 | 568 | 0.489 | -0.716 |
| HY | CACTCC | 1943.40 | 2385 | 1.227 | 0.205 |
| HY | CATTCT | 1145.15 | 1240 | 1.083 | 0.080 |
| HY | CACTAT | 1579.16 | 1378 | 0.873 | -0.136 |
| HY | CATTCC | 1409.29 | 1074 | 0.762 | -0.272 |
| IA | ATTGCT | 1886.56 | 3678 | 1.950 | 0.668 |
| IA | ATAGCA | 759.54 | 1446 | 1.904 | 0.644 |
| IA | ATTGCA | 1651.49 | 2818 | 1.706 | 0.534 |
| IA | ATAGCT | 867.65 | 1289 | 1.486 | 0.396 |
| IA | ATTGCC | 2868.63 | 3435 | 1.197 | 0.180 |
| IA | ATAGCC | 1319.32 | 1191 | 0.903 | -0.102 |
| IA | ATCGCG | 980.82 | 708 | 0.722 | -0.326 |
| IA | ATCGCC | 3627.56 | 2570 | 0.708 | -0.345 |
| IA | ATTGCG | 775.62 | 494 | 0.637 | -0.451 |
| IA | ATAGCG | 356.72 | 198 | 0.555 | -0.589 |
| IA | ATCGCA | 2088.41 | 831 | 0.398 | -0.922 |
| IA | ATCGCT | 2385.67 | 910 | 0.381 | -0.964 |
| IC | ATCTGC | 2115.05 | 3055 | 1.444 | 0.368 |
| IC | ATCTGT | 1781.48 | 2074 | 1.164 | 0.152 |
| IC | ATATGT | 647.91 | 731 | 1.128 | 0.121 |
| IC | ATTTGT | 1408.77 | 1197 | 0.850 | -0.163 |
| IC | ATATGC | 769.23 | 470 | 0.611 | -0.493 |
| IC | ATTTGC | 1672.56 | 868 | 0.519 | -0.656 |
| ID | ATTGAT | 2604.76 | 4341 | 1.667 | 0.511 |
| ID | ATAGAT | 1197.96 | 1947 | 1.625 | 0.486 |
| ID | ATTGAC | 2942.37 | 3938 | 1.338 | 0.291 |
| ID | ATAGAC | 1353.23 | 1476 | 1.091 | 0.087 |
| ID | ATCGAC | 3720.81 | 2270 | 0.610 | -0.494 |
| ID | ATCGAT | 3293.87 | 1141 | 0.346 | -1.060 |
| IE | ATAGAA | 1371.51 | 2939 | 2.143 | 0.762 |
| IE | ATTGAA | 2982.12 | 5518 | 1.850 | 0.615 |
| IE | ATTGAG | 3988.04 | 4634 | 1.162 | 0.150 |
| IE | ATAGAG | 1834.15 | 1898 | 1.035 | 0.034 |
| IE | ATCGAG | 5043.12 | 3007 | 0.596 | -0.517 |
| IE | ATCGAA | 3771.07 | 994 | 0.264 | -1.333 |
| IF | ATATTT | 1144.73 | 1929 | 1.685 | 0.522 |
| IF | ATCTTC | 3602.60 | 4836 | 1.342 | 0.294 |
| IF | ATTTTT | 2489.02 | 2226 | 0.894 | -0.112 |
| IF | ATCTTT | 3147.52 | 2779 | 0.883 | -0.125 |
| IF | ATATTC | 1310.24 | 886 | 0.676 | -0.391 |
| IF | ATTTTC | 2848.89 | 1887 | 0.662 | -0.412 |
| IG | ATTGGT | 1013.16 | 2102 | 2.075 | 0.730 |

Supplemental Table 1

Expected and Observed Codon Pair Frequencies and Codon Pair Scores for 14,795 Human Genes

| amino acid pair | codon pair | expected | observed | observed/expected | CPS |
|---|---|---|---|---|---|
| IG | ATTGGA | 1564.91 | 3151 | 2.014 | 0.700 |
| IG | ATAGGA | 719.72 | 1054 | 1.464 | 0.381 |
| IG | ATTGGG | 1527.75 | 2144 | 1.403 | 0.339 |
| IG | ATAGGT | 465.96 | 596 | 1.279 | 0.246 |
| IG | ATTGGC | 2121.81 | 2706 | 1.275 | 0.243 |
| IG | ATAGGG | 702.63 | 549 | 0.781 | -0.247 |
| IG | ATAGGC | 975.84 | 700 | 0.717 | -0.332 |
| IG | ATCGGG | 1931.93 | 1244 | 0.644 | -0.440 |
| IG | ATCGGC | 2683.15 | 1619 | 0.603 | -0.505 |
| IG | ATCGGT | 1281.20 | 498 | 0.389 | -0.945 |
| IG | ATCGGA | 1978.93 | 604 | 0.305 | -1.187 |
| IH | ATTCAT | 1622.93 | 2242 | 1.381 | 0.323 |
| IH | ATCCAC | 2830.09 | 3367 | 1.190 | 0.174 |
| IH | ATACAT | 746.40 | 760 | 1.018 | 0.018 |
| IH | ATCCAT | 2052.29 | 1814 | 0.884 | -0.123 |
| IH | ATTCAC | 2238.00 | 1778 | 0.794 | -0.230 |
| IH | ATACAC | 1029.28 | 558 | 0.542 | -0.612 |
| II | ATCATC | 3797.03 | 5979 | 1.575 | 0.454 |
| II | ATAATA | 502.24 | 700 | 1.394 | 0.332 |
| II | ATAATT | 1092.04 | 1309 | 1.199 | 0.181 |
| II | ATCATT | 3002.64 | 3321 | 1.106 | 0.101 |
| II | ATTATT | 2374.46 | 2157 | 0.908 | -0.096 |
| II | ATCATA | 1380.95 | 1183 | 0.857 | -0.155 |
| II | ATTATA | 1092.04 | 921 | 0.843 | -0.170 |
| II | ATAATC | 1380.95 | 715 | 0.518 | -0.658 |
| II | ATTATC | 3002.64 | 1340 | 0.446 | -0.807 |
| IK | ATAAAA | 1419.09 | 2244 | 1.581 | 0.458 |
| IK | ATCAAG | 5053.39 | 5884 | 1.164 | 0.152 |
| IK | ATAAAG | 1837.88 | 1943 | 1.057 | 0.056 |
| IK | ATTAAA | 3085.58 | 3107 | 1.007 | 0.007 |
| IK | ATCAAA | 3901.90 | 3830 | 0.982 | -0.019 |
| IK | ATTAAG | 3996.16 | 2286 | 0.572 | -0.559 |
| IL | ATTTTA | 977.08 | 1679 | 1.718 | 0.541 |
| IL | ATATTA | 449.37 | 723 | 1.609 | 0.476 |
| IL | ATTTTG | 1641.41 | 2339 | 1.425 | 0.354 |
| IL | ATTCTT | 1675.18 | 2271 | 1.356 | 0.304 |
| IL | ATCCTC | 3072.14 | 4017 | 1.308 | 0.268 |
| IL | ATCCTG | 6384.29 | 7754 | 1.215 | 0.194 |
| IL | ATTCTA | 903.41 | 1021 | 1.130 | 0.122 |
| IL | ATCTTG | 2075.66 | 2250 | 1.084 | 0.081 |
| IL | ATCCTA | 1142.42 | 1170 | 1.024 | 0.024 |
| IL | ATACTA | 415.49 | 416 | 1.001 | 0.001 |
| IL | ATCCTT | 2118.37 | 2058 | 0.972 | -0.029 |
| IL | ATATTG | 754.90 | 717 | 0.950 | -0.052 |
| IL | ATACTT | 770.44 | 726 | 0.942 | -0.059 |
| IL | ATCTTA | 1235.57 | 1077 | 0.872 | -0.137 |
| IL | ATTCTC | 2429.41 | 1918 | 0.789 | -0.236 |
| IL | ATTCTG | 5048.62 | 3005 | 0.595 | -0.519 |
| IL | ATACTC | 1117.32 | 458 | 0.410 | -0.892 |
| IL | ATACTG | 2321.92 | 934 | 0.402 | -0.911 |
| IM | ATCATG | 3206.80 | 4314 | 1.345 | 0.297 |
| IM | ATAATG | 1166.29 | 1196 | 1.025 | 0.025 |
| IM | ATTATG | 2535.90 | 1399 | 0.552 | -0.595 |
| IN | ATAAAT | 1088.42 | 1649 | 1.515 | 0.415 |
| IN | ATCAAC | 3296.07 | 4599 | 1.395 | 0.333 |
| IN | ATCAAT | 2992.68 | 2890 | 0.966 | -0.035 |
| IN | ATAAAC | 1198.76 | 1113 | 0.928 | -0.074 |
| IN | ATTAAT | 2366.58 | 1967 | 0.831 | -0.185 |
| IN | ATTAAC | 2606.49 | 1331 | 0.511 | -0.672 |
| IP | ATTCCT | 2051.78 | 2787 | 1.358 | 0.306 |
| IP | ATTCCA | 1980.23 | 2644 | 1.335 | 0.289 |
| IP | ATACCA | 910.73 | 1047 | 1.150 | 0.139 |
| IP | ATCCCC | 2896.94 | 3229 | 1.115 | 0.109 |
| IP | ATACCT | 943.64 | 995 | 1.054 | 0.053 |
| IP | ATCCCG | 1049.66 | 1073 | 1.022 | 0.022 |
| IP | ATCCCA | 2504.13 | 2366 | 0.945 | -0.057 |
| IP | ATCCCT | 2594.61 | 2451 | 0.945 | -0.057 |
| IP | ATTCCC | 2290.86 | 1775 | 0.775 | -0.255 |
| IP | ATACCC | 1053.60 | 610 | 0.579 | -0.547 |
| IP | ATTCCG | 830.06 | 386 | 0.465 | -0.766 |

Supplemental Table 1

Expected and Observed Codon Pair Frequencies and Codon Pair Scores for 14,795 Human Genes

| amino acid pair | codon pair | expected | observed | observed/expected | CPS |
|---|---|---|---|---|---|
| IP | ATACCG | 381.76 | 125 | 0.327 | -1.116 |
| IQ | ATACAA | 765.47 | 950 | 1.241 | 0.216 |
| IQ | ATTCAA | 1664.38 | 2045 | 1.229 | 0.206 |
| IQ | ATCCAG | 5877.26 | 6881 | 1.171 | 0.158 |
| IQ | ATTCAG | 4647.67 | 3987 | 0.858 | -0.153 |
| IQ | ATCCAA | 2104.71 | 1765 | 0.839 | -0.176 |
| IQ | ATACAG | 2137.52 | 1569 | 0.734 | -0.309 |
| IR | ATCCGC | 1552.18 | 2623 | 1.690 | 0.525 |
| IR | ATTCGA | 727.72 | 1142 | 1.569 | 0.451 |
| IR | ATCCGA | 920.25 | 1434 | 1.558 | 0.444 |
| IR | ATCCGT | 664.55 | 943 | 1.419 | 0.350 |
| IR | ATAAGA | 622.67 | 877 | 1.408 | 0.342 |
| IR | ATCCGG | 1697.63 | 2265 | 1.334 | 0.288 |
| IR | ATTCGT | 525.51 | 677 | 1.288 | 0.253 |
| IR | ATCAGA | 1712.09 | 1680 | 0.981 | -0.019 |
| IR | ATCAGG | 1680.81 | 1513 | 0.900 | -0.105 |
| IR | ATAAGG | 611.30 | 547 | 0.895 | -0.111 |
| IR | ATACGT | 241.69 | 213 | 0.881 | -0.126 |
| IR | ATACGA | 334.69 | 292 | 0.872 | -0.136 |
| IR | ATTCGG | 1342.46 | 907 | 0.676 | -0.392 |
| IR | ATTAGA | 1353.90 | 900 | 0.665 | -0.408 |
| IR | ATTCGC | 1227.45 | 780 | 0.635 | -0.453 |
| IR | ATACGG | 617.42 | 260 | 0.421 | -0.865 |
| IR | ATTAGG | 1329.16 | 503 | 0.378 | -0.972 |
| IR | ATACGC | 564.52 | 170 | 0.301 | -1.200 |
| IS | ATCTCC | 2689.59 | 3743 | 1.392 | 0.330 |
| IS | ATATCA | 687.92 | 954 | 1.387 | 0.327 |
| IS | ATCAGC | 3047.17 | 3998 | 1.312 | 0.272 |
| IS | ATTTCT | 1850.19 | 2423 | 1.310 | 0.270 |
| IS | ATTTCA | 1495.77 | 1957 | 1.308 | 0.269 |
| IS | ATCAGT | 1922.48 | 2287 | 1.190 | 0.174 |
| IS | ATATCT | 850.92 | 1012 | 1.189 | 0.173 |
| IS | ATCTCG | 711.23 | 773 | 1.087 | 0.083 |
| IS | ATAAGT | 699.19 | 695 | 0.994 | -0.006 |
| IS | ATCTCT | 2339.68 | 2317 | 0.990 | -0.010 |
| IS | ATCTCA | 1891.49 | 1767 | 0.934 | -0.068 |
| IS | ATTTCC | 2126.89 | 1795 | 0.844 | -0.170 |
| IS | ATATCC | 978.18 | 703 | 0.719 | -0.330 |
| IS | ATTAGT | 1520.28 | 906 | 0.596 | -0.518 |
| IS | ATAAGC | 1108.24 | 636 | 0.574 | -0.555 |
| IS | ATATCG | 258.67 | 132 | 0.510 | -0.673 |
| IS | ATTTCG | 562.43 | 255 | 0.453 | -0.791 |
| IS | ATTAGC | 2409.67 | 797 | 0.331 | -1.106 |
| IT | ATCACC | 3094.94 | 4722 | 1.526 | 0.422 |
| IT | ATCACG | 1016.68 | 1306 | 1.285 | 0.250 |
| IT | ATAACT | 805.82 | 1009 | 1.252 | 0.225 |
| IT | ATCACT | 2215.66 | 2751 | 1.242 | 0.216 |
| IT | ATCACA | 2505.48 | 2989 | 1.193 | 0.176 |
| IT | ATAACA | 911.22 | 1079 | 1.184 | 0.169 |
| IT | ATTACT | 1752.12 | 1369 | 0.781 | -0.247 |
| IT | ATTACA | 1981.30 | 1531 | 0.773 | -0.258 |
| IT | ATAACC | 1125.61 | 741 | 0.658 | -0.418 |
| IT | ATAACG | 369.76 | 204 | 0.552 | -0.595 |
| IT | ATTACC | 2447.44 | 1083 | 0.443 | -0.815 |
| IT | ATTACG | 803.98 | 246 | 0.306 | -1.184 |
| IV | ATTGTT | 1261.28 | 2414 | 1.914 | 0.649 |
| IV | ATTGTA | 819.00 | 1478 | 1.805 | 0.590 |
| IV | ATAGTA | 376.67 | 645 | 1.712 | 0.538 |
| IV | ATAGTT | 580.08 | 877 | 1.512 | 0.413 |
| IV | ATTGTC | 1614.84 | 2315 | 1.434 | 0.360 |
| IV | ATTGTG | 3194.65 | 3762 | 1.178 | 0.163 |
| IV | ATCGTC | 2042.07 | 1679 | 0.822 | -0.196 |
| IV | ATAGTG | 1469.26 | 1196 | 0.814 | -0.206 |
| IV | ATAGTC | 742.69 | 575 | 0.774 | -0.256 |
| IV | ATCGTG | 4039.83 | 2922 | 0.723 | -0.324 |
| IV | ATCGTA | 1035.67 | 361 | 0.349 | -1.054 |
| IV | ATCGTT | 1594.97 | 547 | 0.343 | -1.070 |
| IW | ATCTGG | 1887.23 | 2427 | 1.286 | 0.252 |
| IW | ATATGG | 686.37 | 622 | 0.906 | -0.098 |
| IW | ATTTGG | 1492.40 | 1017 | 0.681 | -0.384 |

Supplemental Table 1

Expected and Observed Codon Pair Frequencies and Codon Pair Scores for 14,795 Human Genes

| amino acid pair | codon pair | expected | observed | observed/expected | CPS |
|---|---|---|---|---|---|
| IY | ATCTAC | 2708.47 | 3486 | 1.287 | 0.252 |
| IY | ATATAT | 800.43 | 953 | 1.191 | 0.174 |
| IY | ATTTAT | 1740.39 | 1984 | 1.140 | 0.131 |
| IY | ATCTAT | 2200.83 | 2196 | 0.998 | -0.002 |
| IY | ATTTAC | 2141.83 | 1403 | 0.655 | -0.423 |
| IY | ATATAC | 985.05 | 555 | 0.563 | -0.574 |
| KA | AAAGCA | 3029.93 | 4322 | 1.426 | 0.355 |
| KA | AAAGCT | 3461.21 | 4262 | 1.231 | 0.208 |
| KA | AAGGCC | 6816.15 | 6676 | 0.979 | -0.021 |
| KA | AAGGCG | 1842.96 | 1790 | 0.971 | -0.029 |
| KA | AAGGCA | 3924.10 | 3654 | 0.931 | -0.071 |
| KA | AAAGCC | 5262.99 | 4742 | 0.901 | -0.104 |
| KA | AAGGCT | 4482.65 | 4032 | 0.899 | -0.106 |
| KA | AAAGCG | 1423.01 | 765 | 0.538 | -0.621 |
| KC | AAATGT | 1815.55 | 2671 | 1.471 | 0.386 |
| KC | AAGTGT | 2351.33 | 2267 | 0.964 | -0.037 |
| KC | AAGTGC | 2791.62 | 2498 | 0.895 | -0.111 |
| KC | AAATGC | 2155.50 | 1678 | 0.778 | -0.250 |
| KD | AAAGAT | 4684.00 | 6115 | 1.306 | 0.267 |
| KD | AAGGAC | 6852.58 | 6836 | 0.998 | -0.002 |
| KD | AAGGAT | 6066.30 | 5379 | 0.887 | -0.120 |
| KD | AAAGAC | 5291.12 | 4564 | 0.863 | -0.148 |
| KE | AAAGAA | 6989.41 | 9895 | 1.416 | 0.348 |
| KE | AAGGAG | 12105.47 | 12287 | 1.015 | 0.015 |
| KE | AAGGAA | 9052.06 | 8366 | 0.924 | -0.079 |
| KE | AAAGAG | 9347.06 | 6946 | 0.743 | -0.297 |
| KF | AAATTT | 2631.62 | 3140 | 1.193 | 0.177 |
| KF | AAGTTT | 3408.25 | 3638 | 1.067 | 0.065 |
| KF | AAGTTC | 3901.02 | 3950 | 1.013 | 0.012 |
| KF | AAATTC | 3012.11 | 2225 | 0.739 | -0.303 |
| KG | AAAGGA | 2672.15 | 4509 | 1.687 | 0.523 |
| KG | AAAGGT | 1730.00 | 2402 | 1.388 | 0.328 |
| KG | AAAGGC | 3623.06 | 3435 | 0.948 | -0.053 |
| KG | AAAGGG | 2608.69 | 2465 | 0.945 | -0.057 |
| KG | AAGGGC | 4692.27 | 4309 | 0.918 | -0.085 |
| KG | AAGGGT | 2240.55 | 1978 | 0.883 | -0.125 |
| KG | AAGGGG | 3378.54 | 2740 | 0.811 | -0.209 |
| KG | AAGGGA | 3460.73 | 2568 | 0.742 | -0.298 |
| KH | AAACAT | 1929.29 | 2356 | 1.221 | 0.200 |
| KH | AAGCAC | 3445.60 | 3583 | 1.040 | 0.039 |
| KH | AAGCAT | 2498.64 | 2430 | 0.973 | -0.028 |
| KH | AAACAC | 2660.47 | 2165 | 0.814 | -0.206 |
| KI | AAAATA | 1547.96 | 2667 | 1.723 | 0.544 |
| KI | AAAATT | 3365.76 | 3894 | 1.157 | 0.146 |
| KI | AAGATC | 5512.26 | 5523 | 1.002 | 0.002 |
| KI | AAGATA | 2004.77 | 1943 | 0.969 | -0.031 |
| KI | AAGATT | 4359.03 | 3732 | 0.856 | -0.155 |
| KI | AAAATC | 4256.21 | 3287 | 0.772 | -0.258 |
| KK | AAGAAG | 11070.03 | 13815 | 1.248 | 0.222 |
| KK | AAGAAA | 8547.55 | 10129 | 1.185 | 0.170 |
| KK | AAAAAG | 8547.55 | 6145 | 0.719 | -0.330 |
| KK | AAAAAA | 6599.86 | 4676 | 0.708 | -0.345 |
| KL | AAATTA | 1273.72 | 2084 | 1.636 | 0.492 |
| KL | AAACTA | 1177.70 | 1750 | 1.486 | 0.396 |
| KL | AAACTT | 2183.78 | 3014 | 1.380 | 0.322 |
| KL | AAGCTG | 8523.68 | 9600 | 1.126 | 0.119 |
| KL | AAGCTA | 1525.25 | 1660 | 1.088 | 0.085 |
| KL | AAGCTC | 4101.62 | 4076 | 0.994 | -0.006 |
| KL | AAATTG | 2139.75 | 2113 | 0.987 | -0.013 |
| KL | AAGCTT | 2828.24 | 2772 | 0.980 | -0.020 |
| KL | AAGTTA | 1649.61 | 1459 | 0.884 | -0.123 |
| KL | AAACTC | 3167.00 | 2653 | 0.838 | -0.177 |
| KL | AAGTTG | 2771.21 | 2280 | 0.823 | -0.195 |
| KL | AAACTG | 6581.43 | 4462 | 0.678 | -0.389 |
| KM | AAGATG | 5479.27 | 5650 | 1.031 | 0.031 |
| KM | AAAATG | 4230.73 | 4060 | 0.960 | -0.041 |
| KN | AAAAAT | 3683.47 | 4378 | 1.189 | 0.173 |
| KN | AAGAAC | 5254.13 | 5515 | 1.050 | 0.048 |
| KN | AAGAAT | 4770.51 | 4618 | 0.968 | -0.032 |
| KN | AAAAAC | 4056.89 | 3254 | 0.802 | -0.221 |

Supplemental Table 1

Expected and Observed Codon Pair Frequencies and Codon Pair Scores for 14,795 Human Genes

| amino acid pair | codon pair | expected | observed | observed/expected | CPS |
|---|---|---|---|---|---|
| KP | AAACCA | 2803.51 | 3370 | 1.202 | 0.184 |
| KP | AAGCCC | 4200.41 | 4673 | 1.113 | 0.107 |
| KP | AAGCCA | 3630.85 | 4035 | 1.111 | 0.106 |
| KP | AAACCT | 2904.80 | 3118 | 1.073 | 0.071 |
| KP | AAGCCG | 1521.96 | 1544 | 1.014 | 0.014 |
| KP | AAGCCT | 3762.04 | 3396 | 0.903 | -0.102 |
| KP | AAACCC | 3243.28 | 2624 | 0.809 | -0.212 |
| KP | AAACCG | 1175.16 | 482 | 0.410 | -0.891 |
| KQ | AAACAA | 2178.87 | 3274 | 1.503 | 0.407 |
| KQ | AAGCAA | 2821.88 | 3177 | 1.126 | 0.119 |
| KQ | AAGCCG | 7879.90 | 8081 | 1.026 | 0.025 |
| KQ | AAACAG | 6084.35 | 4433 | 0.729 | -0.317 |
| KR | AAAAGA | 2247.57 | 3147 | 1.400 | 0.337 |
| KR | AAGAGG | 2857.67 | 3975 | 1.391 | 0.330 |
| KR | AAGAGA | 2910.85 | 3511 | 1.206 | 0.187 |
| KR | AAAAGG | 2206.51 | 2325 | 1.054 | 0.052 |
| KR | AAACGT | 872.39 | 862 | 0.988 | -0.012 |
| KR | AAGCGG | 2886.27 | 2828 | 0.980 | -0.020 |
| KR | AAGCGC | 2638.99 | 2532 | 0.959 | -0.041 |
| KR | AAACGA | 1208.07 | 1087 | 0.900 | -0.106 |
| KR | AAGCGT | 1129.84 | 978 | 0.866 | -0.144 |
| KR | AAGCGA | 1564.59 | 1325 | 0.847 | -0.166 |
| KR | AAACGG | 2228.59 | 1178 | 0.529 | -0.638 |
| KR | AAACGC | 2037.65 | 1041 | 0.511 | -0.672 |
| KS | AAATCA | 1871.14 | 2533 | 1.354 | 0.303 |
| KS | AAAAGT | 1901.80 | 2389 | 1.256 | 0.228 |
| KS | AAATCT | 2314.50 | 2793 | 1.207 | 0.188 |
| KS | AAGTCA | 2423.33 | 2566 | 1.059 | 0.057 |
| KS | AAGAGC | 3903.97 | 4045 | 1.036 | 0.035 |
| KS | AAGAGT | 2463.04 | 2459 | 0.998 | -0.002 |
| KS | AAGTCG | 911.22 | 904 | 0.992 | -0.008 |
| KS | AAGTCC | 3445.84 | 3100 | 0.900 | -0.106 |
| KS | AAGTCT | 2997.54 | 2675 | 0.892 | -0.114 |
| KS | AAATCC | 2660.65 | 2304 | 0.866 | -0.144 |
| KS | AAAAGC | 3014.39 | 2381 | 0.790 | -0.236 |
| KS | AAATCG | 703.58 | 462 | 0.657 | -0.421 |
| KT | AAAACA | 2831.74 | 3611 | 1.275 | 0.243 |
| KT | AAGACG | 1488.17 | 1790 | 1.203 | 0.185 |
| KT | AAAACT | 2504.18 | 2969 | 1.186 | 0.170 |
| KT | AAGACC | 4530.26 | 4475 | 0.988 | -0.012 |
| KT | AAGACA | 3667.42 | 3574 | 0.975 | -0.026 |
| KT | AAGACT | 3243.20 | 2876 | 0.887 | -0.120 |
| KT | AAAACC | 3497.97 | 2854 | 0.816 | -0.203 |
| KT | AAAACG | 1149.07 | 763 | 0.664 | -0.409 |
| KV | AAAGTA | 1317.00 | 2214 | 1.681 | 0.519 |
| KV | AAAGTT | 2028.22 | 3042 | 1.500 | 0.405 |
| KV | AAAGTC | 2596.78 | 2642 | 1.017 | 0.017 |
| KV | AAGGTG | 6653.25 | 6512 | 0.979 | -0.021 |
| KV | AAGGTC | 3363.11 | 3016 | 0.897 | -0.109 |
| KV | AAGGTT | 2626.77 | 2294 | 0.873 | -0.135 |
| KV | AAAGTG | 5137.21 | 4417 | 0.860 | -0.151 |
| KV | AAGGTA | 1705.66 | 1291 | 0.757 | -0.279 |
| KW | AAGTGG | 2598.56 | 2701 | 1.039 | 0.039 |
| KW | AAATGG | 2006.44 | 1904 | 0.949 | -0.052 |
| KY | AAATAT | 2319.32 | 2982 | 1.286 | 0.251 |
| KY | AAGTAC | 3696.62 | 3603 | 0.975 | -0.026 |
| KY | AAATAC | 2854.29 | 2763 | 0.968 | -0.033 |
| KY | AAGTAT | 3003.78 | 2526 | 0.841 | -0.173 |
| LA | CTGGCG | 2275.39 | 3643 | 1.601 | 0.471 |
| LA | TTGGCA | 1575.16 | 2350 | 1.492 | 0.400 |
| LA | CTGGCC | 8415.49 | 12456 | 1.480 | 0.392 |
| LA | TTGGCT | 1799.36 | 2643 | 1.469 | 0.384 |
| LA | TTAGCA | 937.64 | 1314 | 1.401 | 0.337 |
| LA | CTTGCT | 1836.39 | 2345 | 1.277 | 0.244 |
| LA | CTAGCA | 866.95 | 1107 | 1.277 | 0.244 |
| LA | CTTGCA | 1607.57 | 1861 | 1.158 | 0.146 |
| LA | TTAGCT | 1071.10 | 1239 | 1.157 | 0.146 |
| LA | CTGGCT | 5534.46 | 6333 | 1.144 | 0.135 |
| LA | CTAGCT | 990.35 | 1099 | 1.110 | 0.104 |
| LA | CTGGCA | 4844.85 | 5013 | 1.035 | 0.034 |

Supplemental Table 1

Expected and Observed Codon Pair Frequencies and Codon Pair Scores for 14,795 Human Genes

| amino acid pair | codon pair | expected | observed | observed/ expected | CPS |
|---|---|---|---|---|---|
| LA | TTGGCC | 2736.04 | 2824 | 1.032 | 0.032 |
| LA | TTGGCG | 739.77 | 623 | 0.842 | -0.172 |
| LA | CTTGCC | 2792.34 | 2201 | 0.788 | -0.238 |
| LA | CTAGCC | 1505.89 | 1159 | 0.770 | -0.262 |
| LA | CTAGCG | 407.16 | 253 | 0.621 | -0.476 |
| LA | TTAGCC | 1628.68 | 941 | 0.578 | -0.549 |
| LA | CTTGCG | 755.00 | 346 | 0.458 | -0.780 |
| LA | TTAGCG | 440.36 | 198 | 0.450 | -0.799 |
| LA | CTCGCC | 4049.56 | 1527 | 0.377 | -0.975 |
| LA | CTCGCG | 1094.93 | 390 | 0.356 | -1.032 |
| LA | CTCGCT | 2663.20 | 605 | 0.227 | -1.482 |
| LA | CTCGCA | 2331.36 | 429 | 0.184 | -1.693 |
| LC | CTCTGC | 1769.27 | 3523 | 1.991 | 0.689 |
| LC | CTCTGT | 1490.23 | 2145 | 1.439 | 0.364 |
| LC | CTTTGT | 1027.58 | 1155 | 1.124 | 0.117 |
| LC | TTATGT | 599.35 | 627 | 1.046 | 0.045 |
| LC | CTGTGC | 3676.77 | 3517 | 0.957 | -0.044 |
| LC | TTGTGT | 1006.86 | 856 | 0.850 | -0.162 |
| LC | CTTTGC | 1219.99 | 974 | 0.798 | -0.225 |
| LC | CTGTGT | 3096.89 | 2370 | 0.765 | -0.268 |
| LC | CTATGT | 554.17 | 417 | 0.752 | -0.284 |
| LC | TTGTGC | 1195.39 | 722 | 0.604 | -0.504 |
| LC | TTATGC | 711.58 | 368 | 0.517 | -0.659 |
| LC | CTATGC | 657.93 | 332 | 0.505 | -0.684 |
| LD | TTGGAT | 2174.51 | 3688 | 1.696 | 0.528 |
| LD | TTAGAT | 1294.41 | 1977 | 1.527 | 0.424 |
| LD | CTGGAC | 7555.23 | 10531 | 1.394 | 0.332 |
| LD | CTAGAT | 1196.83 | 1584 | 1.323 | 0.280 |
| LD | TTGGAC | 2456.35 | 2775 | 1.130 | 0.122 |
| LD | CTTGAT | 2219.25 | 2463 | 1.110 | 0.104 |
| LD | CTGGAT | 6688.33 | 6912 | 1.033 | 0.033 |
| LD | CTAGAC | 1351.95 | 1390 | 1.028 | 0.028 |
| LD | CTTGAC | 2506.90 | 1832 | 0.731 | -0.314 |
| LD | TTAGAC | 1462.19 | 969 | 0.663 | -0.411 |
| LD | CTCGAC | 3635.60 | 981 | 0.270 | -1.310 |
| LD | CTCGAT | 3218.44 | 658 | 0.204 | -1.587 |
| LE | TTAGAA | 1739.66 | 3085 | 1.773 | 0.573 |
| LE | CTAGAA | 1608.51 | 2701 | 1.679 | 0.518 |
| LE | TTGGAA | 2922.49 | 4652 | 1.592 | 0.465 |
| LE | CTGGAG | 12021.09 | 18044 | 1.501 | 0.406 |
| LE | TTGGAG | 3908.29 | 4774 | 1.222 | 0.200 |
| LE | CTAGAG | 2151.09 | 2515 | 1.169 | 0.156 |
| LE | CTTGAA | 2982.63 | 3161 | 1.060 | 0.058 |
| LE | CTGGAA | 8988.96 | 7642 | 0.850 | -0.162 |
| LE | TTAGAG | 2326.48 | 1873 | 0.805 | -0.217 |
| LE | CTTGAG | 3988.72 | 2484 | 0.623 | -0.474 |
| LE | CTCGAG | 5784.58 | 1305 | 0.226 | -1.489 |
| LE | CTCGAA | 4325.51 | 512 | 0.118 | -2.134 |
| LF | CTCTTC | 2629.18 | 6495 | 2.470 | 0.904 |
| LF | TTATTT | 923.85 | 1405 | 1.521 | 0.419 |
| LF | CTCTTT | 2297.07 | 3446 | 1.500 | 0.406 |
| LF | CTTTTT | 1583.93 | 1937 | 1.223 | 0.201 |
| LF | CTTTTC | 1812.93 | 1936 | 1.068 | 0.066 |
| LF | CTATTT | 854.20 | 876 | 1.026 | 0.025 |
| LF | TTGTTT | 1551.99 | 1544 | 0.995 | -0.005 |
| LF | CTGTTT | 4773.59 | 2957 | 0.619 | -0.479 |
| LF | CTGTTC | 5463.77 | 3119 | 0.571 | -0.561 |
| LF | TTATTC | 1057.42 | 583 | 0.551 | -0.595 |
| LF | TTGTTC | 1776.38 | 940 | 0.529 | -0.636 |
| LF | CTATTC | 977.70 | 464 | 0.475 | -0.745 |
| LG | CTTGGA | 1534.14 | 2667 | 1.738 | 0.553 |
| LG | CTTGGT | 993.23 | 1579 | 1.590 | 0.464 |
| LG | CTGGGC | 6268.87 | 9794 | 1.562 | 0.446 |
| LG | CTAGGA | 827.35 | 1087 | 1.314 | 0.273 |
| LG | CTTGGG | 1497.70 | 1881 | 1.256 | 0.228 |
| LG | TTAGGA | 894.81 | 1114 | 1.245 | 0.219 |
| LG | CTGGGG | 4513.74 | 5602 | 1.241 | 0.216 |
| LG | TTGGGT | 973.20 | 1194 | 1.227 | 0.204 |
| LG | TTGGGA | 1503.20 | 1820 | 1.211 | 0.191 |
| LG | CTAGGT | 535.64 | 611 | 1.141 | 0.132 |

Supplemental Table 1

Expected and Observed Codon Pair Frequencies and Codon Pair Scores for 14,795 Human Genes

| amino acid pair | codon pair | expected | observed | observed/expected | CPS |
|---|---|---|---|---|---|
| LG | TTAGGT | 579.32 | 611 | 1.055 | 0.053 |
| LG | TTGGGG | 1467.50 | 1452 | 0.989 | -0.011 |
| LG | CTGGGT | 2993.37 | 2947 | 0.985 | -0.016 |
| LG | CTTGGC | 2080.08 | 2009 | 0.966 | -0.035 |
| LG | CTAGGG | 807.70 | 766 | 0.948 | -0.053 |
| LG | TTGGGC | 2038.13 | 1786 | 0.876 | -0.132 |
| LG | CTGGGA | 4623.54 | 4034 | 0.872 | -0.136 |
| LG | CTAGGC | 1121.77 | 940 | 0.838 | -0.177 |
| LG | TTAGGG | 873.56 | 529 | 0.606 | -0.502 |
| LG | CTCGGG | 2172.02 | 1076 | 0.495 | -0.702 |
| LG | CTCGGC | 3016.60 | 1313 | 0.435 | -0.832 |
| LG | TTAGGC | 1213.24 | 507 | 0.418 | -0.873 |
| LG | CTCGGT | 1440.42 | 365 | 0.253 | -1.373 |
| LG | CTCGGA | 2224.86 | 510 | 0.229 | -1.473 |
| LH | CTTCAT | 1127.31 | 1980 | 1.756 | 0.563 |
| LH | TTACAT | 657.52 | 935 | 1.422 | 0.352 |
| LH | CTACAT | 607.95 | 741 | 1.219 | 0.198 |
| LH | CTGCAC | 4685.05 | 5459 | 1.165 | 0.153 |
| LH | CTCCAC | 2254.46 | 2204 | 0.978 | -0.023 |
| LH | CTTCAC | 1554.55 | 1490 | 0.958 | -0.042 |
| LH | CTCCAT | 1634.86 | 1521 | 0.930 | -0.072 |
| LH | CTACAC | 838.36 | 777 | 0.927 | -0.076 |
| LH | TTGCAT | 1104.58 | 1017 | 0.921 | -0.083 |
| LH | TTGCAC | 1523.20 | 1140 | 0.748 | -0.290 |
| LH | CTGCAT | 3397.45 | 2394 | 0.705 | -0.350 |
| LH | TTACAC | 906.71 | 634 | 0.699 | -0.358 |
| LI | CTCATC | 2602.42 | 6250 | 2.402 | 0.876 |
| LI | TTAATA | 380.66 | 798 | 2.096 | 0.740 |
| LI | TTAATT | 827.68 | 1290 | 1.559 | 0.444 |
| LI | CTCATT | 2057.96 | 3117 | 1.515 | 0.415 |
| LI | CTAATA | 351.96 | 516 | 1.466 | 0.383 |
| LI | CTAATT | 765.28 | 952 | 1.244 | 0.218 |
| LI | CTTATT | 1419.05 | 1761 | 1.241 | 0.216 |
| LI | TTGATA | 639.48 | 791 | 1.237 | 0.213 |
| LI | TTGATT | 1390.44 | 1468 | 1.056 | 0.054 |
| LI | CTTATA | 652.64 | 683 | 1.047 | 0.045 |
| LI | CTCATA | 946.48 | 919 | 0.971 | -0.029 |
| LI | CTTATC | 1794.48 | 1189 | 0.663 | -0.412 |
| LI | TTGATC | 1758.29 | 1135 | 0.646 | -0.438 |
| LI | CTGATC | 5408.15 | 3356 | 0.621 | -0.477 |
| LI | CTGATT | 4276.70 | 2639 | 0.617 | -0.483 |
| LI | CTGATA | 1966.91 | 1193 | 0.607 | -0.500 |
| LI | TTAATC | 1046.66 | 633 | 0.605 | -0.503 |
| LI | CTAATC | 967.75 | 563 | 0.582 | -0.542 |
| LK | TTAAAA | 1429.91 | 2557 | 1.788 | 0.581 |
| LK | CTAAAA | 1322.10 | 1842 | 1.393 | 0.332 |
| LK | TTGAAA | 2402.12 | 3193 | 1.329 | 0.285 |
| LK | CTCAAG | 4604.55 | 6048 | 1.313 | 0.273 |
| LK | CTAAAG | 1712.27 | 2078 | 1.214 | 0.194 |
| LK | TTAAAG | 1851.89 | 2128 | 1.149 | 0.139 |
| LK | CTGAAG | 9568.82 | 10212 | 1.067 | 0.065 |
| LK | TTGAAG | 3111.01 | 3222 | 1.036 | 0.035 |
| LK | CTCAAA | 3555.33 | 2768 | 0.779 | -0.250 |
| LK | CTTAAA | 2451.55 | 1850 | 0.755 | -0.282 |
| LK | CTGAAA | 7388.42 | 5227 | 0.707 | -0.346 |
| LK | CTTAAG | 3175.03 | 1448 | 0.456 | -0.785 |
| LL | TTATTA | 500.55 | 802 | 1.602 | 0.471 |
| LL | CTTCTA | 793.49 | 1132 | 1.427 | 0.355 |
| LL | CTTCTT | 1471.36 | 2099 | 1.427 | 0.355 |
| LL | CTTTTA | 858.19 | 1203 | 1.402 | 0.338 |
| LL | CTGCTG | 13364.10 | 18236 | 1.365 | 0.311 |
| LL | CTTTTG | 1441.69 | 1945 | 1.349 | 0.299 |
| LL | TTACTA | 462.82 | 608 | 1.314 | 0.273 |
| LL | CTCCTC | 3094.54 | 3800 | 1.228 | 0.205 |
| LL | CTCCTG | 6430.85 | 7786 | 1.211 | 0.191 |
| LL | TTACTT | 858.19 | 1039 | 1.211 | 0.191 |
| LL | TTGCTA | 777.49 | 929 | 1.195 | 0.178 |
| LL | CTGCTC | 6430.85 | 7550 | 1.174 | 0.160 |
| LL | CTACTA | 427.93 | 474 | 1.108 | 0.102 |
| LL | CTTCTC | 2133.82 | 2292 | 1.074 | 0.072 |

Supplemental Table 1

Expected and Observed Codon Pair Frequencies and Codon Pair Scores for 14,795 Human Genes

| amino acid pair | codon pair | expected | observed | observed/expected | CPS |
|---|---|---|---|---|---|
| LL | CTACTT | 793.49 | 839 | 1.057 | 0.056 |
| LL | CTCTTG | 2090.79 | 2131 | 1.019 | 0.019 |
| LL | TTGCTT | 1441.69 | 1464 | 1.015 | 0.015 |
| LL | TTATTG | 840.89 | 818 | 0.973 | -0.028 |
| LL | CTCCTT | 2133.82 | 2034 | 0.953 | -0.048 |
| LL | TTGTTA | 840.89 | 771 | 0.917 | -0.087 |
| LL | TTGTTG | 1412.62 | 1289 | 0.912 | -0.092 |
| LL | CTCCTA | 1150.75 | 1034 | 0.899 | -0.107 |
| LL | TTGCTG | 4344.93 | 3820 | 0.879 | -0.129 |
| LL | CTTCTG | 4434.34 | 3837 | 0.865 | -0.145 |
| LL | CTGCTA | 2391.41 | 1913 | 0.800 | -0.223 |
| LL | CTCTTA | 1244.58 | 959 | 0.771 | -0.261 |
| LL | CTATTA | 462.82 | 354 | 0.765 | -0.268 |
| LL | CTGCTT | 4434.34 | 3148 | 0.710 | -0.343 |
| LL | TTGCTC | 2090.79 | 1440 | 0.689 | -0.373 |
| LL | CTACTC | 1150.75 | 792 | 0.688 | -0.374 |
| LL | CTATTG | 777.49 | 532 | 0.684 | -0.379 |
| LL | CTACTG | 2391.41 | 1583 | 0.662 | -0.413 |
| LL | CTGTTG | 4344.93 | 2615 | 0.602 | -0.508 |
| LL | TTACTC | 1244.58 | 657 | 0.528 | -0.639 |
| LL | TTACTG | 2586.40 | 1358 | 0.525 | -0.644 |
| LL | CTGTTA | 2586.40 | 953 | 0.368 | -0.998 |
| LM | CTCATG | 2631.41 | 4030 | 1.531 | 0.426 |
| LM | TTAATG | 1058.32 | 1228 | 1.160 | 0.149 |
| LM | CTAATG | 978.53 | 1101 | 1.125 | 0.118 |
| LM | TTGATG | 1777.88 | 1763 | 0.992 | -0.008 |
| LM | CTGATG | 5468.39 | 4470 | 0.817 | -0.202 |
| LM | CTTATG | 1814.47 | 1137 | 0.627 | -0.467 |
| LN | TTAAAT | 962.36 | 1926 | 2.001 | 0.694 |
| LN | CTCAAC | 2635.40 | 4681 | 1.776 | 0.574 |
| LN | CTAAAT | 889.81 | 1446 | 1.625 | 0.486 |
| LN | TTGAAT | 1616.68 | 2048 | 1.267 | 0.236 |
| LN | CTCAAT | 2392.82 | 2652 | 1.108 | 0.103 |
| LN | CTAAAC | 980.01 | 922 | 0.941 | -0.061 |
| LN | TTAAAC | 1059.92 | 965 | 0.910 | -0.094 |
| LN | CTTAAT | 1649.95 | 1441 | 0.873 | -0.135 |
| LN | TTGAAC | 1780.58 | 1541 | 0.865 | -0.145 |
| LN | CTGAAC | 5476.68 | 4308 | 0.787 | -0.240 |
| LN | CTGAAT | 4972.58 | 3413 | 0.686 | -0.376 |
| LN | CTTAAC | 1817.22 | 891 | 0.490 | -0.713 |
| LP | CTTCCT | 1728.14 | 2795 | 1.617 | 0.481 |
| LP | CTTCCA | 1667.88 | 2369 | 1.420 | 0.351 |
| LP | CTGCCC | 5815.10 | 7856 | 1.351 | 0.301 |
| LP | TTACCT | 1007.96 | 1244 | 1.234 | 0.210 |
| LP | CTGCCG | 2107.02 | 2489 | 1.181 | 0.167 |
| LP | TTACCA | 972.81 | 1140 | 1.172 | 0.159 |
| LP | CTCCCG | 1013.90 | 1184 | 1.168 | 0.155 |
| LP | TTGCCA | 1634.25 | 1897 | 1.161 | 0.149 |
| LP | CTACCT | 931.97 | 1045 | 1.121 | 0.114 |
| LP | TTGCCT | 1693.30 | 1800 | 1.063 | 0.061 |
| LP | CTTCCC | 1929.51 | 1889 | 0.979 | -0.021 |
| LP | CTACCA | 899.47 | 850 | 0.945 | -0.057 |
| LP | CTCCCA | 2418.82 | 2126 | 0.879 | -0.129 |
| LP | CTGCCT | 5208.23 | 4563 | 0.876 | -0.132 |
| LP | CTCCCT | 2506.21 | 2192 | 0.875 | -0.134 |
| LP | CTACCC | 1040.57 | 888 | 0.853 | -0.159 |
| LP | CTCCCC | 2798.25 | 2369 | 0.847 | -0.167 |
| LP | TTGCCC | 1890.60 | 1560 | 0.825 | -0.192 |
| LP | TTGCCG | 685.03 | 478 | 0.698 | -0.360 |
| LP | CTGCCA | 5026.60 | 3348 | 0.666 | -0.406 |
| LP | CTTCCG | 699.13 | 451 | 0.645 | -0.438 |
| LP | TTACCC | 1125.42 | 666 | 0.592 | -0.525 |
| LP | CTACCG | 377.04 | 211 | 0.560 | -0.580 |
| LP | TTACCG | 407.78 | 175 | 0.429 | -0.846 |
| LQ | TTACAA | 864.28 | 1290 | 1.493 | 0.401 |
| LQ | CTACAA | 799.12 | 1188 | 1.487 | 0.397 |
| LQ | CTTCAA | 1481.79 | 2098 | 1.416 | 0.348 |
| LQ | CTACAG | 2231.48 | 2674 | 1.198 | 0.181 |
| LQ | CTGCAG | 12470.36 | 14508 | 1.163 | 0.151 |
| LQ | CTTCAG | 4137.79 | 4363 | 1.054 | 0.053 |

Supplemental Table 1

Expected and Observed Codon Pair Frequencies and Codon Pair Scores for 14,795 Human Genes

| amino acid pair | codon pair | expected | observed | observed/expected | CPS |
|---|---|---|---|---|---|
| LQ | TTGCAA | 1451.91 | 1467 | 1.010 | 0.010 |
| LQ | CTCCAG | 6000.78 | 5430 | 0.905 | -0.100 |
| LQ | TTACAG | 2413.43 | 2107 | 0.873 | -0.136 |
| LQ | TTGCAG | 4054.36 | 3177 | 0.784 | -0.244 |
| LQ | CTCCAA | 2148.94 | 1524 | 0.709 | -0.344 |
| LQ | CTGCAA | 4465.77 | 2694 | 0.603 | -0.505 |
| LR | CTTCGA | 661.43 | 1365 | 2.064 | 0.725 |
| LR | CTTCGT | 477.64 | 784 | 1.641 | 0.496 |
| LR | CTGCGG | 3677.31 | 5467 | 1.487 | 0.397 |
| LR | TTAAGA | 717.74 | 1026 | 1.429 | 0.357 |
| LR | CTGCGC | 3362.26 | 4574 | 1.360 | 0.308 |
| LR | CTCCGA | 959.23 | 1289 | 1.344 | 0.295 |
| LR | CTCCGG | 1769.53 | 2229 | 1.260 | 0.231 |
| LR | CTAAGA | 663.63 | 821 | 1.237 | 0.213 |
| LR | CTCAGG | 1752.00 | 2047 | 1.168 | 0.156 |
| LR | CTTCGG | 1220.17 | 1415 | 1.160 | 0.148 |
| LR | CTCCGT | 692.69 | 771 | 1.113 | 0.107 |
| LR | TTACGA | 385.79 | 427 | 1.107 | 0.101 |
| LR | CTAAGG | 651.51 | 721 | 1.107 | 0.101 |
| LR | CTCCGC | 1617.93 | 1790 | 1.106 | 0.101 |
| LR | TTGAGA | 1205.75 | 1290 | 1.070 | 0.068 |
| LR | CTACGT | 257.59 | 275 | 1.068 | 0.065 |
| LR | CTACGA | 356.70 | 378 | 1.060 | 0.058 |
| LR | CTGAGG | 3640.88 | 3637 | 0.999 | -0.001 |
| LR | TTAAGG | 704.63 | 678 | 0.962 | -0.039 |
| LR | TTACGT | 278.59 | 264 | 0.948 | -0.054 |
| LR | CTGCGT | 1439.50 | 1363 | 0.947 | -0.055 |
| LR | TTGAGG | 1183.72 | 1080 | 0.912 | -0.092 |
| LR | CTACGG | 658.03 | 577 | 0.877 | -0.131 |
| LR | CTCAGA | 1784.60 | 1469 | 0.823 | -0.195 |
| LR | CTTCGC | 1115.63 | 819 | 0.734 | -0.309 |
| LR | CTACGC | 601.65 | 438 | 0.728 | -0.317 |
| LR | CTGCGA | 1993.40 | 1399 | 0.702 | -0.354 |
| LR | TTGCGT | 468.01 | 321 | 0.686 | -0.377 |
| LR | CTGAGA | 3708.63 | 2486 | 0.670 | -0.400 |
| LR | TTGCGG | 1195.56 | 772 | 0.646 | -0.437 |
| LR | TTGCGA | 648.09 | 418 | 0.645 | -0.439 |
| LR | CTTAGA | 1230.56 | 694 | 0.564 | -0.573 |
| LR | TTACGG | 711.68 | 383 | 0.538 | -0.620 |
| LR | TTGCGC | 1093.14 | 542 | 0.496 | -0.702 |
| LR | CTTAGG | 1208.08 | 503 | 0.416 | -0.876 |
| LR | TTACGC | 650.71 | 232 | 0.357 | -1.031 |
| LS | CTCAGC | 2740.30 | 5167 | 1.886 | 0.634 |
| LS | CTTTCT | 1450.83 | 2502 | 1.725 | 0.545 |
| LS | CTCTCC | 2418.72 | 4070 | 1.683 | 0.520 |
| LS | CTCTCG | 639.61 | 1016 | 1.588 | 0.463 |
| LS | CTCAGT | 1728.87 | 2589 | 1.498 | 0.404 |
| LS | TTATCA | 684.12 | 963 | 1.408 | 0.342 |
| LS | TTATCT | 846.22 | 1175 | 1.389 | 0.328 |
| LS | CTTTCA | 1172.91 | 1626 | 1.386 | 0.327 |
| LS | TTAAGT | 695.33 | 886 | 1.274 | 0.242 |
| LS | CTCTCT | 2104.05 | 2553 | 1.213 | 0.193 |
| LS | CTAAGT | 642.91 | 770 | 1.198 | 0.180 |
| LS | CTCTCA | 1701.00 | 2003 | 1.178 | 0.163 |
| LS | CTTTCC | 1667.81 | 1819 | 1.091 | 0.087 |
| LS | TTGTCA | 1149.26 | 1210 | 1.053 | 0.052 |
| LS | CTGTCG | 1329.18 | 1392 | 1.047 | 0.046 |
| LS | TTGTCT | 1421.58 | 1461 | 1.028 | 0.027 |
| LS | CTGAGC | 5694.68 | 5805 | 1.019 | 0.019 |
| LS | CTGTCC | 5026.41 | 4628 | 0.921 | -0.083 |
| LS | TTGAGT | 1168.09 | 1035 | 0.886 | -0.121 |
| LS | TTGTCC | 1634.18 | 1334 | 0.816 | -0.203 |
| LS | CTATCA | 632.54 | 512 | 0.809 | -0.211 |
| LS | CTAAGC | 1019.02 | 791 | 0.776 | -0.253 |
| LS | TTATCC | 972.78 | 727 | 0.747 | -0.291 |
| LS | CTGAGT | 3592.81 | 2665 | 0.742 | -0.299 |
| LS | CTTAGT | 1192.13 | 856 | 0.718 | -0.331 |
| LS | CTATCT | 782.42 | 557 | 0.712 | -0.340 |
| LS | CTGTCT | 4372.48 | 2950 | 0.675 | -0.394 |
| LS | CTTTCG | 441.04 | 291 | 0.660 | -0.416 |

Supplemental Table 1

Expected and Observed Codon Pair Frequencies and Codon Pair Scores for 14,795 Human Genes

| amino acid pair | codon pair | expected | observed | observed/ expected | CPS |
|---|---|---|---|---|---|
| LS | TTGTCG | 432.14 | 278 | 0.643 | -0.441 |
| LS | CTGTCA | 3534.89 | 2228 | 0.630 | -0.462 |
| LS | TTGAGC | 1851.45 | 1128 | 0.609 | -0.496 |
| LS | CTATCC | 899.44 | 541 | 0.601 | -0.508 |
| LS | TTATCG | 257.24 | 152 | 0.591 | -0.526 |
| LS | TTAAGC | 1102.11 | 551 | 0.500 | -0.693 |
| LS | CTATCG | 237.85 | 102 | 0.429 | -0.847 |
| LS | CTTAGC | 1889.55 | 793 | 0.420 | -0.868 |
| LT | CTCACC | 2534.19 | 4959 | 1.957 | 0.671 |
| LT | CTCACG | 832.47 | 1510 | 1.814 | 0.595 |
| LT | TTAACA | 825.09 | 1163 | 1.410 | 0.343 |
| LT | CTCACT | 1814.22 | 2521 | 1.390 | 0.329 |
| LT | TTAACT | 729.65 | 969 | 1.328 | 0.284 |
| LT | CTAACT | 674.64 | 817 | 1.211 | 0.191 |
| LT | CTAACA | 762.89 | 898 | 1.177 | 0.163 |
| LT | CTCACA | 2051.52 | 2374 | 1.157 | 0.146 |
| LT | CTGACG | 1729.98 | 1795 | 1.038 | 0.037 |
| LT | TTGACT | 1225.76 | 1259 | 1.027 | 0.027 |
| LT | TTGACA | 1386.09 | 1401 | 1.011 | 0.011 |
| LT | CTTACT | 1250.98 | 1259 | 1.006 | 0.006 |
| LT | CTGACC | 5266.36 | 5160 | 0.980 | -0.020 |
| LT | CTTACA | 1414.61 | 1109 | 0.784 | -0.243 |
| LT | CTGACT | 3770.17 | 2808 | 0.745 | -0.295 |
| LT | TTGACC | 1712.20 | 1235 | 0.721 | -0.327 |
| LT | CTAACC | 942.38 | 678 | 0.719 | -0.329 |
| LT | TTGACG | 562.45 | 399 | 0.709 | -0.343 |
| LT | CTGACA | 4263.32 | 3003 | 0.704 | -0.350 |
| LT | CTAACG | 309.57 | 215 | 0.695 | -0.365 |
| LT | TTAACC | 1019.22 | 687 | 0.674 | -0.394 |
| LT | CTTACC | 1747.43 | 1104 | 0.632 | -0.459 |
| LT | TTAACG | 334.81 | 164 | 0.490 | -0.714 |
| LT | CTTACG | 574.02 | 247 | 0.430 | -0.843 |
| LV | CTTGTT | 1029.60 | 1741 | 1.691 | 0.525 |
| LV | TTAGTA | 389.95 | 602 | 1.544 | 0.434 |
| LV | TTGGTA | 655.07 | 980 | 1.496 | 0.403 |
| LV | CTTGTA | 668.56 | 993 | 1.485 | 0.396 |
| LV | CTGGTG | 7859.41 | 11424 | 1.454 | 0.374 |
| LV | CTAGTA | 360.55 | 519 | 1.439 | 0.364 |
| LV | TTGGTT | 1008.84 | 1427 | 1.414 | 0.347 |
| LV | CTTGTC | 1318.22 | 1541 | 1.169 | 0.156 |
| LV | TTAGTT | 600.53 | 690 | 1.149 | 0.139 |
| LV | CTGGTC | 3972.81 | 4541 | 1.143 | 0.134 |
| LV | TTGGTG | 2555.25 | 2882 | 1.128 | 0.120 |
| LV | CTAGTT | 555.26 | 580 | 1.045 | 0.044 |
| LV | TTGGTC | 1291.64 | 1345 | 1.041 | 0.040 |
| LV | CTTGTG | 2607.83 | 2540 | 0.974 | -0.026 |
| LV | CTAGTG | 1406.38 | 1272 | 0.904 | -0.100 |
| LV | CTGGTA | 2014.87 | 1720 | 0.854 | -0.158 |
| LV | CTGGTT | 3102.98 | 2576 | 0.830 | -0.186 |
| LV | CTAGTC | 710.90 | 551 | 0.775 | -0.255 |
| LV | TTAGTG | 1521.06 | 947 | 0.623 | -0.474 |
| LV | TTAGTC | 768.87 | 416 | 0.541 | -0.614 |
| LV | CTCGTC | 1911.73 | 1013 | 0.530 | -0.635 |
| LV | CTCGTG | 3781.97 | 1691 | 0.447 | -0.805 |
| LV | CTCGTT | 1493.16 | 373 | 0.250 | -1.387 |
| LV | CTCGTA | 969.56 | 191 | 0.197 | -1.625 |
| LW | CTCTGG | 1742.64 | 2796 | 1.604 | 0.473 |
| LW | CTGTGG | 3621.43 | 3365 | 0.929 | -0.073 |
| LW | CTTTGG | 1201.63 | 1018 | 0.847 | -0.166 |
| LW | CTATGG | 648.03 | 501 | 0.773 | -0.257 |
| LW | TTATGG | 700.87 | 535 | 0.763 | -0.270 |
| LW | TTGTGG | 1177.40 | 877 | 0.745 | -0.295 |
| LY | CTCTAC | 2082.09 | 4204 | 2.019 | 0.703 |
| LY | TTATAT | 680.44 | 1022 | 1.502 | 0.407 |
| LY | CTCTAT | 1691.85 | 2487 | 1.470 | 0.385 |
| LY | CTTTAT | 1166.60 | 1591 | 1.364 | 0.310 |
| LY | CTATAT | 629.14 | 596 | 0.947 | -0.054 |
| LY | TTGTAT | 1143.08 | 1063 | 0.930 | -0.073 |
| LY | CTGTAC | 4326.84 | 3390 | 0.783 | -0.244 |
| LY | CTTTAC | 1435.69 | 1069 | 0.745 | -0.295 |

Supplemental Table 1

Expected and Observed Codon Pair Frequencies and Codon Pair Scores for 14,795 Human Genes

| amino acid pair | codon pair | expected | observed | observed/expected | CPS |
|---|---|---|---|---|---|
| LY | TTGTAC | 1406.74 | 1006 | 0.715 | -0.335 |
| LY | TTATAC | 837.39 | 579 | 0.691 | -0.369 |
| LY | CTGTAT | 3515.88 | 2202 | 0.626 | -0.468 |
| LY | CTATAC | 774.26 | 481 | 0.621 | -0.476 |
| MA | ATGGCG | 1645.46 | 2370 | 1.440 | 0.365 |
| MA | ATGGCA | 3503.58 | 3580 | 1.022 | 0.022 |
| MA | ATGGCT | 4002.27 | 4003 | 1.000 | 0.000 |
| MA | ATGGCC | 6085.70 | 5284 | 0.868 | -0.141 |
| MC | ATGTGT | 1386.67 | 1448 | 1.044 | 0.043 |
| MC | ATGTGC | 1646.33 | 1585 | 0.963 | -0.038 |
| MD | ATGGAT | 4467.48 | 4634 | 1.037 | 0.037 |
| MD | ATGGAC | 5046.52 | 4880 | 0.967 | -0.034 |
| ME | ATGGAG | 8054.28 | 8223 | 1.021 | 0.021 |
| ME | ATGGAA | 6022.72 | 5854 | 0.972 | -0.028 |
| MF | ATGTTT | 2565.53 | 2833 | 1.104 | 0.099 |
| MF | ATGTTC | 2936.47 | 2669 | 0.909 | -0.096 |
| MG | ATGGGC | 3467.73 | 3533 | 1.019 | 0.019 |
| MG | ATGGGT | 1655.83 | 1675 | 1.012 | 0.012 |
| MG | ATGGGA | 2557.59 | 2526 | 0.988 | -0.012 |
| MG | ATGGGG | 2496.85 | 2444 | 0.979 | -0.021 |
| MH | ATGCAT | 1465.33 | 1478 | 1.009 | 0.009 |
| MH | ATGCAC | 2020.67 | 2008 | 0.994 | -0.006 |
| MI | ATGATT | 2305.40 | 2382 | 1.033 | 0.033 |
| MI | ATGATA | 1060.28 | 1094 | 1.032 | 0.031 |
| MI | ATGATC | 2915.32 | 2805 | 0.962 | -0.039 |
| MK | ATGAAG | 6107.32 | 6423 | 1.052 | 0.050 |
| MK | ATGAAA | 4715.68 | 4400 | 0.933 | -0.069 |
| ML | ATGCTG | 5938.40 | 6536 | 1.101 | 0.096 |
| ML | ATGCTA | 1062.63 | 1122 | 1.056 | 0.054 |
| ML | ATGTTG | 1930.69 | 1922 | 0.995 | -0.005 |
| ML | ATGTTA | 1149.28 | 1134 | 0.987 | -0.013 |
| ML | ATGCTT | 1970.42 | 1887 | 0.958 | -0.043 |
| ML | ATGCTC | 2857.58 | 2308 | 0.808 | -0.214 |
| MM | ATGATG | 3925.00 | 3925 | 1.000 | 0.000 |
| MN | ATGAAT | 3249.30 | 3301 | 1.016 | 0.016 |
| MN | ATGAAC | 3578.70 | 3527 | 0.986 | -0.015 |
| MP | ATGCCC | 2676.16 | 2752 | 1.028 | 0.028 |
| MP | ATGCCA | 2313.29 | 2313 | 1.000 | 0.000 |
| MP | ATGCCT | 2396.87 | 2372 | 0.990 | -0.010 |
| MP | ATGCCG | 969.67 | 919 | 0.948 | -0.054 |
| MQ | ATGCAG | 5141.70 | 5165 | 1.005 | 0.005 |
| MQ | ATGCAA | 1841.30 | 1818 | 0.987 | -0.013 |
| MR | ATGAGG | 1626.37 | 2127 | 1.308 | 0.268 |
| MR | ATGAGA | 1656.63 | 1974 | 1.192 | 0.175 |
| MR | ATGCGG | 1642.64 | 1513 | 0.921 | -0.082 |
| MR | ATGCGT | 643.02 | 531 | 0.826 | -0.191 |
| MR | ATGCGA | 890.44 | 684 | 0.768 | -0.264 |
| MR | ATGCGC | 1501.91 | 1132 | 0.754 | -0.283 |
| MS | ATGTCG | 666.33 | 809 | 1.214 | 0.194 |
| MS | ATGTCT | 2191.95 | 2338 | 1.067 | 0.065 |
| MS | ATGTCA | 1772.07 | 1781 | 1.005 | 0.005 |
| MS | ATGTCC | 2519.77 | 2493 | 0.989 | -0.011 |
| MS | ATGAGT | 1801.10 | 1770 | 0.983 | -0.017 |
| MS | ATGAGC | 2854.78 | 2615 | 0.916 | -0.088 |
| MT | ATGACT | 2098.83 | 2195 | 1.046 | 0.045 |
| MT | ATGACC | 2931.75 | 2927 | 0.998 | -0.002 |
| MT | ATGACA | 2373.36 | 2337 | 0.985 | -0.015 |
| MT | ATGACG | 963.07 | 908 | 0.943 | -0.059 |
| MV | ATGGTG | 4813.46 | 5122 | 1.064 | 0.062 |
| MV | ATGGTT | 1900.41 | 1915 | 1.008 | 0.008 |
| MV | ATGGTA | 1234.00 | 1191 | 0.965 | -0.035 |
| MV | ATGGTC | 2433.13 | 2153 | 0.885 | -0.122 |
| MW | ATGTGG | 1876.00 | 1876 | 1.000 | 0.000 |
| MY | ATGTAC | 2354.66 | 2363 | 1.004 | 0.004 |
| MY | ATGTAT | 1913.34 | 1905 | 0.996 | -0.004 |
| NA | AATGCA | 1705.68 | 3344 | 1.961 | 0.673 |
| NA | AATGCT | 1948.47 | 3458 | 1.775 | 0.574 |
| NA | AATGCC | 2962.77 | 4259 | 1.438 | 0.363 |
| NA | AATGCG | 801.08 | 624 | 0.779 | -0.250 |
| NA | AACGCG | 882.29 | 661 | 0.749 | -0.289 |

Supplemental Table 1

Expected and Observed Codon Pair Frequencies and Codon Pair Scores for 14,795 Human Genes

| amino acid pair | codon pair | expected | observed | observed/expected | CPS |
|---|---|---|---|---|---|
| NA | AACGCC | 3263.12 | 1899 | 0.582 | -0.541 |
| NA | AACGCA | 1878.60 | 700 | 0.373 | -0.987 |
| NA | AACGCT | 2146.00 | 643 | 0.300 | -1.205 |
| NC | AACTGC | 1868.57 | 2826 | 1.512 | 0.414 |
| NC | AACTGT | 1573.86 | 2016 | 1.281 | 0.248 |
| NC | AATTGT | 1429.00 | 935 | 0.654 | -0.424 |
| NC | AATTGC | 1696.57 | 791 | 0.466 | -0.763 |
| ND | AATGAT | 2555.01 | 4420 | 1.730 | 0.548 |
| ND | AATGAC | 2886.18 | 4521 | 1.566 | 0.449 |
| ND | AACGAC | 3178.77 | 1654 | 0.520 | -0.653 |
| ND | AACGAT | 2814.03 | 839 | 0.298 | -1.210 |
| NE | AATGAA | 3381.19 | 7367 | 2.179 | 0.779 |
| NE | AATGAG | 4521.72 | 5796 | 1.282 | 0.248 |
| NE | AACGAG | 4980.12 | 2476 | 0.497 | -0.699 |
| NE | AACGAA | 3723.97 | 968 | 0.260 | -1.347 |
| NF | AACTTC | 3150.86 | 4259 | 1.352 | 0.301 |
| NF | AACTTT | 2752.85 | 2846 | 1.034 | 0.033 |
| NF | AATTTT | 2499.46 | 2350 | 0.940 | -0.062 |
| NF | AATTTC | 2860.84 | 1809 | 0.632 | -0.458 |
| NG | AATGGA | 2235.93 | 4484 | 2.005 | 0.696 |
| NG | AATGGT | 1447.59 | 2430 | 1.679 | 0.518 |
| NG | AATGGG | 2182.83 | 3202 | 1.467 | 0.383 |
| NG | AATGGC | 3031.62 | 4001 | 1.320 | 0.277 |
| NG | AACGGG | 2404.12 | 1508 | 0.627 | -0.466 |
| NG | AACGGC | 3338.95 | 1752 | 0.525 | -0.645 |
| NG | AACGGA | 2462.61 | 804 | 0.326 | -1.119 |
| NG | AACGGT | 1594.34 | 517 | 0.324 | -1.126 |
| NH | AACCAC | 2167.68 | 2776 | 1.281 | 0.247 |
| NH | AACCAT | 1571.93 | 1639 | 1.043 | 0.042 |
| NH | AATCAT | 1427.24 | 1456 | 1.020 | 0.020 |
| NH | AATCAC | 1968.15 | 1264 | 0.642 | -0.443 |
| NI | AACATC | 3876.27 | 5487 | 1.416 | 0.348 |
| NI | AACATT | 3065.31 | 3184 | 1.039 | 0.038 |
| NI | AATATA | 1280.01 | 1309 | 1.023 | 0.022 |
| NI | AACATA | 1409.77 | 1384 | 0.982 | -0.018 |
| NI | AATATT | 2783.16 | 2725 | 0.979 | -0.021 |
| NI | AATATC | 3519.48 | 1845 | 0.524 | -0.646 |
| NK | AACAAG | 4824.98 | 5918 | 1.227 | 0.204 |
| NK | AACAAA | 3725.54 | 4221 | 1.133 | 0.125 |
| NK | AATAAA | 3382.62 | 3607 | 1.066 | 0.064 |
| NK | AATAAG | 4380.86 | 2568 | 0.586 | -0.534 |
| NL | AATTTA | 1025.31 | 1571 | 1.532 | 0.427 |
| NL | AACCTC | 2807.78 | 3954 | 1.408 | 0.342 |
| NL | AACTTG | 1897.05 | 2429 | 1.280 | 0.247 |
| NL | AACCTG | 5834.92 | 6690 | 1.147 | 0.137 |
| NL | AATTTG | 1722.43 | 1947 | 1.130 | 0.123 |
| NL | AATCTT | 1757.88 | 1943 | 1.105 | 0.100 |
| NL | AACCTA | 1044.12 | 1135 | 1.087 | 0.083 |
| NL | AACCTT | 1936.08 | 2021 | 1.044 | 0.043 |
| NL | AACTTA | 1129.25 | 1129 | 1.000 | 0.000 |
| NL | AATCTA | 948.01 | 893 | 0.942 | -0.060 |
| NL | AATCTC | 2549.34 | 1713 | 0.672 | -0.398 |
| NL | AATCTG | 5297.84 | 2525 | 0.477 | -0.741 |
| NM | AACATG | 3351.76 | 4374 | 1.305 | 0.266 |
| NM | AATATG | 3043.24 | 2021 | 0.664 | -0.409 |
| NN | AACAAC | 3150.02 | 4430 | 1.406 | 0.341 |
| NN | AACAAT | 2860.08 | 2830 | 0.989 | -0.011 |
| NN | AATAAT | 2596.82 | 2424 | 0.933 | -0.069 |
| NN | AATAAC | 2860.08 | 1783 | 0.623 | -0.473 |
| NP | AACCCC | 2770.02 | 3474 | 1.254 | 0.226 |
| NP | AATCCA | 2174.02 | 2380 | 1.095 | 0.091 |
| NP | AACCCA | 2394.42 | 2612 | 1.091 | 0.087 |
| NP | AATCCT | 2252.58 | 2414 | 1.072 | 0.069 |
| NP | AACCCG | 1003.68 | 1048 | 1.044 | 0.043 |
| NP | AACCCT | 2480.94 | 2578 | 1.039 | 0.038 |
| NP | AATCCC | 2515.05 | 1641 | 0.652 | -0.427 |
| NP | AATCCG | 911.29 | 355 | 0.390 | -0.943 |
| NQ | AATCAA | 1516.57 | 1905 | 1.256 | 0.228 |
| NQ | AACCAA | 1670.31 | 1955 | 1.170 | 0.157 |
| NQ | AACCAG | 4664.22 | 5409 | 1.160 | 0.148 |

Supplemental Table 1

Expected and Observed Codon Pair Frequencies and Codon Pair Scores for 14,795 Human Genes

| amino acid pair | codon pair | expected | observed | observed/expected | CPS |
|---|---|---|---|---|---|
| NQ | AATCAG | 4234.90 | 2817 | 0.665 | −0.408 |
| NR | AACAGA | 1511.98 | 2383 | 1.576 | 0.455 |
| NR | AACCGC | 1370.77 | 1966 | 1.434 | 0.361 |
| NR | AACAGG | 1484.36 | 1903 | 1.282 | 0.248 |
| NR | AACCGA | 812.69 | 998 | 1.228 | 0.205 |
| NR | AACCGT | 586.88 | 706 | 1.203 | 0.185 |
| NR | AACCGG | 1499.21 | 1779 | 1.187 | 0.171 |
| NR | AATCGA | 737.89 | 687 | 0.931 | −0.071 |
| NR | AATCGT | 532.86 | 486 | 0.912 | −0.092 |
| NR | AATAGA | 1372.81 | 1117 | 0.814 | −0.206 |
| NR | AATCGC | 1244.60 | 602 | 0.484 | −0.726 |
| NR | AATAGG | 1347.73 | 643 | 0.477 | −0.740 |
| NR | AATCGG | 1361.22 | 593 | 0.436 | −0.831 |
| NS | AACAGC | 2917.73 | 4490 | 1.539 | 0.431 |
| NS | AACAGT | 1840.81 | 2414 | 1.311 | 0.271 |
| NS | AACTCG | 681.02 | 821 | 1.206 | 0.187 |
| NS | AATTCA | 1644.43 | 1970 | 1.198 | 0.181 |
| NS | AATTCT | 2034.08 | 2383 | 1.172 | 0.158 |
| NS | AACTCC | 2575.33 | 2818 | 1.094 | 0.090 |
| NS | AACTCA | 1811.14 | 1783 | 0.984 | −0.016 |
| NS | AACTCT | 2240.29 | 1981 | 0.884 | −0.123 |
| NS | AATAGT | 1671.38 | 1193 | 0.714 | −0.337 |
| NS | AATTCC | 2338.29 | 1655 | 0.708 | −0.346 |
| NS | AATAGC | 2649.17 | 1273 | 0.481 | −0.733 |
| NS | AATTCG | 618.33 | 241 | 0.390 | −0.942 |
| NT | AACACG | 860.22 | 1238 | 1.439 | 0.364 |
| NT | AACACA | 2119.90 | 2783 | 1.313 | 0.272 |
| NT | AACACC | 2618.65 | 3278 | 1.252 | 0.225 |
| NT | AACACT | 1874.68 | 2099 | 1.120 | 0.113 |
| NT | AATACT | 1702.13 | 1540 | 0.905 | −0.100 |
| NT | AATACA | 1924.77 | 1692 | 0.879 | −0.129 |
| NT | AATACC | 2377.62 | 1312 | 0.552 | −0.595 |
| NT | AATACG | 781.04 | 317 | 0.406 | −0.902 |
| NV | AATGTA | 927.15 | 1710 | 1.844 | 0.612 |
| NV | AATGTT | 1427.85 | 2573 | 1.802 | 0.589 |
| NV | AATGTC | 1828.10 | 2877 | 1.574 | 0.453 |
| NV | AATGTG | 3616.54 | 4314 | 1.193 | 0.176 |
| NV | AACGTG | 3983.18 | 2772 | 0.696 | −0.363 |
| NV | AACGTC | 2013.43 | 1341 | 0.666 | −0.406 |
| NV | AACGTT | 1572.60 | 509 | 0.324 | −1.128 |
| NV | AACGTA | 1021.14 | 294 | 0.288 | −1.245 |
| NW | AACTGG | 1808.22 | 2595 | 1.435 | 0.361 |
| NW | AATTGG | 1641.78 | 855 | 0.521 | −0.652 |
| NY | AACTAC | 2506.72 | 3191 | 1.273 | 0.241 |
| NY | AACTAT | 2036.89 | 2145 | 1.053 | 0.052 |
| NY | AATTAT | 1849.41 | 1795 | 0.971 | −0.030 |
| NY | AATTAC | 2275.98 | 1538 | 0.676 | −0.392 |
| PA | CCGGCG | 470.57 | 1166 | 2.478 | 0.907 |
| PA | CCGGCC | 1740.39 | 2666 | 1.532 | 0.426 |
| PA | CCAGCA | 2390.31 | 3368 | 1.409 | 0.343 |
| PA | CCAGCT | 2730.54 | 3622 | 1.326 | 0.283 |
| PA | CCTGCT | 2829.20 | 3750 | 1.325 | 0.282 |
| PA | CCTGCA | 2476.67 | 3178 | 1.283 | 0.249 |
| PA | CCAGCC | 4151.96 | 4942 | 1.190 | 0.174 |
| PA | CCCGCG | 1298.71 | 1528 | 1.177 | 0.163 |
| PA | CCTGCC | 4301.98 | 5000 | 1.162 | 0.150 |
| PA | CCAGCG | 1122.61 | 1078 | 0.960 | −0.041 |
| PA | CCTGCG | 1163.17 | 1105 | 0.950 | −0.051 |
| PA | CCGGCT | 1144.57 | 1013 | 0.885 | −0.122 |
| PA | CCGGCA | 1001.95 | 777 | 0.775 | −0.254 |
| PA | CCCGCC | 4803.25 | 2690 | 0.560 | −0.580 |
| PA | CCCGCA | 2765.26 | 846 | 0.306 | −1.184 |
| PA | CCCGCT | 3158.86 | 821 | 0.260 | −1.347 |
| PC | CCCTGC | 1550.51 | 2870 | 1.851 | 0.616 |
| PC | CCCTGT | 1305.97 | 1577 | 1.208 | 0.189 |
| PC | CCGTGC | 561.80 | 630 | 1.121 | 0.115 |
| PC | CCTTGT | 1169.67 | 1001 | 0.856 | −0.156 |
| PC | CCATGT | 1128.89 | 831 | 0.736 | −0.306 |
| PC | CCGTGT | 473.20 | 340 | 0.719 | −0.331 |
| PC | CCTTGC | 1388.69 | 937 | 0.675 | −0.393 |

Supplemental Table 1

Expected and Observed Codon Pair Frequencies and Codon Pair Scores for 14,795 Human Genes

| amino acid pair | codon pair | expected | observed | observed/expected | CPS |
|---|---|---|---|---|---|
| PC | CCATGC | 1340.27 | 733 | 0.547 | -0.603 |
| PD | CCAGAT | 2721.60 | 4165 | 1.530 | 0.425 |
| PD | CCTGAT | 2819.94 | 3781 | 1.341 | 0.293 |
| PD | CCGGAC | 1288.69 | 1659 | 1.287 | 0.253 |
| PD | CCAGAC | 3074.36 | 3766 | 1.225 | 0.203 |
| PD | CCTGAC | 3185.44 | 3646 | 1.145 | 0.135 |
| PD | CCGGAT | 1140.82 | 895 | 0.785 | -0.243 |
| PD | CCCGAC | 3556.62 | 2215 | 0.623 | -0.474 |
| PD | CCCGAT | 3148.53 | 809 | 0.257 | -1.359 |
| PE | CCAGAA | 3999.86 | 5699 | 1.425 | 0.354 |
| PE | CCTGAG | 5542.36 | 7122 | 1.285 | 0.251 |
| PE | CCGGAG | 2242.20 | 2870 | 1.280 | 0.247 |
| PE | CCAGAG | 5349.08 | 6777 | 1.267 | 0.237 |
| PE | CCTGAA | 4144.39 | 5108 | 1.233 | 0.209 |
| PE | CCCGAG | 6188.17 | 4149 | 0.670 | -0.400 |
| PE | CCGGAA | 1676.64 | 1032 | 0.616 | -0.485 |
| PE | CCCGAA | 4627.30 | 1013 | 0.219 | -1.519 |
| PF | CCCTTC | 2555.92 | 4301 | 1.683 | 0.520 |
| PF | CCATTT | 1930.27 | 2057 | 1.066 | 0.064 |
| PF | CCTTTT | 2000.01 | 1967 | 0.983 | -0.017 |
| PF | CCCTTT | 2233.06 | 2159 | 0.967 | -0.034 |
| PF | CCTTTC | 2289.18 | 2078 | 0.908 | -0.097 |
| PF | CCGTTC | 926.10 | 662 | 0.715 | -0.336 |
| PF | CCATTC | 2209.35 | 1290 | 0.584 | -0.538 |
| PF | CCGTTT | 809.12 | 439 | 0.543 | -0.611 |
| PG | CCTGGG | 2918.52 | 4310 | 1.477 | 0.390 |
| PG | CCTGGA | 2989.52 | 4317 | 1.444 | 0.367 |
| PG | CCGGGC | 1639.82 | 2353 | 1.435 | 0.361 |
| PG | CCGGGG | 1180.71 | 1657 | 1.403 | 0.339 |
| PG | CCTGGT | 1935.48 | 2673 | 1.381 | 0.323 |
| PG | CCAGGA | 2885.27 | 3897 | 1.351 | 0.301 |
| PG | CCAGGG | 2816.75 | 3472 | 1.233 | 0.209 |
| PG | CCAGGT | 1867.98 | 2259 | 1.209 | 0.190 |
| PG | CCTGGC | 4053.37 | 4622 | 1.140 | 0.131 |
| PG | CCAGGC | 3912.02 | 4106 | 1.050 | 0.048 |
| PG | CCGGGT | 783.01 | 661 | 0.844 | -0.169 |
| PG | CCGGGA | 1209.43 | 963 | 0.796 | -0.228 |
| PG | CCCGGG | 3258.60 | 2136 | 0.655 | -0.422 |
| PG | CCCGGC | 4525.68 | 2555 | 0.565 | -0.572 |
| PG | CCCGGA | 3337.86 | 968 | 0.290 | -1.238 |
| PG | CCCGGT | 2161.00 | 526 | 0.243 | -1.413 |
| PH | CCGCAC | 725.13 | 972 | 1.340 | 0.293 |
| PH | CCCCAC | 2001.25 | 2505 | 1.252 | 0.225 |
| PH | CCTCAT | 1299.79 | 1592 | 1.225 | 0.203 |
| PH | CCACAT | 1254.46 | 1222 | 0.974 | -0.026 |
| PH | CCCCAT | 1451.24 | 1303 | 0.898 | -0.108 |
| PH | CCTCAC | 1792.40 | 1531 | 0.854 | -0.158 |
| PH | CCACAC | 1729.89 | 1366 | 0.790 | -0.236 |
| PH | CCGCAT | 525.84 | 289 | 0.550 | -0.599 |
| PI | CCCATC | 2119.04 | 4651 | 2.195 | 0.786 |
| PI | CCCATT | 1675.71 | 2102 | 1.254 | 0.227 |
| PI | CCAATA | 666.18 | 819 | 1.229 | 0.207 |
| PI | CCCATA | 770.68 | 776 | 1.007 | 0.007 |
| PI | CCAATT | 1448.49 | 1386 | 0.957 | -0.044 |
| PI | CCTATA | 690.25 | 603 | 0.874 | -0.135 |
| PI | CCTATT | 1500.83 | 1266 | 0.844 | -0.170 |
| PI | CCAATC | 1831.71 | 939 | 0.513 | -0.668 |
| PI | CCTATC | 1897.89 | 957 | 0.504 | -0.685 |
| PI | CCGATT | 607.17 | 299 | 0.492 | -0.708 |
| PI | CCGATC | 767.80 | 342 | 0.445 | -0.809 |
| PI | CCGATA | 279.24 | 115 | 0.412 | -0.887 |
| PK | CCCAAG | 3738.47 | 6383 | 1.707 | 0.535 |
| PK | CCCAAA | 2886.60 | 3787 | 1.312 | 0.271 |
| PK | CCAAAA | 2495.20 | 2489 | 0.998 | -0.002 |
| PK | CCAAAG | 3231.55 | 3127 | 0.968 | -0.033 |
| PK | CCTAAA | 2585.35 | 1840 | 0.712 | -0.340 |
| PK | CCGAAG | 1354.58 | 940 | 0.694 | -0.365 |
| PK | CCTAAG | 3348.32 | 1660 | 0.496 | -0.702 |
| PK | CCGAAA | 1045.92 | 460 | 0.440 | -0.821 |
| PL | CCGCTG | 1824.84 | 3343 | 1.832 | 0.605 |

Supplemental Table 1

Expected and Observed Codon Pair Frequencies and Codon Pair Scores for 14,795 Human Genes

| amino acid pair | codon pair | expected | observed | observed/expected | CPS |
|---|---|---|---|---|---|
| PL | CCGCTC | 878.12 | 1254 | 1.428 | 0.356 |
| PL | CCTTTG | 1466.52 | 2054 | 1.401 | 0.337 |
| PL | CCTTTA | 872.97 | 1195 | 1.369 | 0.314 |
| PL | CCCTTG | 1637.40 | 2122 | 1.296 | 0.259 |
| PL | CCTCTT | 1496.70 | 1827 | 1.221 | 0.199 |
| PL | CCCCTG | 5036.31 | 5760 | 1.144 | 0.134 |
| PL | CCCCTC | 2423.49 | 2646 | 1.092 | 0.088 |
| PL | CCTCTA | 807.16 | 871 | 1.079 | 0.076 |
| PL | CCATTA | 842.53 | 826 | 0.980 | -0.020 |
| PL | CCACTT | 1444.51 | 1371 | 0.949 | -0.052 |
| PL | CCACTA | 779.01 | 729 | 0.936 | -0.066 |
| PL | CCTCTC | 2170.57 | 1934 | 0.891 | -0.115 |
| PL | CCTCTG | 4510.71 | 3745 | 0.830 | -0.186 |
| PL | CCATTG | 1415.38 | 1172 | 0.828 | -0.189 |
| PL | CCCCTT | 1671.10 | 1324 | 0.792 | -0.233 |
| PL | CCGCTA | 326.54 | 255 | 0.781 | -0.247 |
| PL | CCCCTA | 901.21 | 689 | 0.765 | -0.268 |
| PL | CCACTG | 4353.41 | 3218 | 0.739 | -0.302 |
| PL | CCCTTA | 974.69 | 709 | 0.727 | -0.318 |
| PL | CCACTC | 2094.88 | 1475 | 0.704 | -0.351 |
| PL | CCGTTG | 593.29 | 402 | 0.678 | -0.389 |
| PL | CCGCTT | 605.50 | 402 | 0.664 | -0.410 |
| PL | CCGTTA | 353.17 | 157 | 0.445 | -0.811 |
| PM | CCCATG | 2307.54 | 3923 | 1.700 | 0.531 |
| PM | CCAATG | 1994.65 | 1552 | 0.778 | -0.251 |
| PM | CCGATG | 836.10 | 520 | 0.622 | -0.475 |
| PM | CCTATG | 2066.72 | 1210 | 0.585 | -0.535 |
| PN | CCCAAC | 2313.61 | 4255 | 1.839 | 0.609 |
| PN | CCAAAT | 1815.81 | 2453 | 1.351 | 0.301 |
| PN | CCCAAT | 2100.65 | 2296 | 1.093 | 0.089 |
| PN | CCAAAC | 1999.90 | 1735 | 0.868 | -0.142 |
| PN | CCTAAT | 1881.42 | 1342 | 0.713 | -0.338 |
| PN | CCTAAC | 2072.16 | 997 | 0.481 | -0.732 |
| PN | CCGAAT | 761.14 | 340 | 0.447 | -0.806 |
| PN | CCGAAC | 838.30 | 365 | 0.435 | -0.831 |
| PP | CCGCCG | 608.57 | 2335 | 3.837 | 1.345 |
| PP | CCGCCC | 1679.58 | 2697 | 1.606 | 0.474 |
| PP | CCCCCG | 1679.58 | 2420 | 1.441 | 0.365 |
| PP | CCTCCA | 3588.72 | 4314 | 1.202 | 0.184 |
| PP | CCTCCT | 3718.39 | 4305 | 1.158 | 0.146 |
| PP | CCACCA | 3463.58 | 3850 | 1.112 | 0.106 |
| PP | CCACCT | 3588.72 | 3798 | 1.058 | 0.057 |
| PP | CCCCCA | 4006.89 | 4095 | 1.022 | 0.022 |
| PP | CCACCC | 4006.89 | 3595 | 0.897 | -0.108 |
| PP | CCGCCA | 1451.84 | 1280 | 0.882 | -0.126 |
| PP | CCACCG | 1451.84 | 1252 | 0.862 | -0.148 |
| PP | CCGCCT | 1504.30 | 1286 | 0.855 | -0.157 |
| PP | CCTCCC | 4151.67 | 3338 | 0.804 | -0.218 |
| PP | CCTCCG | 1504.30 | 1152 | 0.766 | -0.267 |
| PP | CCCCCT | 4151.67 | 3160 | 0.761 | -0.273 |
| PP | CCCCCC | 4635.43 | 2315 | 0.499 | -0.694 |
| PQ | CCCCAG | 5063.98 | 6421 | 1.268 | 0.237 |
| PQ | CCGCAG | 1834.86 | 2187 | 1.192 | 0.176 |
| PQ | CCTCAA | 1624.21 | 1752 | 1.079 | 0.076 |
| PQ | CCTCAG | 4535.49 | 4221 | 0.931 | -0.072 |
| PQ | CCACAA | 1567.57 | 1405 | 0.896 | -0.109 |
| PQ | CCACAG | 4377.33 | 3670 | 0.838 | -0.176 |
| PQ | CCCCAA | 1813.47 | 1497 | 0.825 | -0.192 |
| PQ | CCGCAA | 657.08 | 321 | 0.489 | -0.716 |
| PR | CCGCGC | 563.43 | 1094 | 1.942 | 0.664 |
| PR | CCGCGG | 616.23 | 1113 | 1.806 | 0.591 |
| PR | CCCAGG | 1683.86 | 2927 | 1.738 | 0.553 |
| PR | CCCCGG | 1700.71 | 2608 | 1.533 | 0.428 |
| PR | CCCCGC | 1555.00 | 1979 | 1.273 | 0.241 |
| PR | CCCCGA | 921.92 | 1166 | 1.265 | 0.235 |
| PR | CCTCGA | 825.71 | 1015 | 1.229 | 0.206 |
| PR | CCAAGA | 1482.62 | 1608 | 1.085 | 0.081 |
| PR | CCTCGT | 596.27 | 644 | 1.080 | 0.077 |
| PR | CCCAGA | 1715.19 | 1801 | 1.050 | 0.049 |
| PR | CCGAGG | 610.12 | 636 | 1.042 | 0.042 |

Supplemental Table 1

Expected and Observed Codon Pair Frequencies and Codon Pair Scores for 14,795 Human Genes

| amino acid pair | codon pair | expected | observed | observed/expected | CPS |
|---|---|---|---|---|---|
| PR | CCTCGG | 1523.22 | 1511 | 0.992 | -0.008 |
| PR | CCCCGT | 665.75 | 655 | 0.984 | -0.016 |
| PR | CCAAGG | 1455.54 | 1347 | 0.925 | -0.077 |
| PR | CCACGA | 796.91 | 632 | 0.793 | -0.232 |
| PR | CCGCGT | 241.23 | 191 | 0.792 | -0.233 |
| PR | CCACGT | 575.48 | 418 | 0.726 | -0.320 |
| PR | CCACGG | 1470.10 | 1040 | 0.707 | -0.346 |
| PR | CCGCGA | 334.04 | 226 | 0.677 | -0.391 |
| PR | CCTCGC | 1392.72 | 838 | 0.602 | -0.508 |
| PR | CCACGC | 1344.15 | 701 | 0.522 | -0.651 |
| PR | CCGAGA | 621.48 | 308 | 0.496 | -0.702 |
| PR | CCTAGA | 1536.19 | 692 | 0.450 | -0.797 |
| PR | CCTAGG | 1508.13 | 586 | 0.389 | -0.945 |
| PS | CCCAGC | 3196.25 | 6398 | 2.002 | 0.694 |
| PS | CCCTCG | 746.03 | 1385 | 1.856 | 0.619 |
| PS | CCGTCG | 270.31 | 483 | 1.787 | 0.580 |
| PS | CCCAGT | 2016.53 | 2743 | 1.360 | 0.308 |
| PS | CCTTCA | 1776.97 | 2263 | 1.274 | 0.242 |
| PS | CCTTCT | 2198.02 | 2711 | 1.233 | 0.210 |
| PS | CCCTCC | 2821.16 | 3353 | 1.189 | 0.173 |
| PS | CCATCA | 1715.00 | 1819 | 1.061 | 0.059 |
| PS | CCATCT | 2121.37 | 2183 | 1.029 | 0.029 |
| PS | CCTTCC | 2526.74 | 2594 | 1.027 | 0.026 |
| PS | CCGTCC | 1022.21 | 1048 | 1.025 | 0.025 |
| PS | CCCTCA | 1984.02 | 1945 | 0.980 | -0.020 |
| PS | CCAAGT | 1743.10 | 1582 | 0.908 | -0.097 |
| PS | CCCTCT | 2454.14 | 2113 | 0.861 | -0.150 |
| PS | CCTTCG | 668.17 | 552 | 0.826 | -0.191 |
| PS | CCATCC | 2438.63 | 1995 | 0.818 | -0.201 |
| PS | CCGAGC | 1158.11 | 885 | 0.764 | -0.269 |
| PS | CCATCG | 644.87 | 475 | 0.737 | -0.306 |
| PS | CCAAGC | 2762.85 | 1659 | 0.600 | -0.510 |
| PS | CCGTCT | 889.22 | 523 | 0.588 | -0.531 |
| PS | CCGAGT | 730.66 | 371 | 0.508 | -0.678 |
| PS | CCGTCA | 718.88 | 364 | 0.506 | -0.681 |
| PS | CCTAGT | 1806.08 | 860 | 0.476 | -0.742 |
| PS | CCTAGC | 2862.68 | 968 | 0.338 | -1.084 |
| PT | CCCACG | 829.55 | 1764 | 2.126 | 0.754 |
| PT | CCCACC | 2525.29 | 4586 | 1.816 | 0.597 |
| PT | CCCACA | 2044.32 | 2719 | 1.330 | 0.285 |
| PT | CCCACT | 1807.85 | 2282 | 1.262 | 0.233 |
| PT | CCAACA | 1767.12 | 1895 | 1.072 | 0.070 |
| PT | CCAACT | 1562.71 | 1593 | 1.019 | 0.019 |
| PT | CCGACG | 300.57 | 305 | 1.015 | 0.015 |
| PT | CCTACT | 1619.18 | 1252 | 0.773 | -0.257 |
| PT | CCAACC | 2182.87 | 1514 | 0.694 | -0.366 |
| PT | CCTACA | 1830.97 | 1241 | 0.678 | -0.389 |
| PT | CCGACC | 915.00 | 592 | 0.647 | -0.435 |
| PT | CCAACG | 717.06 | 463 | 0.646 | -0.437 |
| PT | CCTACC | 2261.75 | 1251 | 0.553 | -0.592 |
| PT | CCGACT | 655.05 | 342 | 0.522 | -0.650 |
| PT | CCGACA | 740.73 | 352 | 0.475 | -0.744 |
| PT | CCTACG | 742.97 | 352 | 0.474 | -0.747 |
| PV | CCTGTT | 1493.79 | 2375 | 1.590 | 0.464 |
| PV | CCTGTA | 969.97 | 1482 | 1.528 | 0.424 |
| PV | CCAGTA | 936.15 | 1352 | 1.444 | 0.368 |
| PV | CCTGTG | 3783.57 | 5362 | 1.417 | 0.349 |
| PV | CCAGTT | 1441.70 | 2038 | 1.414 | 0.346 |
| PV | CCTGTC | 1912.53 | 2666 | 1.394 | 0.332 |
| PV | CCGGTG | 1530.67 | 1911 | 1.248 | 0.222 |
| PV | CCAGTG | 3651.63 | 3787 | 1.037 | 0.036 |
| PV | CCAGTC | 1845.84 | 1863 | 1.009 | 0.009 |
| PV | CCGGTC | 773.73 | 778 | 1.006 | 0.006 |
| PV | CCCGTG | 4224.44 | 2576 | 0.610 | -0.495 |
| PV | CCGGTT | 604.32 | 351 | 0.581 | -0.543 |
| PV | CCGGTA | 392.41 | 215 | 0.548 | -0.602 |
| PV | CCCGTC | 2135.39 | 1084 | 0.508 | -0.678 |
| PV | CCCGTT | 1667.85 | 391 | 0.234 | -1.451 |
| PV | CCCGTA | 1083.00 | 216 | 0.199 | -1.612 |
| PW | CCCTGG | 1769.80 | 2753 | 1.556 | 0.442 |

Supplemental Table 1

Expected and Observed Codon Pair Frequencies and Codon Pair Scores for 14,795 Human Genes

| amino acid pair | codon pair | expected | observed | observed/expected | CPS |
|---|---|---|---|---|---|
| PW | CCGTGG | 641.26 | 661 | 1.031 | 0.030 |
| PW | CCATGG | 1529.83 | 1060 | 0.693 | -0.367 |
| PW | CCTTGG | 1585.10 | 1052 | 0.664 | -0.410 |
| PY | CCCTAC | 2166.25 | 3378 | 1.559 | 0.444 |
| PY | CCCTAT | 1760.24 | 2097 | 1.191 | 0.175 |
| PY | CCTTAT | 1576.54 | 1702 | 1.080 | 0.077 |
| PY | CCATAT | 1521.56 | 1513 | 0.994 | -0.006 |
| PY | CCTTAC | 1940.18 | 1485 | 0.765 | -0.267 |
| PY | CCGTAC | 784.91 | 592 | 0.754 | -0.282 |
| PY | CCGTAT | 637.80 | 429 | 0.673 | -0.397 |
| PY | CCATAC | 1872.52 | 1064 | 0.568 | -0.565 |
| QA | CAAGCA | 1597.87 | 2339 | 1.464 | 0.381 |
| QA | CAAGCT | 1825.31 | 2409 | 1.320 | 0.277 |
| QA | CAGGCG | 2095.55 | 2271 | 1.084 | 0.080 |
| QA | CAGGCC | 7750.37 | 7695 | 0.993 | -0.007 |
| QA | CAAGCC | 2775.49 | 2655 | 0.957 | -0.044 |
| QA | CAGGCT | 5097.04 | 4584 | 0.899 | -0.106 |
| QA | CAGGCA | 4461.94 | 3943 | 0.884 | -0.124 |
| QA | CAAGCG | 750.44 | 458 | 0.610 | -0.494 |
| QC | CAGTGT | 2490.13 | 2791 | 1.121 | 0.114 |
| QC | CAGTGC | 2956.40 | 3260 | 1.103 | 0.098 |
| QC | CAATGT | 891.74 | 822 | 0.922 | -0.081 |
| QC | CAATGC | 1058.72 | 524 | 0.495 | -0.703 |
| QD | CAAGAT | 2128.42 | 3326 | 1.563 | 0.446 |
| QD | CAAGAC | 2404.29 | 2506 | 1.042 | 0.041 |
| QD | CAGGAC | 6713.82 | 6642 | 0.989 | -0.011 |
| QD | CAGGAT | 5943.46 | 4716 | 0.793 | -0.231 |
| QE | CAAGAA | 3247.03 | 5286 | 1.628 | 0.487 |
| QE | CAGGAG | 12125.58 | 12556 | 1.035 | 0.035 |
| QE | CAAGAG | 4342.30 | 4206 | 0.969 | -0.032 |
| QE | CAGGAA | 9067.09 | 6734 | 0.743 | -0.297 |
| QF | CAGTTT | 3509.26 | 4032 | 1.149 | 0.139 |
| QF | CAGTTC | 4016.64 | 4205 | 1.047 | 0.046 |
| QF | CAATTT | 1256.70 | 1156 | 0.920 | -0.084 |
| QF | CAATTC | 1438.40 | 828 | 0.576 | -0.552 |
| QG | CAAGGA | 1440.03 | 2837 | 1.970 | 0.678 |
| QG | CAGGGT | 932.30 | 1506 | 1.615 | 0.480 |
| QG | CAGGGG | 1405.83 | 1700 | 1.209 | 0.190 |
| QG | CAGGGC | 1952.47 | 2192 | 1.123 | 0.116 |
| QG | CAGGGC | 5452.14 | 5605 | 1.028 | 0.028 |
| QG | CAGGGT | 2603.39 | 2292 | 0.880 | -0.127 |
| QG | CAGGGA | 4021.17 | 2871 | 0.714 | -0.337 |
| QG | CAGGGG | 3925.67 | 2730 | 0.695 | -0.363 |
| QH | CAACAT | 1067.82 | 1364 | 1.277 | 0.245 |
| QH | CAGCAC | 4111.88 | 4483 | 1.090 | 0.086 |
| QH | CAGCAT | 2981.80 | 2794 | 0.937 | -0.065 |
| QH | CAACAC | 1472.51 | 993 | 0.674 | -0.394 |
| QI | CAAATA | 656.37 | 1125 | 1.714 | 0.539 |
| QI | CAAATT | 1427.17 | 1667 | 1.168 | 0.155 |
| QI | CAGATC | 5039.60 | 5197 | 1.031 | 0.031 |
| QI | CAGATA | 1832.87 | 1802 | 0.983 | -0.017 |
| QI | CAGATT | 3985.26 | 3693 | 0.927 | -0.076 |
| QI | CAAATC | 1804.74 | 1262 | 0.699 | -0.358 |
| QK | CAGGAG | 8990.94 | 9726 | 1.082 | 0.079 |
| QK | CAAGAA | 2486.09 | 2610 | 1.050 | 0.049 |
| QK | CAGGAA | 6942.22 | 6532 | 0.941 | -0.061 |
| QK | CAAGAG | 3219.76 | 2771 | 0.861 | -0.150 |
| QL | CAGCTG | 10304.18 | 12629 | 1.226 | 0.203 |
| QL | CAACTA | 660.31 | 798 | 1.209 | 0.189 |
| QL | CAACTT | 1224.39 | 1479 | 1.208 | 0.189 |
| QL | CAGCTC | 4958.40 | 5986 | 1.207 | 0.188 |
| QL | CAGCTA | 1843.86 | 2002 | 1.086 | 0.082 |
| QL | CAGCTT | 3419.03 | 3476 | 1.017 | 0.017 |
| QL | CAATTA | 714.15 | 642 | 0.899 | -0.107 |
| QL | CAGTTG | 3350.09 | 2597 | 0.775 | -0.255 |
| QL | CAGTTA | 1994.20 | 1518 | 0.761 | -0.273 |
| QL | CAACTC | 1775.66 | 1279 | 0.720 | -0.328 |
| QL | CAACTG | 3690.04 | 2093 | 0.567 | -0.567 |
| QL | CAATTG | 1199.70 | 635 | 0.529 | -0.636 |
| QM | CAGATG | 5587.91 | 5592 | 1.001 | 0.001 |

Supplemental Table 1

Expected and Observed Codon Pair Frequencies and Codon Pair Scores for 14,795 Human Genes

| amino acid pair | codon pair | expected | observed | observed/expected | CPS |
|---|---|---|---|---|---|
| QM | CAAATG | 2001.09 | 1997 | 0.998 | -0.002 |
| QN | CAAAAT | 1720.47 | 2394 | 1.391 | 0.330 |
| QN | CAGAGC | 5291.34 | 5195 | 0.982 | -0.018 |
| QN | CAGAAT | 4804.30 | 4430 | 0.922 | -0.081 |
| QN | CAAAGC | 1894.89 | 1692 | 0.893 | -0.113 |
| QP | CAGCCG | 1816.66 | 2237 | 1.231 | 0.208 |
| QP | CAGCCC | 5013.75 | 6143 | 1.225 | 0.203 |
| QP | CAGCCT | 4490.51 | 4526 | 1.008 | 0.008 |
| QP | CAGCCA | 4333.91 | 4235 | 0.977 | -0.023 |
| QP | CAACCA | 1552.02 | 1441 | 0.928 | -0.074 |
| QP | CAACCT | 1608.10 | 1304 | 0.811 | -0.210 |
| QP | CAACCC | 1795.48 | 1132 | 0.630 | -0.461 |
| QP | CAACCG | 650.57 | 243 | 0.374 | -0.985 |
| QQ | CAACCA | 1545.49 | 1866 | 1.207 | 0.188 |
| QQ | CAGCAG | 12051.19 | 13131 | 1.090 | 0.086 |
| QQ | CAGCCA | 4315.66 | 4034 | 0.935 | -0.067 |
| QQ | CAACAG | 4315.66 | 3197 | 0.741 | -0.300 |
| QR | CAAAGA | 1214.45 | 1863 | 1.534 | 0.428 |
| QR | CAGAGG | 3329.32 | 4331 | 1.301 | 0.263 |
| QR | CAAAGG | 1192.27 | 1360 | 1.141 | 0.132 |
| QR | CAGAGA | 3391.27 | 3777 | 1.114 | 0.108 |
| QR | CAGCGC | 3074.54 | 3169 | 1.031 | 0.030 |
| QR | CAGCGG | 3362.63 | 3352 | 0.997 | -0.003 |
| QR | CAGCGT | 1316.32 | 1215 | 0.923 | -0.080 |
| QR | CAGCGA | 1822.82 | 1469 | 0.806 | -0.216 |
| QR | CAACGT | 471.39 | 327 | 0.694 | -0.366 |
| QR | CAACGA | 652.77 | 413 | 0.633 | -0.458 |
| QR | CAACGG | 1204.20 | 453 | 0.376 | -0.978 |
| QR | CAACGC | 1101.03 | 404 | 0.367 | -1.003 |
| QS | CAAAGT | 904.91 | 1408 | 1.556 | 0.442 |
| QS | CAGAGC | 4005.17 | 5248 | 1.310 | 0.270 |
| QS | CAGAGT | 2526.89 | 2963 | 1.173 | 0.159 |
| QS | CAAAGC | 1434.30 | 1465 | 1.021 | 0.021 |
| QS | CAGTCG | 934.84 | 923 | 0.987 | -0.013 |
| QS | CAGTCA | 2486.15 | 2379 | 0.957 | -0.044 |
| QS | CAGTCT | 3075.24 | 2806 | 0.912 | -0.092 |
| QS | CAATCA | 890.32 | 781 | 0.877 | -0.131 |
| QS | CAGTCC | 3535.16 | 3051 | 0.863 | -0.147 |
| QS | CAATCT | 1101.28 | 765 | 0.695 | -0.364 |
| QS | CAATCC | 1265.98 | 587 | 0.464 | -0.769 |
| QS | CAATCG | 334.78 | 119 | 0.355 | -1.034 |
| QT | CAAACT | 1116.05 | 1463 | 1.311 | 0.271 |
| QT | CAAACA | 1262.03 | 1602 | 1.269 | 0.239 |
| QT | CAGACG | 1430.02 | 1665 | 1.164 | 0.152 |
| QT | CAGACC | 4353.25 | 4301 | 0.988 | -0.012 |
| QT | CAGACA | 3524.12 | 3445 | 0.978 | -0.023 |
| QT | CAGACT | 3116.48 | 2792 | 0.896 | -0.110 |
| QT | CAAACC | 1558.95 | 1232 | 0.790 | -0.235 |
| QT | CAAACG | 512.11 | 373 | 0.728 | -0.317 |
| QV | CAAGTA | 657.01 | 1210 | 1.842 | 0.611 |
| QV | CAAGTT | 1011.82 | 1737 | 1.717 | 0.540 |
| QV | CAAGTC | 1295.45 | 1468 | 1.133 | 0.125 |
| QV | CAAGTG | 2562.79 | 2712 | 1.058 | 0.057 |
| QV | CAGGTG | 7156.41 | 7062 | 0.987 | -0.013 |
| QV | CAGGTC | 3617.45 | 3213 | 0.888 | -0.119 |
| QV | CAGGTT | 2825.43 | 2269 | 0.803 | -0.219 |
| QV | CAGGTA | 1834.65 | 1290 | 0.703 | -0.352 |
| QW | CAGTGG | 3057.92 | 3447 | 1.127 | 0.120 |
| QW | CAATGG | 1095.08 | 706 | 0.645 | -0.439 |
| QY | CAATAT | 1029.01 | 1120 | 1.088 | 0.085 |
| QY | CAGTAC | 3536.21 | 3820 | 1.080 | 0.077 |
| QY | CAGTAT | 2873.43 | 2979 | 1.037 | 0.036 |
| QY | CAATAC | 1266.36 | 786 | 0.621 | -0.477 |
| RA | CGGGCG | 659.18 | 1185 | 1.798 | 0.587 |
| RA | CGGGCC | 2437.97 | 3513 | 1.441 | 0.365 |
| RA | AGAGCA | 1415.51 | 1970 | 1.392 | 0.331 |
| RA | CGCGCG | 602.71 | 827 | 1.372 | 0.316 |
| RA | CGTGCC | 954.35 | 1266 | 1.327 | 0.283 |
| RA | CGAGCA | 760.84 | 970 | 1.275 | 0.243 |
| RA | CGAGCT | 869.13 | 1108 | 1.275 | 0.243 |

Supplemental Table 1

Expected and Observed Codon Pair Frequencies and Codon Pair Scores for 14,795 Human Genes

| amino acid pair | codon pair | expected | observed | observed/expected | CPS |
|---|---|---|---|---|---|
| RA | CGAGCC | 1321.57 | 1595 | 1.207 | 0.188 |
| RA | AGAGCT | 1616.99 | 1949 | 1.205 | 0.187 |
| RA | CGTGCT | 627.63 | 744 | 1.185 | 0.170 |
| RA | CGGGCA | 1403.55 | 1612 | 1.149 | 0.138 |
| RA | CGTGCA | 549.43 | 570 | 1.037 | 0.037 |
| RA | CGTGCG | 258.04 | 250 | 0.969 | -0.032 |
| RA | CGAGCG | 357.33 | 341 | 0.954 | -0.047 |
| RA | AGGGCC | 2413.81 | 2173 | 0.900 | -0.105 |
| RA | AGAGCC | 2458.73 | 2202 | 0.896 | -0.110 |
| RA | CGGGCT | 1603.33 | 1435 | 0.895 | -0.111 |
| RA | AGGGCA | 1389.65 | 1242 | 0.894 | -0.112 |
| RA | AGGGCT | 1587.45 | 1311 | 0.826 | -0.191 |
| RA | AGGGCG | 652.65 | 524 | 0.803 | -0.220 |
| RA | CGCGCC | 2229.09 | 1712 | 0.768 | -0.264 |
| RA | AGAGCG | 664.79 | 384 | 0.578 | -0.549 |
| RA | CGCGCA | 1283.30 | 331 | 0.258 | -1.355 |
| RA | CGCGCT | 1465.97 | 369 | 0.252 | -1.379 |
| RC | CGCTGC | 986.26 | 2873 | 2.913 | 1.069 |
| RC | CGCTGT | 830.71 | 1313 | 1.581 | 0.458 |
| RC | CGTTGT | 355.66 | 320 | 0.900 | -0.106 |
| RC | CGTTGC | 422.25 | 372 | 0.881 | -0.127 |
| RC | AGATGT | 916.29 | 806 | 0.880 | -0.128 |
| RC | CGATGT | 492.51 | 421 | 0.855 | -0.157 |
| RC | AGGTGT | 899.55 | 671 | 0.746 | -0.293 |
| RC | AGGTGC | 1067.99 | 758 | 0.710 | -0.343 |
| RC | CGATGC | 584.73 | 381 | 0.652 | -0.428 |
| RC | CGGTGC | 1078.67 | 660 | 0.612 | -0.491 |
| RC | AGATGC | 1087.86 | 642 | 0.590 | -0.527 |
| RC | CGGTGT | 908.55 | 414 | 0.456 | -0.786 |
| RD | AGAGAT | 2027.66 | 2952 | 1.456 | 0.376 |
| RD | CGGGAC | 2271.13 | 3231 | 1.423 | 0.353 |
| RD | CGAGAT | 1089.87 | 1500 | 1.376 | 0.319 |
| RD | CGAGAC | 1231.14 | 1693 | 1.375 | 0.319 |
| RD | CGTGAC | 889.05 | 1044 | 1.174 | 0.161 |
| RD | AGAGAC | 2290.48 | 2433 | 1.062 | 0.060 |
| RD | CGTGAT | 787.04 | 833 | 1.058 | 0.057 |
| RD | AGGGAC | 2248.63 | 2322 | 1.033 | 0.032 |
| RD | AGGGAT | 1990.62 | 1732 | 0.870 | -0.139 |
| RD | CGGGAT | 2010.54 | 1606 | 0.799 | -0.225 |
| RD | CGCGAC | 2076.56 | 1092 | 0.526 | -0.643 |
| RD | CGCGAT | 1838.29 | 313 | 0.170 | -1.770 |
| RE | AGAGAA | 2644.21 | 4195 | 1.586 | 0.462 |
| RE | CGGGAG | 3506.29 | 5344 | 1.524 | 0.421 |
| RE | CGAGAG | 1900.69 | 2475 | 1.302 | 0.264 |
| RE | CGAGAA | 1421.27 | 1844 | 1.297 | 0.260 |
| RE | CGTGAG | 1372.55 | 1453 | 1.059 | 0.057 |
| RE | AGGGAG | 3471.55 | 3469 | 0.999 | -0.001 |
| RE | AGAGAG | 3536.15 | 3392 | 0.959 | -0.042 |
| RE | CGTGAA | 1026.35 | 947 | 0.923 | -0.080 |
| RE | AGGGAA | 2595.91 | 2343 | 0.903 | -0.103 |
| RE | CGGGAA | 2621.88 | 2131 | 0.813 | -0.207 |
| RE | CGCGAG | 3205.89 | 1839 | 0.574 | -0.556 |
| RE | CGCGAA | 2397.25 | 268 | 0.112 | -2.191 |
| RF | CGCTTC | 1446.49 | 3411 | 2.358 | 0.858 |
| RF | CGTTTC | 619.29 | 823 | 1.329 | 0.284 |
| RF | CGTTTT | 541.07 | 705 | 1.303 | 0.265 |
| RF | AGATTT | 1393.96 | 1531 | 1.098 | 0.094 |
| RF | CGCTTT | 1263.77 | 1366 | 1.081 | 0.078 |
| RF | CGATTT | 749.26 | 772 | 1.030 | 0.030 |
| RF | AGGTTT | 1368.50 | 1295 | 0.946 | -0.055 |
| RF | AGGTTC | 1566.36 | 1192 | 0.761 | -0.273 |
| RF | CGATTC | 857.59 | 632 | 0.737 | -0.305 |
| RF | CGGTTC | 1582.03 | 951 | 0.601 | -0.509 |
| RF | AGATTC | 1595.50 | 944 | 0.592 | -0.525 |
| RF | CGGTTT | 1382.19 | 744 | 0.538 | -0.619 |
| RG | CGTGGT | 370.38 | 685 | 1.849 | 0.615 |
| RG | CGTGGG | 558.50 | 980 | 1.755 | 0.562 |
| RG | CGTGGC | 775.66 | 1315 | 1.695 | 0.528 |
| RG | CGAGGA | 792.21 | 1266 | 1.598 | 0.469 |
| RG | CGAGGG | 773.39 | 1219 | 1.576 | 0.455 |

Supplemental Table 1

Expected and Observed Codon Pair Frequencies and Codon Pair Scores for 14,795 Human Genes

| amino acid pair | codon pair | expected | observed | observed/expected | CPS |
|---|---|---|---|---|---|
| RG | AGAGGA | 1473.87 | 2281 | 1.548 | 0.437 |
| RG | CGAGGT | 512.89 | 789 | 1.538 | 0.431 |
| RG | CGGGGC | 1981.48 | 2952 | 1.490 | 0.399 |
| RG | CGTGGA | 572.08 | 844 | 1.475 | 0.389 |
| RG | CGAGGC | 1074.12 | 1569 | 1.461 | 0.379 |
| RG | AGAGGT | 954.21 | 1128 | 1.182 | 0.167 |
| RG | CGGGGT | 946.15 | 918 | 0.970 | -0.030 |
| RG | CGCGGC | 1811.72 | 1574 | 0.869 | -0.141 |
| RG | AGGGGC | 1961.86 | 1660 | 0.846 | -0.167 |
| RG | AGAGGC | 1998.36 | 1680 | 0.841 | -0.174 |
| RG | AGAGGG | 1438.87 | 1203 | 0.836 | -0.179 |
| RG | AGGGGT | 936.78 | 777 | 0.829 | -0.187 |
| RG | CGGGGG | 1426.72 | 1146 | 0.803 | -0.219 |
| RG | CGGGGA | 1461.42 | 1140 | 0.780 | -0.248 |
| RG | CGCGGG | 1304.48 | 904 | 0.693 | -0.367 |
| RG | AGGGGA | 1446.94 | 923 | 0.638 | -0.450 |
| RG | AGGGGG | 1412.58 | 683 | 0.484 | -0.727 |
| RG | CGCGGT | 865.09 | 248 | 0.287 | -1.249 |
| RG | CGCGGA | 1336.22 | 302 | 0.226 | -1.487 |
| RH | CGCCAC | 1288.00 | 1861 | 1.445 | 0.368 |
| RH | CGGCAC | 1408.69 | 1707 | 1.212 | 0.192 |
| RH | AGACAT | 1030.24 | 1201 | 1.166 | 0.153 |
| RH | CGTCAT | 399.89 | 447 | 1.118 | 0.111 |
| RH | AGGCAT | 1011.41 | 988 | 0.977 | -0.023 |
| RH | CGACAT | 553.75 | 530 | 0.957 | -0.044 |
| RH | AGGCAC | 1394.73 | 1292 | 0.926 | -0.077 |
| RH | AGACAC | 1420.69 | 1212 | 0.853 | -0.159 |
| RH | CGTCAC | 551.44 | 468 | 0.849 | -0.164 |
| RH | CGACAC | 763.62 | 614 | 0.804 | -0.218 |
| RH | CGCCAT | 934.02 | 728 | 0.779 | -0.249 |
| RH | CGGCAT | 1021.53 | 730 | 0.715 | -0.336 |
| RI | CGCATC | 1625.56 | 2948 | 1.814 | 0.595 |
| RI | AGAATA | 652.11 | 1175 | 1.802 | 0.589 |
| RI | AGAATT | 1417.90 | 2185 | 1.541 | 0.432 |
| RI | AGGATA | 640.20 | 804 | 1.256 | 0.228 |
| RI | CGAATA | 350.51 | 439 | 1.252 | 0.225 |
| RI | CGAATT | 762.13 | 850 | 1.115 | 0.109 |
| RI | AGGATT | 1392.00 | 1366 | 0.981 | -0.019 |
| RI | AGGATC | 1760.27 | 1662 | 0.944 | -0.057 |
| RI | CGAATC | 963.75 | 802 | 0.832 | -0.184 |
| RI | CGGATC | 1777.88 | 1479 | 0.832 | -0.184 |
| RI | AGAATC | 1793.03 | 1389 | 0.775 | -0.255 |
| RI | CGTATT | 550.36 | 408 | 0.741 | -0.299 |
| RI | CGCATT | 1285.48 | 913 | 0.710 | -0.342 |
| RI | CGGATA | 646.60 | 451 | 0.697 | -0.360 |
| RI | CGTATC | 695.96 | 440 | 0.632 | -0.459 |
| RI | CGTATA | 253.12 | 152 | 0.601 | -0.510 |
| RI | CGGATT | 1405.93 | 825 | 0.587 | -0.533 |
| RI | CGCATA | 591.21 | 276 | 0.467 | -0.762 |
| RK | AGGAAG | 3199.71 | 4856 | 1.518 | 0.417 |
| RK | AGGAAA | 2470.61 | 3737 | 1.513 | 0.414 |
| RK | AGAAAA | 2516.58 | 3482 | 1.384 | 0.325 |
| RK | CGCAAG | 2954.85 | 2981 | 1.009 | 0.009 |
| RK | CGGAAG | 3231.73 | 3225 | 0.998 | -0.002 |
| RK | AGAAAG | 3259.25 | 2909 | 0.893 | -0.114 |
| RK | CGAAAA | 1352.67 | 1189 | 0.879 | -0.129 |
| RK | CGGAAA | 2495.33 | 1834 | 0.735 | -0.308 |
| RK | CGAAAG | 1751.85 | 1265 | 0.722 | -0.326 |
| RK | CGTAAA | 976.81 | 566 | 0.579 | -0.546 |
| RK | CGCAAA | 2281.54 | 1209 | 0.530 | -0.635 |
| RK | CGTAAG | 1265.08 | 503 | 0.398 | -0.922 |
| RL | CGCCTC | 1491.12 | 2511 | 1.684 | 0.521 |
| RL | CGCCTG | 3098.73 | 4809 | 1.552 | 0.439 |
| RL | CGGCTG | 3389.08 | 5029 | 1.484 | 0.395 |
| RL | CGGCTC | 1630.84 | 2301 | 1.411 | 0.344 |
| RL | CGTTTA | 256.76 | 337 | 1.313 | 0.272 |
| RL | AGATTA | 661.49 | 862 | 1.303 | 0.265 |
| RL | CGTCTT | 440.20 | 562 | 1.277 | 0.244 |
| RL | CGTCTA | 237.40 | 296 | 1.247 | 0.221 |
| RL | CGTTTG | 431.33 | 526 | 1.219 | 0.198 |

Supplemental Table 1

Expected and Observed Codon Pair Frequencies and Codon Pair Scores for 14,795 Human Genes

| amino acid pair | codon pair | expected | observed | observed/expected | CPS |
|---|---|---|---|---|---|
| RL | CGTCTC | 638.40 | 723 | 1.133 | 0.124 |
| RL | AGGCTA | 600.44 | 669 | 1.114 | 0.108 |
| RL | AGACTT | 1134.11 | 1227 | 1.082 | 0.079 |
| RL | AGGCTG | 3355.51 | 3531 | 1.052 | 0.051 |
| RL | AGACTA | 611.62 | 617 | 1.009 | 0.009 |
| RL | AGGCTT | 1113.39 | 1104 | 0.992 | -0.008 |
| RL | CGACTA | 328.75 | 324 | 0.986 | -0.015 |
| RL | CGGCTA | 606.45 | 593 | 0.978 | -0.022 |
| RL | CGTCTG | 1326.68 | 1281 | 0.966 | -0.035 |
| RL | AGGCTC | 1614.68 | 1540 | 0.954 | -0.047 |
| RL | CGATTA | 355.55 | 337 | 0.948 | -0.054 |
| RL | CGACTT | 609.59 | 576 | 0.945 | -0.057 |
| RL | CGCCTA | 554.49 | 501 | 0.904 | -0.101 |
| RL | AGGTTA | 649.40 | 586 | 0.902 | -0.103 |
| RL | CGCCTT | 1028.19 | 862 | 0.838 | -0.176 |
| RL | CGCTTG | 1007.46 | 804 | 0.798 | -0.226 |
| RL | CGGCTT | 1124.53 | 866 | 0.770 | -0.261 |
| RL | AGATTG | 1111.24 | 839 | 0.755 | -0.281 |
| RL | CGACTC | 884.04 | 663 | 0.750 | -0.288 |
| RL | AGGTTG | 1090.94 | 774 | 0.709 | -0.343 |
| RL | AGACTC | 1644.73 | 1142 | 0.694 | -0.365 |
| RL | CGATTG | 597.29 | 408 | 0.683 | -0.381 |
| RL | CGACTG | 1837.15 | 1128 | 0.614 | -0.488 |
| RL | CGCTTA | 599.71 | 345 | 0.575 | -0.553 |
| RL | CGGTTG | 1101.86 | 566 | 0.514 | -0.666 |
| RL | AGACTG | 3417.95 | 1701 | 0.498 | -0.698 |
| RL | CGGTTA | 655.90 | 297 | 0.453 | -0.792 |
| RM | CGCATG | 1558.32 | 1961 | 1.258 | 0.230 |
| RM | AGGATG | 1687.45 | 1974 | 1.170 | 0.157 |
| RM | CGAATG | 923.88 | 932 | 1.009 | 0.009 |
| RM | AGAATG | 1718.85 | 1690 | 0.983 | -0.017 |
| RM | CGGATG | 1704.33 | 1374 | 0.806 | -0.215 |
| RM | CGTATG | 667.17 | 329 | 0.493 | -0.707 |
| RN | AGAAAT | 1568.88 | 2627 | 1.674 | 0.515 |
| RN | AGGAAC | 1696.37 | 2200 | 1.297 | 0.260 |
| RN | AGGAAT | 1540.22 | 1796 | 1.166 | 0.154 |
| RN | AGAAAC | 1727.93 | 1949 | 1.128 | 0.120 |
| RN | CGAAAT | 843.28 | 930 | 1.103 | 0.098 |
| RN | CGCAAC | 1566.55 | 1575 | 1.005 | 0.005 |
| RN | CGGAAC | 1713.34 | 1621 | 0.946 | -0.055 |
| RN | CGAAAC | 928.77 | 784 | 0.844 | -0.169 |
| RN | CGGAAT | 1555.63 | 1002 | 0.644 | -0.440 |
| RN | CGTAAT | 608.96 | 340 | 0.558 | -0.583 |
| RN | CGCAAT | 1422.36 | 711 | 0.500 | -0.693 |
| RN | CGTAAC | 670.70 | 308 | 0.459 | -0.778 |
| RP | CGGCCG | 587.88 | 1226 | 2.085 | 0.735 |
| RP | CGGCCC | 1622.47 | 2939 | 1.811 | 0.594 |
| RP | CGCCCG | 537.51 | 717 | 1.334 | 0.288 |
| RP | AGGCCC | 1606.39 | 1982 | 1.234 | 0.210 |
| RP | AGGCCG | 582.05 | 666 | 1.144 | 0.135 |
| RP | AGGCCT | 1438.75 | 1642 | 1.141 | 0.132 |
| RP | AGGCCA | 1388.57 | 1511 | 1.088 | 0.084 |
| RP | CGTCCT | 568.84 | 589 | 1.035 | 0.035 |
| RP | AGACCA | 1414.41 | 1387 | 0.981 | -0.020 |
| RP | CGGCCT | 1453.14 | 1390 | 0.957 | -0.044 |
| RP | AGACCT | 1465.52 | 1398 | 0.954 | -0.047 |
| RP | CGTCCC | 635.12 | 582 | 0.916 | -0.087 |
| RP | CGGCCA | 1402.47 | 1285 | 0.916 | -0.087 |
| RP | CGCCCC | 1483.46 | 1320 | 0.890 | -0.117 |
| RP | CGTCCA | 549.00 | 487 | 0.887 | -0.120 |
| RP | AGACCC | 1636.29 | 1283 | 0.784 | -0.243 |
| RP | CGACCA | 760.25 | 591 | 0.777 | -0.252 |
| RP | CGACCC | 879.51 | 671 | 0.763 | -0.271 |
| RP | CGACCT | 787.72 | 580 | 0.736 | -0.306 |
| RP | CGCCCA | 1282.31 | 887 | 0.692 | -0.369 |
| RP | CGTCCG | 230.13 | 159 | 0.691 | -0.370 |
| RP | CGCCCT | 1328.65 | 830 | 0.625 | -0.470 |
| RP | CGACCG | 318.68 | 184 | 0.577 | -0.549 |
| RP | AGACCG | 592.88 | 246 | 0.415 | -0.880 |
| RQ | AGACAA | 1054.78 | 1456 | 1.380 | 0.322 |

Supplemental Table 1

Expected and Observed Codon Pair Frequencies and Codon Pair Scores for 14,795 Human Genes

| amino acid pair | codon pair | expected | observed | observed/expected | CPS |
|---|---|---|---|---|---|
| RQ | CGGCAG | 2920.52 | 3950 | 1.352 | 0.302 |
| RQ | CGCCAG | 2670.31 | 3160 | 1.183 | 0.168 |
| RQ | AGGCAA | 1035.51 | 1177 | 1.137 | 0.128 |
| RQ | AGGCAG | 2891.59 | 3013 | 1.042 | 0.041 |
| RQ | CGACAA | 566.95 | 522 | 0.921 | -0.083 |
| RQ | CGTCAG | 1143.25 | 953 | 0.834 | -0.182 |
| RQ | CGTCAA | 409.41 | 327 | 0.799 | -0.225 |
| RQ | CGACAG | 1583.16 | 1249 | 0.789 | -0.237 |
| RQ | CGGCAA | 1045.87 | 763 | 0.730 | -0.315 |
| RQ | AGACAG | 2945.39 | 2062 | 0.700 | -0.357 |
| RQ | CGCCAA | 956.27 | 591 | 0.618 | -0.481 |
| RR | CGCCGC | 1172.08 | 2232 | 1.904 | 0.644 |
| RR | CGGCGG | 1402.02 | 2316 | 1.652 | 0.502 |
| RR | AGAAGA | 1426.00 | 2307 | 1.618 | 0.481 |
| RR | CGGCGC | 1281.90 | 2064 | 1.610 | 0.476 |
| RR | AGGAGG | 1374.38 | 1973 | 1.436 | 0.362 |
| RR | CGCCGG | 1281.90 | 1679 | 1.310 | 0.270 |
| RR | CGAAGA | 766.48 | 987 | 1.288 | 0.253 |
| RR | AGGAGA | 1399.95 | 1758 | 1.256 | 0.228 |
| RR | CGCAGG | 1269.20 | 1565 | 1.233 | 0.209 |
| RR | CGGAGG | 1388.13 | 1670 | 1.203 | 0.185 |
| RR | CGTCGT | 214.84 | 228 | 1.061 | 0.059 |
| RR | CGAAGG | 752.48 | 770 | 1.023 | 0.023 |
| RR | CGCCGT | 501.81 | 502 | 1.000 | 0.000 |
| RR | AGAAGG | 1399.95 | 1325 | 0.946 | -0.055 |
| RR | CGGCGT | 548.83 | 498 | 0.907 | -0.097 |
| RR | CGTCGA | 297.51 | 265 | 0.891 | -0.116 |
| RR | CGGCGA | 760.01 | 675 | 0.888 | -0.119 |
| RR | CGTCGC | 501.81 | 438 | 0.873 | -0.136 |
| RR | AGGCGG | 1388.13 | 1177 | 0.848 | -0.165 |
| RR | CGTCGG | 548.83 | 450 | 0.820 | -0.199 |
| RR | CGACGT | 297.51 | 241 | 0.810 | -0.211 |
| RR | CGCCGA | 694.89 | 547 | 0.787 | -0.239 |
| RR | AGGCGA | 752.48 | 570 | 0.757 | -0.278 |
| RR | CGGAGA | 1413.96 | 1068 | 0.755 | -0.281 |
| RR | AGACGA | 766.48 | 557 | 0.727 | -0.319 |
| RR | AGGCGT | 543.39 | 383 | 0.705 | -0.350 |
| RR | AGGCGC | 1269.20 | 889 | 0.700 | -0.356 |
| RR | AGACGT | 553.50 | 376 | 0.679 | -0.387 |
| RR | CGACGA | 411.98 | 272 | 0.660 | -0.415 |
| RR | CGCAGA | 1292.82 | 771 | 0.596 | -0.517 |
| RR | CGACGG | 760.01 | 411 | 0.541 | -0.615 |
| RR | CGACGC | 694.89 | 368 | 0.530 | -0.636 |
| RR | CGTAGA | 553.50 | 271 | 0.490 | -0.714 |
| RR | CGTAGG | 543.39 | 235 | 0.432 | -0.838 |
| RR | AGACGC | 1292.82 | 524 | 0.405 | -0.903 |
| RR | AGACGG | 1413.96 | 569 | 0.402 | -0.910 |
| RS | CGCTCG | 332.61 | 817 | 2.456 | 0.899 |
| RS | CGCAGC | 1425.00 | 2853 | 2.002 | 0.694 |
| RS | CGCTCC | 1257.78 | 2184 | 1.736 | 0.552 |
| RS | AGAAGT | 991.66 | 1532 | 1.545 | 0.435 |
| RS | CGTTCT | 468.44 | 687 | 1.467 | 0.383 |
| RS | CGAAGT | 533.02 | 728 | 1.366 | 0.312 |
| RS | CGTTCC | 538.50 | 707 | 1.313 | 0.272 |
| RS | AGGAGC | 1543.09 | 1992 | 1.291 | 0.255 |
| RS | CGTTCA | 378.71 | 471 | 1.244 | 0.218 |
| RS | CGGAGC | 1558.53 | 1856 | 1.191 | 0.175 |
| RS | AGGAGT | 973.54 | 1071 | 1.100 | 0.095 |
| RS | AGAAGC | 1571.80 | 1628 | 1.036 | 0.035 |
| RS | AGATCA | 975.67 | 1000 | 1.025 | 0.025 |
| RS | CGAAGC | 844.85 | 859 | 1.017 | 0.017 |
| RS | CGCTCA | 884.55 | 860 | 0.972 | -0.028 |
| RS | CGCAGT | 899.04 | 853 | 0.949 | -0.053 |
| RS | AGATCT | 1206.86 | 1106 | 0.916 | -0.087 |
| RS | CGCTCT | 1094.14 | 942 | 0.861 | -0.150 |
| RS | CGTTCG | 142.40 | 121 | 0.850 | -0.163 |
| RS | AGGTCA | 957.85 | 808 | 0.844 | -0.170 |
| RS | CGATCA | 524.43 | 416 | 0.793 | -0.232 |
| RS | AGGTCT | 1184.81 | 939 | 0.793 | -0.233 |
| RS | AGGTCG | 360.17 | 284 | 0.789 | -0.238 |

Supplemental Table 1

Expected and Observed Codon Pair Frequencies and Codon Pair Scores for 14,795 Human Genes

| amino acid pair | codon pair | expected | observed | observed/expected | CPS |
|---|---|---|---|---|---|
| RS | CGATCT | 648.69 | 497 | 0.766 | −0.266 |
| RS | AGGTCC | 1362.00 | 1036 | 0.761 | −0.274 |
| RS | CGGAGT | 983.28 | 745 | 0.758 | −0.278 |
| RS | CGTAGT | 384.91 | 278 | 0.722 | −0.325 |
| RS | CGGTCG | 363.77 | 235 | 0.646 | −0.437 |
| RS | CGATCC | 745.70 | 455 | 0.610 | −0.494 |
| RS | AGATCC | 1387.35 | 830 | 0.598 | −0.514 |
| RS | CGGTCC | 1375.63 | 821 | 0.597 | −0.516 |
| RS | CGATCG | 197.19 | 107 | 0.543 | −0.611 |
| RS | CGGTCA | 967.43 | 507 | 0.524 | −0.646 |
| RS | CGTAGC | 610.09 | 317 | 0.520 | −0.655 |
| RS | AGATCG | 366.87 | 177 | 0.482 | −0.729 |
| RS | CGGTCT | 1196.66 | 518 | 0.433 | −0.837 |
| RT | CGCACG | 450.78 | 858 | 1.903 | 0.644 |
| RT | AGAACT | 1083.61 | 1467 | 1.354 | 0.303 |
| RT | CGCACC | 1372.27 | 1821 | 1.327 | 0.283 |
| RT | AGGACG | 488.14 | 646 | 1.323 | 0.280 |
| RT | AGGACT | 1063.81 | 1389 | 1.306 | 0.267 |
| RT | AGAACA | 1225.34 | 1575 | 1.285 | 0.251 |
| RT | AGGACA | 1202.96 | 1523 | 1.266 | 0.236 |
| RT | AGGACC | 1485.98 | 1773 | 1.193 | 0.177 |
| RT | CGGACG | 493.02 | 537 | 1.089 | 0.085 |
| RT | CGAACA | 658.62 | 661 | 1.004 | 0.004 |
| RT | CGAACT | 582.44 | 556 | 0.955 | −0.046 |
| RT | CGGACC | 1500.85 | 1408 | 0.938 | −0.064 |
| RT | CGCACA | 1110.90 | 984 | 0.886 | −0.121 |
| RT | CGGACA | 1215.00 | 949 | 0.781 | −0.247 |
| RT | AGAACC | 1513.63 | 1166 | 0.770 | −0.261 |
| RT | CGTACT | 420.60 | 313 | 0.744 | −0.295 |
| RT | CGAACC | 813.58 | 599 | 0.736 | −0.306 |
| RT | CGGACT | 1074.45 | 712 | 0.663 | −0.411 |
| RT | CGCACT | 982.40 | 638 | 0.649 | −0.432 |
| RT | CGTACC | 587.52 | 361 | 0.614 | −0.487 |
| RT | AGAACG | 497.22 | 302 | 0.607 | −0.499 |
| RT | CGTACA | 475.62 | 288 | 0.606 | −0.502 |
| RT | CGAACG | 267.26 | 154 | 0.576 | −0.551 |
| RT | CGTACG | 193.00 | 79 | 0.409 | −0.893 |
| RV | CGTGTG | 889.90 | 1699 | 1.909 | 0.647 |
| RV | CGTGTC | 449.83 | 826 | 1.836 | 0.608 |
| RV | CGAGTA | 315.92 | 562 | 1.779 | 0.576 |
| RV | CGTGTA | 228.14 | 391 | 1.714 | 0.539 |
| RV | CGTGTT | 351.34 | 565 | 1.608 | 0.475 |
| RV | AGAGTT | 905.17 | 1350 | 1.491 | 0.400 |
| RV | AGAGTA | 587.76 | 876 | 1.490 | 0.399 |
| RV | CGAGTC | 622.91 | 914 | 1.467 | 0.383 |
| RV | CGAGTT | 486.53 | 681 | 1.400 | 0.336 |
| RV | CGAGTG | 1232.31 | 1576 | 1.279 | 0.246 |
| RV | CGGGTC | 1149.12 | 1310 | 1.140 | 0.131 |
| RV | AGGGTC | 1137.73 | 1221 | 1.073 | 0.071 |
| RV | CGGGTG | 2273.30 | 2328 | 1.024 | 0.024 |
| RV | AGAGTC | 1158.91 | 1154 | 0.996 | −0.004 |
| RV | CGCGTG | 2078.54 | 1725 | 0.830 | −0.186 |
| RV | AGGGTA | 577.02 | 471 | 0.816 | −0.203 |
| RV | AGAGTG | 2292.67 | 1750 | 0.763 | −0.270 |
| RV | CGGGTA | 582.79 | 438 | 0.752 | −0.286 |
| RV | AGGGTG | 2250.78 | 1658 | 0.737 | −0.306 |
| RV | CGCGTC | 1050.67 | 763 | 0.726 | −0.320 |
| RV | AGGGTT | 888.63 | 645 | 0.726 | −0.320 |
| RV | CGGGTT | 897.52 | 548 | 0.611 | −0.493 |
| RV | CGCGTA | 532.86 | 132 | 0.248 | −1.395 |
| RV | CGCGTT | 820.63 | 178 | 0.217 | −1.528 |
| RW | CGCTGG | 1038.00 | 2199 | 2.118 | 0.751 |
| RW | CGTTGG | 444.40 | 380 | 0.855 | −0.157 |
| RW | AGGTGG | 1124.01 | 876 | 0.779 | −0.249 |
| RW | CGATGG | 615.40 | 466 | 0.757 | −0.278 |
| RW | AGATGG | 1144.93 | 804 | 0.702 | −0.353 |
| RW | CGGTGG | 1135.26 | 777 | 0.684 | −0.379 |
| RY | CGCTAC | 1173.12 | 2612 | 2.227 | 0.800 |
| RY | CGCTAT | 953.25 | 1198 | 1.257 | 0.229 |
| RY | CGTTAC | 502.25 | 565 | 1.125 | 0.118 |

Supplemental Table 1

Expected and Observed Codon Pair Frequencies and Codon Pair Scores for 14,795 Human Genes

| amino acid pair | codon pair | expected | observed | observed/expected | CPS |
|---|---|---|---|---|---|
| RY | CGTTAT | 408.12 | 459 | 1.125 | 0.117 |
| RY | AGATAT | 1051.45 | 1018 | 0.968 | -0.032 |
| RY | AGATAC | 1293.97 | 1239 | 0.958 | -0.043 |
| RY | CGATAT | 565.15 | 509 | 0.901 | -0.105 |
| RY | CGATAC | 695.51 | 584 | 0.840 | -0.175 |
| RY | AGGTAC | 1270.33 | 1007 | 0.793 | -0.232 |
| RY | AGGTAT | 1032.24 | 769 | 0.745 | -0.294 |
| RY | CGGTAC | 1283.04 | 856 | 0.667 | -0.405 |
| RY | CGGTAT | 1042.57 | 455 | 0.436 | -0.829 |
| SA | TCGGCG | 241.39 | 778 | 3.223 | 1.170 |
| SA | TCGGCC | 892.76 | 1976 | 2.213 | 0.795 |
| SA | TCAGCA | 1366.87 | 2526 | 1.848 | 0.614 |
| SA | TCTGCA | 1690.75 | 3035 | 1.795 | 0.585 |
| SA | TCTGCT | 1931.41 | 3350 | 1.734 | 0.551 |
| SA | TCAGCT | 1561.43 | 2630 | 1.684 | 0.521 |
| SA | AGTGCT | 1587.01 | 2487 | 1.567 | 0.449 |
| SA | AGTGCA | 1389.27 | 2040 | 1.468 | 0.384 |
| SA | AGTGCC | 2413.15 | 3437 | 1.424 | 0.354 |
| SA | TCAGCC | 2374.25 | 3294 | 1.387 | 0.327 |
| SA | TCGGCT | 587.12 | 808 | 1.376 | 0.319 |
| SA | TCTGCC | 2936.83 | 3480 | 1.185 | 0.170 |
| SA | TCGGCA | 513.97 | 598 | 1.163 | 0.151 |
| SA | TCTGCG | 794.06 | 745 | 0.938 | -0.064 |
| SA | TCAGCG | 641.95 | 584 | 0.910 | -0.095 |
| SA | AGTGCG | 652.47 | 532 | 0.815 | -0.204 |
| SA | AGCGCG | 1034.18 | 802 | 0.775 | -0.254 |
| SA | AGCGCC | 3824.90 | 2428 | 0.635 | -0.454 |
| SA | TCCGCG | 912.82 | 577 | 0.632 | -0.459 |
| SA | TCCGCC | 3376.05 | 1230 | 0.364 | -1.010 |
| SA | AGCGCT | 2515.45 | 709 | 0.282 | -1.266 |
| SA | AGCGCA | 2202.02 | 601 | 0.273 | -1.299 |
| SA | TCCGCA | 1943.61 | 476 | 0.245 | -1.407 |
| SA | TCCGCT | 2220.26 | 481 | 0.217 | -1.530 |
| SC | TCCTGC | 1640.34 | 2828 | 1.724 | 0.545 |
| SC | AGCTGC | 1858.43 | 3034 | 1.633 | 0.490 |
| SC | TCCTGT | 1381.63 | 1779 | 1.288 | 0.253 |
| SC | AGCTGT | 1565.33 | 1922 | 1.228 | 0.205 |
| SC | TCGTGC | 433.77 | 361 | 0.832 | -0.184 |
| SC | TCTTGT | 1201.89 | 941 | 0.783 | -0.245 |
| SC | AGTTGT | 987.57 | 698 | 0.707 | -0.347 |
| SC | TCGTGT | 365.36 | 225 | 0.616 | -0.485 |
| SC | TCATGT | 971.65 | 584 | 0.601 | -0.509 |
| SC | TCTTGC | 1426.94 | 758 | 0.531 | -0.633 |
| SC | TCATGC | 1153.59 | 525 | 0.455 | -0.787 |
| SC | AGTTGC | 1172.49 | 504 | 0.430 | -0.844 |
| SD | TCAGAT | 1978.63 | 3706 | 1.873 | 0.628 |
| SD | AGTGAT | 2011.05 | 3683 | 1.831 | 0.605 |
| SD | AGTGAC | 2271.71 | 4040 | 1.778 | 0.576 |
| SD | TCGGAC | 840.43 | 1438 | 1.711 | 0.537 |
| SD | TCTGAT | 2447.46 | 3578 | 1.462 | 0.380 |
| SD | TCAGAC | 2235.09 | 2906 | 1.300 | 0.262 |
| SD | TCGGAT | 744.00 | 840 | 1.129 | 0.121 |
| SD | TCTGAC | 2764.69 | 2949 | 1.067 | 0.065 |
| SD | AGCGAC | 3600.71 | 2017 | 0.560 | -0.580 |
| SD | TCCGAC | 3178.17 | 1336 | 0.420 | -0.867 |
| SD | AGCGAT | 3187.56 | 920 | 0.289 | -1.243 |
| SD | TCCGAT | 2813.50 | 660 | 0.235 | -1.450 |
| SE | TCAGAA | 2420.84 | 4815 | 1.989 | 0.688 |
| SE | AGTGAA | 2460.50 | 4686 | 1.904 | 0.644 |
| SE | TCGGAG | 1217.33 | 2184 | 1.794 | 0.584 |
| SE | TCTGAA | 2994.45 | 4621 | 1.543 | 0.434 |
| SE | TCAGAG | 3237.43 | 4683 | 1.447 | 0.369 |
| SE | AGTGAG | 3290.47 | 4410 | 1.340 | 0.293 |
| SE | TCTGAG | 4004.54 | 4891 | 1.221 | 0.200 |
| SE | TCGGAA | 910.28 | 879 | 0.966 | -0.035 |
| SE | AGCGAG | 5215.47 | 2961 | 0.568 | -0.566 |
| SE | TCCGAG | 4603.44 | 2005 | 0.436 | -0.831 |
| SE | AGCGAA | 3899.95 | 847 | 0.217 | -1.527 |
| SE | TCCGAA | 3442.29 | 715 | 0.208 | -1.572 |
| SF | TCCTTC | 2645.79 | 4407 | 1.666 | 0.510 |

Supplemental Table 1

Expected and Observed Codon Pair Frequencies and Codon Pair Scores for 14,795 Human Genes

| amino acid pair | codon pair | expected | observed | observed/expected | CPS |
|---|---|---|---|---|---|
| SF | AGCTTC | 2997.56 | 3942 | 1.315 | 0.274 |
| SF | TCATTT | 1625.65 | 1773 | 1.091 | 0.087 |
| SF | TCCTTT | 2311.58 | 2487 | 1.076 | 0.073 |
| SF | AGTTTT | 1652.29 | 1695 | 1.026 | 0.026 |
| SF | AGCTTT | 2618.91 | 2370 | 0.905 | -0.100 |
| SF | TCTTTT | 2010.85 | 1809 | 0.900 | -0.106 |
| SF | TCTTTC | 2301.58 | 1728 | 0.751 | -0.287 |
| SF | AGTTTC | 1891.18 | 1353 | 0.715 | -0.335 |
| SF | TCGTTT | 611.27 | 342 | 0.559 | -0.581 |
| SF | TCATTC | 1860.69 | 991 | 0.533 | -0.630 |
| SF | TCGTTC | 699.65 | 330 | 0.472 | -0.751 |
| SG | AGTGGT | 1051.00 | 2094 | 1.992 | 0.689 |
| SG | TCGGGG | 586.31 | 1117 | 1.905 | 0.645 |
| SG | TCGGGC | 814.29 | 1487 | 1.826 | 0.602 |
| SG | AGTGGA | 1623.36 | 2932 | 1.806 | 0.591 |
| SG | TCAGGA | 1597.19 | 2760 | 1.728 | 0.547 |
| SG | TCTGGA | 1975.64 | 3391 | 1.716 | 0.540 |
| SG | AGTGGG | 1584.81 | 2584 | 1.630 | 0.489 |
| SG | TCTGGG | 1928.73 | 2974 | 1.542 | 0.433 |
| SG | AGTGGC | 2201.05 | 3314 | 1.506 | 0.409 |
| SG | TCTGGT | 1279.07 | 1902 | 1.487 | 0.397 |
| SG | TCAGGG | 1559.26 | 2161 | 1.386 | 0.326 |
| SG | TCAGGT | 1034.06 | 1351 | 1.307 | 0.267 |
| SG | TCGGGA | 600.57 | 684 | 1.139 | 0.130 |
| SG | TCGGGT | 388.82 | 410 | 1.054 | 0.053 |
| SG | TCTGGC | 2678.70 | 2734 | 1.021 | 0.020 |
| SG | TCAGGC | 2165.57 | 2114 | 0.976 | -0.024 |
| SG | AGCGGC | 3488.72 | 2475 | 0.709 | -0.343 |
| SG | AGCGGG | 2511.96 | 1464 | 0.583 | -0.540 |
| SG | TCCGGG | 2217.18 | 1117 | 0.504 | -0.686 |
| SG | TCCGGC | 3079.31 | 1163 | 0.378 | -0.974 |
| SG | AGCGGT | 1665.85 | 536 | 0.322 | -1.134 |
| SG | AGCGGA | 2573.06 | 663 | 0.258 | -1.356 |
| SG | TCCGGA | 2271.11 | 560 | 0.247 | -1.400 |
| SG | TCCGGT | 1470.37 | 359 | 0.244 | -1.410 |
| SH | AGCCAC | 2202.27 | 3210 | 1.458 | 0.377 |
| SH | TCTCAT | 1226.22 | 1426 | 1.163 | 0.151 |
| SH | TCCCAC | 1943.83 | 2233 | 1.149 | 0.139 |
| SH | AGTCAT | 1007.57 | 1082 | 1.074 | 0.071 |
| SH | AGCCAT | 1597.01 | 1606 | 1.006 | 0.006 |
| SH | TCGCAC | 514.03 | 512 | 0.996 | -0.004 |
| SH | TCCCAT | 1409.60 | 1349 | 0.957 | -0.044 |
| SH | TCACAT | 991.32 | 929 | 0.937 | -0.065 |
| SH | AGTCAC | 1389.42 | 1077 | 0.775 | -0.255 |
| SH | TCACAC | 1367.03 | 956 | 0.699 | -0.358 |
| SH | TCTCAC | 1690.94 | 1158 | 0.685 | -0.379 |
| SH | TCGCAT | 372.75 | 174 | 0.467 | -0.762 |
| SI | TCCATC | 2374.96 | 4526 | 1.906 | 0.645 |
| SI | AGCATC | 2690.72 | 4471 | 1.662 | 0.508 |
| SI | TCCATT | 1878.09 | 2383 | 1.269 | 0.238 |
| SI | AGCATT | 2127.79 | 2384 | 1.120 | 0.114 |
| SI | TCCATA | 863.76 | 963 | 1.115 | 0.109 |
| SI | AGTATA | 617.40 | 640 | 1.037 | 0.036 |
| SI | TCAATA | 607.45 | 618 | 1.017 | 0.017 |
| SI | AGTATT | 1342.43 | 1299 | 0.968 | -0.033 |
| SI | AGCATA | 978.60 | 943 | 0.964 | -0.037 |
| SI | TCTATA | 751.38 | 658 | 0.876 | -0.133 |
| SI | TCTATT | 1633.75 | 1215 | 0.744 | -0.296 |
| SI | TCAATT | 1320.79 | 957 | 0.725 | -0.322 |
| SI | AGTATC | 1697.59 | 924 | 0.544 | -0.608 |
| SI | TCGATA | 228.41 | 109 | 0.477 | -0.740 |
| SI | TCTATC | 2065.98 | 958 | 0.464 | -0.769 |
| SI | TCGATT | 496.64 | 185 | 0.373 | -0.988 |
| SI | TCAATC | 1670.22 | 557 | 0.333 | -1.098 |
| SI | TCGATC | 628.03 | 184 | 0.293 | -1.228 |
| SK | TCCAAG | 3563.99 | 5021 | 1.409 | 0.343 |
| SK | TCCAAA | 2751.88 | 3634 | 1.321 | 0.278 |
| SK | AGCAAG | 4037.83 | 5128 | 1.270 | 0.239 |
| SK | AGCAAA | 3117.75 | 3736 | 1.198 | 0.181 |
| SK | TCAAAA | 1935.30 | 2282 | 1.179 | 0.165 |

Supplemental Table 1

Expected and Observed Codon Pair Frequencies and Codon Pair Scores for 14,795 Human Genes

| amino acid pair | codon pair | expected | observed | observed/expected | CPS |
|---|---|---|---|---|---|
| SK | AGTAAA | 1967.01 | 2149 | 1.093 | 0.088 |
| SK | TCAAAG | 2506.42 | 2082 | 0.831 | -0.186 |
| SK | TCTAAA | 2393.86 | 1838 | 0.768 | -0.264 |
| SK | TCGAAG | 942.46 | 522 | 0.554 | -0.591 |
| SK | AGTAAG | 2547.49 | 1300 | 0.510 | -0.673 |
| SK | TCTAAG | 3100.32 | 1569 | 0.506 | -0.681 |
| SK | TCGAAA | 727.71 | 331 | 0.455 | -0.788 |
| SL | AGTTTA | 709.05 | 1103 | 1.556 | 0.442 |
| SL | TCGCTG | 1355.42 | 2104 | 1.552 | 0.440 |
| SL | TCCTTG | 1666.44 | 2462 | 1.477 | 0.390 |
| SL | TCTTTA | 862.92 | 1267 | 1.468 | 0.384 |
| SL | AGCCTC | 2794.39 | 4013 | 1.436 | 0.362 |
| SL | TCTTTG | 1449.64 | 2009 | 1.386 | 0.326 |
| SL | TCATTA | 697.62 | 862 | 1.236 | 0.212 |
| SL | AGCCTG | 5807.08 | 7014 | 1.208 | 0.189 |
| SL | AGTTTG | 1191.15 | 1427 | 1.198 | 0.181 |
| SL | TCGCTC | 652.23 | 777 | 1.191 | 0.175 |
| SL | TCTCTA | 797.87 | 950 | 1.191 | 0.175 |
| SL | TCTCTT | 1479.47 | 1750 | 1.183 | 0.168 |
| SL | TCCCTG | 5125.62 | 6034 | 1.177 | 0.163 |
| SL | TCCCTC | 2466.46 | 2805 | 1.137 | 0.129 |
| SL | TCCTTA | 991.98 | 1076 | 1.085 | 0.081 |
| SL | AGTCTT | 1215.66 | 1242 | 1.022 | 0.021 |
| SL | AGCCTT | 1926.85 | 1959 | 1.017 | 0.017 |
| SL | TCACTA | 645.03 | 630 | 0.977 | -0.024 |
| SL | AGCTTG | 1888.00 | 1786 | 0.946 | -0.056 |
| SL | TCACTT | 1196.06 | 1111 | 0.929 | -0.074 |
| SL | TCCCTT | 1700.73 | 1545 | 0.908 | -0.096 |
| SL | TCCCTA | 917.19 | 810 | 0.883 | -0.124 |
| SL | AGTCTA | 655.60 | 569 | 0.868 | -0.142 |
| SL | TCATTG | 1171.95 | 1015 | 0.866 | -0.144 |
| SL | AGCCTA | 1039.14 | 875 | 0.842 | -0.172 |
| SL | TCTCTC | 2145.58 | 1760 | 0.820 | -0.198 |
| SL | TCTCTG | 4458.78 | 3418 | 0.767 | -0.266 |
| SL | AGCTTA | 1123.86 | 758 | 0.674 | -0.394 |
| SL | AGTCTC | 1763.00 | 1158 | 0.657 | -0.420 |
| SL | TCGTTG | 440.67 | 280 | 0.635 | -0.454 |
| SL | TCACTC | 1734.58 | 1100 | 0.634 | -0.455 |
| SL | TCACTG | 3604.66 | 2254 | 0.625 | -0.470 |
| SL | TCGCTT | 449.74 | 279 | 0.620 | -0.477 |
| SL | TCGCTA | 242.54 | 143 | 0.590 | -0.528 |
| SL | TCGTTA | 262.32 | 140 | 0.534 | -0.628 |
| SL | AGTCTG | 3663.72 | 1808 | 0.493 | -0.706 |
| SM | TCCATG | 2282.65 | 3908 | 1.712 | 0.538 |
| SM | AGCATG | 2586.13 | 3300 | 1.276 | 0.244 |
| SM | TCAATG | 1605.31 | 1129 | 0.703 | -0.352 |
| SM | TCGATG | 603.62 | 365 | 0.605 | -0.503 |
| SM | AGTATG | 1631.61 | 966 | 0.592 | -0.524 |
| SM | TCTATG | 1985.68 | 1027 | 0.517 | -0.659 |
| SN | AGCAAC | 2539.42 | 3717 | 1.464 | 0.381 |
| SN | TCCAAC | 2241.42 | 3216 | 1.435 | 0.361 |
| SN | TCAAAT | 1431.22 | 1883 | 1.316 | 0.274 |
| SN | AGCAAT | 2305.68 | 2513 | 1.090 | 0.086 |
| SN | TCCAAT | 2035.11 | 2000 | 0.983 | -0.017 |
| SN | AGTAAT | 1454.67 | 1425 | 0.980 | -0.021 |
| SN | AGTAAC | 1602.14 | 1339 | 0.836 | -0.179 |
| SN | TCAAAC | 1576.31 | 1194 | 0.757 | -0.278 |
| SN | TCTAAT | 1770.34 | 1297 | 0.733 | -0.311 |
| SN | TCTAAC | 1949.81 | 955 | 0.490 | -0.714 |
| SN | TCGAAT | 538.16 | 258 | 0.479 | -0.735 |
| SN | TCGAAC | 592.72 | 240 | 0.405 | -0.904 |
| SP | TCGCCG | 282.21 | 549 | 1.945 | 0.665 |
| SP | TCGCCC | 778.87 | 1221 | 1.568 | 0.450 |
| SP | TCCCCG | 1067.21 | 1621 | 1.519 | 0.418 |
| SP | TCTCCA | 2214.76 | 3119 | 1.408 | 0.342 |
| SP | AGCCCC | 3336.96 | 4654 | 1.395 | 0.333 |
| SP | TCTCCT | 2294.78 | 2888 | 1.259 | 0.230 |
| SP | AGCCCG | 1209.10 | 1432 | 1.184 | 0.169 |
| SP | TCCCCA | 2545.99 | 2968 | 1.166 | 0.153 |
| SP | TCACCA | 1790.50 | 1869 | 1.044 | 0.043 |

Supplemental Table 1

Expected and Observed Codon Pair Frequencies and Codon Pair Scores for 14,795 Human Genes

| amino acid pair | codon pair | expected | observed | observed/expected | CPS |
|---|---|---|---|---|---|
| SP | AGCCCT | 2988.71 | 3086 | 1.033 | 0.032 |
| SP | AGTCCT | 1885.59 | 1904 | 1.010 | 0.010 |
| SP | TCACCT | 1855.20 | 1752 | 0.944 | -0.057 |
| SP | AGCCCA | 2884.48 | 2607 | 0.904 | -0.101 |
| SP | TCCCCT | 2637.98 | 2238 | 0.848 | -0.164 |
| SP | AGTCCA | 1819.84 | 1473 | 0.809 | -0.211 |
| SP | TCGCCT | 697.59 | 562 | 0.806 | -0.216 |
| SP | TCGCCA | 673.26 | 541 | 0.804 | -0.219 |
| SP | TCTCCC | 2562.18 | 2036 | 0.795 | -0.230 |
| SP | TCACCC | 2071.37 | 1568 | 0.757 | -0.278 |
| SP | AGTCCC | 2105.31 | 1534 | 0.729 | -0.317 |
| SP | TCTCCG | 928.37 | 664 | 0.715 | -0.335 |
| SP | TCCCCC | 2945.37 | 2058 | 0.699 | -0.358 |
| SP | TCACCG | 750.53 | 426 | 0.568 | -0.566 |
| SP | AGTCCG | 762.83 | 319 | 0.418 | -0.872 |
| SQ | TCCCAG | 4427.95 | 5592 | 1.263 | 0.233 |
| SQ | AGCCAG | 5016.65 | 6041 | 1.204 | 0.186 |
| SQ | TCTCAA | 1379.40 | 1644 | 1.192 | 0.175 |
| SQ | AGTCAA | 1133.44 | 1293 | 1.141 | 0.132 |
| SQ | TCACAA | 1115.16 | 1196 | 1.072 | 0.070 |
| SQ | AGCCAA | 1796.52 | 1819 | 1.013 | 0.012 |
| SQ | TCCCAA | 1585.70 | 1474 | 0.930 | -0.073 |
| SQ | TCTCAG | 3851.88 | 3430 | 0.890 | -0.116 |
| SQ | TCGCAG | 1170.92 | 1015 | 0.867 | -0.143 |
| SQ | TCACAG | 3114.02 | 2271 | 0.729 | -0.316 |
| SQ | AGTCAG | 3165.04 | 2215 | 0.700 | -0.357 |
| SQ | TCGCAA | 419.32 | 186 | 0.444 | -0.813 |
| SR | AGCCGC | 1540.23 | 2828 | 1.836 | 0.608 |
| SR | TCCAGG | 1472.14 | 2309 | 1.568 | 0.450 |
| SR | AGCCGG | 1684.56 | 2353 | 1.397 | 0.334 |
| SR | TCCCGG | 1486.87 | 1976 | 1.329 | 0.284 |
| SR | AGCAGG | 1667.87 | 2186 | 1.311 | 0.271 |
| SR | AGCCGT | 659.43 | 857 | 1.300 | 0.262 |
| SR | TCGCGC | 359.50 | 446 | 1.241 | 0.216 |
| SR | TCCAGA | 1499.54 | 1850 | 1.234 | 0.210 |
| SR | TCAAGA | 1054.57 | 1294 | 1.227 | 0.205 |
| SR | TCGCGG | 393.19 | 481 | 1.223 | 0.202 |
| SR | TCCCGC | 1359.49 | 1605 | 1.181 | 0.166 |
| SR | TCTCGA | 701.14 | 826 | 1.178 | 0.164 |
| SR | AGTCGT | 416.04 | 484 | 1.163 | 0.151 |
| SR | TCCCGA | 806.00 | 937 | 1.163 | 0.151 |
| SR | AGCAGA | 1698.90 | 1925 | 1.133 | 0.125 |
| SR | AGCCGA | 913.16 | 1020 | 1.117 | 0.111 |
| SR | TCTCGT | 506.32 | 493 | 0.974 | -0.027 |
| SR | AGTCGA | 576.12 | 553 | 0.960 | -0.041 |
| SR | TCCCGT | 582.04 | 553 | 0.950 | -0.051 |
| SR | TCAAGG | 1035.31 | 922 | 0.891 | -0.116 |
| SR | TCGAGG | 389.29 | 324 | 0.832 | -0.184 |
| SR | TCTCGG | 1293.43 | 1062 | 0.821 | -0.197 |
| SR | TCACGT | 409.33 | 323 | 0.789 | -0.237 |
| SR | AGTAGA | 1071.85 | 746 | 0.696 | -0.362 |
| SR | TCGCGT | 153.92 | 102 | 0.663 | -0.411 |
| SR | AGTCGG | 1062.80 | 675 | 0.635 | -0.454 |
| SR | AGTCGC | 971.74 | 591 | 0.608 | -0.497 |
| SR | TCACGA | 566.83 | 344 | 0.607 | -0.499 |
| SR | TCGAGA | 396.54 | 240 | 0.605 | -0.502 |
| SR | TCTAGA | 1304.45 | 750 | 0.575 | -0.553 |
| SR | TCGCGA | 213.14 | 115 | 0.540 | -0.617 |
| SR | TCTCGC | 1182.62 | 636 | 0.538 | -0.620 |
| SR | TCACGG | 1045.66 | 534 | 0.511 | -0.672 |
| SR | TCTAGG | 1280.62 | 574 | 0.448 | -0.802 |
| SR | TCACGC | 956.08 | 406 | 0.425 | -0.856 |
| SR | AGTAGG | 1052.27 | 443 | 0.421 | -0.865 |
| SS | AGCAGC | 3919.72 | 7160 | 1.827 | 0.602 |
| SS | TCGTCG | 213.54 | 376 | 1.761 | 0.566 |
| SS | TCCTCG | 807.53 | 1302 | 1.612 | 0.478 |
| SS | TCCAGC | 3459.74 | 4832 | 1.397 | 0.334 |
| SS | TCTTCA | 1868.19 | 2596 | 1.390 | 0.329 |
| SS | AGCAGT | 2472.97 | 3417 | 1.382 | 0.323 |
| SS | TCCTCC | 3053.74 | 4162 | 1.363 | 0.310 |

Supplemental Table 1

Expected and Observed Codon Pair Frequencies and Codon Pair Scores for 14,795 Human Genes

| amino acid pair | codon pair | expected | observed | observed/expected | CPS |
|---|---|---|---|---|---|
| SS | TCTTCT | 2310.85 | 2896 | 1.253 | 0.226 |
| SS | TCCAGT | 2182.77 | 2691 | 1.233 | 0.209 |
| SS | TCATCA | 1510.32 | 1795 | 1.188 | 0.173 |
| SS | AGCTCC | 3459.74 | 4024 | 1.163 | 0.151 |
| SS | TCATCT | 1868.19 | 2118 | 1.134 | 0.126 |
| SS | TCCTCA | 2147.58 | 2413 | 1.124 | 0.117 |
| SS | AGCTCG | 914.89 | 1001 | 1.094 | 0.090 |
| SS | TCCTCT | 2656.45 | 2744 | 1.033 | 0.032 |
| SS | TCGTCC | 807.53 | 818 | 1.013 | 0.013 |
| SS | TCTTCC | 2656.45 | 2600 | 0.979 | -0.021 |
| SS | AGTTCT | 1898.79 | 1856 | 0.977 | -0.023 |
| SS | AGTTCA | 1535.06 | 1498 | 0.976 | -0.024 |
| SS | TCAAGT | 1535.06 | 1404 | 0.915 | -0.089 |
| SS | AGCTCA | 2433.11 | 2075 | 0.853 | -0.159 |
| SS | AGCTCT | 3009.63 | 2465 | 0.819 | -0.200 |
| SS | TCTTCG | 702.47 | 556 | 0.791 | -0.234 |
| SS | TCATCC | 2147.58 | 1632 | 0.760 | -0.275 |
| SS | AGTAGT | 1560.21 | 1030 | 0.660 | -0.415 |
| SS | AGTTCC | 2182.77 | 1405 | 0.644 | -0.441 |
| SS | TCGTCT | 702.47 | 434 | 0.618 | -0.482 |
| SS | TCATCG | 567.91 | 343 | 0.604 | -0.504 |
| SS | TCGTCA | 567.91 | 313 | 0.551 | -0.596 |
| SS | TCTAGT | 1898.79 | 957 | 0.504 | -0.685 |
| SS | TCGAGC | 914.89 | 440 | 0.481 | -0.732 |
| SS | AGTAGC | 2472.97 | 1158 | 0.468 | -0.759 |
| SS | TCAAGC | 2433.11 | 1117 | 0.459 | -0.779 |
| SS | TCGAGT | 577.21 | 259 | 0.449 | -0.801 |
| SS | AGTTCG | 577.21 | 251 | 0.435 | -0.833 |
| SS | TCTAGC | 3009.63 | 899 | 0.299 | -1.208 |
| ST | TCCACG | 785.52 | 1434 | 1.826 | 0.602 |
| ST | AGCACC | 2709.18 | 4149 | 1.531 | 0.426 |
| ST | TCCACC | 2391.25 | 3527 | 1.475 | 0.389 |
| ST | AGCACG | 889.95 | 1180 | 1.326 | 0.282 |
| ST | AGCACA | 2193.18 | 2692 | 1.227 | 0.205 |
| ST | TCCACA | 1935.81 | 2329 | 1.203 | 0.185 |
| ST | TCCACT | 1711.89 | 1937 | 1.131 | 0.124 |
| ST | AGCACT | 1939.49 | 2193 | 1.131 | 0.123 |
| ST | TCAACA | 1361.39 | 1485 | 1.091 | 0.087 |
| ST | TCAACT | 1203.91 | 1270 | 1.055 | 0.053 |
| ST | TCTACT | 1489.18 | 1390 | 0.933 | -0.069 |
| ST | TCTACA | 1683.97 | 1461 | 0.868 | -0.142 |
| ST | AGTACT | 1223.64 | 1036 | 0.847 | -0.166 |
| ST | AGTACA | 1383.69 | 1061 | 0.767 | -0.266 |
| ST | TCGACG | 207.72 | 145 | 0.698 | -0.359 |
| ST | TCTACC | 2080.15 | 1218 | 0.586 | -0.535 |
| ST | TCGACC | 632.34 | 365 | 0.577 | -0.550 |
| ST | AGTACC | 1709.24 | 976 | 0.571 | -0.560 |
| ST | TCGACT | 452.69 | 240 | 0.530 | -0.635 |
| ST | TCAACC | 1681.68 | 873 | 0.519 | -0.656 |
| ST | TCAACG | 552.43 | 275 | 0.498 | -0.698 |
| ST | TCGACA | 511.90 | 236 | 0.461 | -0.774 |
| ST | TCTACG | 683.32 | 302 | 0.442 | -0.817 |
| ST | AGTACG | 561.48 | 201 | 0.358 | -1.027 |
| SV | TCGGTG | 935.47 | 1822 | 1.948 | 0.667 |
| SV | TCTGTA | 788.92 | 1398 | 1.772 | 0.572 |
| SV | TCTGTT | 1214.96 | 2136 | 1.758 | 0.564 |
| SV | TCAGTA | 637.79 | 1121 | 1.758 | 0.564 |
| SV | AGTGTT | 998.32 | 1719 | 1.722 | 0.543 |
| SV | TCAGTT | 982.23 | 1591 | 1.620 | 0.482 |
| SV | TCTGTC | 1555.54 | 2367 | 1.522 | 0.420 |
| SV | AGTGTC | 1278.17 | 1943 | 1.520 | 0.419 |
| SV | TCTGTG | 3077.33 | 4672 | 1.518 | 0.418 |
| SV | AGTGTA | 648.24 | 976 | 1.506 | 0.409 |
| SV | TCGGTC | 472.87 | 683 | 1.444 | 0.368 |
| SV | TCAGTG | 2487.84 | 2925 | 1.176 | 0.162 |
| SV | AGTGTG | 2528.60 | 2901 | 1.147 | 0.137 |
| SV | TCAGTC | 1257.56 | 1351 | 1.074 | 0.072 |
| SV | TCGGTA | 239.82 | 231 | 0.963 | -0.037 |
| SV | TCGGTT | 369.33 | 266 | 0.720 | -0.328 |
| SV | AGCGTC | 2025.93 | 1298 | 0.641 | -0.445 |

Supplemental Table 1

Expected and Observed Codon Pair Frequencies and Codon Pair Scores for 14,795 Human Genes

| amino acid pair | codon pair | expected | observed | observed/expected | CPS |
|---|---|---|---|---|---|
| SV | TCCGTG | 3537.57 | 2065 | 0.584 | −0.538 |
| SV | AGCGTG | 4007.89 | 2221 | 0.554 | −0.590 |
| SV | TCCGTC | 1788.18 | 829 | 0.464 | −0.769 |
| SV | AGCGTT | 1582.36 | 446 | 0.282 | −1.266 |
| SV | TCCGTA | 906.91 | 239 | 0.264 | −1.334 |
| SV | TCCGTT | 1396.67 | 329 | 0.236 | −1.446 |
| SV | AGCGTA | 1027.48 | 217 | 0.211 | −1.555 |
| SW | TCCTGG | 1756.97 | 2825 | 1.608 | 0.475 |
| SW | AGCTGG | 1990.56 | 2404 | 1.208 | 0.189 |
| SW | TCGTGG | 464.61 | 444 | 0.956 | −0.045 |
| SW | TCTTGG | 1528.39 | 1137 | 0.744 | −0.296 |
| SW | TCATGG | 1235.61 | 778 | 0.630 | −0.463 |
| SW | AGTTGG | 1255.86 | 644 | 0.513 | −0.668 |
| SY | TCCTAC | 1871.53 | 3038 | 1.623 | 0.484 |
| SY | AGCTAC | 2120.35 | 2864 | 1.351 | 0.301 |
| SY | TCCTAT | 1520.75 | 1869 | 1.229 | 0.206 |
| SY | AGCTAT | 1722.94 | 1609 | 0.934 | −0.068 |
| SY | AGTTAT | 1087.01 | 1010 | 0.929 | −0.073 |
| SY | AGTTAC | 1337.74 | 1153 | 0.862 | −0.149 |
| SY | TCATAT | 1069.49 | 897 | 0.839 | −0.176 |
| SY | TCTTAT | 1322.91 | 1100 | 0.832 | −0.185 |
| SY | TCTTAC | 1628.04 | 1204 | 0.740 | −0.302 |
| SY | TCGTAC | 494.91 | 304 | 0.614 | −0.487 |
| SY | TCGTAT | 402.15 | 204 | 0.507 | −0.679 |
| SY | TCATAC | 1316.18 | 642 | 0.488 | −0.718 |
| TA | ACGGCG | 348.71 | 734 | 2.105 | 0.744 |
| TA | ACAGCA | 1829.79 | 3283 | 1.794 | 0.585 |
| TA | ACGGCC | 1289.71 | 2090 | 1.621 | 0.483 |
| TA | ACTGCA | 1618.13 | 2557 | 1.580 | 0.458 |
| TA | ACAGCT | 2090.24 | 3295 | 1.576 | 0.455 |
| TA | ACTGCT | 1848.45 | 2764 | 1.495 | 0.402 |
| TA | ACAGCC | 3178.34 | 3912 | 1.231 | 0.208 |
| TA | ACGGCA | 742.49 | 804 | 1.083 | 0.080 |
| TA | ACTGCC | 2810.69 | 3015 | 1.073 | 0.070 |
| TA | ACGGCT | 848.18 | 804 | 0.948 | −0.053 |
| TA | ACAGCG | 859.36 | 803 | 0.934 | −0.068 |
| TA | ACTGCG | 759.96 | 623 | 0.820 | −0.199 |
| TA | ACCGCG | 1061.55 | 584 | 0.550 | −0.598 |
| TA | ACCGCC | 3926.11 | 1648 | 0.420 | −0.868 |
| TA | ACCGCA | 2260.29 | 561 | 0.248 | −1.394 |
| TA | ACCGCT | 2582.01 | 577 | 0.223 | −1.498 |
| TC | ACCTGC | 1892.82 | 3247 | 1.715 | 0.540 |
| TC | ACCTGT | 1594.30 | 1994 | 1.251 | 0.224 |
| TC | ACGTGC | 621.78 | 691 | 1.111 | 0.106 |
| TC | ACGTGT | 523.72 | 484 | 0.924 | −0.079 |
| TC | ACTTGT | 1141.35 | 1033 | 0.905 | −0.100 |
| TC | ACATGT | 1290.64 | 938 | 0.727 | −0.319 |
| TC | ACTTGC | 1355.07 | 815 | 0.601 | −0.508 |
| TC | ACATGC | 1532.31 | 750 | 0.489 | −0.714 |
| TD | ACAGAT | 2415.25 | 4195 | 1.737 | 0.552 |
| TD | ACAGAC | 2728.31 | 3765 | 1.380 | 0.322 |
| TD | ACTGAT | 2135.87 | 2913 | 1.364 | 0.310 |
| TD | ACGGAC | 1107.10 | 1446 | 1.306 | 0.267 |
| TD | ACTGAC | 2412.71 | 2615 | 1.084 | 0.081 |
| TD | ACGGAT | 980.07 | 922 | 0.941 | −0.061 |
| TD | ACCGAC | 3370.20 | 1547 | 0.459 | −0.779 |
| TD | ACCGAT | 2983.49 | 730 | 0.245 | −1.408 |
| TE | ACAGAA | 3127.33 | 5307 | 1.697 | 0.529 |
| TE | ACGGAG | 1697.07 | 2517 | 1.483 | 0.394 |
| TE | ACTGAA | 2765.58 | 4093 | 1.480 | 0.392 |
| TE | ACAGAG | 4182.23 | 5419 | 1.296 | 0.259 |
| TE | ACTGAG | 3698.46 | 4124 | 1.115 | 0.109 |
| TE | ACGGAA | 1269.01 | 1080 | 0.851 | −0.161 |
| TE | ACCGAG | 5166.20 | 2450 | 0.474 | −0.746 |
| TE | ACCGAA | 3863.10 | 779 | 0.202 | −1.601 |
| TF | ACCTTC | 3026.54 | 4955 | 1.637 | 0.493 |
| TF | ACATTT | 2140.61 | 2275 | 1.063 | 0.061 |
| TF | ACTTTT | 1893.00 | 1904 | 1.006 | 0.006 |
| TF | ACCTTT | 2644.23 | 2518 | 0.952 | −0.049 |
| TF | ACTTTC | 2166.69 | 1822 | 0.841 | −0.173 |

Supplemental Table 1

Expected and Observed Codon Pair Frequencies and Codon Pair Scores for 14,795 Human Genes

| amino acid pair | codon pair | expected | observed | observed/expected | CPS |
|---|---|---|---|---|---|
| TF | ACGTTT | 868.62 | 650 | 0.748 | -0.290 |
| TF | ACGTTC | 994.21 | 666 | 0.670 | -0.401 |
| TF | ACATTC | 2450.10 | 1394 | 0.569 | -0.564 |
| TG | ACTGGA | 1710.74 | 3660 | 2.139 | 0.761 |
| TG | ACTGGT | 1107.57 | 1887 | 1.704 | 0.533 |
| TG | ACAGGA | 1934.51 | 2970 | 1.535 | 0.429 |
| TG | ACGGGC | 1064.34 | 1583 | 1.487 | 0.397 |
| TG | ACTGGG | 1670.12 | 2322 | 1.390 | 0.330 |
| TG | ACGGGG | 766.35 | 1049 | 1.369 | 0.314 |
| TG | ACAGGT | 1252.44 | 1694 | 1.353 | 0.302 |
| TG | ACAGGG | 1888.57 | 2148 | 1.137 | 0.129 |
| TG | ACTGGC | 2319.53 | 2620 | 1.130 | 0.122 |
| TG | ACAGGC | 2622.93 | 2664 | 1.016 | 0.016 |
| TG | ACGGGT | 508.22 | 484 | 0.952 | -0.049 |
| TG | ACGGGA | 784.99 | 710 | 0.904 | -0.100 |
| TG | ACCGGG | 2332.90 | 1093 | 0.469 | -0.758 |
| TG | ACCGGC | 3240.03 | 1373 | 0.424 | -0.859 |
| TG | ACCGGT | 1547.11 | 355 | 0.229 | -1.472 |
| TG | ACCGGA | 2389.65 | 528 | 0.221 | -1.510 |
| TH | ACTCAT | 1054.95 | 1291 | 1.224 | 0.202 |
| TH | ACCCAC | 2032.09 | 2408 | 1.185 | 0.170 |
| TH | ACGCAC | 667.53 | 764 | 1.145 | 0.135 |
| TH | ACACAT | 1192.94 | 1186 | 0.994 | -0.006 |
| TH | ACTCAC | 1454.76 | 1384 | 0.951 | -0.050 |
| TH | ACCCTT | 1473.60 | 1287 | 0.873 | -0.135 |
| TH | ACACAC | 1645.05 | 1383 | 0.841 | -0.174 |
| TH | ACGCAT | 484.07 | 302 | 0.624 | -0.472 |
| TI | ACCATC | 2842.70 | 5915 | 2.081 | 0.733 |
| TI | ACCATT | 2247.97 | 2878 | 1.280 | 0.247 |
| TI | ACAATA | 836.96 | 980 | 1.171 | 0.158 |
| TI | ACCATA | 1033.87 | 1137 | 1.100 | 0.095 |
| TI | ACAATT | 1819.82 | 1579 | 0.868 | -0.142 |
| TI | ACTATA | 740.14 | 642 | 0.867 | -0.142 |
| TI | ACTATT | 1609.31 | 1337 | 0.831 | -0.185 |
| TI | ACGATA | 339.62 | 190 | 0.559 | -0.581 |
| TI | ACGATT | 738.45 | 389 | 0.527 | -0.641 |
| TI | ACGATC | 933.81 | 463 | 0.496 | -0.702 |
| TI | ACTATC | 2035.08 | 942 | 0.463 | -0.770 |
| TI | ACAATC | 2301.27 | 1027 | 0.446 | -0.807 |
| TK | ACCAAG | 3878.56 | 6678 | 1.722 | 0.543 |
| TK | ACCAAA | 2994.77 | 3789 | 1.265 | 0.235 |
| TK | ACAAAA | 2424.38 | 2546 | 1.050 | 0.049 |
| TK | ACAAAG | 3139.84 | 2507 | 0.798 | -0.225 |
| TK | ACTAAA | 2143.95 | 1684 | 0.785 | -0.241 |
| TK | ACGAAG | 1274.09 | 708 | 0.556 | -0.588 |
| TK | ACGAAA | 983.77 | 511 | 0.519 | -0.655 |
| TK | ACTAAG | 2776.65 | 1193 | 0.430 | -0.845 |
| TL | ACGCTG | 1815.48 | 3357 | 1.849 | 0.615 |
| TL | ACTTTA | 765.72 | 1207 | 1.576 | 0.455 |
| TL | ACTTTG | 1286.34 | 1876 | 1.458 | 0.377 |
| TL | ACATTA | 865.87 | 1115 | 1.288 | 0.253 |
| TL | ACCTTG | 1796.82 | 2257 | 1.256 | 0.228 |
| TL | ACTCTA | 707.99 | 876 | 1.237 | 0.213 |
| TL | ACGCTC | 873.61 | 1057 | 1.210 | 0.191 |
| TL | ACCCTC | 2659.44 | 3133 | 1.178 | 0.164 |
| TL | ACCCTG | 5526.65 | 6354 | 1.150 | 0.140 |
| TL | ACTCTT | 1312.81 | 1469 | 1.119 | 0.112 |
| TL | ACACTA | 800.60 | 799 | 0.998 | -0.002 |
| TL | ACGCTA | 324.87 | 307 | 0.945 | -0.057 |
| TL | ACCTTA | 1069.59 | 957 | 0.895 | -0.111 |
| TL | ACACTT | 1484.53 | 1316 | 0.886 | -0.121 |
| TL | ACGTTG | 590.25 | 505 | 0.856 | -0.156 |
| TL | ACATTG | 1454.60 | 1210 | 0.832 | -0.184 |
| TL | ACCCTT | 1833.80 | 1515 | 0.826 | -0.191 |
| TL | ACCCTA | 988.95 | 802 | 0.811 | -0.210 |
| TL | ACTCTG | 3956.51 | 3120 | 0.789 | -0.238 |
| TL | ACGTTA | 351.36 | 262 | 0.746 | -0.293 |
| TL | ACTCTC | 1903.88 | 1391 | 0.731 | -0.314 |
| TL | ACGCTT | 602.39 | 427 | 0.709 | -0.344 |
| TL | ACACTG | 4474.03 | 3013 | 0.673 | -0.395 |

Supplemental Table 1

Expected and Observed Codon Pair Frequencies and Codon Pair Scores for 14,795 Human Genes

| amino acid pair | codon pair | expected | observed | observed/expected | CPS |
|---|---|---|---|---|---|
| TL | ACACTC | 2152.92 | 1274 | 0.592 | -0.525 |
| TM | ACCATG | 2733.42 | 4467 | 1.634 | 0.491 |
| TM | ACAATG | 2212.81 | 1641 | 0.742 | -0.299 |
| TM | ACGATG | 897.92 | 655 | 0.729 | -0.315 |
| TM | ACTATG | 1956.85 | 1038 | 0.530 | -0.634 |
| TN | ACCAAC | 2378.62 | 4300 | 1.808 | 0.592 |
| TN | ACAAAT | 1748.34 | 2194 | 1.255 | 0.227 |
| TN | ACCAAT | 2159.68 | 2454 | 1.136 | 0.128 |
| TN | ACAAAC | 1925.59 | 1486 | 0.772 | -0.259 |
| TN | ACTAAT | 1546.11 | 1077 | 0.697 | -0.362 |
| TN | ACGAAT | 709.45 | 336 | 0.474 | -0.747 |
| TN | ACTAAC | 1702.85 | 789 | 0.463 | -0.769 |
| TN | ACGAAC | 781.37 | 316 | 0.404 | -0.905 |
| TP | ACGCCG | 349.03 | 632 | 1.811 | 0.594 |
| TP | ACGCCC | 963.29 | 1491 | 1.548 | 0.437 |
| TP | ACTCCA | 1814.66 | 2359 | 1.300 | 0.262 |
| TP | ACCCCG | 1062.52 | 1331 | 1.253 | 0.225 |
| TP | ACTCCT | 1880.23 | 2186 | 1.163 | 0.151 |
| TP | ACACCA | 2052.02 | 2361 | 1.151 | 0.140 |
| TP | ACCCCA | 2534.80 | 2784 | 1.098 | 0.094 |
| TP | ACACCT | 2126.17 | 2104 | 0.990 | -0.010 |
| TP | ACCCCT | 2626.39 | 2415 | 0.920 | -0.084 |
| TP | ACGCCA | 832.67 | 748 | 0.898 | -0.107 |
| TP | ACCCCC | 2932.43 | 2380 | 0.812 | -0.209 |
| TP | ACACCC | 2373.91 | 1922 | 0.810 | -0.211 |
| TP | ACGCCT | 862.76 | 697 | 0.808 | -0.213 |
| TP | ACTCCC | 2099.31 | 1649 | 0.785 | -0.241 |
| TP | ACTCCG | 760.66 | 538 | 0.707 | -0.346 |
| TP | ACACCG | 860.15 | 534 | 0.621 | -0.477 |
| TQ | ACTCAA | 1103.35 | 1368 | 1.240 | 0.215 |
| TQ | ACCCAG | 4303.71 | 5173 | 1.202 | 0.184 |
| TQ | ACGCAG | 1413.75 | 1518 | 1.074 | 0.071 |
| TQ | ACACAA | 1247.67 | 1328 | 1.064 | 0.062 |
| TQ | ACTCAG | 3081.01 | 2839 | 0.921 | -0.082 |
| TQ | ACCCAA | 1541.21 | 1410 | 0.915 | -0.089 |
| TQ | ACACAG | 3484.02 | 2765 | 0.794 | -0.231 |
| TQ | ACGCAA | 506.28 | 280 | 0.553 | -0.592 |
| TR | ACCAGG | 1331.08 | 2049 | 1.539 | 0.431 |
| TR | ACGCGC | 403.79 | 605 | 1.498 | 0.404 |
| TR | ACGCGG | 441.63 | 661 | 1.497 | 0.403 |
| TR | ACTCGA | 521.72 | 717 | 1.374 | 0.318 |
| TR | ACAAGA | 1097.61 | 1429 | 1.302 | 0.264 |
| TR | ACCCGC | 1229.22 | 1547 | 1.259 | 0.230 |
| TR | ACCCGG | 1344.40 | 1668 | 1.241 | 0.216 |
| TR | ACTCGT | 376.76 | 448 | 1.189 | 0.173 |
| TR | ACCAGA | 1355.85 | 1599 | 1.179 | 0.165 |
| TR | ACCCGA | 728.77 | 758 | 1.040 | 0.039 |
| TR | ACCCGT | 526.27 | 535 | 1.017 | 0.016 |
| TR | ACAAGG | 1077.56 | 1072 | 0.995 | -0.005 |
| TR | ACGAGG | 437.25 | 433 | 0.990 | -0.010 |
| TR | ACTCGG | 962.45 | 823 | 0.855 | -0.157 |
| TR | ACGCGT | 172.88 | 141 | 0.816 | -0.204 |
| TR | ACACGT | 426.04 | 329 | 0.772 | -0.258 |
| TR | ACGAGA | 445.39 | 331 | 0.743 | -0.297 |
| TR | ACACGA | 589.97 | 432 | 0.732 | -0.312 |
| TR | ACACGG | 1088.34 | 756 | 0.695 | -0.364 |
| TR | ACTCGC | 879.99 | 607 | 0.690 | -0.371 |
| TR | ACTAGA | 970.65 | 624 | 0.643 | -0.442 |
| TR | ACGCGA | 239.40 | 150 | 0.627 | -0.468 |
| TR | ACACGC | 995.10 | 498 | 0.500 | -0.692 |
| TR | ACTAGG | 952.91 | 383 | 0.402 | -0.911 |
| TS | ACCAGC | 2807.29 | 4575 | 1.630 | 0.488 |
| TS | ACCTCG | 655.24 | 1060 | 1.618 | 0.481 |
| TS | ACGTCG | 215.24 | 348 | 1.617 | 0.480 |
| TS | ACTTCA | 1247.51 | 1844 | 1.478 | 0.391 |
| TS | ACTTCT | 1543.11 | 1974 | 1.279 | 0.246 |
| TS | ACATCA | 1410.69 | 1754 | 1.243 | 0.218 |
| TS | ACCAGT | 1771.14 | 2194 | 1.239 | 0.214 |
| TS | ACCTCC | 2477.85 | 3050 | 1.231 | 0.208 |
| TS | ACCTCA | 1742.59 | 1938 | 1.112 | 0.106 |

Supplemental Table 1

Expected and Observed Codon Pair Frequencies and Codon Pair Scores for 14,795 Human Genes

| amino acid pair | codon pair | expected | observed | observed/expected | CPS |
|---|---|---|---|---|---|
| TS | ACATCT | 1744.95 | 1911 | 1.095 | 0.091 |
| TS | ACGTCC | 813.96 | 840 | 1.032 | 0.031 |
| TS | ACCTCT | 2155.49 | 2072 | 0.961 | -0.040 |
| TS | ACAAGT | 1433.80 | 1335 | 0.931 | -0.071 |
| TS | ACTTCC | 1773.89 | 1524 | 0.859 | -0.152 |
| TS | ACGTCA | 572.43 | 450 | 0.786 | -0.241 |
| TS | ACATCC | 2005.92 | 1570 | 0.783 | -0.245 |
| TS | ACTTCG | 469.09 | 353 | 0.753 | -0.284 |
| TS | ACGTCT | 708.07 | 527 | 0.744 | -0.295 |
| TS | ACATCG | 530.44 | 361 | 0.681 | -0.385 |
| TS | ACTAGT | 1267.95 | 725 | 0.572 | -0.559 |
| TS | ACAAGC | 2272.61 | 1275 | 0.561 | -0.578 |
| TS | ACGAGT | 581.81 | 297 | 0.510 | -0.672 |
| TS | ACGAGC | 922.18 | 469 | 0.509 | -0.676 |
| TS | ACTAGC | 2009.73 | 687 | 0.342 | -1.073 |
| TT | ACCACG | 875.88 | 1567 | 1.789 | 0.582 |
| TT | ACCACC | 2666.32 | 4767 | 1.788 | 0.581 |
| TT | ACCACA | 2158.49 | 2882 | 1.335 | 0.289 |
| TT | ACCACT | 1908.81 | 2309 | 1.210 | 0.190 |
| TT | ACAACA | 1747.38 | 1793 | 1.026 | 0.026 |
| TT | ACAACT | 1545.26 | 1567 | 1.014 | 0.014 |
| TT | ACGACG | 287.72 | 252 | 0.876 | -0.133 |
| TT | ACTACT | 1366.51 | 1065 | 0.779 | -0.249 |
| TT | ACTACA | 1545.26 | 1196 | 0.774 | -0.256 |
| TT | ACGACC | 875.88 | 575 | 0.656 | -0.421 |
| TT | ACGACA | 709.06 | 437 | 0.616 | -0.484 |
| TT | ACAACC | 2158.49 | 1310 | 0.607 | -0.499 |
| TT | ACGACT | 627.04 | 357 | 0.569 | -0.563 |
| TT | ACTACC | 1908.81 | 992 | 0.520 | -0.655 |
| TT | ACAACG | 709.06 | 365 | 0.515 | -0.664 |
| TT | ACTACG | 627.04 | 283 | 0.451 | -0.796 |
| TV | ACTGTA | 845.20 | 1425 | 1.686 | 0.522 |
| TV | ACTGTT | 1301.64 | 2058 | 1.581 | 0.458 |
| TV | ACGGTG | 1512.80 | 2306 | 1.524 | 0.422 |
| TV | ACAGTA | 955.76 | 1371 | 1.434 | 0.361 |
| TV | ACTGTC | 1666.51 | 2289 | 1.374 | 0.317 |
| TV | ACAGTT | 1471.90 | 2019 | 1.372 | 0.316 |
| TV | ACTGTG | 3296.87 | 4505 | 1.366 | 0.312 |
| TV | ACGGTC | 764.70 | 911 | 1.191 | 0.175 |
| TV | ACAGTG | 3728.11 | 4108 | 1.102 | 0.097 |
| TV | ACAGTC | 1884.50 | 1933 | 1.026 | 0.025 |
| TV | ACGGTA | 387.83 | 286 | 0.737 | -0.305 |
| TV | ACGGTT | 597.27 | 415 | 0.695 | -0.364 |
| TV | ACCGTG | 4605.23 | 2640 | 0.573 | -0.556 |
| TV | ACCGTC | 2327.87 | 1285 | 0.552 | -0.594 |
| TV | ACCGTT | 1818.19 | 496 | 0.273 | -1.299 |
| TV | ACCGTA | 1180.62 | 298 | 0.252 | -1.377 |
| TW | ACGTGG | 606.25 | 837 | 1.381 | 0.323 |
| TW | ACCTGG | 1845.52 | 2403 | 1.302 | 0.264 |
| TW | ACATGG | 1494.02 | 1089 | 0.729 | -0.316 |
| TW | ACTTGG | 1321.21 | 938 | 0.710 | -0.343 |
| TY | ACCTAC | 2130.11 | 3648 | 1.713 | 0.538 |
| TY | ACCTAT | 1730.88 | 1778 | 1.027 | 0.027 |
| TY | ACTTAC | 1524.94 | 1383 | 0.907 | -0.098 |
| TY | ACGTAC | 699.73 | 621 | 0.887 | -0.119 |
| TY | ACATAT | 1401.21 | 1136 | 0.811 | -0.210 |
| TY | ACTTAT | 1239.13 | 907 | 0.732 | -0.312 |
| TY | ACGTAT | 568.59 | 408 | 0.718 | -0.332 |
| TY | ACATAC | 1724.41 | 1138 | 0.660 | -0.416 |
| VA | GTGGCC | 6082.92 | 9316 | 1.532 | 0.426 |
| VA | GTAGCA | 897.78 | 1347 | 1.500 | 0.406 |
| VA | GTTGCT | 1579.41 | 2217 | 1.404 | 0.339 |
| VA | GTAGCT | 1025.57 | 1407 | 1.372 | 0.316 |
| VA | GTGGCT | 4000.44 | 5252 | 1.313 | 0.272 |
| VA | GTGGCG | 1644.71 | 2099 | 1.276 | 0.244 |
| VA | GTTGCA | 1382.62 | 1728 | 1.250 | 0.223 |
| VA | GTGGCA | 3501.98 | 3859 | 1.102 | 0.097 |
| VA | GTAGCC | 1559.44 | 1363 | 0.874 | -0.135 |
| VA | GTTGCC | 2401.60 | 1808 | 0.753 | -0.284 |
| VA | GTAGCG | 421.64 | 216 | 0.512 | -0.669 |

Supplemental Table 1

Expected and Observed Codon Pair Frequencies and Codon Pair Scores for 14,795 Human Genes

| amino acid pair | codon pair | expected | observed | observed/expected | CPS |
|---|---|---|---|---|---|
| VA | GTTGCG | 649.35 | 234 | 0.360 | -1.021 |
| VA | GTCGCG | 831.37 | 284 | 0.342 | -1.074 |
| VA | GTCGCC | 3074.82 | 992 | 0.323 | -1.131 |
| VA | GTCGCT | 2022.16 | 406 | 0.201 | -1.606 |
| VA | GTCGCA | 1770.19 | 318 | 0.180 | -1.717 |
| VC | GTCTGC | 1410.66 | 2160 | 1.531 | 0.426 |
| VC | GTCTGT | 1188.18 | 1572 | 1.323 | 0.280 |
| VC | GTTTGT | 928.03 | 942 | 1.015 | 0.015 |
| VC | GTATGT | 602.60 | 594 | 0.986 | -0.014 |
| VC | GTGTGC | 2790.71 | 2583 | 0.926 | -0.077 |
| VC | GTGTGT | 2350.57 | 1996 | 0.849 | -0.164 |
| VC | GTTTGC | 1101.80 | 830 | 0.753 | -0.283 |
| VC | GTATGC | 715.44 | 411 | 0.574 | -0.554 |
| VD | GTAGAT | 1225.65 | 1924 | 1.570 | 0.451 |
| VD | GTGGAC | 5400.58 | 7734 | 1.432 | 0.359 |
| VD | GTTGAT | 1887.55 | 2389 | 1.266 | 0.236 |
| VD | GTGGAT | 4780.91 | 5727 | 1.198 | 0.181 |
| VD | GTAGAC | 1384.52 | 1346 | 0.972 | -0.028 |
| VD | GTTGAC | 2132.21 | 1791 | 0.840 | -0.174 |
| VD | GTCGAC | 2729.91 | 602 | 0.221 | -1.512 |
| VD | GTCGAT | 2416.67 | 445 | 0.184 | -1.692 |
| VE | GTAGAA | 1456.83 | 2855 | 1.960 | 0.673 |
| VE | GTGGAG | 7599.48 | 11579 | 1.524 | 0.421 |
| VE | GTTGAA | 2243.56 | 2905 | 1.295 | 0.258 |
| VE | GTGGAA | 5682.64 | 6229 | 1.096 | 0.092 |
| VE | GTAGAG | 1948.24 | 2002 | 1.028 | 0.027 |
| VE | GTTGAG | 3000.36 | 1987 | 0.662 | -0.412 |
| VE | GTCGAG | 3841.42 | 721 | 0.188 | -1.673 |
| VE | GTCGAA | 2872.48 | 367 | 0.128 | -2.058 |
| VF | GTCTTC | 2309.08 | 4216 | 1.826 | 0.602 |
| VF | GTATTT | 1023.16 | 1512 | 1.478 | 0.391 |
| VF | GTCTTT | 2017.40 | 2238 | 1.109 | 0.104 |
| VF | GTTTTT | 1575.70 | 1706 | 1.083 | 0.079 |
| VF | GTTTTC | 1803.52 | 1604 | 0.889 | -0.117 |
| VF | GTGTTT | 3991.02 | 3257 | 0.816 | -0.203 |
| VF | GTGTTC | 4568.05 | 3205 | 0.702 | -0.354 |
| VF | GTATTC | 1171.09 | 721 | 0.616 | -0.485 |
| VG | GTTGGT | 779.74 | 1617 | 2.074 | 0.729 |
| VG | GTTGGA | 1204.37 | 2315 | 1.922 | 0.653 |
| VG | GTGGGC | 4136.07 | 5977 | 1.445 | 0.368 |
| VG | GTAGGA | 782.04 | 1089 | 1.393 | 0.331 |
| VG | GTTGGG | 1175.77 | 1510 | 1.284 | 0.250 |
| VG | GTTGGC | 1632.96 | 1794 | 1.099 | 0.094 |
| VG | GTAGGT | 506.31 | 554 | 1.094 | 0.090 |
| VG | GTGGGG | 2978.07 | 3255 | 1.093 | 0.089 |
| VG | GTGGGT | 1974.96 | 2009 | 1.017 | 0.017 |
| VG | GTAGGG | 763.47 | 683 | 0.895 | -0.111 |
| VG | GTGGGA | 3050.51 | 2599 | 0.852 | -0.160 |
| VG | GTAGGC | 1060.34 | 676 | 0.638 | -0.450 |
| VG | GTCGGG | 1505.36 | 734 | 0.488 | -0.718 |
| VG | GTCGGC | 2090.72 | 734 | 0.351 | -1.047 |
| VG | GTCGGT | 998.31 | 292 | 0.292 | -1.229 |
| VG | GTCGGA | 1541.98 | 343 | 0.222 | -1.503 |
| VH | GTTCAT | 911.79 | 1418 | 1.555 | 0.442 |
| VH | GTACAT | 592.06 | 773 | 1.306 | 0.267 |
| VH | GTCCAC | 1609.82 | 2085 | 1.295 | 0.259 |
| VH | GTCCAT | 1167.39 | 1313 | 1.125 | 0.118 |
| VH | GTTCAC | 1257.35 | 1319 | 1.049 | 0.048 |
| VH | GTGCAC | 3184.70 | 2856 | 0.897 | -0.109 |
| VH | GTACAC | 816.44 | 613 | 0.751 | -0.287 |
| VH | GTGCAT | 2309.44 | 1472 | 0.637 | -0.450 |
| VI | GTCATC | 2367.78 | 5207 | 2.199 | 0.788 |
| VI | GTCATT | 1872.41 | 2827 | 1.510 | 0.412 |
| VI | GTAATA | 436.74 | 614 | 1.406 | 0.341 |
| VI | GTAATT | 949.63 | 1074 | 1.131 | 0.123 |
| VI | GTTATT | 1462.46 | 1595 | 1.091 | 0.087 |
| VI | GTCATA | 861.15 | 904 | 1.050 | 0.049 |
| VI | GTTATA | 672.60 | 702 | 1.044 | 0.043 |
| VI | GTGATT | 3704.20 | 2742 | 0.740 | -0.301 |
| VI | GTGATC | 4684.19 | 3353 | 0.716 | -0.334 |

Supplemental Table 1

Expected and Observed Codon Pair Frequencies and Codon Pair Scores for 14,795 Human Genes

| amino acid pair | codon pair | expected | observed | observed/expected | CPS |
|---|---|---|---|---|---|
| VI | GTGATA | 1703.61 | 1117 | 0.656 | -0.422 |
| VI | GTTATC | 1849.37 | 1053 | 0.569 | -0.563 |
| VI | GTAATC | 1200.86 | 577 | 0.480 | -0.733 |
| VK | GTAAAA | 1288.46 | 1945 | 1.510 | 0.412 |
| VK | GTCAAG | 3290.24 | 3982 | 1.210 | 0.191 |
| VK | GTGAAG | 6509.08 | 7513 | 1.154 | 0.143 |
| VK | GTAAAG | 1668.70 | 1704 | 1.021 | 0.021 |
| VK | GTCAAA | 2540.51 | 2376 | 0.935 | -0.067 |
| VK | GTTAAA | 1984.27 | 1777 | 0.896 | -0.110 |
| VK | GTGAAA | 5025.89 | 4409 | 0.877 | -0.131 |
| VK | GTTAAG | 2569.85 | 1171 | 0.456 | -0.786 |
| VL | GTTTTA | 668.83 | 1311 | 1.960 | 0.673 |
| VL | GTTCTT | 1146.70 | 1859 | 1.621 | 0.483 |
| VL | GTTTTG | 1123.58 | 1737 | 1.546 | 0.436 |
| VL | GTATTA | 434.30 | 646 | 1.487 | 0.397 |
| VL | GTCCTC | 2129.16 | 3019 | 1.418 | 0.349 |
| VL | GTTCTA | 618.41 | 832 | 1.345 | 0.297 |
| VL | GTCCTG | 4424.65 | 5574 | 1.260 | 0.231 |
| VL | GTCCTT | 1468.14 | 1722 | 1.173 | 0.159 |
| VL | GTGCTG | 8753.31 | 10107 | 1.155 | 0.144 |
| VL | GTCTTG | 1438.54 | 1628 | 1.132 | 0.124 |
| VL | GTACTA | 401.55 | 447 | 1.113 | 0.107 |
| VL | GTCCTA | 791.76 | 874 | 1.104 | 0.099 |
| VL | GTCTTA | 856.32 | 863 | 1.008 | 0.008 |
| VL | GTATTG | 729.58 | 711 | 0.975 | -0.026 |
| VL | GTACTT | 744.59 | 693 | 0.931 | -0.072 |
| VL | GTTCTC | 1662.99 | 1501 | 0.903 | -0.102 |
| VL | GTGCTC | 4212.12 | 3765 | 0.894 | -0.112 |
| VL | GTGCTA | 1566.34 | 1286 | 0.821 | -0.197 |
| VL | GTTCTG | 3455.90 | 2350 | 0.680 | -0.386 |
| VL | GTGTTG | 2845.87 | 1910 | 0.671 | -0.399 |
| VL | GTGCTT | 2904.43 | 1933 | 0.666 | -0.407 |
| VL | GTGTTA | 1694.06 | 965 | 0.570 | -0.563 |
| VL | GTACTC | 1079.84 | 541 | 0.501 | -0.691 |
| VL | GTACTG | 2244.04 | 1121 | 0.500 | -0.694 |
| VM | GTCATG | 2149.52 | 3308 | 1.539 | 0.431 |
| VM | GTGATG | 4252.41 | 3872 | 0.911 | -0.094 |
| VM | GTAATG | 1090.17 | 935 | 0.858 | -0.154 |
| VM | GTTATG | 1678.90 | 1056 | 0.629 | -0.464 |
| VN | GTCAAC | 2052.00 | 3311 | 1.614 | 0.478 |
| VN | GTAAAT | 944.92 | 1518 | 1.606 | 0.474 |
| VN | GTCAAT | 1863.13 | 2155 | 1.157 | 0.146 |
| VN | GTTAAT | 1455.20 | 1325 | 0.911 | -0.094 |
| VN | GTGAAC | 4059.49 | 3551 | 0.875 | -0.134 |
| VN | GTGAAT | 3685.83 | 3110 | 0.844 | -0.170 |
| VN | GTAAAC | 1040.71 | 854 | 0.821 | -0.198 |
| VN | GTTAAC | 1602.73 | 880 | 0.549 | -0.600 |
| VP | GTTCCT | 1434.04 | 2257 | 1.574 | 0.454 |
| VP | GTTCCA | 1384.03 | 1911 | 1.381 | 0.323 |
| VP | GTGCCC | 4055.45 | 4998 | 1.232 | 0.209 |
| VP | GTACCT | 931.17 | 1048 | 1.125 | 0.118 |
| VP | GTCCCC | 2049.96 | 2260 | 1.102 | 0.098 |
| VP | GTCCCT | 1836.02 | 2014 | 1.097 | 0.093 |
| VP | GTACCA | 898.70 | 963 | 1.072 | 0.069 |
| VP | GTCCCG | 742.77 | 786 | 1.058 | 0.057 |
| VP | GTTCCC | 1601.13 | 1506 | 0.941 | -0.061 |
| VP | GTCCCA | 1772.00 | 1596 | 0.901 | -0.105 |
| VP | GTGCCT | 3632.21 | 3062 | 0.843 | -0.171 |
| VP | GTGCCG | 1469.43 | 1228 | 0.836 | -0.179 |
| VP | GTACCC | 1039.67 | 809 | 0.778 | -0.251 |
| VP | GTGCCA | 3505.55 | 2431 | 0.693 | -0.366 |
| VP | GTTCCG | 580.15 | 279 | 0.481 | -0.732 |
| VP | GTACCG | 376.71 | 161 | 0.427 | -0.850 |
| VQ | GTACAA | 633.37 | 1049 | 1.656 | 0.505 |
| VQ | GTTCAA | 975.42 | 1485 | 1.522 | 0.420 |
| VQ | GTCCAG | 3487.32 | 3907 | 1.120 | 0.114 |
| VQ | GTACAG | 1768.65 | 1752 | 0.991 | -0.009 |
| VQ | GTTCAG | 2723.79 | 2689 | 0.987 | -0.013 |
| VQ | GTGCAG | 6898.98 | 6734 | 0.976 | -0.024 |
| VQ | GTCCAA | 1248.85 | 1067 | 0.854 | -0.157 |

Supplemental Table 1

Expected and Observed Codon Pair Frequencies and Codon Pair Scores for 14,795 Human Genes

| amino acid pair | codon pair | expected | observed | observed/expected | CPS |
|---|---|---|---|---|---|
| VQ | GTGCAA | 2470.60 | 1524 | 0.617 | -0.483 |
| VR | GTTCGA | 463.33 | 867 | 1.871 | 0.627 |
| VR | GTTCGT | 334.59 | 580 | 1.733 | 0.550 |
| VR | GTCCGA | 593.21 | 805 | 1.357 | 0.305 |
| VR | GTCCGC | 1000.57 | 1332 | 1.331 | 0.286 |
| VR | GTGCGC | 1979.43 | 2543 | 1.285 | 0.251 |
| VR | GTCCGT | 428.38 | 549 | 1.282 | 0.248 |
| VR | GTCCGG | 1094.32 | 1346 | 1.230 | 0.207 |
| VR | GTACGA | 300.86 | 361 | 1.200 | 0.182 |
| VR | GTAAGA | 559.73 | 660 | 1.179 | 0.165 |
| VR | GTGCGG | 2164.91 | 2552 | 1.179 | 0.164 |
| VR | GTCAGA | 1103.65 | 1291 | 1.170 | 0.157 |
| VR | GTACGT | 217.26 | 253 | 1.165 | 0.152 |
| VR | GTCAGG | 1083.48 | 1238 | 1.143 | 0.133 |
| VR | GTGAGG | 2143.46 | 1986 | 0.927 | -0.076 |
| VR | GTGCGT | 847.46 | 761 | 0.898 | -0.108 |
| VR | GTAAGG | 549.51 | 444 | 0.808 | -0.213 |
| VR | GTTCGG | 854.73 | 650 | 0.760 | -0.274 |
| VR | GTGCGA | 1173.55 | 826 | 0.704 | -0.351 |
| VR | GTTCGC | 781.50 | 545 | 0.697 | -0.360 |
| VR | GTGAGA | 2183.35 | 1511 | 0.692 | -0.368 |
| VR | GTACGG | 555.00 | 377 | 0.679 | -0.387 |
| VR | GTTAGA | 862.01 | 556 | 0.645 | -0.438 |
| VR | GTACGC | 507.46 | 286 | 0.564 | -0.573 |
| VR | GTTAGG | 846.26 | 309 | 0.365 | -1.007 |
| VS | GTTTCT | 1206.81 | 2161 | 1.791 | 0.583 |
| VS | GTCTCC | 1776.18 | 2936 | 1.653 | 0.503 |
| VS | GTCAGC | 2012.32 | 3223 | 1.602 | 0.471 |
| VS | GTTTCA | 975.63 | 1465 | 1.502 | 0.407 |
| VS | GTCAGT | 1269.59 | 1841 | 1.450 | 0.372 |
| VS | GTATCT | 783.62 | 1093 | 1.395 | 0.333 |
| VS | GTATCA | 633.51 | 806 | 1.272 | 0.241 |
| VS | GTCTCT | 1545.10 | 1847 | 1.195 | 0.178 |
| VS | GTTTCC | 1387.29 | 1604 | 1.156 | 0.145 |
| VS | GTCTCG | 469.69 | 542 | 1.154 | 0.143 |
| VS | GTCTCA | 1249.12 | 1333 | 1.067 | 0.065 |
| VS | GTGTCC | 3513.81 | 3722 | 1.059 | 0.058 |
| VS | GTGTCG | 929.19 | 860 | 0.926 | -0.077 |
| VS | GTGTCT | 3056.67 | 2784 | 0.911 | -0.093 |
| VS | GTATCC | 900.82 | 763 | 0.847 | -0.166 |
| VS | GTAAGT | 643.89 | 499 | 0.775 | -0.255 |
| VS | GTGAGC | 3980.98 | 2901 | 0.729 | -0.316 |
| VS | GTGTCA | 2471.14 | 1710 | 0.692 | -0.368 |
| VS | GTTAGT | 991.62 | 640 | 0.645 | -0.438 |
| VS | GTATCG | 238.21 | 138 | 0.579 | -0.546 |
| VS | GTTTCG | 366.85 | 202 | 0.551 | -0.597 |
| VS | GTGAGT | 2511.63 | 1371 | 0.546 | -0.605 |
| VS | GTAAGC | 1020.58 | 514 | 0.504 | -0.686 |
| VS | GTTAGC | 1571.73 | 551 | 0.351 | -1.048 |
| VT | GTCACC | 2294.69 | 4477 | 1.951 | 0.668 |
| VT | GTCACT | 1642.76 | 2452 | 1.493 | 0.401 |
| VT | GTCACG | 753.80 | 997 | 1.323 | 0.280 |
| VT | GTAACT | 833.15 | 1046 | 1.255 | 0.228 |
| VT | GTCACA | 1857.64 | 2207 | 1.188 | 0.172 |
| VT | GTAACA | 942.13 | 1096 | 1.163 | 0.151 |
| VT | GTTACT | 1283.09 | 1208 | 0.941 | -0.060 |
| VT | GTGACC | 4539.59 | 4223 | 0.930 | -0.072 |
| VT | GTGACG | 1491.24 | 1318 | 0.884 | -0.123 |
| VT | GTGACT | 3249.88 | 2758 | 0.849 | -0.164 |
| VT | GTGACA | 3674.98 | 2947 | 0.802 | -0.221 |
| VT | GTTACA | 1450.92 | 1111 | 0.766 | -0.267 |
| VT | GTAACC | 1163.79 | 758 | 0.651 | -0.429 |
| VT | GTTACC | 1792.28 | 969 | 0.541 | -0.615 |
| VT | GTAACG | 382.30 | 191 | 0.500 | -0.694 |
| VT | GTTACG | 588.76 | 183 | 0.311 | -1.169 |
| VV | GTTGTA | 655.54 | 1109 | 1.692 | 0.526 |
| VV | GTTGTT | 1009.55 | 1701 | 1.685 | 0.522 |
| VV | GTAGTA | 425.66 | 698 | 1.640 | 0.495 |
| VV | GTGGTG | 6476.64 | 9025 | 1.393 | 0.332 |
| VV | GTGGTC | 3273.84 | 4256 | 1.300 | 0.262 |

Supplemental Table 1

Expected and Observed Codon Pair Frequencies and Codon Pair Scores for 14,795 Human Genes

| amino acid pair | codon pair | expected | observed | observed/expected | CPS |
|---|---|---|---|---|---|
| VV | GTAGTT | 655.54 | 800 | 1.220 | 0.199 |
| VV | GTTGTC | 1292.55 | 1561 | 1.208 | 0.189 |
| VV | GTGGTA | 1660.38 | 1777 | 1.070 | 0.068 |
| VV | GTGGTT | 2557.05 | 2613 | 1.022 | 0.022 |
| VV | GTTGTG | 2557.05 | 2261 | 0.884 | -0.123 |
| VV | GTAGTG | 1660.38 | 1161 | 0.699 | -0.358 |
| VV | GTAGTC | 839.30 | 553 | 0.659 | -0.417 |
| VV | GTCGTC | 1654.87 | 858 | 0.518 | -0.657 |
| VV | GTCGTG | 3273.84 | 1250 | 0.382 | -0.963 |
| VV | GTCGTA | 839.30 | 213 | 0.254 | -1.371 |
| VV | GTCGTT | 1292.55 | 288 | 0.223 | -1.501 |
| VW | GTCTGG | 1316.29 | 1763 | 1.339 | 0.292 |
| VW | GTGTGG | 2604.03 | 2451 | 0.941 | -0.061 |
| VW | GTATGG | 667.58 | 578 | 0.866 | -0.144 |
| VW | GTTTGG | 1028.10 | 824 | 0.801 | -0.221 |
| VY | GTCTAC | 1602.79 | 2490 | 1.554 | 0.441 |
| VY | GTTTAT | 1017.23 | 1438 | 1.414 | 0.346 |
| VY | GTATAT | 660.53 | 875 | 1.325 | 0.281 |
| VY | GTCTAT | 1302.39 | 1544 | 1.186 | 0.170 |
| VY | GTGTAC | 3170.80 | 2654 | 0.837 | -0.178 |
| VY | GTTTAC | 1251.87 | 1008 | 0.805 | -0.217 |
| VY | GTATAC | 812.88 | 582 | 0.716 | -0.334 |
| VY | GTGTAT | 2576.51 | 1804 | 0.700 | -0.356 |
| WA | TGGGCA | 1469.77 | 1535 | 1.044 | 0.043 |
| WA | TGGGCG | 690.28 | 695 | 1.007 | 0.007 |
| WA | TGGGCT | 1678.97 | 1664 | 0.991 | -0.009 |
| WA | TGGGCC | 2552.98 | 2498 | 0.978 | -0.022 |
| WC | TGGTGC | 1057.38 | 1066 | 1.008 | 0.008 |
| WC | TGGTGT | 890.62 | 882 | 0.990 | -0.010 |
| WD | TGGGAC | 2699.37 | 2807 | 1.040 | 0.039 |
| WD | TGGGAT | 2389.63 | 2282 | 0.955 | -0.046 |
| WE | TGGGAG | 3580.00 | 3650 | 1.020 | 0.019 |
| WE | TGGGAA | 2677.00 | 2607 | 0.974 | -0.026 |
| WF | TGGTTT | 1639.95 | 1735 | 1.058 | 0.056 |
| WF | TGGTTC | 1877.05 | 1782 | 0.949 | -0.052 |
| WG | TGGGGT | 955.95 | 1064 | 1.113 | 0.107 |
| WG | TGGGGC | 2002.00 | 2179 | 1.088 | 0.085 |
| WG | TGGGGA | 1476.56 | 1454 | 0.985 | -0.015 |
| WG | TGGGGG | 1441.49 | 1179 | 0.818 | -0.201 |
| WH | TGGCAT | 971.42 | 1000 | 1.029 | 0.029 |
| WH | TGGCAC | 1339.58 | 1311 | 0.979 | -0.022 |
| WI | TGGATT | 1537.91 | 1627 | 1.058 | 0.056 |
| WI | TGGATA | 707.30 | 714 | 1.009 | 0.009 |
| WI | TGGATC | 1944.78 | 1849 | 0.951 | -0.051 |
| WK | TGGAAG | 3491.83 | 3645 | 1.044 | 0.043 |
| WK | TGGAAA | 2696.17 | 2543 | 0.943 | -0.058 |
| WL | TGGCTA | 683.88 | 798 | 1.167 | 0.154 |
| WL | TGGCTG | 3821.78 | 4228 | 1.106 | 0.101 |
| WL | TGGCTT | 1268.11 | 1334 | 1.052 | 0.051 |
| WL | TGGCTC | 1839.05 | 1879 | 1.022 | 0.021 |
| WL | TGGTTG | 1242.54 | 855 | 0.688 | -0.374 |
| WL | TGGTTA | 739.64 | 501 | 0.677 | -0.390 |
| WM | TGGCTG | 2335.00 | 2335 | 1.000 | 0.000 |
| WN | TGGAAT | 1978.70 | 2005 | 1.013 | 0.013 |
| WN | TGGAAC | 2179.30 | 2153 | 0.988 | -0.012 |
| WP | TGGCCC | 1302.21 | 1381 | 1.061 | 0.059 |
| WP | TGGCCG | 471.84 | 486 | 1.030 | 0.030 |
| WP | TGGCCA | 1125.64 | 1123 | 0.998 | -0.002 |
| WP | TGGCCT | 1166.31 | 1076 | 0.923 | -0.081 |
| WQ | TGGCAG | 2983.56 | 2997 | 1.005 | 0.004 |
| WQ | TGGCAA | 1068.44 | 1055 | 0.987 | -0.013 |
| WR | TGGAGG | 1198.99 | 1665 | 1.389 | 0.328 |
| WR | TGGAGA | 1221.30 | 1472 | 1.205 | 0.187 |
| WR | TGGCGG | 1210.98 | 979 | 0.808 | -0.213 |
| WR | TGGCGC | 1107.23 | 895 | 0.808 | -0.213 |
| WR | TGGCGT | 474.05 | 377 | 0.795 | -0.229 |
| WR | TGGCGA | 656.45 | 481 | 0.733 | -0.311 |
| WS | TGGAGT | 1031.75 | 1239 | 1.201 | 0.183 |
| WS | TGGAGC | 1635.35 | 1956 | 1.196 | 0.179 |
| WS | TGGTCA | 1015.12 | 898 | 0.885 | -0.123 |

Supplemental Table 1

Expected and Observed Codon Pair Frequencies and Codon Pair Scores for 14,795 Human Genes

| amino acid pair | codon pair | expected | observed | observed/expected | CPS |
|---|---|---|---|---|---|
| WS | TGGTCC | 1443.44 | 1271 | 0.881 | −0.127 |
| WS | TGGTCT | 1255.65 | 1076 | 0.857 | −0.154 |
| WS | TGGTCG | 381.70 | 323 | 0.846 | −0.167 |
| WT | TGGACG | 598.07 | 674 | 1.127 | 0.120 |
| WT | TGGACA | 1473.88 | 1559 | 1.058 | 0.056 |
| WT | TGGACT | 1303.39 | 1240 | 0.951 | −0.050 |
| WT | TGGACC | 1820.65 | 1723 | 0.946 | −0.055 |
| WV | TGGGTC | 1318.64 | 1378 | 1.045 | 0.044 |
| WV | TGGGTG | 2608.66 | 2633 | 1.009 | 0.009 |
| WV | TGGGTA | 668.77 | 665 | 0.994 | −0.006 |
| WV | TGGGTT | 1029.93 | 950 | 0.922 | −0.081 |
| WW | TGGTGG | 1559.00 | 1559 | 1.000 | 0.000 |
| WY | TGGTAC | 1444.91 | 1520 | 1.052 | 0.051 |
| WY | TGGTAT | 1174.09 | 1099 | 0.936 | −0.066 |
| YA | TATGCA | 1120.39 | 2249 | 2.007 | 0.697 |
| YA | TATGCT | 1279.86 | 2296 | 1.794 | 0.584 |
| YA | TATGCC | 1946.11 | 2862 | 1.471 | 0.386 |
| YA | TACGCG | 647.56 | 622 | 0.961 | −0.040 |
| YA | TATGCG | 526.19 | 482 | 0.916 | −0.088 |
| YA | TACGCC | 2395.00 | 1402 | 0.585 | −0.535 |
| YA | TACGCA | 1378.81 | 512 | 0.371 | −0.991 |
| YA | TACGCT | 1575.07 | 444 | 0.282 | −1.266 |
| YC | TACTGC | 1588.07 | 2411 | 1.518 | 0.418 |
| YC | TACTGT | 1337.61 | 1587 | 1.186 | 0.171 |
| YC | TATTGT | 1086.90 | 659 | 0.606 | −0.500 |
| YC | TATTGC | 1290.42 | 646 | 0.501 | −0.692 |
| YD | TATGAT | 2091.17 | 3707 | 1.773 | 0.572 |
| YD | TATGAC | 2362.22 | 3731 | 1.579 | 0.457 |
| YD | TACGAC | 2907.08 | 1653 | 0.569 | −0.565 |
| YD | TACGAT | 2573.52 | 843 | 0.328 | −1.116 |
| YE | TATGAA | 2515.85 | 5225 | 2.077 | 0.731 |
| YE | TATGAG | 3364.48 | 4722 | 1.403 | 0.339 |
| YE | TACGAG | 4140.53 | 2309 | 0.558 | −0.584 |
| YE | TACGAA | 3096.14 | 861 | 0.278 | −1.280 |
| YF | TACTTC | 2766.63 | 3380 | 1.222 | 0.200 |
| YF | TATTTT | 1964.12 | 2124 | 1.081 | 0.078 |
| YF | TACTTT | 2417.16 | 2201 | 0.911 | −0.094 |
| YF | TATTTC | 2248.09 | 1691 | 0.752 | −0.285 |
| YG | TATGGA | 1472.35 | 2874 | 1.952 | 0.669 |
| YG | TATGGT | 953.23 | 1665 | 1.747 | 0.558 |
| YG | TATGGG | 1437.38 | 2129 | 1.481 | 0.393 |
| YG | TATGGC | 1996.30 | 2749 | 1.377 | 0.320 |
| YG | TACGGG | 1768.93 | 1088 | 0.615 | −0.486 |
| YG | TACGGC | 2456.76 | 1484 | 0.604 | −0.504 |
| YG | TACGGT | 1173.10 | 448 | 0.382 | −0.963 |
| YG | TACGGA | 1811.96 | 633 | 0.349 | −1.052 |
| YH | TACCAC | 1862.81 | 2378 | 1.277 | 0.244 |
| YH | TACCAT | 1350.85 | 1420 | 1.051 | 0.050 |
| YH | TATCAT | 1097.67 | 1021 | 0.930 | −0.072 |
| YH | TATCAC | 1513.67 | 1006 | 0.665 | −0.409 |
| YI | TACATC | 2684.66 | 3935 | 1.466 | 0.382 |
| YI | TACATT | 2122.99 | 2162 | 1.018 | 0.018 |
| YI | TATATT | 1725.09 | 1554 | 0.901 | −0.104 |
| YI | TACATA | 976.39 | 846 | 0.866 | −0.143 |
| YI | TATATA | 793.39 | 648 | 0.817 | −0.202 |
| YI | TATATC | 2181.48 | 1339 | 0.614 | −0.488 |
| YK | TACGAG | 3508.58 | 4372 | 1.246 | 0.220 |
| YK | TACGAA | 2709.10 | 2847 | 1.051 | 0.050 |
| YK | TATGAA | 2201.34 | 2262 | 1.028 | 0.027 |
| YK | TATAAG | 2850.98 | 1789 | 0.628 | −0.466 |
| YL | TACCTG | 4522.42 | 6324 | 1.398 | 0.335 |
| YL | TATTTA | 711.20 | 966 | 1.358 | 0.306 |
| YL | TACCTC | 2176.20 | 2598 | 1.194 | 0.177 |
| YL | TACTTG | 1470.33 | 1701 | 1.157 | 0.146 |
| YL | TATTTG | 1194.75 | 1358 | 1.137 | 0.128 |
| YL | TACCTA | 809.25 | 876 | 1.082 | 0.079 |
| YL | TACCTT | 1500.58 | 1449 | 0.966 | −0.035 |
| YL | TATCTT | 1219.33 | 1166 | 0.956 | −0.045 |
| YL | TACTTA | 875.24 | 763 | 0.872 | −0.137 |
| YL | TATCTA | 657.58 | 541 | 0.823 | −0.195 |

Supplemental Table 1

Expected and Observed Codon Pair Frequencies and Codon Pair Scores for 14,795 Human Genes

| amino acid pair | codon pair | expected | observed | observed/expected | CPS |
|---|---|---|---|---|---|
| YL | TATCTC | 1768.32 | 1087 | 0.615 | −0.487 |
| YL | TATCTG | 3674.80 | 1751 | 0.476 | −0.741 |
| YM | TACATG | 2325.97 | 3055 | 1.313 | 0.273 |
| YM | TATATG | 1890.03 | 1161 | 0.614 | −0.487 |
| YN | TACAGC | 2442.24 | 3341 | 1.368 | 0.313 |
| YN | TACAAT | 2217.44 | 2200 | 0.992 | −0.008 |
| YN | TATAAT | 1801.83 | 1629 | 0.904 | −0.101 |
| YN | TATAAC | 1984.50 | 1276 | 0.643 | −0.442 |
| YP | TACCCG | 668.65 | 1004 | 1.502 | 0.406 |
| YP | TACCCA | 1595.15 | 1925 | 1.207 | 0.188 |
| YP | TATCCA | 1296.18 | 1438 | 1.109 | 0.104 |
| YP | TACCCC | 1845.38 | 1961 | 1.063 | 0.061 |
| YP | TATCCT | 1343.02 | 1379 | 1.027 | 0.026 |
| YP | TACCCT | 1652.79 | 1558 | 0.943 | −0.059 |
| YP | TATCCC | 1499.51 | 937 | 0.625 | −0.470 |
| YP | TATCCG | 543.32 | 242 | 0.445 | −0.809 |
| YQ | TACCTG | 3987.12 | 5013 | 1.257 | 0.229 |
| YQ | TATCTA | 1160.22 | 1179 | 1.016 | 0.016 |
| YQ | TACCTA | 1427.83 | 1397 | 0.978 | −0.022 |
| YQ | TATCAG | 3239.83 | 2226 | 0.687 | −0.375 |
| YR | TACCGC | 1307.70 | 2153 | 1.646 | 0.499 |
| YR | TACCGA | 775.30 | 990 | 1.277 | 0.244 |
| YR | TACAGA | 1442.41 | 1834 | 1.271 | 0.240 |
| YR | TACCGG | 1430.23 | 1796 | 1.256 | 0.228 |
| YR | TACAGG | 1416.06 | 1671 | 1.180 | 0.166 |
| YR | TACCGT | 559.87 | 642 | 1.147 | 0.137 |
| YR | TATCGA | 629.99 | 570 | 0.905 | −0.100 |
| YR | TATCGT | 454.94 | 383 | 0.842 | −0.172 |
| YR | TATAGA | 1172.07 | 827 | 0.706 | −0.349 |
| YR | TATCGG | 1162.17 | 629 | 0.541 | −0.614 |
| YR | TATAGG | 1150.66 | 560 | 0.487 | −0.720 |
| YR | TATCGC | 1062.60 | 509 | 0.479 | −0.736 |
| YS | TACAGC | 2204.13 | 3590 | 1.629 | 0.488 |
| YS | TACTCG | 514.46 | 783 | 1.522 | 0.420 |
| YS | TACAGT | 1390.60 | 1887 | 1.357 | 0.305 |
| YS | TATTCA | 1111.75 | 1210 | 1.088 | 0.085 |
| YS | TACTCC | 1945.47 | 2088 | 1.073 | 0.071 |
| YS | TATTCT | 1375.18 | 1466 | 1.066 | 0.064 |
| YS | TACTCA | 1368.18 | 1188 | 0.868 | −0.141 |
| YS | TATTCC | 1580.84 | 1306 | 0.826 | −0.191 |
| YS | TACTCT | 1692.37 | 1173 | 0.693 | −0.367 |
| YS | TATAGT | 1129.96 | 728 | 0.644 | −0.440 |
| YS | TATTCG | 418.04 | 229 | 0.548 | −0.602 |
| YS | TATAGC | 1791.02 | 874 | 0.488 | −0.717 |
| YT | TACACG | 697.26 | 1311 | 1.880 | 0.631 |
| YT | TACACC | 2122.58 | 2696 | 1.270 | 0.239 |
| YT | TACACA | 1718.31 | 2158 | 1.256 | 0.228 |
| YT | TACACT | 1519.54 | 1409 | 0.927 | −0.076 |
| YT | TATACT | 1234.74 | 1049 | 0.850 | −0.163 |
| YT | TATACA | 1396.25 | 1049 | 0.751 | −0.286 |
| YT | TATACC | 1724.75 | 1063 | 0.616 | −0.484 |
| YT | TATACG | 566.57 | 245 | 0.432 | −0.838 |
| YV | TATGTT | 986.79 | 1723 | 1.746 | 0.557 |
| YV | TATGTA | 640.76 | 1113 | 1.737 | 0.552 |
| YV | TATGTC | 1263.40 | 1862 | 1.474 | 0.388 |
| YV | TATGTG | 2499.39 | 3382 | 1.353 | 0.302 |
| YV | TACGTG | 3075.90 | 2279 | 0.741 | −0.300 |
| YV | TACGTC | 1554.82 | 991 | 0.637 | −0.450 |
| YV | TACGTA | 788.55 | 284 | 0.360 | −1.021 |
| YV | TACGTT | 1214.40 | 390 | 0.321 | −1.136 |
| YW | TACTGG | 1609.87 | 2212 | 1.374 | 0.318 |
| YW | TATTGG | 1308.13 | 706 | 0.540 | −0.617 |
| YY | TACTAC | 2256.03 | 2854 | 1.265 | 0.235 |
| YY | TATTAT | 1489.60 | 1459 | 0.979 | −0.021 |
| YY | TACTAT | 1833.19 | 1760 | 0.960 | −0.041 |
| YY | TATTAC | 1833.19 | 1339 | 0.730 | −0.314 |

We claim:

1. A modified influenza virus in which expression of hemagglutinin (HA) and neuraminidase (NA) is reduced compared to a parent virus, wherein the reduction in expression is the result of recoding the HA protein-encoding sequence and recoding the NA protein-encoding sequence, and wherein the other influenza proteins are not recoded.

2. The modified influenza virus of claim 1, wherein both of the HA protein-encoding sequence and the NA protein-encoding sequence are recoded by lowering the codon pair bias of the protein-encoding sequence.

3. The modified influenza virus of claim 2, wherein reducing the codon-pair bias comprises identifying a codon pair in the parent protein-encoding sequence having a codon-pair score that can be reduced, and reducing the codon-pair bias by substituting the codon pair with a codon pair that encodes the same codon and has a lower codon-pair score.

4. The modified influenza virus of claim 2, wherein reducing the codon-pair bias comprises rearranging the codons of a parent protein-encoding sequence, wherein the rearranged sequence encodes the same protein as the parent protein-encoding sequence.

5. The modified influenza virus of claim 1, wherein each of the recoded HA protein-encoding sequence and the recoded NA protein-encoding sequence have a codon pair bias less than −0.1, or less than −0.2, or less than −0.3, or less than −0.4.

6. The modified influenza virus of claim 1, wherein one or both of the HA protein-encoding sequence and the NA protein-encoding sequence are recoded by replacing one or more codons with synonymous codons that are less frequent in the viral host.

7. An influenza vaccine composition for inducing a protective immune response in a subject, which comprises the modified virus of claim 1.

8. A method of eliciting a protective immune response in a subject comprising administering to the subject a prophylactically or therapeutically effective dose of a vaccine composition comprising the modified virus of claim 1.

9. The method of claim 8, further comprising administering to the subject at least one adjuvant.

10. The method of claim 8, wherein the immune response is cross-protective against a heterologous influenza virus.

11. A method of making a modified influenza virus genome comprising:
 a) obtaining the nucleotide sequence encoding the hemagglutinin protein of an influenza virus and the nucleotide sequence encoding the neuraminidase protein of an influenza virus;
 b) recoding the hemagglutinin-encoding nucleotide sequence to reduce protein expression and recoding the neuraminidase-encoding nucleotide sequence to reduce protein expression, and
 c) substituting a nucleic acid having the recoded hemagglutinin-encoding nucleotide sequence and a nucleic acid having the recoded neuraminidase-encoding nucleotide sequence into a parent influenza virus genome to make an attenuated influenza virus genome; whereby expression of the recoded hemagglutinin-encoding nucleotide sequence and expression of the recoded neuraminidase-encoding nucleotide sequence is reduced compared to the parent virus; wherein the other influenza proteins are not recoded.

12. The method of claim 11, wherein recoding the hemagglutinin-encoding nucleotide sequence to reduce protein expression and recoding the neuraminidase-encoding nucleotide sequence to reduce protein expression comprises lowering the codon pair bias of the hemagglutinin-encoding nucleotide sequence and the neuraminidase-encoding nucleotide sequence.

13. The method of claim 11, wherein recoding the hemagglutinin-encoding nucleotide sequence to reduce protein expression and recoding the neuraminidase-encoding nucleotide sequence to reduce protein expression comprises replacing one or more codons with synonymous codons that are less frequent in the viral host.

* * * * *

SEQUENCE LISTING

<160> NUMBER OF SEQ ID NOS: 63

<210> SEQ ID NO 1
<211> LENGTH: 1683
<212> TYPE: DNA
<213> ORGANISM: Influenza A Virus

<400> SEQUENCE: 1

| | | | | | |
|---|---|---|---|---|---|
| atgtacaaaa | tagtactagt | acttgcgctc | cttggagcgg | tgcatggtct | tgacaaaata | 60 |
| tgccttggac | atcatgcagt | ccccaatggc | accatcgtaa | agactctcac | aaacgaaaag | 120 |
| gaagaggtga | ccaatgctac | tgaaacggtg | gaaagtaaaa | gcctggacaa | actttgcatg | 180 |
| aaaagtcgga | attacaagga | cctaggtaat | tgccacccga | tagggatggt | gatagggact | 240 |
| cctgcttgtg | acttacacct | caccggaaca | tgggacactt | tgatagagag | agacaattcc | 300 |
| attgcctact | gttacccagg | tgccactgtg | aatgaagaag | cattaaggca | gaaaattatg | 360 |
| gaaagtggag | agattgacaa | gataagcacc | gggtttacat | atgaatcatc | catcaatcca | 420 |
| gctggaacca | ctaaagcatg | catgagaaat | gggaaaaaca | gtttctatgc | agagctaaag | 480 |
| tggctagtgt | cgaaggacaa | aggacggaac | ttcccacaaa | caacaaacac | atacaggaat | 540 |
| acagattcaa | cagaacacct | tataatctgg | ggaattcatc | acccgtcaag | cacacaagaa | 600 |
| aagaatgatc | tgtatggaac | acaatcactt | tccatttcag | tagggagttc | tacttatcaa | 660 |
| aacaactttg | tgcctgtggt | gggagcaaga | ccacaggtga | atggccaaag | tgggcggatt | 720 |
| gatttccatt | gggcgatggt | acaaccgggt | gataacatca | cttttcgca | taacggcgga | 780 |
| ctaatagcac | ctagtagagt | gagtaaaacta | aagggaagag | gccttggcat | tcaatcagga | 840 |
| gcttcagtag | ataatgactg | tgaatcaaaa | tgttttttgga | aaggtggatc | catcaacacc | 900 |
| aaactccctt | ttcagaatct | ttccccaaga | actgtgggtc | aatgccccaa | gtatgtgaac | 960 |
| aaaaagagcc | tgttgcttgc | taccggaatg | aggaatgtgc | cagaggttgt | ccaaggaaga | 1020 |
| ggcctgttcg | gagcaattgc | tggattcata | gaaaatggat | gggaagggat | ggtagatggt | 1080 |
| tggtatggtt | tccgacatca | aaatgcccaa | ggcactggtc | aggctgcgga | ttacaaaagc | 1140 |
| actcaggcag | ctatagatca | aatcaccggg | aaattgaaca | gactgatagaa | gaagacaaac | 1200 |
| acagagttcg | aatccataga | atctgagttc | agtgaaattg | aacatcaaat | tggcaatgta | 1260 |
| ataaactgga | ctaaggattc | gataacagac | attttggacgt | atcaagctga | attactggta | 1320 |
| gcaatggaaa | accagcatac | aatcgacatg | gctgattcag | aaatgctgaa | tctatatgag | 1380 |
| agagtgagga | agcaactgag | gcaaaatgca | gaagaagatg | ggaaagggtg | ctttgaaata | 1440 |
| tatcacaaat | gcgacgacaa | ctgcatggaa | agcatcagaa | acaacaccta | tgaccataca | 1500 |
| caatacagag | aagaagcact | cttgaacaga | ctcaacatta | atccggtgaa | actctcttct | 1560 |
| gggtacaaag | atgttatact | gtggtttagc | ttcggggcgt | catgctttgt | acttttggct | 1620 |
| gtcatcatgg | ggcttgtttt | cttctgtctg | aaaaatggaa | acatgcgatg | cacaatctgt | 1680 |
| att | | | | | | 1683 |

<210> SEQ ID NO 2
<211> LENGTH: 1683
<212> TYPE: DNA
<213> ORGANISM: Unknown
<220> FEATURE:
<223> OTHER INFORMATION: deoptimized Influenza A Virus

<400> SEQUENCE: 2

| | | | | | |
|---|---|---|---|---|---|
| atgtataaga | tagtgctcgt | actcgcacta | ttaggcgcag | tgcacggact | cgacaaaatt | 60 |

```
tgcctagggc atcacgcagt gcctaacgga actatcgtta agacacttac taacgaaaaa    120
gaggaagtga ctaacgctac cgaaacagtc gaatcaaaat cactcgacaa attgtgtatg    180
aaaagtcgga attataaaga cctaggcaat tgccatccga tagggatggt gatagggact    240
cccgcttgcg atctgcatct gacagggaca tgggatacac ttatcgaacg ggacaatagt    300
atagcgtatt gttatccagg cgctacagtg aacgaagagg cacttagaca aaaaattatg    360
gaatccggcg aaatcgataa gattagtacc ggattcacat acgaatcctc tattaatccc    420
gcaggaacaa ctaaggcttg tatgcgaaac ggtaagaatt cgttttacgc tgaactgaaa    480
tggcttgtga gtaaggacaa aggtaggaat tccccacaaa ctactaatac ttataggaat    540
accgattcaa ccgaacatct gattatatgg gggatacacc atccaagttc gacacaagag    600
aaaaacgatc tatacggaac gcaatccctt agcattagcg tagggtctag tacttatcag    660
aataatttcg taccggtagt gggcgctaga ccgcaagtga acggacaatc cggtagaatc    720
gatttccatt gggctatggt gcaaccaggc gataacataa cttttagcca taacggcgga    780
ctgatagcgc ctagtagagt gagtaagctt aagggaaggg ggttggggat acaatccggc    840
gctagcgtag acaacgattg cgaatcaaaa tgcttttgga aagggggtc aattaatact    900 aaattgccat ttcagaatct gtcacctaga acagtgggac aatgccctaa atacgttaat    960
aagaaaagtc tgttactcgc aaccggtatg cgaaacgtac cagaggtagt gcaaggtagg   1020
gggctattcg gagcgatagc gggatttatc gaaaacggat gggagggtat ggtcgacgga   1080
tggtacgggt ttagacacca aaacgcacag ggaaccggac aggcagcaga ctataaatcg   1140
acacaagccg ctatagacca aattaccggt aagcttaaca gactgatcga aaagactaat   1200
accgaattcg aatcaatcga atccgaattt agcgaaatcg aacaccaaat cggaaacgta   1260
attaattgga caaaagactc aattaccgat atatggacat atcaagccga actgttagtc   1320
gctatggaga atcagcatac aatcgatatg gccgatagcg aaatgcttaa cctttacgaa   1380
agggtgagaa aacagcttag acaaaacgct gaagaggacg gtaaggggtg tttcgaaata   1440
taccataaat gcgacgataa ttgtatggag tctatacgga ataacacata cgaccatacg   1500
caatatagag aggaagcact actgaataga cttaacatta tccggttaa gctatctagc   1560 ggatataaag acgtgatatt gtggttctca ttcggagcgt catgtttcgt attgctcgca   1620
gtgattatgg gactcgtatt cttttgcctt aaaaacggta atatgagatg cacaatttgc   1680
ata                                                                 1683
```

<210> SEQ ID NO 3
<211> LENGTH: 1410
<212> TYPE: DNA
<213> ORGANISM: Influenza A virus

<400> SEQUENCE: 3

```
atgaatccta atcaaaaatt attcgcactc tctggggtgg ccatagcact gagtatcctc     60
aacctactaa taggaatatc caatgtggga ctgaatgtct cactcaccct gaagggaagc    120
agtgaccagg ataagaattg acatgcacg agtgtaacac aaaccaacac gactttaatc    180
gaaaacacgt atgtcaacaa taccactgtc atcaataagg aaacagggac tacaaagcaa    240
aattatctaa tgctgaacaa gagtttatgc aaagttgaag gatgggtagt ggtggccaag    300
gacaatgcca taagattcgg tgaaagtgaa caaataatag tgacaaggga gccgtatgtg    360
tcatgtgatc cattaggatg taagacgtac gcactgcatc aagggacaac cattagaaac    420
```

| aagcactcaa acggaacaat acacgacagg actgctttca gagggttgat atcaactcct | 480 |
| ttggggagcc cccctgtagt cagcaatagt gactttcttt gtgtagggtg gtcaagcacc | 540 |
| agttgccatg acggcatcgg gcggatgacc atttgcgtgc agggaaataa taacaacgca | 600 |
| acagctacag tgtactatga ccgaaggctc actaccacaa taaaaacatg ggcagggaaa | 660 |
| atccttagga cgcaagagtc ggaatgtgta tgccacaatg aacatgtgt agtaataatg | 720 |
| accgatggat cggcaagcag ccaggcacat acaaaagttc tgtatttcca caaaggacta | 780 |
| gtaataaaag aggaagccct caagggatca gccagacaca tagaggagtg ctcatgctat | 840 |
| gggcacaatt caaaggtgac ttgtgtatgc agggacaact ggcaaggagc caatagacca | 900 |
| gtgattgaaa tagatatgaa tgccatggag catacaagtc agtatctatg tacaggagtt | 960 |
| ctcactgaca cgagcagacc atcagacaaa tcaatgggcg actgtaataa tccgatcact | 1020 |
| gggagtccgg gagcccctgg ggtcaaagga ttcggcttcc tggatagtga caatacatgg | 1080 |
| ttgggccgca caataagtcc tcgttccagg agtggttttg agatgttgaa gatacctaat | 1140 |
| gctgggacag acccaaattc tagaatcact gagaggcaag aaatagttga caacaacaat | 1200 |
| tggtcaggat actcaggaag tttcattgac tattgggatg aaagcagtgt gtgctacaac | 1260 |
| ccctgttttt atgttgaatt aataagagga aggcctgaag aagccaagta tgtttggtgg | 1320 |
| acgagcaaca gtttagttgc actatgtgga agcccaatct cagttgggtc cggttccttc | 1380 |
| cccgatgggg cacaaatcca atactttcg | 1410 |

<210> SEQ ID NO 4
<211> LENGTH: 1410
<212> TYPE: DNA
<213> ORGANISM: Unknown
<220> FEATURE:
<223> OTHER INFORMATION: Deoptimized Influenza A virus

<400> SEQUENCE: 4

| atgaatccta accaaaagct attcgcacta agcggagtcg ccatagccct atcaatactg | 60 |
| aatctgttaa tcggaatatc gaacgttggg ttgaacgtta gtttgcacct taaggggtca | 120 |
| tccgaccaag acaaaaattg gacatgtact agcgttacgc aaacaaatac gactttgatc | 180 |
| gaaaatacat acgttaacaa tacgacagtg ataaataaag gaccggaac tactaagcaa | 240 |
| aactatctga tgctgaataa gtcactatgt aaggtcgagg gatgggtggt agtcgctaaa | 300 |
| gacaacgcaa taaggttcgg cgaaagcgaa cagataatcg tgacacgcga accatacgtt | 360 |
| agttgcgatc cgttagggtg taagacatac gcattacacc aagggactac gatacggaat | 420 |
| aaacactcta acggaacgat acacgacaga accgcattta gggggttgat atcgacacct | 480 |
| ctcggatcac ctcccgtagt gagtaatagc gatttcttat gcgtggggtg gtcaagtact | 540 |
| agttgtcacg acggaatcgg acgtatgaca atatgcgtac aggggaataa caataacgca | 600 |
| accgcaacag tgtattacga taggagactg actacaacaa ttaagacttg ggccggtaag | 660 |
| atactgagaa cacaggaaag cgaatgcgtt tgccataacg tacatgcgt agtgattatg | 720 |
| acagacggat ccgcaagttc gcaagcccat acgaaagtgc tatattttca caagggctc | 780 |
| gtaatcaaag aggaagccct taaggatcc gctagacata tcgaagagtg tagttgttac | 840 |
| ggacacaata gtaaggttac atgcgtatgt agggacaatt ggcaaggcgc aaatagacca | 900 |
| gtgatagaga tagacatgaa cgctatggag catacgagtc agtatctatg taccggagtg | 960 |
| ttaaccgaca ctagtagacc tagcgataag agtatgggcg attgcaataa tccgataacc | 1020 |
| ggatcacccg gagcaccagg cgttaagggg ttcgggtttc tcgatagcga taatacatgg | 1080 |

```
ttaggtagga caatctcacc taggtcaaga tccggattcg aaatgctcaa aatccctaac      1140
gccggaacag accctaatag taggattacc gaacgacaag agatagtcga caataacaat      1200
tggtcagggt atagcggatc tttcatagac tattgggacg aatcaagcgt atgttataac      1260
ccatgtttct atgtcgaact gattaggggg agacccgaag aggccaaata tgtgtggtgg      1320
actagtaata gtctcgtagc cctatgcgga tcaccgataa gcgtagggtc agggtcattc      1380
ccagacggag cccaaatcca atattttagt                                      1410

<210> SEQ ID NO 5
<211> LENGTH: 1698
<212> TYPE: DNA
<213> ORGANISM: Influenza A virus

<400> SEQUENCE: 5
atgaaggcaa tactagtagt tctgctatat acatttgcaa ccgcaaatgc agacacatta       60
tgtataggtt atcatgcgaa caattcaaca gacactgtag acacagtact agaaaagaat      120
gtaacagtaa cacactctgt taaccttcta agagacaagc ataacgggaa actatgcaaa      180
ctaagagggg tagccccatt gcatttgggt aaatgtaaca ttgctggctg gatcctggga      240
aatccagagt gtgaatcact ctccacagca agctcatggt cctacattgt ggaaacatct      300
agttcagaca atggaacgtg ttacccagga gatttcatcg attatgagga gctaagagag      360
caattgagct cagtgtcatc atttgaaagg tttgagatat tccccaagac aagttcatgg      420
cccaatcatg actcgaacaa aggtgtaacg gcagcatgtc ctcatgctgg agcaaaaagc      480
ttctacaaaa atttaatatg gctagttaaa aaggaaatt catacccaaa gctcagcaaa      540
tcctacatta atgataaagg gaaagaagtc ctcgtgctat ggggcattca ccatccatct      600
actagtgctg accaacaaag tctctatcag aatgcagatg catatgtttt tgtggggaca      660
tcaagataca gcaagaagtt caagccggaa atagcaataa gacccaaagt gagggatcaa      720
gaagggagaa tgaactatta ctggacacta gtagagccgg gagacaaaat aacattcgaa      780
gcaactggaa atctagtggt accgagatat gcattcgcaa tggaaagaaa tgctgggtct      840
ggtattatca tttcagatac accagtccac gattgcaata caacttgtca gacacccaag      900
ggtgctataa acaccagcct cccatttcag aatatacatc cgatcacaat tggaaaatgt      960
ccaaaatatg taaaaagcac aaaattgaga ctggccacag gattgaggaa tgtcccgtct     1020
attcaatcta gaggcctatt tggggccatt gccggtttca ttgaaggggg gtggacaggg     1080
atggtagatg gatggtacgg ttatcaccat caaaatgagc aggggtcagg atatgcagcc     1140
gacctgaaga gcacacagaa tgccattgac gagattacta acaaagtaaa ttctgttatt     1200
gaaaagatga tacacagtt cacagcagta ggtaaagagt caaccaccct ggaaaaaaga     1260
atagagaatt aaataaaaa agttgatgat ggtttcctgg acatttggac ttacaatgcc     1320
gaactgttgg ttctattgga aaatgaaaga actttggact accacgattc aaatgtgaag     1380
aacttatatg aaaaggtaag aagccagtta aaaaacaatg ccaaggaaat tggaaacggc     1440
tgctttgaat ttaccacaa atgcgataac acgtgcatgg aaagtgtcaa aatgggact     1500 tatgactacc caaatactc agaggaagca aaattaaaca gagaagaaat agatggggta     1560
aagctggaat caacaaggat ttaccagatt ttggcgatct attcaactgt cgccagttca     1620
ttggtactgg tagtctccct gggggcaatc agtttctgga tgtgctctaa tgggtctcta     1680
cagtgtagaa tatgtatt                                                  1698
```

<210> SEQ ID NO 6
<211> LENGTH: 1698
<212> TYPE: DNA
<213> ORGANISM: Unknown
<220> FEATURE:
<223> OTHER INFORMATION: Deoptimized Influenza A virus

<400> SEQUENCE: 6

| | | | | | |
|---|---|---|---|---|---|
| atgaaagcga | ttctagtcgt | actgctatat | acattcgcta | ccgctaacgc | cgatacacta | 60 |
| tgcatagggt | atcacgctaa | taatagtaca | gacacagtag | acacagtact | cgaaaaaaac | 120 |
| gttacggtta | cacattccgt | taatctgtta | gaggataagc | ataacggtaa | gctatgtaaa | 180 |
| ctgagaggcg | tagcaccatt | gcatttgggt | aagtgtaata | tagccggatg | gatactaggt | 240 |
| aatcccgaat | gcgaatcact | atcaactgca | agttcatggt | cttatatagt | cgaaactagt | 300 |
| tcaagcgata | acggtacatg | ttatcccgga | gactttatcg | attacgaaga | gttgagagag | 360 |
| caattgtcta | gcgtaagctc | attcgaaaga | ttcgaaattt | ttccgaaaac | tagttcatgg | 420 |
| cctaatcacg | attcaaataa | gggggtaaca | gccgcatgcc | cacacgcagg | cgctaagtca | 480 |
| ttctataaaa | atctgatatg | gctagtgaaa | aaagggaatt | cttatccgaa | actatcaaaa | 540 |
| tcatatatta | acgataaggg | taaggaggta | ctcgtattgt | gggggataca | ccatccatca | 600 |
| actagcgcag | accaacaatc | tctgtatcag | aatgccgacg | catacgtatt | cgtagggact | 660 |
| agtaggtact | ctaaaaaatt | taaacccgaa | atcgctatta | gaccgaaagt | gagagaccag | 720 |
| gagggaagaa | tgaattacta | ttggacacta | gtcgaaccag | gcgataagat | tacattcgaa | 780 |
| gcgacaggga | atctagtggt | accgagatac | gcattcgcaa | tggagagaaa | cgccggatcc | 840 |
| ggaattatta | ttagcgatac | tcccgtacac | gattgcaata | caacatgtca | gacaccaaaa | 900 |
| ggggcaatta | atactagcct | accatttcag | aatatacacc | caattacaat | cggtaagtgt | 960 |
| ccaaaatacg | ttaagtctac | gaaacttaga | ttggcaacag | ggttgagaaa | cgtaccatca | 1020 |
| atacagtcta | gagggttgtt | cggagcaatc | gccggattca | tagagggggg | gtggaccggt | 1080 |
| atggtcgacg | gatggtacgg | ataccatcat | caaaacgaac | aggggtccgg | atacgcagcc | 1140 |
| gatctgaaat | caacacagaa | cgcaatcgac | gaaattacga | ataaagtgaa | tagcgtaatc | 1200 |
| gaaaaaatga | atactcagtt | tacagccgta | ggtaaggaat | ttaatcatct | cgaaaaaaga | 1260 |
| attgagaatc | tgaataaaaa | ggtagacgac | gggtttctag | acatttggac | atataatgcc | 1320 |
| gaactgttag | tgttactcga | aaacgaaaga | acattagact | atcacgattc | taacgttaag | 1380 |
| aatctatacg | aaaagtgag | atcgcaattg | aagaataacg | caaagagat | agggaatggg | 1440 |
| tgtttcgaat | tctaccataa | atgcgataat | acatgtatgg | aatccgtaaa | aaacggtaca | 1500 |
| tacgattatc | cgaaatatag | cgaagaagca | aaactgaata | gggaagagat | tgacggagtt | 1560 |
| aagttggagt | caactaggat | ttaccagata | ctcgcaattt | actctacagt | cgcatcaagt | 1620 |
| ctagtgttag | tcgttagctt | aggcgcaatt | agttttggga | tgtgttcaaa | cggatcactg | 1680 |
| caatgtagga | tttgcata | | | | | 1698 |

<210> SEQ ID NO 7
<211> LENGTH: 1407
<212> TYPE: DNA
<213> ORGANISM: Influenza A virus

<400> SEQUENCE: 7

| | | | | | |
|---|---|---|---|---|---|
| atgaatccaa | accaaaagat | aataaccatt | ggttcggtct | gtatgacaat | tggaatggct | 60 |
| aacttaatat | tacaaattgg | aaacataatc | tcaatatgga | ttagccactc | aattcaactt | 120 |

```
gggaatcaaa atcagattga aacatgcaat caaagcgtca ttacttatga aaacaacact      180
tgggtaaatc agacatatgt taacatcagc aacaccaact ttgctgctgg acagtcagtg      240
gtttccgtga aattagcggg caattcctct ctctgccctg ttagtggatg ggctatatac      300
agtaaagaca acagtataag aatcggttcc aaggggatg tgtttgtcat aagggaacca       360
ttcatatcat gctccccctt ggaatgcaga accttcttct tgactcaagg ggccttgcta      420
aatgacaaac attccaatgg aaccattaaa gacaggagcc catatcgaac cctaatgagc      480
tgtcctattg gtgaagttcc ctctccatac aactcaagat ttgagtcagt cgcttggtca      540
gcaagtgctt gtcatgatgg catcaattgg ctaacaattg gaatttctgg cccagacaat      600
ggggcagtgg ctgtgttaaa gtacaacggc ataataacag acactatcaa gagttggaga      660
aacaatatat tgagaacaca agagtctgaa tgtgcatgtg taaatggttc ttgctttact      720
gtaatgaccg atggaccaag tgatggacag gcctcataca agatcttcag aatagaaaag      780
ggaaagatag tcaaatcagt cgaaatgaat gcccctaatt atcactatga ggaatgctcc      840
tgttatcctg attctagtga aatcacatgt gtgtgcaggg ataactggca tggctcgaat      900
cgaccgtggg tgtctttcaa ccagaatctg gaatatcaga taggatacat atgcagtggg      960
attttcggag acaatccacg ccctaatgat aagacaggca gttgtggtcc agtatcgtct     1020
aatggagcaa atggagtaaa aggattttca ttcaaatacg gcaatggtgt ttggataggg     1080
agaactaaaa gcattagttc aagaaacggt tttgagatga tttgggatcc gaacggatgg     1140
actgggacag acaataactt ctcaataaag caagatatcg taggaataaa tgagtggtca     1200
ggatatagcg ggagttttgt tcagcatcca gaactaacag ggctggattg tataagacct     1260
tgcttctggg ttgaactaat cagagggcga cccaaagaga acacaatctg gactagcggg     1320
agcagcatat cctttgtgg tgtaaacagt gacactgtgg gttggtcttg ccagacggt      1380 gctgagttgc catttaccat tgacaag                                          1407
```

<210> SEQ ID NO 8
<211> LENGTH: 1407
<212> TYPE: DNA
<213> ORGANISM: Unknown
<220> FEATURE:
<223> OTHER INFORMATION: Deoptimized Influenza A virus

<400> SEQUENCE: 8

```
atgaatccta ccaaaaaaat tataacaatc ggatccgttt gtatgacaat cggtatggct       60
aacctaatac tgcaaatcgg taatattata tcgatttgga tctcacatag tatacaattg      120
ggtaatcaga atcagataga gacatgcaat caatccgtta ttacatacga aaataatact      180
tgggttaatc agacatacgt taacatatcg aatactaatt tcgctgccgg acaatccgtc      240
gttagcgtta agttagccgg taatagttca ctatgccccg ttagcgggtg ggctatatac      300
tctaaagaca attcgattag aatcggatct aagggcgacg tattcgtaat acgcgaacca      360
ttcataagtt gtagtccatt agagtgtaga acttttttc taacacaagg cgctctattg      420
aacgataagc atagtaacgg tacaattaag gatagatcac cttatagaac attgatgtca      480
tgtcctatcg gcgaagtgcc tagtccatac aatagtagat tcgaatccgt cgcatggtcc      540
gctagcgcat gtcacgacgg gattaattgg ttgactatag ggattagcgg acccgataac      600
ggcgcagtcg ctgtgcttaa gtataacggt attattaccg acactataaa gagttggcga      660
aataacatac tgagaacaca ggaatccgaa tgcgcatgcg taaacggttc atgttttacc      720
```

| | |
|---|---:|
| gtaatgactg acggacctag cgacggacaa gcgtcatata agattttag aatcgaaaaa | 780 |
| ggtaagatag tgaaatctgt cgagatgaac gctccgaatt atcattacga agagtgtagt | 840 |
| tgttatcccg attctagcga aattacatgc gtatgtaggg acaattggca cgggtctaat | 900 |
| cgaccatggg tgtcattcaa tcagaactta gagtatcaga tagggtatat atgctcaggg | 960 |
| atattcggcg ataatcctag accgaacgat aaaaccggat catgcggacc agtgtcatct | 1020 |
| aacggcgcta acgagtgaaa agggtttagt ttcaaatacg gtaacggcgt atggatcgga | 1080 |
| cgaactaagt ctatatctag taggaacgga ttcgaaatga tatgggaccc aaacgggtgg | 1140 |
| accggtaccg ataataactt ttcaatcaaa caggacatag tcggaattaa cgaatggtcc | 1200 |
| gggtatagcg gatcattcgt gcaacatcca gagttaaccg gactcgattg cataagacca | 1260 |
| tgttttggg tcgaattgat tagggggaga ccaaaagaga atactatatg gactagcgga | 1320 |
| tctagtatta gcttttgcgg agtgaatagc gataccgtag ggtggtcatg gccagacgga | 1380 |
| gccgaactac catttacaat cgataag | 1407 |

<210> SEQ ID NO 9
<211> LENGTH: 1698
<212> TYPE: DNA
<213> ORGANISM: Influenza A virus

<400> SEQUENCE: 9

| | |
|---|---:|
| atgaaagtaa aactactgat cctgttatgt acatttacag ctacatatgc agacacaata | 60 |
| tgtataggct accatgccaa caactcaacc gacactgttg acacagtact tgagaagaat | 120 |
| gtgacagtga cacactctgt caacctactt gaggacagtc acaatggaaa actgtgccta | 180 |
| ctaaaaggaa tagccccct acaattgggt aattgcagcg ttgccggatg gatcttagga | 240 |
| aacccagaat gcgaattact gatttccaag gaatcatggt cctacattgt agaaacacca | 300 |
| aatcctgaga atggagcatg ttacccaggg tatttcgccg actatgagga gctaagggag | 360 |
| caattgagtt cagtatcttc atttgagaga ttcgaaatat tccccaaaga aagctcatgg | 420 |
| cccaaccaca ccgtaaccgg agtatcagca tcatgctccc ataatgggaa aagcagtttt | 480 |
| tacaaaaatt tgctatggct gacggggaag aatggtttgt acccaaacct gagcaagtcc | 540 |
| tatgcaaaca acaaagagaa agaagtcctt atactatggg gtgttcatca cccgcctaac | 600 |
| ataggggacc aaaggaccct ctatcacaca gaaaatgctt atgtctctgt agtgtcttca | 660 |
| cattatagca gaagattcac cccagaaata accaaaaggc ccaaagtaag agatcaggaa | 720 |
| ggaagaatca actactactg gactctgctg gaacccgggg atacaataat atttgaggca | 780 |
| aatggaaatc taatagcgcc atggtatgct ttcgcactga gtagaggctt tggatcagga | 840 |
| atcatcacct caaatgcacc aatggatgaa tgtgatgcta agtgtcaaac acctcaggga | 900 |
| gctataaaca gcagtcttcc tttccagaat gtacacccag tcacaatagg agagtgtcca | 960 |
| aagtatgtca ggagtgcaaa attaaggatg gttacaggac taaggaacat cccatccatt | 1020 |
| caatccagag gtttgtttgg agccattgcc ggtttcattg aagggggtg gactggaatg | 1080 |
| gtagatgggt ggtatggtta tcatcatcag aatgagcaag gatctggcta tgctgcagat | 1140 |
| caaaaaagca cacaaaatgc cattaacggg attacaaaca aggtgaattc tgtaattgag | 1200 |
| aaaatgaaca ctcaattcac agctgtgggc aaagaattca acaaattgga agaaggatg | 1260 |
| gaaaacttaa ataaaaaggt tgatgatggg tttctagaca tttggacata taatgcagaa | 1320 |
| ttgttggttc tactggaaaa tgaaaggact ttggatttcc acgactccaa tgtgaagaat | 1380 |
| ctgtacgaga aagtaaaaag ccaattaaag aataatgcca agaaatagg aaatgggtgt | 1440 |

```
tttgaattct atcacaagtg taacaatgaa tgcatggaga gtgtgaaaaa tggaacttat    1500
gactatccaa atattccga agaatcaaag ttaaacaggg aaaaaattga tggagtgaaa    1560
ttggactcaa tggggtcta tcagattctg gcgatctact caactgtcgc cagttccctg    1620
gttcttttgg tctccctggg ggcaatcagc ttctggatgt gttccaatgg gtctttgcag    1680
tgtagaatat gcatctga                                                 1698
```

<210> SEQ ID NO 10
<211> LENGTH: 1698
<212> TYPE: DNA
<213> ORGANISM: Unknown
<220> FEATURE:
<223> OTHER INFORMATION: Deoptimized Influenza A virus

<400> SEQUENCE: 10

```
atgaaagtga aactgttaat actgttgtgc acttttaccg ctacatacgc cgatacaatt      60
tgcatagggt atcacgctaa taatagtacc gatacagtcg acactgtgtt ggaaaagaac     120
gtaaccgtta cacactccgt taatctgtta gaggattccc ataacggtaa gttgtgtctg     180
ttgaaaggga tcgcaccatt gcaattgggt aattgtagcg tagccggatg gatattgggg     240
aatcccgaat gcgaactatt gattagtaaa gagtcatggt catatatagt cgagacacct     300
aatcccgaaa acggagcatg ctatcccgga tatttcgccg attacgaaga gcttagagag     360
caattgtcta gcgtaagctc attcgaaaga ttcgaaattt ttccaaaaga gtcaagttgg     420
cctaatcata ccgtaacagg cgtatccgca tcatgtagtc ataacggtaa gtcaagcttt     480
tataagaatc tgttatggtt aaccggtaaa aacggactgt atccaaatct atctaagtca     540
tacgcaaata ataaagagaa agaggtactg attctatggg gggtgcatca cccacctaat     600
ataggcgatc aaagaacatt gtatcatacc gaaaacgcat acgtatccgt cgttagctca     660
cactatagta aaggtttac acccgaaatt actaagagac ctaaggtaag ggatcaggag     720
ggtaggatta ttattattg gactctactt gaaccaggcg atactatcat attcgaagct     780
aacggaaatc taatcgcacc atggtacgca ttcgcactat ctaggggtt cggatccggg     840 attattactt ctaacgctcc aatggacgaa tgcgacgcaa agtgtcagac accacaggga     900
gcgattaata gttccctacc attccaaaac gtacaccccg ttacaatcgg cgaatgtccg     960
aaatacgtta gatccgctaa acttagaatg gtgaccggac tgagaaatat accatcaatc    1020
caatctaggg ggctattcgg agccatagcc ggatttatcg aagggggggtg gacagggatg    1080 gtcgacggat ggtatgggta tcaccaccaa acgaacagg gatccggata cgccgccgat    1140
cagaaatcca cacaaaacgc tattaacgga attacgaata agtgaatag cgtaatcgaa    1200 aaaatgaata cacaatttac tgccgtaggt aaggaattca ataagttaga gaaggatg    1260 gagaatctga ataaaaagt cgacgacgga ttcctagaca tatggacata taacgccgaa    1320
ctgttagtgt tgcttgagaa cgaaaggaca ctagactttc acgattcaaa cgttaaaaat    1380
ctatacgaaa aagtcaaatc ccaattgaaa aataacgcta aagagatagg gaatgggtgt    1440
ttcgaattct atcataagtg taataacgaa tgtatggaat ccgttaaaaaa cggaacatac    1500 gattatccaa agtatagcga agagtcaaaa ctgaataggg aaaaaatcga cggagtcaaa    1560
cttgactcaa tggggtgta tcagatactc gcaatctata gtacagtcgc atctagccta    1620
gtactgttag tgagtctggg agcgataagc ttttggatgt gttctaacgg atcactgcaa    1680
tgtaggatat gcatatga                                                 1698
```

<210> SEQ ID NO 11
<211> LENGTH: 1410
<212> TYPE: DNA
<213> ORGANISM: Influenza A virus

<400> SEQUENCE: 11

| | | | | | |
|---|---|---|---|---|---|
| atgaatccaa | atcaaaaaat | aataacgatt | ggctctgttt | ctctcaccat | tgccacaata | 60 |
| tgcttcctta | cgcaaattgc | catcctggta | actactgtaa | cattgcattt | caagcaatat | 120 |
| gaatgcaact | ccccccaaa | caaccaagtg | atgctgtgtg | aaccaacaat | aatagaaaga | 180 |
| aacataacag | agatagtgta | tctgaccaac | accaccatag | agaaggaaat | atgccccaaa | 240 |
| ctagcagaat | acagaaattg | gtcaaagccg | caatgcaaca | ttactggatt | tgcacctttt | 300 |
| tctaaggaca | attcgattcg | ctttccgct | ggtggggaca | tctgggttac | aagagaacct | 360 |
| tatgtgtcat | gcgatcctga | caagtgttat | caatttgccc | ttggacaggg | aacaacacta | 420 |
| aacaacggc | attcaaatga | cacagtacat | gataggaccc | cttataggac | cctattgatg | 480 |
| aatgagttgg | gtgttccatt | tcatttggga | accaagcaag | tgtgcatagc | atggtccagc | 540 |
| tcaagttgtc | acgatggaaa | agcatggctg | catgtttgtg | taacggggga | tgataaaaat | 600 |
| gcaactgcta | gcttcattta | caatgggagg | cttgtagata | gtataggttc | atggtccaaa | 660 |
| aaaatcctca | ggacccagga | gtcggaatgc | gtttgtatca | atggaacttg | tacagtagta | 720 |
| atgactgatg | gagtgcttc | aggaaaagct | gatactaaaa | tactattcat | tgaggagggg | 780 |
| aaaatcgttc | atactagcct | attgtcaggg | agtgctcagc | atgtcgagga | gtgctcctgt | 840 |
| tatcctcgat | atcctggtgt | cagatgtgtc | tgcagagaca | actggaaagg | ctccaatagg | 900 |
| cccatcgtag | atataaatgt | aaaggattat | agcattgttt | ccagttatgt | gtgctcagga | 960 |
| cttgttggag | acacacccag | aaaaaacgac | agctccagca | gtagccattg | cttggatcct | 1020 |
| aacaatgagg | aaggtggtca | tggagtgaaa | ggctgggcct | tgatgatgg | aaatgacgtg | 1080 |
| tggatgggaa | gaacgatcag | cgagaagtta | cgctcaggat | atgaacctt | caaagtcatt | 1140 |
| gaaggctggt | ccaaacctaa | ctccaaactg | cagataaata | ggcaagtcat | agttgacaga | 1200 |
| gataataggt | ccggttattc | tggtattttc | tctgttgaag | gcaaaagctg | catcaatcgg | 1260 |
| tgcttttatg | tggagttgat | aaggggaagg | aaccaggaaa | ctgaagtctt | gtggacctca | 1320 |
| aacagtattt | tgtgttttg | tggcacctca | ggtacatatg | aacaggctc | atggcctgat | 1380 |
| ggggcggaca | tcaatctcat | gcctatataa | | | | 1410 |

<210> SEQ ID NO 12
<211> LENGTH: 1410
<212> TYPE: DNA
<213> ORGANISM: Unknown
<220> FEATURE:
<223> OTHER INFORMATION: Deoptimized Influenza A virus

<400> SEQUENCE: 12

| | | | | | |
|---|---|---|---|---|---|
| atgaaccta | atcaaaaaat | aattacaatc | ggatccgtta | gtctgacaat | cgctactata | 60 |
| tgttttctga | ctcagatagc | gatactcgtt | acaaccgtta | cattgcattt | caaacaatac | 120 |
| gaatgcaatt | cccccctaa | caatcaggta | atgttgtgcg | aacctacaat | aatcgaacgg | 180 |
| aatattaccg | agatagtgta | tctgactaat | acgactatcg | aaaagagat | atgcccaaaa | 240 |
| ctagccgaat | atcggaattg | gtcaaaaccg | caatgtaaca | taccggatt | cgcaccattt | 300 |
| tcgaaagaca | attcgattag | gttgtccgcc | ggaggcgata | tttgggttac | acgcgaacct | 360 |
| tatgtgtcat | gcgatcccga | taaatgctat | caattcgcac | tcggacaggg | gactacccct | 420 |

```
aataacggac attctaacga taccgtacac gatagaactc catatcgaac attgctaatg    480
aacgagttag gcgtaccatt ccatttgggc actaaacagg tatgtatcgc atggtctagc    540
tctagttgcc atgacggtaa ggcttggttg catgtgtgcg ttaccggcga cgataagaac    600
gcaaccgcta gctttatata taacggtagg ttggtcgact caatcgggtc atggtcaaaa    660
aaaatactta gaacgcaaga gtccgaatgc gtatgcataa acggtacatg caccgtagtg    720
atgaccgacg gatccgctag cggtaaggcc gatacgaaaa tactgtttat cgaagagggt    780
aagatagtgc atacgagtct actatccgga tccgctcaac atgtcgaaga gtgttcatgt    840
tatcctaggt atcccggcgt tagatgcgta tgtagggata attggaaagg gagtaataga    900
cctatagtcg atattaacgt taaggattat tcaatcgtaa gtagttatgt gtgtagcgga    960
ctcgtaggcg atacacctag aaaaaacgat agctctagta gctcacattg cctagaccct   1020
aataacgaag aggggggcga tggcgttaag ggatgggcat tcgacgacgg taacgacgtt   1080
tggatgggta ggactattag cgaaaagctt agatccgggt atgagacatt caaagtgata   1140
gagggatggt ctaaacctaa ttcaaaactg caaattaata ggcaagtgat agtcgatagg   1200
gataatagat ccgggtattc cggaattttt agcgttgagg gtaagtcatg tattaatagg   1260
tgtttttatg tcgagcttat taggggggaga aatcaggaaa ccgaagtgtt gtggacatcc   1320
aattcaatcg tcgtttttttg cggaactagc ggaacatacg gtaccggatc atggcccgac   1380
ggagccgata ttaaccttat gcctatataa                                     1410
```

<210> SEQ ID NO 13
<211> LENGTH: 1689
<212> TYPE: DNA
<213> ORGANISM: Influenza A virus

<400> SEQUENCE: 13

```
atggccatca tttatctcat tctcctgttc acagcagtga gaggggacca gatatgcatt     60
ggataccatg ccaataattc cacagagaag gtcgacacaa ttctagagcg gaacgtcact    120
gtgactcatg ccaaggacat tcttgagaag acccataacg gaaagttatg caaactaaac    180
ggaatccctc cacttgaact aggggactgt agcattgccg gatggctcct tggaaatcca    240
gaatgtgata ggcttctaag tgtgccagaa tggtcctata taatggagaa agaaaacccg    300
agagacggtt tgtgttatcc aggcagcttc aatgattatg aagaattgaa acatctcctc    360
agcagcgtga aacatttcga gaaagtaaag attctgccca aagatagatg gacacagcat    420
acaacaactg gaggttcacg ggcctgcgcg gtgtctggta atccatcatt cttcaggaac    480
atggtctggc tgacaaagaa aggatcaaat tatccggttg ccaaaggatc gtacaacaat    540
acaagcggag aacaaatgct aataatttgg ggggtgcacc atcccaatga tgagacagaa    600
caaagaacat tgtaccagaa tgtgggaacc tatgtttccg taggcacacc aacattgaac    660
aaaaggtcaa ccccagacat agcaacaagg cctaaagtga atggacaagg aggtagaatg    720
gaattctctt ggaccctatt ggatatgtgg gacaccataa attttgagag tactggtaat    780
ctaattgcac cagagtatgg attcaaaata tcgaaaagag gtagttcagg gatcatgaaa    840
acagaaggaa cacttgggaa ctgtgagacc aaatgccaaa ctcctttggg agcaataaat    900
acaacattgc cttttcacaa tgtccaccca ctgacaatag gtgagtgccc caaatatgta    960
aaatcggaga agttggtctt agcaacagga ctaaggaatg ttccccagat tgaatcaaga   1020
ggattgtttg gggcaatagc tggttttata gaaggaggat ggcaaggaat ggttgatggt   1080
```

```
tggtatggat accatcacag caatgaccag ggatcagggt atgcagcaga caaagaatcc    1140
actcaaaagg catttgatgg aatcaccaac aaggtaaatt ctgtgattga aaagatgaat    1200
acccaatttg aagctgttgg gaaagaattc agtaacttag agagaagact ggagaacttg    1260
aacaaaaaga tggaagacgg gtttctagat gtgtggacat acaatgctga gcttctagtt    1320
ctgatggaaa atgagaggac acttgacttt catgattcta atgtcaagaa tctgtatgat    1380
aaagtcagaa tgcagctgag agacaacgtc aaagaactag gaatggatg ttttgaattt    1440 tatcacaaat gtgatgatga atgcatgaat agtgtgaaaa acgggacgta tgattatccc    1500
aagtatgaag aagagtctaa actaaataga atgaaaatca aaggggtaaa attgagcagc    1560 atggggggttt atcaaatcct tgccatttat gctacagtag caggttctct gtcactggca    1620
atcatgatgg ctgggatctc tttctggatg tgctccaacg ggtctctgca gtgcaggatc    1680
tgcatatga                                                             1689

<210> SEQ ID NO 14
<211> LENGTH: 1689
<212> TYPE: DNA
<213> ORGANISM: Unknown
<220> FEATURE:
<223> OTHER INFORMATION: Deoptimized Influenza A virus

<400> SEQUENCE: 14
atggcaataa tctatctgat actgttgttt acagccgtta ggggcgatca gatatgcata      60
gggtatcacg ctaataatag taccgaaaaa gtcgatacaa tactcgaaag aaacgtaacc     120
gttacacacg ctaagatat actcgaaaag acacataacg gtaagctatg caaacttaac     180
ggtataccac cacttgagtt aggcgattgc tcaatcgcag gatggttgtt ggggaatccc     240
gaatgcgata ggctattgag cgtacccgaa tggtctttata ttatggaaaa agagaatcct     300
agagacggat tgtgttatcc cggatctttt aacgattacg aagagcttaa acatctgcta     360
tctagcgtta acatttcga aaagtgaaa attctgccaa agataggtg acacagcat      420 acgactaccg gaggatctag ggcatgcgcc gttagcggta atccgtcatt ctttagaaat     480
atggtatggt tgacaaaaaa ggggtctaat tatccagtcg ctaagggatc gtataataat     540
acaagcggag agcaaatgtt gattatatgg ggagtgcatc accctaacga cgaaaccgaa     600
caacggacac tgtatcaaaa cgtcggaaca tacgttagcg tcggtacacc aactctgaat     660
aaaagatcga ctcccgatat cgcaactaga ccaaaagtga acggacaggg ggggagaatg     720
gagtttagtt ggacactact cgatatgtgg gatacaatta atttcgaatc aaccggtaat     780
ctgatcgcac ccgaatacgg gtttaagatt agtaaaaggg ggtcatccgg tattatgaaa     840
accgaaggta cactagggaa ttgcgaaact aagtgtcaga caccactagg ggctattaat     900
acaacactac catttcataa tgtgcatcca ttgacaatcg gagagtgtcc taagtatgtg     960
aaatccgaaa aactagtgct tgcaaccgga ctgagaaacg taccgcaaat cgaatccaga    1020
gggttgttcg gagcaatcgc agggtttatc gaagggggggt ggcagggaat ggtcgacgga    1080
tggtatgggt atcatcactc taacgatcag ggatccggat acgcagccga taaggagtca    1140
acccaaaaag cattcgacgg aattactaat aaggtaata gcgtaatcga aaaaatgaat    1200
acacaattcg aagccgtcgg taaagagttt tcgaatctcg aaaggagact tgagaatctg    1260
aataaaaaaa tggaggacgg attcttagac gtatggacat ataatgccga actgttagtc    1320
cttatggaga cgaacggac actagacttt cacgatagta acgttaagaa tctgtatgac    1380
aaagtgagaa tgcaattgag agacaatgtg aaagagctag gtaacggatg tttcgaattc    1440
```

```
tatcataaat gcgacgacga gtgtatgaat agcgttaaaa acggtacata tgactatcct    1500
aagtatgagg aagagtcaaa gcttaataga aacgagatta agggagtgaa actatctagt    1560
atgggagtgt atcagatact cgcaatatac gctacagtcg ccggatccct atcacttgcg    1620
attatgatgg ccggaattag cttttggatg tgctctaacg gatcattgca atgtaggatt    1680
tgcatatga                                                             1689
```

<210> SEQ ID NO 15
<211> LENGTH: 1410
<212> TYPE: DNA
<213> ORGANISM: Influenza A virus

<400> SEQUENCE: 15

```
atgaatccaa atcaaaagat aataacaatt ggctctgtct ctctcaccat tgcaacagta      60
tgcttcatca tgcagattgc catcctggca actactgtga cattgcattt taaacaacat     120
gagtgcgact cccccgcgag caaccaagta atgccatgtg aaccaataat aatagaaagg     180
aacataacag agatagtgta tttgaataac accaccatag agaaagagat tgccccgaa     240 gcagtggaat acgaaaattg gtcaaagccg caatgtcaaa ttacaggatt tgcaccttt     300 tctaaggaca attcaatccg gctttctgct ggtgggggaca tttgggtgac gagagaacct    360
tatgtgtcat gcgatcctgg caagtgttat caatttgcac tcgggcaggg gaccacacta    420
gacaacaaac attcaaatgg cacaatacat gatagaatcc ctcaccgaac cctattaatg    480
aatgagttgg gtgttccatt tcatttagga accaaacaag tgtgtgtagc atggtccagc    540
tcaagttgtc acgatggaaa agcatggttg catgtttgtg tcactgggga tgatagaaat    600
gcgactgcta gcttcattta tgacgggagg cttgtggaca gtattggttc atggtctcaa    660
aatatcctca ggacccagga gtcggaatgc gttttgtatca atgggacttg cacagtagta    720
atgactgatg gaagtgcatc aggaagagcc gatactagaa tactattcat taaagagggg    780
aaaattgtcc atattagccc attgtcagga agtgctcagc atatagagga gtgttcctgt    840
taccctcgat atcctgacgt cagatgtatc tgcagagaca actggaaagg ctctaatagg    900
cccgttatag acataaatat ggaagattat agcattgatt ccagttatgt gtgctcaggg    960
cttgttggcg acacacccag gaacgacgac agctctagca atagcaattg cagggatcct   1020
aacaatgaga gagggaatcc aggagtgaaa ggctgggcct tgacaatgga agatgatgta   1080
tggatgggaa gaacaatcaa caagattca cgctcaggtt atgaaacttt caaagtcatt   1140
ggtggttggt ccacacctaa ttccaaatcg caggtcaata gacaggtcat agttgacaac   1200
aataattggt ctggttactc tggtattttc tctgttgagg gcaaaagctg catcaatagg   1260
tgcttttatg tggagttgat aaggggaagg ccacaggaga ctagagtatg gtggacctca   1320
aacagtattg ttgtgttttg tggcacttca ggtacttatg aacaggctc atggcctgat   1380 ggggcgaaca tcaatttcat gcctatataa                                    1410
```

<210> SEQ ID NO 16
<211> LENGTH: 1410
<212> TYPE: DNA
<213> ORGANISM: Unknown
<220> FEATURE:
<223> OTHER INFORMATION: Deoptimized Influenza A virus

<400> SEQUENCE: 16

```
atgaatccta accagaaaat tattactata gggtcagtgt cattgactat cgcaaccgta      60
```

| | |
|---|---|
| tgctttatta tgcaaatagc gatactcgca actaccgtaa cattgcattt taaacaacac | 120 |
| gaatgcgata gtcccgctag caatcaggta atgccatgcg aacctattat aatcgaacgg | 180 |
| aatattaccg agatagtgta tcttaacaat actactatcg aaaaagagat atgcccagag | 240 |
| gccgtcgagt atagaaattg gtctaaacct caatgtcaga ttaccggatt cgcaccattc | 300 |
| tctaaagaca attcgattag attgtccgcc ggaggcgata tatgggtgac acgcgaacct | 360 |
| tatgtgtcat gcgatcccgg taagtgttat caattcgcac tcggacaggg gactacactc | 420 |
| gataataaac attctaacgg tacgatacac gataggattc cacataggac actattgatg | 480 |
| aacgagttag gcgtaccgtt tcatctaggc actaaacagg tatgcgttgc gtggtctagc | 540 |
| tcatcatgtc atgacggtaa ggcatggttg catgtgtgcg taaccggcga cgatagaaac | 600 |
| gctaccgcta gttttatata cgacggtagg ctagtcgatt caatcggatc atggtcacag | 660 |
| aatatactta gaacacagga atccgaatgc gtttgtatta acggtacatg tacagtcgtt | 720 |
| atgaccgacg gatccgcatc cggtagggcc gatactagga tactgtttat aaaagagggc | 780 |
| aaaatcgtgc atattagccc acttagcgga tccgcacaac atatcgaaga gtgtagttgc | 840 |
| tatcctaggt atcctgacgt tagatgtatt tgcagagaca attggaaagg gtctaataga | 900 |
| cccgtaatcg atatcaatat ggaggattat tcaatcgata gctcttatgt gtgtagcgga | 960 |
| ttagtcggcg atacacctag aaacgacgat agctctagta attcgaattg tagggaccct | 1020 |
| aataacgaga gaggcaatcc cggcgttaaa gggtgggcat tcgataacgg cgacgacgtt | 1080 |
| tggatggggc gaacaattaa taaggactct agatccgggt atgagacatt caaagtgata | 1140 |
| gggggtggt ctacacctaa ctcaaaatct caagtgaata ggcaagtgat agtcgacaat | 1200 |
| aacaattggt cagggtatag cggtatattc tcagtcgagg gtaagtcatg tattaataga | 1260 |
| tgttttacg ttgagttgat taggggcga ccacaagaga ctagagtgtg gtggactagt | 1320 |
| aatagtatag tcgttttttg cggaactagc ggtacatacg gaaccggatc atggcctgac | 1380 |
| ggagcgaata ttaattttat gccaatctaa | 1410 |

<210> SEQ ID NO 17
<211> LENGTH: 1701
<212> TYPE: DNA
<213> ORGANISM: Influenza A virus

<400> SEQUENCE: 17

| | |
|---|---|
| atgaagacta tcattgcttt gagctacatt ctatgtctgg ttttcgctca aaaacttccc | 60 |
| ggaaatgaca acagcacggc aacgctgtgc cttgggcacc atgcagtacc aaacggaacg | 120 |
| atagtgaaaa caatcacgaa tgaccaaatt gaagttacta atgctactga gctggttcag | 180 |
| agttcctcaa caggtgaaat atgcgacagt cctcatcaga tccttgatgg agaaaactgc | 240 |
| acactaatag atgctctatt gggagaccct cagtgtgatg gcttccaaaa taagaaatgg | 300 |
| gacctttttg ttgaacgcag caaagcctac agcaactgtt acccttatga tgtgccggat | 360 |
| tatgcctccc ttaggtcact agttgcctca tccggcacac tggagtttaa caatgaaagc | 420 |
| ttcaattgga ctggagtcac tcaaaatgga acaagctctg cttgcaaaag gagatctaat | 480 |
| aacagtttct ttagtagact gaattggttg acccacttaa aattcaaata cccagcattg | 540 |
| aacgtgacta tgccaaacaa tgaaaaattt gacaaattgt acatttgggg ggttcaccac | 600 |
| ccgggtacgg acaatgacca atcttcttg tatgctcaag catcaggaag aatcacagtc | 660 |
| tctaccaaaa gaagccaaca aactgtaatc ccgaatatcg gatccagacc tagagtaagg | 720 |
| ratatcccca gcagaataag catctattgg acaatagtaa aaccgggaga catacttttg | 780 |

```
attaacagca cagggaatct aattgctcct aggggttact tcaaaatacg aagtgggaaa      840
agctcaataa tgagatcaga tgcacccatt ggcaaatgca attctgaatg catcactcca      900
aatggaagca ttcccaatga caaaccattt caaaatgtaa acagaatcac atatggggcc      960
tgtcccagat atgttaagca aaacactctg aaattggcaa cagggatgag aaatgtacca     1020
gagaaacaaa ctagaggcat atttggcgca atcgcgggtt tcatagaaaa tggttgggag     1080
ggaatggtgg atggttggta cggtttcagg catcaaaatt ctgagggaat aggacaagca     1140
gcagatctca aaagcactca agcagcaatc aatcaaatca tgggaagct gaataggttg      1200
atcgggaaaa ccaacgagaa attccatcag attgaaaaag aattctcaga agtagaaggg     1260
agaattcagg acctcgagaa atatgttgag gacactaaaa tagatctctg gtcatacaac     1320
gcggagcttc ttgttgccct ggagaaccaa catacaattg atctaactga ctcagaaatg     1380
aacaaactgt ttgaaagaac aaagaagcaa ctgagggaaa atgctgagga tatgggcaat     1440
ggttgtttca aaatatacca caaatgtgac aatgcctgca taggatcaat cagaaatgga     1500
acttatgacc atgatgtata cagagatgaa gcattaaaca accggttcca gatcaaaggc     1560
gttgagctga gtcaggata caaagattgg atcctatgga tttcctttgc catatcatgt     1620
tttttgcttt gtgttgtttt gttggggttc atcatgtggg cctgccaaaa aggcaacatt     1680
aggtgcaaca tttgcatttg a                                                1701

<210> SEQ ID NO 18
<211> LENGTH: 1701
<212> TYPE: DNA
<213> ORGANISM: Unknown
<220> FEATURE:
<223> OTHER INFORMATION: Deoptimized Influenza A virus

<400> SEQUENCE: 18
atgaaaacaa ttatcgcact gtcatacata ctgtgtctgg tattcgctca aaaattgccc       60
ggtaacgaca attcaaccgc tacattgtgc ttagggcatc acgccgtacc gaacggaact      120
atcgttaaga caattactaa cgaccaaatc gaagtgacta cgctacaga gttggtgcaa       180
tcctctagta caggcgaaat atgcgattca ccacaccaaa tccttgacgg agagaattgt      240
acacttatcg acgcactatt aggcgatcca caatgcgacg gatttcagaa taaaaaatgg      300
gatctattcg ttgagagatc caaagcttat tcaaattgtt atccatacga cgtaccggat      360
tacgctagcc ttaggtcact cgttgcgtca agcggtactc tcgaattcaa taacgagtca      420
ttcaattgga ctggcgttac gcaaaacgga actagtagcg catgtaaaag acggtctaat      480
aatagctttt ttagcagact gaattggttg actcatctga aattcaaata tcccgcactt      540
aacgttacta tgcctaataa cgaaaaattc gataagctat atatatgggg cgtacaccat      600
cccggaacgg ataacgatca gatattcttg tacgctcaag ctagcggtag gattaccgtt      660
agtactaaaa gatcccaaca aaccgtaatt ccgaatatcg gatctagacc tagggtgaga     720
ratataccgt ctaggattag catatattgg actatcgtta aacccggaga catactgttg      780
atcaatagta caggcaatct gatcgcacct aggggtatt tcaaaattag atccggtaag       840
tctagcatta tgagatccga cgcaccaatc ggtaaatgta tagcgaatg cattacacca      900
aacggatcaa tccctaacga taagccattc caaaacgtaa ataggattac atcggcgca     960
tgccctagat acgttaaaca gaatacgctt aaacttgcga caggtatgcg aaacgtaccc    1020
gaaaaacaga ctaggggat attcggcgca atcgccggat ttatcgaaaa cggatgggag    1080
```

```
ggtatggtcg acggatggta cggatttaga catcaaaata gcgaagggat agggcaagcc    1140
gccgatctga atcaacgca agccgctatt aatcaaatta acggaaaact gaatagattg    1200
atcggtaaga ctaacgaaaa atttcaccaa atcgaaaaag agtttagcga agttgaggga    1260
aggatacaag accttgagaa atacgttgag gatactaaga tcgacctatg gtcatataat    1320
gccgagttgc tagtcgcact cgagaatcag catacaatcg atctgactga tagcgaaatg    1380
aataaattgt tcgaaagaac gaaaaaacaa ttgcgcgaaa acgccgaaga catggggaat    1440
gggtgtttta agatatacca taaatgcgat aacgcatgca tagggtcaat cagaaacgga    1500
acatacgatc acgacgtata tagagacgaa gcccttaata atagattcca aattaaaggc    1560
gttgagctta aaagcggata caaagactgg atactgtgga ttagtttcgc aatctcatgc    1620
tttctattgt gcgttgtgct attggggttc ataatgtggg catgtcagaa agggaatatt    1680
agatgcaata tttgtatatg a                                              1701
```

```
<210> SEQ ID NO 19
<211> LENGTH: 1410
<212> TYPE: DNA
<213> ORGANISM: Influenza A virus

<400> SEQUENCE: 19
atgaatccaa atcaaaagat aataacgatt ggctctgttt ctctcaccat ttccacaata     60
tgcttcttca tgcaaattgc catcttgata actactgtaa cattgcattt caagcaatat    120
gaattcaact cccccccaaa caaccaagtg atgctgtgtg aaccaacaat aatagaaaga    180
aacataacag atagtgtata tctgaccaac accaccatag agaaggaaat atgccccaaa    240
ctagcagaat acagaaattg gtcaaagccg caatgtgaca ttacaggatt tgcacctttt    300
tctaaggaca attcgattag ctttccgct ggtggggaca tctgggtgac aagagaacct    360
tatgtgtcat gcgatcctga caagtgttat caatttgccc ttggacaggg aacaacacta    420
aacaacgtgc attcaaacga cacagtacat gataggaccc cttatcggac cctattgatg    480
aatgagttag gtgttccatt tcatctgggg accaagcaag tgtgcatagc atggtccagc    540
tcaagttgtc acgatggaaa agcatggctg catgtttgtg taacggggga tgataaaaat    600
gcaactgcta gcttcattta caatgggagg cttgtagata tgttgttc atggtccaaa    660 gatatcctca ggacccagga gtcagaatgc gtttgtatca atggaacttg tacagtagta    720
atgactgatg ggagtgcttc aggaaaagct gatactaaaa tactattcat tgaggagggg    780
aaaatcgttc atactagcac attgtcagga agtgctcagc atgtcgagga gtgctcctgc    840
tatcctcgat atcctggtgt cagatgtgtc tgcagagaca actggaaagg ctccaatagg    900
cccattgtag atataaacat aaagaattat agcattgttt ccagttatgt gtgctcagga    960
cttgttggag acacacccag aaaaaccgac agctccagca gtagccattg cttggatcct   1020
aacaatgaag aaggtggtca tggagtgaaa ggctgggcct ttgatgatgg aaatgacgtg   1080
tggatgggaa gaacgatcag cgagaagtta cgcttaggat atgaaccctt caaagtcatt   1140
gaaggctggt ccaaccctaa ttccaaattg cagataaata ggcaagtcat agttgacaga   1200
ggtaataggt ccggttattc tggtattttc tctgttgaag caaaagctg catcaatcgg   1260 tgcttttatg tggagttgat aaggggaaga aaagaggaaa ctgaagtctt gtggacctca   1320
aacagtattg ttgtatttg tggaacctca ggtacatatg aacaggctc atggcctgat   1380 ggggcggaca tcaatctcat gcctatataa                                     1410
```

<210> SEQ ID NO 20
<211> LENGTH: 1410
<212> TYPE: DNA
<213> ORGANISM: Unknown
<220> FEATURE:
<223> OTHER INFORMATION: Deoptimized Influenza A virus

<400> SEQUENCE: 20

| | | | | | |
|---|---|---|---|---|---|
| atgaatccta | accaaaagat | tattacaatc | ggatccgtta | gccttactat | atccacaatt | 60 |
| tgttttttta | tgcaaatagc | gatactgata | actaccgtta | cattgcattt | caaacaatac | 120 |
| gaattcaatt | cacccccctaa | taatcaggtt | atgttgtgcg | aacctactat | tatcgaacgg | 180 |
| aatataaccg | agatagtgta | tctaacgaac | actacaatcg | aaaagagat | atgccctaag | 240 |
| ctcgcagagt | atagaaattg | gtcaaaaccc | caatgcgata | taaccggatt | cgcaccattt | 300 |
| agtaaggata | atagtattag | gttgtccgcc | ggaggcgata | tatgggttac | acgcgaacca | 360 |
| tacgtgtcat | gcgatcccga | taaatgctat | caattcgctc | tcggacaggg | aacgacattg | 420 |
| aataacgtac | attcaaacga | taccgtacac | gataggacac | cttatagaac | actattgatg | 480 |
| aacgaactag | gcgtaccttt | ccatctcgga | actaaacagg | tttgtatcgc | ttggtctagt | 540 |
| agctcatgcc | atgacggtaa | ggcatggttg | catgtgtgcg | ttaccggcga | cgataaaaac | 600 |
| gcaaccgcta | gtttcatata | taacggtagg | ttagtcgata | gcgtagtgag | ttggtctaaa | 660 |
| gacatactgc | gaacacagga | atccgagtgc | gtatgcataa | acggtacatg | taccgtagtg | 720 |
| atgaccgacg | gatccgctag | cggtaaggcc | gatacgaaaa | tattgttcat | agaggagggt | 780 |
| aagatagtgc | atacaagtac | actatccgga | tccgctcaac | atgtcgaaga | gtgctcatgt | 840 |
| tatcctagat | atcccggcgt | tagatgcgta | tgtagagaca | attggaaagg | gtctaataga | 900 |
| ccgatagtcg | acattaatat | taaaaactat | tcaatcgtta | gctcatatgt | gtgttccgga | 960 |
| ttagtcggcg | atacccctag | aaaaaccgat | agctctagct | catcccattg | tcttgaccct | 1020 |
| aataacgaag | agggggggca | tggcgttaag | ggatgggcat | tcgacgacgg | taacgacgtt | 1080 |
| tggatgggac | ggacaattag | cgaaaaactt | agattggggt | atgagacttt | taaggtaatc | 1140 |
| gaagggtggt | ctaatcctaa | ttcgaaactg | caaattaata | ggcaagtgat | agtcgatagg | 1200 |
| gggaataggt | ccggatatag | cggaatcttt | tccgttgagg | gtaagtcatg | tattaatagg | 1260 |
| tgttttatg | tcgaactgat | taggggagga | aaagaggaaa | ccgaagtgtt | atggactagt | 1320 |
| aactcaatcg | ttgtgttttg | cggtacatcc | ggtacttatg | gaaccggatc | atggccagac | 1380 |
| ggagccgata | taaaccttat | gccaatttaa | | | | 1410 |

<210> SEQ ID NO 21
<211> LENGTH: 1704
<212> TYPE: DNA
<213> ORGANISM: Influenza A virus

<400> SEQUENCE: 21

| | | | | | |
|---|---|---|---|---|---|
| atggagaaaa | tagtgcttct | tcttgcaata | gtcagccttg | ttaaaagtga | tcagatttgc | 60 |
| atcggttacc | atgcaaacaa | ctcgacagag | caggttgaca | caataatgga | aaagaacgtt | 120 |
| actgttacac | atgcccaaga | catactggag | aagacacata | acgggaaact | ctgcgatcta | 180 |
| gatggagtga | agcctctgat | tctacgagat | tgtagtgtag | ctggatggct | cctcggaaac | 240 |
| ccaatgtgtg | acgaattcat | caatgtgccg | gaatggtctt | acatagtgga | gaaggccaac | 300 |
| ccagccaatg | acctctgtta | cccagggaat | ttcaacgact | atgaagaact | gaaacaccta | 360 |
| ttgagcagaa | taaaccattt | tgagaaaatt | cagatcatcc | ccaaaagttc | ttggtccgat | 420 |

| | |
|---|---|
| catgaagcct catcagggt gagctcagca tgtccatacc agggaacgcc ctccttttc | 480 |
| agaaatgtgg tatggcttat caaaaagaac aatacatacc caacaataaa gagaagctac | 540 |
| aataatacca accaggaaaa tcttttgata ctgtgggga ttcatcattc taatgatgca | 600 |
| gcagagcaga taaagctcta tcaaaaccca accacctata tttccgttgg gacatcaaca | 660 |
| ctaaaccaga gattggtacc aaaaatagcc actagatcca aagtaaacgg caaagtgga | 720 |
| aggatggatt tcttctggac aattttaaaa ccgaatgatg caatcaactt cgagagtaat | 780 |
| ggaaatttca ttgctccaga atatgcatac aaaattgtca aggaaggaga ctcagcaatt | 840 |
| atgaaaagtg aagtgaata tggtaactgc aacaccaagt gtcaaactcc aatggggcg | 900 |
| ataaactcta gtatgccatt ccacaacata caccctctca ccatcgggga atgccccaaa | 960 |
| tatgtgaaat caaacaaatt agtccttgct actgggctca gaaatagtcc tctaagagaa | 1020 |
| agaagaagaa aaagaggact atttggagct atagcagggt ttatagaggg aggatggcag | 1080 |
| ggaatggtag atggttggta tgggtaccac catagcaatg agcaggggag tgggtacgct | 1140 |
| gcagacaaag aatccactca aaaggcaata gatgagtca ccaataaggt caactcgatc | 1200 |
| attgacaaaa tgaacactca gtttgaggcc gttggaaggg aatttaataa cttggaaagg | 1260 |
| agaatagaga acttaaacaa gaaaatggaa gacggattcc tagatgtctg gacttataat | 1320 |
| gctgaacttc tggttctcat ggaaaatgag agaactctag acttccatga ctcaaatgtc | 1380 |
| aagaacctt acgacagggt ccgactacag cttagggata atgcaaagga ctgggtaac | 1440 |
| ggttgtttcg agttctatca caatgtgat aatgaatgta tggaaagtgt aagaaacgga | 1500 |
| acgtatgact acccgcagta ttcagaagaa gcaagattaa aaagagagga aataagtgga | 1560 |
| gtaaaattgg aatcaatggg aacttaccaa atactgtcaa tttattcaac agttgcgagt | 1620 |
| tctctagcac tggcaatcat ggtggctggt ctatctttgt ggatgtgctc caatgggtcg | 1680 |
| ttacaatgca gaatttgcat ttaa | 1704 |

<210> SEQ ID NO 22
<211> LENGTH: 1704
<212> TYPE: DNA
<213> ORGANISM: Unknown
<220> FEATURE:
<223> OTHER INFORMATION: Deoptimized Influenza A virus

<400> SEQUENCE: 22

| | |
|---|---|
| atggagaaaa tagtgctact actcgcaatc gttagtctgg ttaagtccga tcagatatgc | 60 |
| atagggtatc acgctaacaa tagtaccgaa caggtcgaca ctattatgga aaaaaacgtt | 120 |
| accgttacac acgcacagga catactcgaa aaaacccata acggtaagtt atgcgattta | 180 |
| gacggagtta agccactgat acttagggat tgttcagtcg ccggatggtt gttagggaat | 240 |
| ccaatgtgcg acgaattcat taacgtaccc gaatggtcat acatagtcga aaaagcgaat | 300 |
| cccgctaacg atctatgtta tccagggaat tttaacgatt acgaagagct taagcatcta | 360 |
| ctatctagaa taaaccattt cgaaaagatt cagataatac cgaaatcgag ttggtccgat | 420 |
| cacgaagcgt caagcggagt gagtagcgca tgcccatacc aaggaacacc atcattcttt | 480 |
| agaaacgtcg tttggttgat taaaaaaaat aatacatatc cgactattaa gagatcatat | 540 |
| aataatacaa accaagagaa tctactgata ctatggggga tacaccatag taacgacgca | 600 |
| gccgaacaga ttaagctata tcagaatcca actacataca ttagcgtagg gactagtaca | 660 |
| cttaatcaga gactcgtacc taaatcgct actagatcga aggtaaacgg acaatccggt | 720 |
| agaatggact tttttggac tatactgaaa cctaacgacg caattaattt cgaatctaac | 780 | ggaaatttta tcgctcccga atacgcatat aagatagtga aagaggggga tagcgcaatt 840 atgaaatccg aagtcgaata cggaaattgc aatactaagt gtcagacacc aatcggagca 900 attaactcta gtatgccatt ccataacata catccactta caatcggaga atgccctaaa 960 tacgttaagt ctaacaaact cgtactcgca accggactta ggaatagtcc acttagagag 1020 agacgaagaa agagagggtt gttcggagca atcgcagggt tcatagaggg ggggtggcag 1080 ggtatggtcg acggatggta cgggtatcat cattctaacg aacagggatc cggatacgca 1140 gccgataaag agagtactca gaaagcaatc gacggagtga cgaataaagt gaattcgata 1200 atcgataaga tgaatacgca attcgaagcc gtaggtaggg aattcaataa tctcgagaga 1260 cgaatcgaaa accttaacaa aaaaatggaa gacggattcc tagacgtatg gacttataac 1320 gccgaactgt tagtgcttat ggagaacgaa agaacccttg actttcacga ttctaacgtt 1380 aagaatctat acgatagagt gagactgcaa ttgagggata acgctaaaga gttagggaac 1440 gggtgtttcg aattctatca taaatgcgat aacgaatgta tggagtcagt gagaaacggt 1500 acatacgact atccgcaata ttccgaagag gctagattga aaagagagga gattagcgga 1560 gtgaaacttg agtcaatggg gacatatcag atattgtcaa tatactcaac cgtcgctagt 1620 agtctcgcac tcgcaattat ggtcgccgga ctgtcactat ggatgtgttc aaacggtagt 1680 ctgcaatgta ggatttgtat ataa 1704

<210> SEQ ID NO 23
<211> LENGTH: 1350
<212> TYPE: DNA
<213> ORGANISM: Influenza A virus

<400> SEQUENCE: 23
atgaatccaa atcagaagat aataaccatt gggtcaatct gtatggtaat tggaatagtt 60
agcttaatgt tacaaattgg gaacataatc tcaatatggg tcagtcattc aattcaaaca 120
gggaatcaac accaagatga accaatcaga aatgctaatt ttcttactga gaacgctgtg 180
gcttcagtaa cattagcggg caattcatct ctttgccccg ttagaggatg ggctgtacac 240
agtaaagaca acagtataag gattggttcc aaggggggatg tgtttgttat tagagagccg 300
ttcatctcat gctcccactt ggaatgcaga actttctttt tgactcaggg agccttactg 360
aatgacaagc actccaatgg gactgtcaaa gacagaagcc ctcacagaac attaatgagt 420
tgtcctgtgg gtgaggctcc ctccccatat aactcaaggt ttgagtctgt tgcttggtca 480
gcaagtgctt gccatgatgg caccagttgg ttgacaattg gaatttctgg cccagacaat 540
ggggctgtgg ctgtattgaa atacaatggc ataataacag acaccatcaa gagttggagg 600
aacaacatac tgagaactca agagtctgaa tgtgcatgtg taaatggctc ttgctttact 660
gtaatgactg atggaccaag taatgggcag gcatcatata agatcttcaa aatggaaaaa 720
ggaaaagtgg ttaaatcagt cgaattgaat gccccctaatt atcactatga ggaatgctcc 780
tgttatcctg atgctggcga aatcacatgt gtgtgcaggg ataattggca tggctcaaat 840
aggccatggg tatctttcaa tcagaatttg gagtatcaaa taggatatat atgtagtgga 900
gttttcggag acaatccacg ccccaatgat ggaacaggta gttgtgatcc agtgtcccct 960
aacggggcat atgggataaa agggttttca tttaaatacg gcaatggtgt ttggatcgga 1020
agaaccaaaa gcactaattc caggagtggt tttgaaatga tttgggatcc aaatgggtgg 1080
actgaaacgg acagtagctt ttcagtgaaa caagatatag tagcaataac tgattggtca 1140

```
gggtatagcg ggagttttgt tcagcatcca gaactgacag gattagattg cataagacct   1200
tgcttctggg ttgagttaat cagagggcgg cccaaagaga gcacaatttg gactagtggg   1260
agcagcatat cttttgtgg tgtaaatagc gacactgtga gttggtcttg gccagacggt    1320
gctgagttgc cattcaccat tgacaagtag                                    1350

<210> SEQ ID NO 24
<211> LENGTH: 1350
<212> TYPE: DNA
<213> ORGANISM: Unknown
<220> FEATURE:
<223> OTHER INFORMATION: Deoptimized Influenza A virus

<400> SEQUENCE: 24
atgaatccga atcaaaaaat tataacaata gggtcaatct gtatggtaat cggtatagtg    60
tcacttatgt tacaaatcgg gaatattata tctatttggg tgtcacactc aatccaaacc   120
ggtaatcaac accaagacga acctatacgg aatgcgaatt tcttaacaga gaatgccgta   180
gctagcgtta cgttagccgg taatagttca ttgtgtcccg ttaggggtg ggctgtgcat    240 agtaaggata atagtattag gatagggtct aaaggcgacg tattcgtgat acgcgaacct   300
tttatctctt gctcacactt agagtgtaga acatttttc tgactcaagg cgcactgtta    360
aacgataaac actctaacgg tacagttaag gataggtcac cacataggac attgatgtca   420
tgtcccgtag gcgaagctcc tagtccatat aatagtagat cgaaagcgt tgcatggtcc    480 gctagcgctt gtcacgacgg aactagttgg ttgacaatcg ggatatccgg acccgataat   540
ggcgcagtcg cagtgttgaa gtataatggg attataaccg atactatcaa atcatggaga   600
aataatatac tgagaacaca ggagtccgaa tgcgcttgcg ttaacggatc atgctttacc   660
gttatgactg acgaccatc taacgggcaa gctagttata aaattttcaa aatggagaaa    720
ggtaaggtag tgaaatccgt tgagcttaac gctccaaatt atcattacga agagtgtagt   780
tgctatccag acgctggcga aattacttgc gtatgtagag acaattggca cggatctaat   840
agaccatggg ttagctttaa tcagaattta gagtatcaga tagggtatat atgttccgga   900
gtgttcggcg ataatcctag acctaacgac ggtacaggt catgcgatcc agtgagtcca    960
aacggcgcat acggaattaa agggtttagc tttaagtatg gaatggcgt atggatcggt   1020 aggactaagt ctactaatag tagatccgga ttcgaaatga tatgggaccc taatgggtgg   1080
actgagactg atagtagttt tagcgtaaaa caggatatag tcgctataac cgattggagc   1140
gggtatagcg gatcattcgt acagcatccc gaattgactg ggttagactg tattagacca   1200
tgcttttggg tcgaattgat tagggggaga ccaaaagagt caactatatg gactagcgga   1260
tctagtatta gttttgcgg agtgaattcc gataccgtta gttggtcatg gccagacgga   1320
gctgagttgc catttacaat cgataaatag                                   1350

<210> SEQ ID NO 25
<211> LENGTH: 1659
<212> TYPE: DNA
<213> ORGANISM: Influenza A virus

<400> SEQUENCE: 25
atgaacattc aaattctggc attcattgct tgtgtgctga ctggagctaa aggagacaaa    60
atatgtcttg gcaccatgc tgtggcaaat ggaacaaaag tgaacacatt aacagagagg   120
gggattgaag tagtgaatgc cacagagaca gttgaaactg cgaatatcaa gaaaatatgt   180
actcaaggga aaagaccaac agatctggga caatgtggac ttctagggac cctaataggga   240
```

```
cctccccaat gtgatcaatt cctggagttt tcctctgatt tgataattga gcgaagagaa      300
ggaaccgatg tatgctatcc cggtaaattc acaaatgaag aatcactgag acagatcctt      360
cgaagatcag gaggaattgg taaggagtca atgggcttca cctatagtgg aataaggacc      420
aatggagcga caagtgcctg cacaagatca ggttcttctt tctatgcaga gatgaagtgg      480
ttgctgtcga attcagacaa tgcagcattc ccacagatga caaaatcgta tagaaatccc      540
agaaacaaac cagctctgat aatttgggga gttcatcact ctgaatcggt tagcgagcag      600
accaaactct atggaagtgg aaacaagttg ataaagtaa gaagctcaaa ataccaacaa       660
tcatttaccc caaatcctgg agcacggaga atcgatttcc actggctact cctggatccc      720
aatgacacag tgaccttcac tttcaatggg gcattcatag cccctgacag ggcaagtttc      780
tttagaggag aatcaatagg agtccagagt gatgctcctt tggattctag ttgtggaggg      840
aattgctttc acagtggggg tacgatagtc agttccctgc cattccaaaa catcaaccct      900
agaactgtgg gaaaatgccc tcggtatgtc aaacagaaaa gcctccttct ggctacagga      960
atgagaaatg ttccagagaa accaagaaaa agaggccttt ttggagcaat gctggattc      1020 atagagaacg gatgggaggg tctcatcaat ggatggtatg gtttcagaca tcaaaatgca      1080
caaggagagg gaactgcagc tgactacaaa agcacccagt ctgcaataga tcagatcaca      1140
ggcaaattga atcgtctaat tggcaaaaca aatcagcagt ttgggctgat agacaatgag      1200
ttcaatgagg tagaacaaca aataggaaat gtcattaatt ggacacaaga cgcaatgact      1260
gagatatggt cgtataatgc tgagctgttg gtggcaatgg aaaatcaaca tacaatagat      1320
cttacggatt cagaaatgag caaactttat gagcgtgtca gaaacaact gagggagaat      1380 gctgaagaag atgggactgg atgtttcgaa atattccata gtgtgatga tcattgtatg      1440 gagagcataa gaaacaacac ttatgaccat actcaataca gaacagagtc actgcagaat      1500
agaatacaga tagacccagt gaaattgagt agtggataca agacataat cttatggttt      1560 agcttcgggg catcatgttt tcttcttcta gccattgcaa tgggattggt tttcatttgc      1620
ataaaaaatg gaaacatgca gtgcactatt tgtatatag                            1659

<210> SEQ ID NO 26
<211> LENGTH: 1659
<212> TYPE: DNA
<213> ORGANISM: Unknown
<220> FEATURE:
<223> OTHER INFORMATION: Deoptimized Influenza A virus

<400> SEQUENCE: 26
atgaatatac agatactcgc attcatagct tgcgtactta ccggagctaa aggcgataag      60
atatgtctag gcatcacgc agtcgcaaac ggaacgaaag tgaatacact tacagagaga       120
gggatagagg tcgttaacgc tacagagaca gtcgaaaccg caaatattaa aaaatttgt       180 acacaaggaa aacgaccaac cgatctggga caatgcggac tgttagggac actgatagga      240
ccaccacaat gcgatcaatt ccttgagttt agtagcgatc tgataatcga acgaagagag      300
ggaactgacg tttgttatcc cggtaagttc actaacgaag agagtcttag acagatactg      360
agacggtcag ggggaatcgg aaaagagtca atggggttta cgtattctgg gattaggact      420
aatggcgcaa ctagcgcatg tactagaagc ggatcatcat tctatgccga atgaaatgg      480 ttgttgtcga attccgataa cgctgcattc ccacaaatga ctaaatcgta tagaaatcct      540
aggaataaac ccgcactgat aatatgggga gtgcatcata gcgaatccgt aagtgaacag      600
```

```
actaaattgt acggatcagg taataaactg attaaagtga gatctagtaa gtatcagcaa    660
tcgtttacac ctaatcccgg agctagacgt atcgatttcc attggctatt gctcgaccct    720
aacgataccg ttacattcac attcaatggc gcattcatag cgccagatag ggcaagtttt    780
tttagaggcg aatcaatcgg agtgcaatca gacgcaccac ttgactcaag ttgcggaggg    840
aattgtttcc atagcggagg gactatagtg agtagtctgc cattccaaaa tattaatcct    900
agaacagtgg gtaagtgtcc tagatacgtt aaacagaaaa gtctgttact cgcaaccgga    960
atgcgtaacg tacccgaaaa acctaaaaaa aggggattgt tcggagcgat agccggattc   1020
atagagaatg gatgggaggg actgattaac ggatggtacg gatttagaca ccaaaacgct   1080
cagggagagg gaaccgcagc cgattataaa tcgacacaat ctgcaatcga tcagattacc   1140
ggtaagctta atagattgat tggtaagact aatcagcaat tcggactgat agacaatgag   1200
tttaacgaag tcgagcaaca gatagggaat gtgattaatt ggacacaaga cgctatgact   1260
gagatttggt cttataatgc cgaactgcta gtcgctatgg agaatcaaca cacaatcgat   1320
ctaaccgata gcgaaatgtc aaaattgtat gagagagtga gaaaacagct tagagagaat   1380
gcagaggaag acggaactgg ggtgtttcgag atattccata aatgcgacga tcactgtatg   1440
gaatctatta gaaataatac atacgatcat acacagtata gaacagagtc acttcaaaat   1500
cggatacaga tagacccagt taaactatct agcggatata agacataat   actgtggttc   1560
tcattcggag ctagttgttt tctgttgctc gcaatcgcta tgggacttgt attcatatgt   1620
attaaaaacg gtaatatgca atgtacaatt tgcatatag                          1659

<210> SEQ ID NO 27
<211> LENGTH: 1362
<212> TYPE: DNA
<213> ORGANISM: Influenza A virus

<400> SEQUENCE: 27
atgaatccaa atcagaagat aataacaatt ggctccgtct ctctaaccat tgcaacagta     60
tgtttcctca tgcagattgc cattctagca atgactgtaa cactgcattt caggcaaaat    120
gaatgcagca tttccgcgaa cagtcaggta gtgccgtgtg aaccaactac agagaaagag    180
gtctgttcga acgtagtaga ctatagaagc tggtcaaagc cgcagtgtca aattacagga    240
tttgccccctt tttccaagga caactcaatt cgactttctg ctggtggaga catttggata    300
acaagagagc cttatgtgtc gtgtgacacc agcaaatgtt accaatttgc acttgggcag    360
gggaccacac tggataacaa acattcaaac ggaacaatac atgatagaat ctcccatcgg    420
acccttttga tgaatgaact gggtgttcca tttcacttgg gaaccaaaca gtttgcata    480
gcatggtcca gctcaagttg ccatgatggg aaagcatggt tgcacgtttg tgtcactggg    540
gatgatagaa atgcaactgc tagtttcatt tacaatggga tgcttgttga cagtattggt    600
tcatggtctc aaaatatcct caggacccag gagtcagaat gcgtttgcat caatgggtct    660
tgtacagtag tgatgactga tggaagtgcc tcagggaagg ccgatactag gatattattc    720
gtcaaagaag gaaagattgt tcacattagc ccattgtcag gaagtgctca gcatatagag    780
gaatgttcct gttatcccg atacccaaac gtcagatgtg tctgcaggga caactggaag    840
ggctctaata ggcctgttat agacataaac atggcagatt atagcatcga ctccagttat    900
gtgtgctcag gactcgttgg ggacacacca aggaatgagg atagttctag cagcagcaac    960
tgtagggatc ccaatgaaga gaggggaaac ccaggagtga aggatgggc  ctttgacagt   1020
ggagatgatg tttggatggg tagaacaatc agtagggatt cgcggtcagg ctatgagaca   1080
```

```
tttagggtca ttggtggttg gaccactgcc aattccaaat cacagaccag cagacaagtc      1140
atagttgata ataacaattg gtctggttat tctggtattt tctctgttga acacaaaagc      1200
tgtatcaata ggtgttttta tgtggagtta ataagaggaa ggccgaaaga aactagagta      1260
tggtggacct caaacagtat tgtcgtgttt tgtggcactt ctggcactta tggaacaggc      1320
tcatggcctg atggggcgaa catcaatttc atgcctatat aa                         1362
```

```
<210> SEQ ID NO 28
<211> LENGTH: 1362
<212> TYPE: DNA
<213> ORGANISM: Unknown
<220> FEATURE:
<223> OTHER INFORMATION: Deoptimized Influenza A virus

<400> SEQUENCE: 28
atgaatccga atcagaaaat cattactatc ggatccgtta gcttgacaat cgcaaccgta       60
tgttttctta tgcagattgc gatactcgca atgaccgtta cattgcattt tagacaaaac      120
gagtgttcta ttagcgctaa ctctcaggtc gtgccatgcg aacctacaac cgaaaaagag      180
gtttgttcaa acgtagtcga ttataggtca tggtctaaac cgcaatgtca gattaccgga      240
ttcgcaccat tttcgaaaga caattcgatt agactatccg ccggaggcga tatttggata      300
actagggaac catacgtgtc atgcgataca agtaagtgtt atcaattcgc actcggccaa      360
gggactacac tcgataacaa acactctaac ggtacaatac acgataggat tagtcatagg      420
acactgctta tgaacgagtt aggcgtacca ttccatctgg gaactaaaca ggtatgcata      480
gcctggtcat ctagttcatg tcacgacggt aaggcatggt tgcacgtatg cgtaaccggc      540
gacgatagaa acgctaccgc ctcattcata tataacggta tgctagtcga ctcaatcggg      600
tcatggtcac aaaatatact taggacacag gaatccgaat gcgtatgtat taacggatca      660
tgtacagtcg ttatgaccga cggatccgct agcggtaagg ccgatacacg gatactgttc      720
gttaaagagg gtaagatagt gcatattagc ccacttagcg gatccgccca acatatcgaa      780
gagtgttcat gttatcctag atatccgaac gttaggtgcg tttgtaggga taattggaaa      840
gggtctaatc gacccgttat cgatattaat atggccgatt atagtatcga tagttcatac      900
gtttgttccg gattagtcgg cgatactcct agaaacgaag atagttctag ctctagtaat      960
tgtagagacc caaacgaaga gagagggaat cccggagtga aagggtgggc attcgatagc     1020
ggtgacgacg tttggatggg taggacaatt agtagggact ctagatccgg gtatgagact     1080
tttagggtga taggcggatg gacaaccgca aactctaaga gtcagactag tagacaggtg     1140
atagtcgata taataattg gtccgggtat agcgggattt ttagcgtcga gcataagtca      1200
tgtattaatc ggtgttttta tgtcgaattg attaggggc gacctaaaga gactagggtg      1260
tggtggacta gcaattcgat agtcgttttt tgcggtacta gcggaacata cggaaccgga     1320
agttggccag acggagcgaa tattaatttt atgcctatat aa                         1362
```

```
<210> SEQ ID NO 29
<211> LENGTH: 1704
<212> TYPE: DNA
<213> ORGANISM: Influenza A virus

<400> SEQUENCE: 29
atgaatactc aaattttggc attcattgct tgtatgctga ttggaactaa aggagacaaa       60
atatgtcttg gcaccatgc tgtggcaaat gggacaaaag tgaacacact aacagagagg      120
```

| | |
|---|---|
| ggaattgaag tagtcaatgc cacggagacg gtggaaactg taaatattaa gaaaatatgc | 180 |
| actcaaggaa aaaggccaac agatctggga caatgtggac ttctaggaac cctaatagga | 240 |
| cctccccaat gcgatcaatt tctggagttt gacgctaatt tgataattga acgaagagaa | 300 |
| ggaaccgatg tgtgctatcc cgggaagttc acaaatgaag aatcactgag gcagatcctt | 360 |
| cgagggtcag gaggaattga taaagagtca atgggtttca cctatagtgg aataagaacc | 420 |
| aatggggcga cgagtgcctg cagaagatca ggttcttctt tctatgcgga gatgaaatgg | 480 |
| ttactgtcga attcagacaa tgcggcattt ccccaaatga ctaagtcgta taggaatccc | 540 |
| aggaacaaac cagctctgat aatctgggga gtgcatcact ctggatcagc tactgagcag | 600 |
| accaaactct atggaagtgg aaacaagttg ataacagtag gaagctcgaa ataccagcaa | 660 |
| tcattcactc caagtccggg agcacggcca caagtgaatg gacaatcagg aaggattgat | 720 |
| tttcattggc tactccttga ccccaatgac acagtgacct tcactttcaa tgggcattc | 780 |
| atagccctg acagggcaag tttctttaga ggagaatcgc taggagtcca gagtgatgtt | 840 |
| cctttggatt ctggttgtga aggggattgc ttccacagtg ggggtacgat agtcagttcc | 900 |
| ctgccattcc aaaacatcaa ccctagaaca gtggggaaat gccctcgata tgtcaaacag | 960 |
| acaagcctcc ttttggctac aggaatgaga aacgtcccag agaaccccaa gcaggcctac | 1020 |
| cagaaacgga tgaccagagg cctttttgga gcgattgctg gattcataga gaatggatgg | 1080 |
| gaaggtctca tcgatggatg gtatggtttc agacatcaaa atgcacaagg agaaggaact | 1140 |
| gcagctgact acaaaagcac ccaatctgca atagatcaga tcacaggcaa attgaatcgt | 1200 |
| ctgattgaca aaacaaacca gcagtttgaa ctgatagaca tgaattcag tgagatagaa | 1260 |
| caacaaatcg gaatgtcat taactggaca cgagactcaa tgactgaggt atggtcgtat | 1320 |
| aatgctgagc tgttggtggc aatggagaat cagcatacaa tagatcttgc agactcagaa | 1380 |
| atgaacaaac tttacgaacg cgtcagaaaa caactaaggg aaaatgctga agaagatgga | 1440 |
| actggatgct ttgagatatt ccataagtgt gatgatcagt gtatggagag cataaggaac | 1500 |
| aacacttatg accatacccca atacaggaca gagtcattgc agaatagaat acagatagac | 1560 |
| ccagtgaaat tgagtagtgg atacaaagac ataatcttat ggtttagctt cggggcatca | 1620 |
| tgttttcttc ttctagccat tgcaatggga ttggttttca tttgcataaa gaatggaaac | 1680 |
| atgcggtgca ctatttgtat atag | 1704 |

<210> SEQ ID NO 30
<211> LENGTH: 1704
<212> TYPE: DNA
<213> ORGANISM: Unknown
<220> FEATURE:
<223> OTHER INFORMATION: Deoptimized Influenza A virus

<400> SEQUENCE: 30

| | |
|---|---|
| atgaatacac agatactcgc attcatagcg tgtatgctta tcggaactaa aggcgataaa | 60 |
| atttgcttag ggcatcacgc agtcgctaac ggaactaaag tgaatacgct taccgaacgc | 120 |
| ggaatagagg tcgtgaacgc taccgagaca gtcgaaacag tcaatataaa aaaaatttgt | 180 |
| acacagggaa aaagaccaac cgatctggga caatgcggac tgttagggac actaatcgga | 240 |
| ccaccacaat gcgatcaatt cctcgaattc gacgctaatc tgataatcga acggagagag | 300 |
| ggaactgacg tatgctatcc cggtaagttt acgaacgaag agtcacttag acagatactt | 360 |
| agggggtcag ggggatagacaaagagtct atggggttta catatagcgg aatacggact | 420 |
| aacggagcta caagtgcatg tagacgatcc ggatcatcgt tttacgccga aatgaaatgg | 480 |

```
ttgttgtcta atagcgataa cgctgcattc ccacaaatga ctaagtctta taggaatcct    540
agaaataaac ccgcactgat tatttgggga gtgcatcata gtggatcagc aaccgaacag    600
actaagttgt acggatcagg taataaactg attacagtcg gatcgagtaa atatcagcaa    660
tcgttcacac ctagtcccgg agctagaccg caagtgaacg gacaatctgg taggattgac    720
tttcattggt tgcttctaga cccaaacgat acagtgacat tcacttttaa cggagcattt    780
atcgcacccg atagggctag tttctttagg ggagagtcac tcggagtgca atcagacgta    840
ccacttgata gcggatgcga aggcgattgt tttcactcag gggaactat agtgagtagt    900
ctgccattcc aaaatattaa tcctagaacc gtcggtaagt gtcctaggta cgttaaacag    960
actagtctat tgctcgcaac cggaatgcgt aacgtacccg aaaatcctaa acaggcatat   1020
cagaaacgga tgactagggg gctattcgga gcgattgccg gattcataga gaatgggtgg   1080
gagggactga tagacggatg gtacgggttc agacaccaaa acgctcaggg agagggaaca   1140
gccgcagact ataagtctac gcaatcggca atcgatcaga ttaccggtaa gcttaataga   1200
ctgatagaca aaactaatca gcaattcgaa ctgatagaca acgaatttag tgagatagag   1260
caacagatag ggaatgtgat aaattggact agagactcaa tgactgaggt atggtcatat   1320
aacgccgaac tgttggtcgc aatggagaat cagcatacaa tcgatctagc cgatagcgaa   1380
atgaataaac tttacgaaag ggtgcgaaaa caattgcgag agaatgcgga agaggacgga   1440
accggatgtt tcgaaatttt ccataaatgc gacgatcaat gtatggaatc gattaggaat   1500
aatacatacg atcatacaca atatagaacc gaatcacttc agaataggat tcaaatcgat   1560
cccgttaagt tgagtagcgg atataaagac attatactat ggttctcatt cggagctagt   1620
tgctttctat tgcttgcgat agctatggga ttggtgttca tatgcataaa aaacggtaat   1680
atgcgatgta cgatttgcat atag                                          1704
```

<210> SEQ ID NO 31
<211> LENGTH: 1410
<212> TYPE: DNA
<213> ORGANISM: Influenza A virus

<400> SEQUENCE: 31

```
atgaatccga atcagaagat aataacaatc ggggtagtga ataccactct gtcaacaata     60
gcccttctca ttggagtggg aaacttagtt ttcaacacag tcatacatga gaaaatagga    120
gaccatcaaa tagtgaccca tccaacaata atgacccctg aagtaccgaa ctgcagtgac    180
actataataa catacaataa cactgttata aacaacataa caacaacaat aataactgaa    240
gcagaaaggc ctttcaagtc tccactaccg ctgtgcccct tcagaggatt cttccctttt    300
cacaaggaca atgcaatacg actgggtgaa aacaaagacg tcatagtcac aagggagcct    360
tatgttagct gcgataatga caactgctgg tcctttgctc tcgcacaagg agcattgcta    420
gggactaaac atagcaatgg gaccattaaa gacagaacac catataggtc tctaattcgt    480
ttcccaatag gaacagctcc agtactagga aattacaaag agatatgcat tgcttggtcg    540
agcagcagtt gctttgacgg gaaagagtgg atgcatgtgt gcatgacagg gaatgataat    600
gatgcaagtg cccagataat atatggagga agaatgacag actccattaa atcatggagg    660
aaagacatac taagaaccca ggagtctgaa tgtcaatgca ttgacgggac ttgtgttgtt    720
gctgtcacag atggccctgc tgctaatagt gcagatcaca gggtttactg gatacgggag    780
ggaagaataa taaagtatga aaatgttccc aaaacaaaga tacaacactt agaagaatgt    840
```

```
tcctgctatg tggacattga tgtttactgt atatgtaggg acaattggaa gggctctaac    900
agaccttgga tgagaatcaa caacgagact atactggaaa caggatatgt atgtagtaaa    960
tttcactcag acaccccag gccagctgac ccttcaataa tgtcatgtga ctccccaagc    1020
aatgtcaatg gaggacccgg agtgaagggg tttggtttca agctggcaa tgatgtatgg     1080
ttaggtagaa cagtgtcaac tagtggtaga tcgggctttg aaattatcaa agttacagaa    1140
gggtggatca actctcctaa ccatgtcaaa tcaattacac aaacactagt gtccaacaat    1200
gactggtcag gctattcagg tagcttcatt gtcaaagcca aggactgttt tcagccctgt    1260
ttttatgttg agcttatacg agggaggccc aacaagaatg atgacgtctc ttggacaagt    1320
aatagtatag ttactttctg tggactagac aatgaacctg gatcgggaaa ttggccagat    1380
ggttctaaca ttgggtttat gcccaagtaa                                     1410
```

<210> SEQ ID NO 32
<211> LENGTH: 1410
<212> TYPE: DNA
<213> ORGANISM: Unknown
<220> FEATURE:
<223> OTHER INFORMATION: Deoptimized Influenza A virus

<400> SEQUENCE: 32

```
atgaatccta atcagaaaat aattactata ggggtcgtta atactacact atctacaatc    60
gctctactaa tcggagtcgg taatctagtc tttaatacag tgatacacga aaagataggc    120
gaccatcaga tagtgacaca tcctacaatt atgacacccg aagtgcctaa ttgtagcgat    180
acaataatta catataacaa taccgttata aacaatatta caacaacaat tataaccgaa    240
gccgaacgac cattcaaaag tccactaccc ctatgtccat taggggggtt ttttccgttt    300
cataaggata cgctatacg gttaggcgaa ataaagacg taatcgttac tagggagcca    360
tacgttagtt gcgataacga taattgttgg tcattcgcac tcgctcaagg cgcactgtta    420
gggactaaac actctaacgg aacaattaaa gacagaacac cttataggtc actgataaga    480
ttccctatcg gaaccgctcc cgtactaggc aattataaag agatatgcat agcatggtca    540
agttcgtcat gtttcgacgg taaagagtgg atgcacgtat gtatgaccgg taacgataac    600
gacgctagcg cacagataat atacggaggg cgaatgacag actcaattaa gagttggcgt    660
aaagacatac tgagaacaca agagtccgaa tgccaatgca tagacggaac ttgcgtagtc    720
gccgttacag acggacccgc agctaactcc gctgaccata gagtgtattg gattagggag    780
ggaaggataa taaagtatga gaacgtgcct aagactaaga tacaacatct tgaagagtgt    840
tcatgttatg tcgacataga cgtgtattgc atatgtagag acaattggaa agggtctaat    900
aggccatgga tgagaataaa taacgaaact atactcgaaa ccggatacgt atgttctaag    960
ttccatagcg atacacctag acccgcagac ccatctatta tgtcatgcga tagcccatct    1020
aacgttaacg gcgacccgg agtcaaaggg ttcggattca agccggtaa cgacgtttgg    1080
ttagggagaa ccgttagtac tagcggtagg tccggattcg aaattataaa ggttacagag    1140
gggtggataa atagtccgaa tcacgttaag tcaattacac aaacacttgt gtctaataac    1200
gattggtccg gatatagcgg atcattcata gtcaaagcta aggattgctt tcagccatgt    1260
ttttacgtcg aactgataag ggggagaccg aataaaaacg acgacgttag ttggactagt    1320
aattcgatag tgcattttg cggattggac aacgaacccg gatccggtaa ttggcctgac    1380
ggatcgaata tagggtttat gcctaaataa                                     1410
```

<210> SEQ ID NO 33
<211> LENGTH: 1710
<212> TYPE: DNA
<213> ORGANISM: Influenza A virus

<400> SEQUENCE: 33

| | | | | | |
|---|---|---|---|---|---|
| agcaaaagca | ggggatacaa | aatgaacact | caaatcctgg | tattcgctct | ggtggcgagc | 60 |
| attccgacaa | atgcagacaa | gatctgcctt | gggcatcatg | ccgtgtcaaa | cgggactaaa | 120 |
| gtaaacacat | taactgagag | aggagtggaa | gtcgttaatg | caactgaaac | ggtggaacga | 180 |
| acaaacgttc | ccaggatctg | ctcaaaaggg | aaaaggacag | ttgacctcgg | tcaatgtgga | 240 |
| cttctgggaa | caatcactgg | gccaccccaa | tgtgaccaat | tcctagaatt | ttcggccgac | 300 |
| ttaattattg | agaggcgaga | aggaagtgat | gtctgttatc | ctgggaaatt | cgtgaatgaa | 360 |
| gaagctctga | ggcaaattct | cagagagtca | ggcggaattg | acaaggagac | aatgggattc | 420 |
| acctacagcg | gaataagaac | taatggaaca | accagtgcat | gtaggagatc | aggatcttca | 480 |
| ttctatgcag | agatgaaatg | gctcctgtca | aacacagaca | atgctgcttt | cccgcaaatg | 540 |
| actaagtcat | acaagaacac | aaggaaagac | ccagctctga | taatatgggg | gatccaccat | 600 |
| tccggatcaa | ctacagaaca | gaccaagcta | tatgggagtg | gaaacaaact | gataacagtt | 660 |
| gggagttcta | attaccaaca | gtcctttgta | ccgagtccag | gagcgagacc | acaagtgaat | 720 |
| ggccaatctg | gaagaattga | cttttcattgg | ctgatactaa | accctaatga | cacggtcact | 780 |
| ttcagtttca | atggggcctt | catagctcca | gaccgtgcaa | gctttctgag | agggaagtcc | 840 |
| atggaattc | agagtgaagt | acaggttgat | gccaattgtg | aaggagattg | ctatcatagt | 900 |
| ggagggacaa | taataagtaa | tttgcccttt | cagaacataa | atagcagggc | agtaggaaaa | 960 |
| tgtccgagat | atgttaagca | agagagtctg | ctgttggcaa | caggaatgaa | gaatgttccc | 1020 |
| gaaatcccaa | agaggaggag | gagaggccta | tttggtgcta | tagcgggttt | cattgaaaat | 1080 |
| ggatgggaag | gtttgattga | tgggtggtat | ggcttcaggc | atcaaaatgc | acaaggggag | 1140 |
| ggaactgctg | cagattacaa | aagcacccaa | tcagcaattg | atcaaataac | agggaaatta | 1200 |
| aatcggctta | tagaaaaaac | taaccaacag | tttgagttaa | tagacaacga | attcactgag | 1260 |
| gttgaaaggc | aaattggcaa | tgtgataaac | tggaccagag | attccatgac | agaagtgtgg | 1320 |
| tcctataacg | ctgaactctt | agtagcaatg | gagaatcagc | acacaattga | tctggccgac | 1380 |
| tcagaaatga | acaaactgta | cgaacgagtg | aagagacaac | tgagagagaa | tgccgaagaa | 1440 |
| gatggcactg | gttgcttcga | aatatttcac | aagtgtgatg | acgactgcat | ggccagtatt | 1500 |
| agaaacaaca | cctatgatca | cagcaagtac | agggaagaag | caatacaaaa | tagaatacag | 1560 |
| attgacccag | tcaaactaag | cagcggctac | aaagatgtga | actttggtt | tagcttcggg | 1620 |
| gcatcatgtt | tcatacttct | ggccattgca | atgggccttg | tcttcatatg | tgtgaagaat | 1680 |
| ggaaacatgc | ggtgcactat | ttgtatataa | | | | 1710 |

<210> SEQ ID NO 34
<211> LENGTH: 1710
<212> TYPE: DNA
<213> ORGANISM: Unknown
<220> FEATURE:
<223> OTHER INFORMATION: Deoptimized Influenza A virus

<400> SEQUENCE: 34

| | | | | | |
|---|---|---|---|---|---|
| agtaagagta | gggggtataa | aatgaataca | cagatactcg | tattcgcact | cgttgcgtca | 60 |
| ataccgacaa | acgccgataa | gatttgccta | gggcatcacg | cagtgtcaaa | cggaactaaa | 120 |

-continued

```
gtgaatacac ttaccgaaag gggcgttgag gtagtgaacg ctacagagac tgtcgaacgg 180
actaacgtac ctaggatttg tagtaagggt aaaagaacag tcgacctagg gcaatgcgga 240
ctgttaggca caattaccgg accaccacaa tgcgaccaat ttctcgaatt tagcgctgat 300
ctgattatcg aacggagaga gggatccgac gtttgttatc ccggtaaatt cgttaacgaa 360
gaggcactga gacagatact tagagaatcc ggagggatag acaaagagac aatggggttt 420
acatatagcg gaattagaac taacggaact actagcgcat gtaggagatc cggatctagc 480
ttttacgccg aaatgaaatg gttactgtca aataccgata acgccgcatt tccgcaaatg 540
actaagtcat ataagaatac taggaaagac cccgcactga taatttgggg gatacaccat 600
agcggatcga ctaccgaaca gacaaagcta tacggtagcg ggaataaact gataacagtg 660
ggatcaagta attaccaaca gtcattcgta ccgagtccag gcgctagacc acaagtgaac 720
ggacaatccg gacgtataga tttccattgg ttgatactga atccgaacga tacagtgaca 780
tttagcttta acggcgcatt catagcaccc gatagggcat cattccttag ggtaagagt 840
atggggatac aaagcgaagt gcaagtcgac gctaattgcg aaggcgattg ttatcatagc 900
ggggggacta ttattagtaa tctgccattc caaaatatta atagtagggc agtgggaaag 960
tgtccaaggt acgttaaaca ggaatcactg ttactcgcaa ccggaatgaa aaacgtacca 1020
```
gagataccta agagacgaag aagggggttg ttcggcgcta tagccggatt catagagaac 1080
ggatgggagg gactgataga cggatggtac gggttcagac accaaaacgc tcaaggcgaa 1140
gggacagccg cagactataa gagtacacaa tccgctatcg atcaaattac cggtaagctt 1200
aatagactga tcgaaaaaac taatcaacaa ttcgaactaa tcgataacga atttacggaa 1260
gtcgaaagac agattggcaa tgtgataaat tggactagag actctatgac tgaggtttgg 1320
tcatataacg ccgaactgtt agtcgcaatg gaaaatcagc atacgataga ccttgccgat 1380
agcgaaatga ataagctata cgaaagggtg aaacgacaat tgagggaaaa cgccgaagag 1440
gacggaacag ggtgtttcga aatttttcac aaatgcgacg acgattgtat ggctagtatt 1500
aggaataata catacgacca tagtaagtat agagaggaag cgatacagaa taggattcaa 1560
atcgatcccg taaaactgtc tagcggatac aaagacgtta tactgtggtt ctcattcgga 1620
gcgtcatgtt tcatactgct tgcaatcgct atggggttag tgttcatatg cgttaaaaac 1680
ggaaatatgc gatgtactat ttgtatttaa 1710

<210> SEQ ID NO 35
<211> LENGTH: 1416
<212> TYPE: DNA
<213> ORGANISM: Influenza A virus
<400> SEQUENCE: 35
atgaatccaa atcagaaact atttgcatta tctggagtgg caatagcact tagtgtactg 60
aacttattga taggaatctc aaacgtcgga ttgaacgtat ctctacatct aaaggaaaaa 120
ggacccaaac aggaggagaa tttaacatgc acgaccatta atcaaaacaa cactactgta 180
gtagaaaaca catatgtaaa taatacaaca ataattacca agggaactga tttgaaaaca 240
ccaagctatc tgctgttgaa caagagcctg tgcaatgttg aagggtgggt cgtgatagca 300
aaagacaatg cagtaagatt tggggaaagt gaacaaatca ttgttaccag ggagccatat 360
gtatcatgcg acccaacagg atgcaaaatg tatgccttgc accaagggac taccattagg 420
aacaaacatt caaatggaac gattcatgac agaacagctt tcagaggtct catctccact 480
ccattgggca ctccaccaac cgtaagtaac agtgacttta tgtgtgttgg atggtcaagc 540

```
acaacttgcc atgatgggat tgctaggatg actatctgta tacaaggaaa taatgacaat    600
gctacagcaa cggtttatta caacagaagg ctgaccacta ccattaagac ctgggccaga    660
aacattctga ggactcaaga atcagaatgt gtgtgccaca atggcacatg tgcagttgta    720
atgaccgacg gatcggctag tagtcaagcc tatacaaaag taatgtattt ccacaaggga    780
ttagtagtta aggaggagga gttaagggga tcagccagac atattgagga atgctcctgt    840
tatgdacaca atcaaaaggt gacctgtgtg tgcagagata actggcaggg agcaaacagg    900
cctattatag aaattgatat gagcacattg gagcacacaa gtagatacgt gtgcactgga    960
attctcacag acaccagcag acctggggac aaatctagtg gtgattgttc caatccaata   1020
actgggagtc ccggcgttcc gggagtgaag ggattcgggt ttctaaatgg ggataacaca   1080
tggcttggta ggaccatcag ccccagatca agaagtggat tcgaaatgtt gaaaatacct   1140
aatgcaggta ctgatcccaa ttctagaata gcagaacgac aggaaattgt cgacaataac   1200
aattggtcag gctattccgg aagctttatt gactattgga atgataacag tgaatgctac   1260
aatccatgct tttacgtaga gttaattaga ggaagacccg aagaggctaa atacgtatgg   1320
tgggcaagta acagtctaat tgccctatgt ggaagcccat tcccagttgg gtctggttcc   1380
ttccccgatg gggcacaaat ccaatacttt tcgtaa                              1416
```

<210> SEQ ID NO 36
<211> LENGTH: 1416
<212> TYPE: DNA
<213> ORGANISM: Unknown
<220> FEATURE:
<223> OTHER INFORMATION: Deoptimized Influenza A virus

<400> SEQUENCE: 36

```
atgaatccga accaaaaatt gttcgcatta agcggagtcg caatcgcact aagcgtactg     60
aatctgttga tagggataag taacgtaggg ttgaacgtat cactacattt gaaagagaaa    120
gggcctaaac aggaagagaa tttgacatgt actacaatta atcagaataa tactaccgta    180
gtcgaaaata catacgttaa caatacaaca attattacta agggaaccga tctgaaaact    240
ccaagttatc tgttactgaa taaatctcta tgtaacgttg agggatgggt agtgatcgca    300
aaggataacg ccgttagatt cggcgaaagc gaacagatta tagtgactag agagccatac    360
gtatcatgcg atccaaccgg atgcaaaatg tacgcattac accaagggac aactattagg    420
ataaaacact ctaacggtac gatacacgat agaaccgcat ttaggggggtt gattagtaca    480 ccactcgggta caccaccaac cgtttcgaat agcgacttta tgtgcgtagg gtggtctagt    540
actacatgtc acgacggaat cgctagaatg acaatttgca tacaggggaa taacgataac    600
gctaccgcaa ccgtatatta ataragaaga ctaactacta ctattaagac atgggctagg    660
aatatactga gaacgcaaga atccgaatgc gtttgtcata acggtacatg cgccgtagtg    720
atgaccgacg gatccgctag ttcgcaagca tatactaagg taatgtattt tcacaaaggg    780
ttagtagtga agaggaaga gttgaggggg tccgctagac atattgagga atgctcatgt    840
tacggacata atcaaaaggt gacatgcgta tgtagagaca attggcaagg cgcaaataga    900
cccattatcg aaatcgatat gagtacactc gaacatacta gtagatatgt gtgtaccgga    960
atactaaccg atacgagtag acccggcgat aagtctagcg gagattgctc aaacccaatt   1020
accggatcac ccggagtgcc aggcgttaag ggattcggat ccttaacgg agacaataca   1080 tggttaggga gaactattag tcctaggagt aggtccggat tcgaaatgct taagatacct   1140
```

```
aacgccggaa ccgacccaaa tagtaggatt gccgaacgac aagagattgt cgacaataac    1200
aattggtccg gatatagcgg atcattcata gactattgga acgacaatag cgaatgctat    1260
aacccatgtt tttacgttga gttgattagg ggtagacccg aagaggcaaa atacgtttgg    1320
tgggcatcta acagtctaat cgcattatgc ggatcaccat ttcccgtagg tagcggatca    1380
tttcccgacg gagcccaaat tcaatatttt agttaa                              1416
```

<210> SEQ ID NO 37
<211> LENGTH: 1683
<212> TYPE: DNA
<213> ORGANISM: Influenza A virus

<400> SEQUENCE: 37

```
atggaaacaa tatcactaat aactatacta ctagtagtaa cagcaagcaa tgcagataaa      60
atctgcatcg gccaccagtc aacaaactcc acagaaactg tggacacgct aacagaaacc     120
aatgttcctg tgacacatgc caaagaattg ctccacacag agcataatgg aatgctgtgt     180
gcaacaagcc tgggacatcc cctcattcta gacacatgca ctattgaagg actagtctat     240
ggcaacccct tcttgtgacct gctgttggga ggaagagaat ggtcctacat cgtcgaaaga     300
tcatcagctg taaatggaac gtgttaccct gggaatgtag aaaacctaga ggaactcagg     360
acacttttta gttccgctag ttcctaccaa agaatcccaaa tcttcccaga cacaacctgg     420
aatgtgactt acactggaac aagcagagca tgttcaggtt cattctacag gagtatgaga     480
tggctgactc aaaagagcgg ttttttaccct gttcaagacg cccaatacac aaataacagg     540
ggaaagagca ttcttttcgt gtggggcata catcacccac ccacctatac cgagcaaaca     600
aatttgtaca agaaaacga cacaacaaca agcgtgacaa cagaagattt gaataggacc     660
ttcaaaccag tgatagggcc aaggccccctt gtcaatggtc tgcagggaag aattgattat     720
tattggtcgg tactaaaacc aggccaaaca ttgcgagtac gatccaatgg gaatctaatt     780
gctccatggt atggacacgt tctttcagga gggagccatg gaagaatcct gaagactgat     840
ttaaaaggtg gtaattgtgt agtgcaatgt cagactgaaa aaggtggctt aaacagtaca     900
ttgccattcc acaatatcag taaatatgca tttggaacct gccccaaata tgtaagagtt     960
aatagtctca aactggcagt cggtctgagg aacgtgcctg ctagatcaag tagaggacta    1020 tttgagcca tagctggatt catagaagga ggttggccag gactagtcgc tggctggtat    1080
ggtttccagc attcaaatga tcaagggggt tggtatggctg cagataggga ttcaactcaa    1140
aaggcaattg ataaaataac atccaaggt aataatatag tcgacaagat gaacaagcaa    1200
tatgaaataa ttgatcatga attcagtgag gttgaaacta gactcaatat gatcaataat    1260
aagattgatg accaaataca agacgtatgg gcatataatg cagaattgct agtactactt    1320
gaaaatcaaa aacactcga tgagcatgat gcgaacgtga acaatctata taacaaggtg    1380
aagagggcac tgggctccaa tgctatggaa gatgggaaag ctgtttcga gctataccat    1440 aaatgtgatg atcagtgcat ggaaacaatt cggaacggga cctataatag agagaagtat    1500
agagaggaat caagactaga aaggcagaaa atagagggg ttaagctgga atctgaggga    1560
acttacaaaa tcctcaccat ttattcgact gtcgcctcat ctcttgtgct tgcaatgggg    1620
tttgctgcct tcctgttctg ggccatgtcc aatggatctt gcagatgcaa catttgtata    1680
taa                                                                 1683
```

<210> SEQ ID NO 38
<211> LENGTH: 1683

<212> TYPE: DNA
<213> ORGANISM: Unknown
<220> FEATURE:
<223> OTHER INFORMATION: Deoptimized Influenza A virus

<400> SEQUENCE: 38

| | |
|---|---|
| atggagacaa ttagtctgat tactatacta ttggtcgtta cagcgtcaaa cgctgacaaa | 60 |
| atatgtatag gccatcaatc cactaattca accgaaacag tcgatacact aaccgaaacg | 120 |
| aatgtgccag tgacacacgc taaagagcta ctgcataccg aacataacgg aatgctatgc | 180 |
| gctactagcc tagggcatcc actgatactc gatacatgta ctatcgaggg actcgtatac | 240 |
| ggtaatccta gttgcgatct actgttaggc ggtagggaat ggtcatacat agtcgaacga | 300 |
| tcatccgccg taaacggaac atgttatccc ggtaatgtcg agaatctcga agagcttagg | 360 |
| acactattct catccgctag ctcataccaa cgaatacaga ttttttcccga tactacatgg | 420 |
| aatgtgacat ataccggaac tagtagggca tgttccggat cattctatag atcaatgaga | 480 |
| tggttgacac aaaaatccgg cttttaccct gtgcaagacg cacaatatac gaataatagg | 540 |
| ggtaaatcta tactattcgt atggggtata catcatccac ctacttatac cgaacagact | 600 |
| aatctgtata ttagaaacga tacaactaca tccgttacaa ccgaagactt gaataggaca | 660 |
| ttcaaacccg taatcggacc tagaccacta gtgaacggat tgcagggtag aatcgattac | 720 |
| tattggtccg tacttaagcc agggcaaaca cttagagtga gatctaacgg taatctaatc | 780 |
| gcaccatggt acggacacgt acttagcgga gggtcacacg gtaggatact taagaccgat | 840 |
| ctgaaagggg ggaattgcgt agtgcaatgc caaaccgaaa aaggcggact gaattcgaca | 900 |
| ctaccattcc ataatattag caaatacgca ttcggaacat gtcctaagta cgttagggtg | 960 |
| aatagtctga actcgcagt gggattgaga aacgtacccg ctagatcgag taggggcta | 1020 |
| ttcggcgcaa tcgcagggtt tatcgaaggc ggatggccag gactagttgc cggatggtac | 1080 |
| ggattccaac atagtaacga tcaaggcgta gggatggccg ccgatagggga tagcacacaa | 1140 |
| aaagcaatcg ataagattac tagtaaggtt aataatatag tcgataagat gaataagcaa | 1200 |
| tacgaaatta tcgatcacga atttagcgaa gtcgaaacta gactgaatat gataaataat | 1260 |
| aagatagacg atcagataca agacgtatgg gcatataacg ccgaactgtt agtgttgctt | 1320 |
| gagaatcaga agacactcga cgaacacgac gcaaacgtta ataatctgta taataaagtg | 1380 |
| aaaagagcac tagggtctaa cgctatggag gacggtaagg gatgtttcga actatatcat | 1440 |
| aaatgcgacg atcaatgcat ggagacaatt agaaacggta catataatcg gagaaagtat | 1500 |
| agagaggaat ctagactcga aagacagaaa atcgaaggcg ttaaactcga atccgaagga | 1560 |
| acatataaga tactgactat ttatagtaca gtcgctagct cactagtgct tgctatggga | 1620 |
| ttcgccgcat tcttgttttg ggctatgtca acggatcat gtaggtgtaa tatttgtatt | 1680 |
| taa | 1683 |

<210> SEQ ID NO 39
<211> LENGTH: 1404
<212> TYPE: DNA
<213> ORGANISM: Influenza A virus

<400> SEQUENCE: 39

| | |
|---|---|
| atgaatccaa atcaaaagat aatagcactt ggctctgttt ctataactat tgcgacaata | 60 |
| tgtttactca tgcagattgc catcttagca acgactatga cactacattt caatgaatgt | 120 |
| accaacccat cgaacaatca agcagtgcca tgtgaaccaa tcataataga aaggaacata | 180 |

| | |
|---|---|
| acagagatag tgcatttgaa taatactacc atagagaagg aaagttgtcc taaagtagca | 240 |
| gaatacaaga attggtcaaa accgcaatgt caaattacag ggttcgcccc tttctccaag | 300 |
| gacaactcaa ttaggctttc tgcaggcggg gatatttggg tgacaagaga accttatgta | 360 |
| tcgtgcggtc ttggtaaatg ttaccaattt gcacttgggc agggaaccac tttgaacaac | 420 |
| aaacactcaa atggcacaat acatgatagg agtccccata gaacccttt aatgaacgag | 480 |
| ttgggtgttc catttcattt gggaaccaaa caagtgtgca tagcatggtc cagctcaagc | 540 |
| tgccatgatg ggaaggcatg gttacatgtt tgtgtcactg gggatgatag aaatgcgact | 600 |
| gctagcatca tttatgatgg gatgcttacc gacagtattg gttcatggtc taagaacatc | 660 |
| ctcagaactc aggagtcaga atgcgtttgc atcaatggaa cttgtacagt agtaatgact | 720 |
| gatggaagtg catcaggaag ggctgatact aaaatactat tcattagaga agggaaaatt | 780 |
| gtccacattg gtccactgtc aggaagtgct cagcatgtgg aggaatgctc ctgttacccc | 840 |
| cggtatccag aagttagatg tgttgcaga gacaattgga agggctccaa tagacccgtg | 900 |
| ctatatataa atgtggcaga ttatagtgtt gattctagtt atgtgtgctc aggacttgtt | 960 |
| ggcgacacac caagaaatga cgatagctcc agcagcagta actgcaggga tcctaataac | 1020 |
| gagagagggg gcccaggagt gaaagggtgg gcctttgaca atgaaatga tgtttggatg | 1080 |
| ggacgaacaa tcaagaaaga ttcgcgctct ggttatgaga ctttcagggt cgttggtggt | 1140 |
| tggactacgg ctaattccaa gtcacaaata aataggcaag tcatagttga cagtgataac | 1200 |
| tggtctgggt attctggtat attctctgtt gaaggaaaaa cctgcatcaa caggtgtttt | 1260 |
| tatgtggagt tgataagagg gagaccacag gagaccagag tatggtggac ttcaaatagc | 1320 |
| atcattgtat tttgtggaac ttcaggtacc tatggaacag gctcatggcc tgatggagcg | 1380 |
| aatatcaatt tcatgtctat ataa | 1404 |

<210> SEQ ID NO 40
<211> LENGTH: 1404
<212> TYPE: DNA
<213> ORGANISM: Unknown
<220> FEATURE:
<223> OTHER INFORMATION: Deoptimized Influenza A virus

<400> SEQUENCE: 40

| | |
|---|---|
| atgaatccga atcagaaaat aatcgcatta gggtccgttt cgattactat agcgactata | 60 |
| tgcctattga tgcaaatcgc aatactcgca acgactatga cattgcattt taacgaatgc | 120 |
| actaatccct ctaataatca ggccgttcca tgcgaaccaa tcataatcga acggaatatt | 180 |
| accgagatag tgcatcttaa caatacgact atcgaaaaag agtcatgccc taaggtagcg | 240 |
| gaatataaaa attggtctaa gcctcaatgt cagattaccg gattcgcacc attctctaaa | 300 |
| gataattcaa ttaggcttag cgcaggcgga gatatatggg tgactagaga gccatacgta | 360 |
| agttgcggac tcgtaagtg ttatcaattc gcattaggcc aagggacaac ccttaataat | 420 |
| aagcatagta acggtactat acacgatagg agtccacata ggactcttct tatgaacgag | 480 |
| ttaggcgtac cattccattt agggactaaa caggtttgta tcgcatggtc tagtagttca | 540 |
| tgtcatgacg gtaaggcatg gttgcatgtt tgcgttaccg gcgacgatag aaacgctacc | 600 |
| gcttcaatca tatcgacgg tatgcttacc gattcaatcg gatcatggtc taaaaatata | 660 |
| cttagaaccc aagagtccga atgcgtatgt attaacggta catgtacagt cgttatgaca | 720 |
| gacggatccg ctagcggtag ggccgataca agatatactat tcatacgcga aggtaagata | 780 |
| gtgcatatcg gaccattgtc cggatccgca caacacgttg aggaatgctc atgttatcct | 840 |

-continued

```
agatatcccg aagtgagatg cgtatgtaga gataattgga aagggtcaaa tagacccgta      900
ctgtatataa acgttgccga ttatagcgtc gatagttcat atgtgtgtag cggactagtg      960
ggcgatacac ctagaaacga cgattcatct agtagttcga attgtaggga tcctaataac     1020
gaaagaggcg gaccaggcgt taaagggtgg gcattcgata acggtaacga cgtttggatg     1080
gggagaacta ttaaaaaaga ttctagatca gggtatgaga cattcagagt ggtgggggggg     1140 tggactaccg ctaactctaa gtctcaaatt aatagacagg tgatagtcga tagcgataat     1200
tggtcagggt attccggtat ttttagcgtt gagggtaaga catgtattaa taggtgtttt     1260
tatgtcgaat tgattagggg gcgaccacaa gagactaggg tttggtggac tagtaattcg     1320
attatagtgt tttgcggaac tagcggaaca tacggaaccg gatcatggcc agacggagcg     1380
aatataaatt ttatgtctat ataa                                            1404
```

<210> SEQ ID NO 41
<211> LENGTH: 2341
<212> TYPE: DNA
<213> ORGANISM: Influenza virus
<220> FEATURE:
<221> NAME/KEY: CDS
<222> LOCATION: (25)..(2298)

<400> SEQUENCE: 41

```
agcgaaagca ggcaaaccat ttga atg gat gtc aat ccg acc tta ctt ttc        51
                          Met Asp Val Asn Pro Thr Leu Leu Phe
                          1               5 tta aaa gtg cca gca caa aat gct ata agc aca act ttc cct tat act       99
Leu Lys Val Pro Ala Gln Asn Ala Ile Ser Thr Thr Phe Pro Tyr Thr
 10                  15                  20                  25 gga gac cct cct tac agc cat ggg aca gga aca gga tac acc atg gat      147
Gly Asp Pro Pro Tyr Ser His Gly Thr Gly Thr Gly Tyr Thr Met Asp
                 30                  35                  40 act gtc aac agg aca cat cag tac tca gaa aag gga aga tgg aca aca      195
Thr Val Asn Arg Thr His Gln Tyr Ser Glu Lys Gly Arg Trp Thr Thr
             45                  50                  55 aac acc gaa act gga gca ccg caa ctc aac ccg att gat ggg cca ctg      243
Asn Thr Glu Thr Gly Ala Pro Gln Leu Asn Pro Ile Asp Gly Pro Leu
         60                  65                  70 cca gaa gac aat gaa cca agt ggt tat gcc caa aca gat tgt gta ttg      291
Pro Glu Asp Asn Glu Pro Ser Gly Tyr Ala Gln Thr Asp Cys Val Leu
     75                  80                  85 gaa gca atg gct ttc ctt gag gaa tcc cat cct ggt att ttt gaa aac      339
Glu Ala Met Ala Phe Leu Glu Glu Ser His Pro Gly Ile Phe Glu Asn
 90                  95                 100                 105 tcg tgt att gaa acg atg gag gtt gtt cag caa aca cga gta gac aag      387
Ser Cys Ile Glu Thr Met Glu Val Val Gln Gln Thr Arg Val Asp Lys
                110                 115                 120 ctg aca caa ggc cga cag acc tat gac tgg act cta aat aga aac caa      435
Leu Thr Gln Gly Arg Gln Thr Tyr Asp Trp Thr Leu Asn Arg Asn Gln
            125                 130                 135 cct gct gca aca gca ttg gcc aac aca ata gaa gtg ttc aga tca aat      483
Pro Ala Ala Thr Ala Leu Ala Asn Thr Ile Glu Val Phe Arg Ser Asn
        140                 145                 150 ggc ctc acg gcc aat gag tct gga agg ctc ata gac ttc ctt aag gat      531
Gly Leu Thr Ala Asn Glu Ser Gly Arg Leu Ile Asp Phe Leu Lys Asp
    155                 160                 165 gta atg gag tca atg aaa aaa gaa gaa atg ggg atc aca act cat ttt      579
Val Met Glu Ser Met Lys Lys Glu Glu Met Gly Ile Thr Thr His Phe
170                 175                 180                 185
```

```
cag aga aag aga cgg gtg aga gac aat atg act aag aaa atg ata aca       627
Gln Arg Lys Arg Arg Val Arg Asp Asn Met Thr Lys Lys Met Ile Thr
            190                 195                 200 cag aga aca ata ggt aaa aag aag cag aga ttg aac aaa agg agt tat       675
Gln Arg Thr Ile Gly Lys Lys Lys Gln Arg Leu Asn Lys Arg Ser Tyr
        205                 210                 215 cta att aga gca ttg acc ctg aac aca atg acc aaa gat gct gag aga       723
Leu Ile Arg Ala Leu Thr Leu Asn Thr Met Thr Lys Asp Ala Glu Arg
    220                 225                 230 ggg aag cta aaa cgg aga gca att gca acc cca ggg atg caa ata agg       771
Gly Lys Leu Lys Arg Arg Ala Ile Ala Thr Pro Gly Met Gln Ile Arg
235                 240                 245 ggg ttt gta tac ttt gtt gag aca ctg gca agg agt ata tgt gag aaa       819
Gly Phe Val Tyr Phe Val Glu Thr Leu Ala Arg Ser Ile Cys Glu Lys
250                 255                 260                 265 ctt gaa caa tca ggg ttg cca gtt gga ggc aat gag aag aaa gca aag       867
Leu Glu Gln Ser Gly Leu Pro Val Gly Gly Asn Glu Lys Lys Ala Lys
                270                 275                 280 ttg gca aat gtt gta agg aag atg atg acc aat tct cag gac acc gaa       915
Leu Ala Asn Val Val Arg Lys Met Met Thr Asn Ser Gln Asp Thr Glu
            285                 290                 295 ctt tct ttc acc atc act gga gat aac acc aaa tgg aac gaa aat cag       963
Leu Ser Phe Thr Ile Thr Gly Asp Asn Thr Lys Trp Asn Glu Asn Gln
        300                 305                 310 aat cct cgg atg ttt ttg gcc atg atc aca tat atg aca aga aat cag      1011
Asn Pro Arg Met Phe Leu Ala Met Ile Thr Tyr Met Thr Arg Asn Gln
    315                 320                 325 ccc gaa tgg ttc aga aat gtt cta agt att gct cca ata atg ttc tca      1059
Pro Glu Trp Phe Arg Asn Val Leu Ser Ile Ala Pro Ile Met Phe Ser
330                 335                 340                 345 aac aaa atg gcg aga ctg gga aaa ggg tat atg ttt gag agc aag agt      1107
Asn Lys Met Ala Arg Leu Gly Lys Gly Tyr Met Phe Glu Ser Lys Ser
                350                 355                 360 atg aaa ctt aga act caa ata cct gca gaa atg cta gca agc atc gat      1155
Met Lys Leu Arg Thr Gln Ile Pro Ala Glu Met Leu Ala Ser Ile Asp
            365                 370                 375 ttg aaa tat ttc aat gat tca aca aga aag aag att gaa aaa atc cga      1203
Leu Lys Tyr Phe Asn Asp Ser Thr Arg Lys Lys Ile Glu Lys Ile Arg
        380                 385                 390 ccg ctc tta ata gag ggg act gca tca ttg agc cct gga atg atg atg      1251
Pro Leu Leu Ile Glu Gly Thr Ala Ser Leu Ser Pro Gly Met Met Met
    395                 400                 405 ggc atg ttc aat atg tta agc act gta tta ggc gtc tcc atc ctg aat      1299
Gly Met Phe Asn Met Leu Ser Thr Val Leu Gly Val Ser Ile Leu Asn
410                 415                 420                 425 ctt gga caa aag aga tac acc aag act act tac tgg tgg gat ggt ctt      1347
Leu Gly Gln Lys Arg Tyr Thr Lys Thr Thr Tyr Trp Trp Asp Gly Leu
                430                 435                 440 caa tcc tct gac gat ttt gct ctg att gtg aat gca ccc aat cat gaa      1395
Gln Ser Ser Asp Asp Phe Ala Leu Ile Val Asn Ala Pro Asn His Glu
            445                 450                 455 ggg att caa gcc gga gtc gac agg ttt tat cga acc tgt aag cta ctt      1443
Gly Ile Gln Ala Gly Val Asp Arg Phe Tyr Arg Thr Cys Lys Leu Leu
        460                 465                 470 gga atc aat atg agc aag aaa aag tct tac ata aac aga aca ggt aca      1491
Gly Ile Asn Met Ser Lys Lys Lys Ser Tyr Ile Asn Arg Thr Gly Thr
    475                 480                 485 ttt gaa ttc aca agt ttt ttc tat cgt tat ggg ttt gtt gcc aat ttc      1539
Phe Glu Phe Thr Ser Phe Phe Tyr Arg Tyr Gly Phe Val Ala Asn Phe
```

```
                 490                 495                 500                 505
agc atg gag ctc ccc agt ttt ggg gtg tct ggg atc aac gag tca gcg    1587
Ser Met Glu Leu Pro Ser Phe Gly Val Ser Gly Ile Asn Glu Ser Ala
                510                 515                 520 gac atg agt att gga gtt act gtc atc aaa aac aat atg ata aac aat    1635
Asp Met Ser Ile Gly Val Thr Val Ile Lys Asn Asn Met Ile Asn Asn
            525                 530                 535 gat ctt ggt cca gca aca gct caa atg gcc ctt cag ttg ttc atc aaa    1683
Asp Leu Gly Pro Ala Thr Ala Gln Met Ala Leu Gln Leu Phe Ile Lys
        540                 545                 550 gat tac agg tac acg tac cga tgc cat aga ggt gac aca caa ata caa    1731
Asp Tyr Arg Tyr Thr Tyr Arg Cys His Arg Gly Asp Thr Gln Ile Gln
    555                 560                 565 acc cga aga tca ttt gaa ata aag aaa ctg tgg gag caa acc cgt tcc    1779
Thr Arg Arg Ser Phe Glu Ile Lys Lys Leu Trp Glu Gln Thr Arg Ser
570                 575                 580                 585 aaa gct gga ctg ctg gtc tcc gac gga ggc cca aat tta tac aac att    1827
Lys Ala Gly Leu Leu Val Ser Asp Gly Gly Pro Asn Leu Tyr Asn Ile
                590                 595                 600 aga aat ctc cac att cct gaa gtc tgc cta aaa tgg gaa ttg atg gat    1875
Arg Asn Leu His Ile Pro Glu Val Cys Leu Lys Trp Glu Leu Met Asp
            605                 610                 615 gag gat tac cag ggg cgt tta tgc aac cca ctg aac cca ttt gtc agc    1923
Glu Asp Tyr Gln Gly Arg Leu Cys Asn Pro Leu Asn Pro Phe Val Ser
        620                 625                 630 cat aaa gaa att gaa tca atg aac aat gca gtg atg atg cca gca cat    1971
His Lys Glu Ile Glu Ser Met Asn Asn Ala Val Met Met Pro Ala His
    635                 640                 645 ggt cca gcc aaa aac atg gag tat gat gct gtt gca aca aca cac tcc    2019
Gly Pro Ala Lys Asn Met Glu Tyr Asp Ala Val Ala Thr Thr His Ser
650                 655                 660                 665 tgg atc ccc aaa aga aat cga tcc atc ttg aat aca agt caa aga gga    2067
Trp Ile Pro Lys Arg Asn Arg Ser Ile Leu Asn Thr Ser Gln Arg Gly
                670                 675                 680 gta ctt gaa gat gaa caa atg tac caa agg tgc tgc aat tta ttt gaa    2115
Val Leu Glu Asp Glu Gln Met Tyr Gln Arg Cys Cys Asn Leu Phe Glu
            685                 690                 695 aaa ttc ttc ccc agc agt tca tac aga aga cca gtg ggg ata tcc agt    2163
Lys Phe Phe Pro Ser Ser Ser Tyr Arg Arg Pro Val Gly Ile Ser Ser
        700                 705                 710 atg gtg gag gct atg gtt tcc aga gcc cga att gat gca cgg att gat    2211
Met Val Glu Ala Met Val Ser Arg Ala Arg Ile Asp Ala Arg Ile Asp
    715                 720                 725 ttc gaa tct gga agg ata aag aaa gaa gag ttc act gag atc atg aag    2259
Phe Glu Ser Gly Arg Ile Lys Lys Glu Glu Phe Thr Glu Ile Met Lys
730                 735                 740                 745 atc tgt tcc acc att gaa gag ctc aga cgg caa aaa tag tgaatttagc    2308
Ile Cys Ser Thr Ile Glu Glu Leu Arg Arg Gln Lys
                750                 755 ttgtccttca tgaaaaaatg ccttgtttct act                               2341

<210> SEQ ID NO 42
<211> LENGTH: 757
<212> TYPE: PRT
<213> ORGANISM: Influenza virus

<400> SEQUENCE: 42

Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
```

```
                20                  25                  30
Gly Thr Gly Thr Gly Tyr Thr Met Asp Thr Val Asn Arg Thr His Gln
            35                  40                  45
Tyr Ser Glu Lys Gly Arg Trp Thr Thr Asn Thr Glu Thr Gly Ala Pro
        50                  55                  60
Gln Leu Asn Pro Ile Asp Gly Pro Leu Pro Glu Asp Asn Glu Pro Ser
65                  70                  75                  80
Gly Tyr Ala Gln Thr Asp Cys Val Leu Glu Ala Met Ala Phe Leu Glu
                85                  90                  95
Glu Ser His Pro Gly Ile Phe Glu Asn Ser Cys Ile Glu Thr Met Glu
            100                 105                 110
Val Val Gln Gln Thr Arg Val Asp Lys Leu Thr Gln Gly Arg Gln Thr
        115                 120                 125
Tyr Asp Trp Thr Leu Asn Arg Asn Gln Pro Ala Ala Thr Ala Leu Ala
    130                 135                 140
Asn Thr Ile Glu Val Phe Arg Ser Asn Gly Leu Thr Ala Asn Glu Ser
145                 150                 155                 160
Gly Arg Leu Ile Asp Phe Leu Lys Asp Val Met Glu Ser Met Lys Lys
                165                 170                 175
Glu Glu Met Gly Ile Thr Thr His Phe Gln Arg Lys Arg Arg Val Arg
            180                 185                 190
Asp Asn Met Thr Lys Lys Met Ile Thr Gln Arg Thr Ile Gly Lys Lys
        195                 200                 205
Lys Gln Arg Leu Asn Lys Arg Ser Tyr Leu Ile Arg Ala Leu Thr Leu
    210                 215                 220
Asn Thr Met Thr Lys Asp Ala Glu Arg Gly Lys Leu Lys Arg Arg Ala
225                 230                 235                 240
Ile Ala Thr Pro Gly Met Gln Ile Arg Gly Phe Val Tyr Phe Val Glu
                245                 250                 255
Thr Leu Ala Arg Ser Ile Cys Glu Lys Leu Glu Gln Ser Gly Leu Pro
            260                 265                 270
Val Gly Gly Asn Glu Lys Lys Ala Lys Leu Ala Asn Val Val Arg Lys
        275                 280                 285
Met Met Thr Asn Ser Gln Asp Thr Glu Leu Ser Phe Thr Ile Thr Gly
    290                 295                 300
Asp Asn Thr Lys Trp Asn Glu Asn Gln Asn Pro Arg Met Phe Leu Ala
305                 310                 315                 320
Met Ile Thr Tyr Met Thr Arg Asn Gln Pro Glu Trp Phe Arg Asn Val
                325                 330                 335
Leu Ser Ile Ala Pro Ile Met Phe Ser Asn Lys Met Ala Arg Leu Gly
            340                 345                 350
Lys Gly Tyr Met Phe Glu Ser Lys Ser Met Lys Leu Arg Thr Gln Ile
        355                 360                 365
Pro Ala Glu Met Leu Ala Ser Ile Asp Leu Lys Tyr Phe Asn Asp Ser
    370                 375                 380
Thr Arg Lys Lys Ile Glu Lys Ile Arg Pro Leu Leu Ile Glu Gly Thr
385                 390                 395                 400
Ala Ser Leu Ser Pro Gly Met Met Gly Met Phe Asn Met Leu Ser
                405                 410                 415
Thr Val Leu Gly Val Ser Ile Leu Asn Leu Gly Gln Lys Arg Tyr Thr
            420                 425                 430
Lys Thr Thr Tyr Trp Trp Asp Gly Leu Gln Ser Ser Asp Asp Phe Ala
        435                 440                 445
```

```
Leu Ile Val Asn Ala Pro Asn His Glu Gly Ile Gln Ala Gly Val Asp
    450                 455                 460

Arg Phe Tyr Arg Thr Cys Lys Leu Leu Gly Ile Asn Met Ser Lys Lys
465                 470                 475                 480

Lys Ser Tyr Ile Asn Arg Thr Gly Thr Phe Glu Phe Thr Ser Phe Phe
                485                 490                 495

Tyr Arg Tyr Gly Phe Val Ala Asn Phe Ser Met Glu Leu Pro Ser Phe
            500                 505                 510

Gly Val Ser Gly Ile Asn Glu Ser Ala Asp Met Ser Ile Gly Val Thr
        515                 520                 525

Val Ile Lys Asn Asn Met Ile Asn Asn Asp Leu Gly Pro Ala Thr Ala
    530                 535                 540

Gln Met Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Ile
                565                 570                 575

Lys Lys Leu Trp Glu Gln Thr Arg Ser Lys Ala Gly Leu Leu Val Ser
            580                 585                 590

Asp Gly Gly Pro Asn Leu Tyr Asn Ile Arg Asn Leu His Ile Pro Glu
        595                 600                 605

Val Cys Leu Lys Trp Glu Leu Met Asp Glu Asp Tyr Gln Gly Arg Leu
    610                 615                 620

Cys Asn Pro Leu Asn Pro Phe Val Ser His Lys Glu Ile Glu Ser Met
625                 630                 635                 640

Asn Asn Ala Val Met Met Pro Ala His Gly Pro Ala Lys Asn Met Glu
                645                 650                 655

Tyr Asp Ala Val Ala Thr Thr His Ser Trp Ile Pro Lys Arg Asn Arg
            660                 665                 670

Ser Ile Leu Asn Thr Ser Gln Arg Gly Val Leu Glu Asp Glu Gln Met
        675                 680                 685

Tyr Gln Arg Cys Cys Asn Leu Phe Glu Lys Phe Phe Pro Ser Ser Ser
    690                 695                 700

Tyr Arg Arg Pro Val Gly Ile Ser Ser Met Val Glu Ala Met Val Ser
705                 710                 715                 720

Arg Ala Arg Ile Asp Ala Arg Ile Asp Phe Glu Ser Gly Arg Ile Lys
                725                 730                 735

Lys Glu Glu Phe Thr Glu Ile Met Lys Ile Cys Ser Thr Ile Glu Glu
            740                 745                 750

Leu Arg Arg Gln Lys
        755

<210> SEQ ID NO 43
<211> LENGTH: 2341
<212> TYPE: DNA
<213> ORGANISM: unknown
<220> FEATURE:
<223> OTHER INFORMATION: synthetic
<220> FEATURE:
<221> NAME/KEY: CDS
<222> LOCATION: (25)..(2298)
<220> FEATURE:
<221> NAME/KEY: misc_difference
<222> LOCATION: (531)..(2143)

<400> SEQUENCE: 43
agcgaaagca ggcaaaccat ttga atg gat gtc aat ccg acc tta ctt ttc      51
                          Met Asp Val Asn Pro Thr Leu Leu Phe
```

```
                                                                -continued
1           5
tta aaa gtg cca gca caa aat gct ata agc aca act ttc cct tat act      99
Leu Lys Val Pro Ala Gln Asn Ala Ile Ser Thr Thr Phe Pro Tyr Thr
10              15              20              25 gga gac cct cct tac agc cat ggg aca gga aca gga tac acc atg gat     147
Gly Asp Pro Pro Tyr Ser His Gly Thr Gly Thr Gly Tyr Thr Met Asp
                30              35              40 act gtc aac agg aca cat cag tac tca gaa aag gga aga tgg aca aca     195
Thr Val Asn Arg Thr His Gln Tyr Ser Glu Lys Gly Arg Trp Thr Thr
        45              50              55 aac acc gaa act gga gca ccg caa ctc aac ccg att gat ggg cca ctg     243
Asn Thr Glu Thr Gly Ala Pro Gln Leu Asn Pro Ile Asp Gly Pro Leu
            60              65              70 cca gaa gac aat gaa cca agt ggt tat gcc caa aca gat tgt gta ttg     291
Pro Glu Asp Asn Glu Pro Ser Gly Tyr Ala Gln Thr Asp Cys Val Leu
    75              80              85 gaa gca atg gct ttc ctt gag gaa tcc cat cct ggt att ttt gaa aac     339
Glu Ala Met Ala Phe Leu Glu Glu Ser His Pro Gly Ile Phe Glu Asn
90              95              100             105 tcg tgt att gaa acg atg gag gtt gtt cag caa aca cga gta gac aag     387
Ser Cys Ile Glu Thr Met Glu Val Val Gln Gln Thr Arg Val Asp Lys
                110             115             120 ctg aca caa ggc cga cag acc tat gac tgg act cta aat aga aac caa     435
Leu Thr Gln Gly Arg Gln Thr Tyr Asp Trp Thr Leu Asn Arg Asn Gln
        125             130             135 cct gct gca aca gca ttg gcc aac aca ata gaa gtg ttc aga tca aat     483
Pro Ala Ala Thr Ala Leu Ala Asn Thr Ile Glu Val Phe Arg Ser Asn
            140             145             150 ggc ctc acg gcc aat gag tct gga agg ctc ata gac ttc ctt aag gac     531
Gly Leu Thr Ala Asn Glu Ser Gly Arg Leu Ile Asp Phe Leu Lys Asp
    155             160             165 gtt atg gag tct atg aaa aaa gag gaa atg ggg att acg aca cat ttt     579
Val Met Glu Ser Met Lys Lys Glu Glu Met Gly Ile Thr Thr His Phe
170             175             180             185 caa cga aaa aga cgg gtt agg gat aat atg aca aaa aaa atg att acg     627
Gln Arg Lys Arg Arg Val Arg Asp Asn Met Thr Lys Lys Met Ile Thr
                190             195             200 caa cga aca atc gga aag aaa aaa cag aga ctg aat aag cga tca tac     675
Gln Arg Thr Ile Gly Lys Lys Lys Gln Arg Leu Asn Lys Arg Ser Tyr
        205             210             215 ttg att agg gca ctt aca ctt aac act atg act aag gac gcc gaa agg     723
Leu Ile Arg Ala Leu Thr Leu Asn Thr Met Thr Lys Asp Ala Glu Arg
            220             225             230 gga aag cta aag cgt aga gca att gca aca ccc gga atg caa att agg     771
Gly Lys Leu Lys Arg Arg Ala Ile Ala Thr Pro Gly Met Gln Ile Arg
    235             240             245 ggg ttc gta tac ttc gtc gag aca ctc gct aga tcc ata tgc gaa aag     819
Gly Phe Val Tyr Phe Val Glu Thr Leu Ala Arg Ser Ile Cys Glu Lys
250             255             260             265 tta gag caa tcc gga ctg cca gtc ggg ggg aac gaa aaa aaa gcg aaa     867
Leu Glu Gln Ser Gly Leu Pro Val Gly Gly Asn Glu Lys Lys Ala Lys
                270             275             280 ctc gct aac gtc gtt aga aaa atg atg act aat agt cag gat acc gaa     915
Leu Ala Asn Val Val Arg Lys Met Met Thr Asn Ser Gln Asp Thr Glu
        285             290             295 ctg tca ttt acg att acc ggc gat aat act aag tgg aac gag aat cag     963
Leu Ser Phe Thr Ile Thr Gly Asp Asn Thr Lys Trp Asn Glu Asn Gln
            300             305             310 aat cct aga atg ttt ctc gca atg atc aca tat atg aca cgt aac caa    1011
```

```
                Asn Pro Arg Met Phe Leu Ala Met Ile Thr Tyr Met Thr Arg Asn Gln
                    315                 320                 325 ccc gaa tgg ttt aga aac gta ctg tca atc gca cca att atg ttt agc         1059
Pro Glu Trp Phe Arg Asn Val Leu Ser Ile Ala Pro Ile Met Phe Ser
330                 335                 340                 345 aat aag atg gct aga ttg ggc aag ggg tat atg ttt gaa tct aag agt         1107
Asn Lys Met Ala Arg Leu Gly Lys Gly Tyr Met Phe Glu Ser Lys Ser
                    350                 355                 360 atg aaa ttg cga aca cag ata cct gcc gaa atg cta gca tca atc gat         1155
Met Lys Leu Arg Thr Gln Ile Pro Ala Glu Met Leu Ala Ser Ile Asp
                365                 370                 375 cta aag tac ttt aac gat agt aca cga aaa aaa atc gaa aag att aga         1203
Leu Lys Tyr Phe Asn Asp Ser Thr Arg Lys Lys Ile Glu Lys Ile Arg
            380                 385                 390 ccg tta ctg ata gag gga acc gcc agc cta tcc ccc gga atg atg atg         1251
Pro Leu Leu Ile Glu Gly Thr Ala Ser Leu Ser Pro Gly Met Met Met
        395                 400                 405 ggg atg ttt aat atg ctt agt acc gtg tta ggc gtt agc ata ctt aac         1299
Gly Met Phe Asn Met Leu Ser Thr Val Leu Gly Val Ser Ile Leu Asn
410                 415                 420                 425 tta ggg caa aaa cgt tat act aag act aca tat tgg tgg gac gga ctg         1347
Leu Gly Gln Lys Arg Tyr Thr Lys Thr Thr Tyr Trp Trp Asp Gly Leu
                    430                 435                 440 caa tct agc gac gat ttc gca cta atc gtt aac gca cct aac cat gag         1395
Gln Ser Ser Asp Asp Phe Ala Leu Ile Val Asn Ala Pro Asn His Glu
                    445                 450                 455 ggg ata caa gcc gga gtc gat aga ttc tat aga aca tgc aaa ctg tta         1443
Gly Ile Gln Ala Gly Val Asp Arg Phe Tyr Arg Thr Cys Lys Leu Leu
                460                 465                 470 ggg att aat atg tct aaa aaa aag tca tac ata aat aga acc gga aca         1491
Gly Ile Asn Met Ser Lys Lys Lys Ser Tyr Ile Asn Arg Thr Gly Thr
475                 480                 485 ttt gaa ttc act agc ttt ttt tac aga tac gga ttc gtt gct aat ttt         1539
Phe Glu Phe Thr Ser Phe Phe Tyr Arg Tyr Gly Phe Val Ala Asn Phe
490                 495                 500                 505 agt atg gag tta cct agt ttc gga gtt agc gga att aac gaa tcc gcc         1587
Ser Met Glu Leu Pro Ser Phe Gly Val Ser Gly Ile Asn Glu Ser Ala
                    510                 515                 520 gat atg tca atc ggc gta acc gtt att aag aat aat atg att aat aac         1635
Asp Met Ser Ile Gly Val Thr Val Ile Lys Asn Asn Met Ile Asn Asn
                525                 530                 535 gat cta ggg cca gca acc gca caa atg gca ttg cag ttg ttc ata aag         1683
Asp Leu Gly Pro Ala Thr Ala Gln Met Ala Leu Gln Leu Phe Ile Lys
            540                 545                 550 gat tat cgt tat aca tat aga tgt cat aga ggc gat aca cag ata cag         1731
Asp Tyr Arg Tyr Thr Tyr Arg Cys His Arg Gly Asp Thr Gln Ile Gln
        555                 560                 565 act aga cga tca ttt gaa atc aaa aaa ttg tgg gag caa act agg tct         1779
Thr Arg Arg Ser Phe Glu Ile Lys Lys Leu Trp Glu Gln Thr Arg Ser
570                 575                 580                 585 aaa gcc gga ctg tta gtg tcc gac gga ggg cct aat cta tac aat att         1827
Lys Ala Gly Leu Leu Val Ser Asp Gly Gly Pro Asn Leu Tyr Asn Ile
                    590                 595                 600 agg aat ctg cat ata ccc gaa gtg tgt cta aag tgg gag ctt atg gac         1875
Arg Asn Leu His Ile Pro Glu Val Cys Leu Lys Trp Glu Leu Met Asp
                    605                 610                 615 gaa gac tat cag ggg aga ttg tgc aat ccg ctt aac cca ttc gtt agc         1923
Glu Asp Tyr Gln Gly Arg Leu Cys Asn Pro Leu Asn Pro Phe Val Ser
                620                 625                 630
```

-continued

| | | | | | | | | | | | | | | | | |
|---|---|---|---|---|---|---|---|---|---|---|---|---|---|---|---|---|
| cat | aaa | gag | ata | gag | tca | atg | aat | aac | gcc | gtt | atg | atg | cca | gca | cac | 1971 |
| His | Lys | Glu | Ile | Glu | Ser | Met | Asn | Asn | Ala | Val | Met | Met | Pro | Ala | His | |
| | 635 | | | | 640 | | | | | 645 | | | | | | |
| gga | ccc | gct | aag | aat | atg | gaa | tac | gac | gca | gtc | gca | act | aca | cat | agt | 2019 |
| Gly | Pro | Ala | Lys | Asn | Met | Glu | Tyr | Asp | Ala | Val | Ala | Thr | Thr | His | Ser | |
| 650 | | | | | 655 | | | | | 660 | | | | | 665 | |
| tgg | ata | ccg | aaa | cgg | aat | cga | tcc | ata | ctg | aat | aca | tcc | caa | aga | ggc | 2067 |
| Trp | Ile | Pro | Lys | Arg | Asn | Arg | Ser | Ile | Leu | Asn | Thr | Ser | Gln | Arg | Gly | |
| | | | 670 | | | | | 675 | | | | | 680 | | | |
| gta | ctc | gaa | gac | gaa | caa | atg | tac | caa | cgg | tgt | tgc | aat | cta | ttt | gaa | 2115 |
| Val | Leu | Glu | Asp | Glu | Gln | Met | Tyr | Gln | Arg | Cys | Cys | Asn | Leu | Phe | Glu | |
| | | | 685 | | | | | 690 | | | | | 695 | | | |
| aaa | ttt | ttt | cct | agt | agt | agc | tat | aga | cga | cca | gtc | ggg | ata | tcc | agt | 2163 |
| Lys | Phe | Phe | Pro | Ser | Ser | Ser | Tyr | Arg | Arg | Pro | Val | Gly | Ile | Ser | Ser | |
| | | 700 | | | | | 705 | | | | | 710 | | | | |
| atg | gtg | gag | gct | atg | gtt | tcc | aga | gcc | cga | att | gat | gca | cgg | att | gat | 2211 |
| Met | Val | Glu | Ala | Met | Val | Ser | Arg | Ala | Arg | Ile | Asp | Ala | Arg | Ile | Asp | |
| | 715 | | | | 720 | | | | | 725 | | | | | | |
| ttc | gaa | tct | gga | agg | ata | aag | aaa | gaa | gag | ttc | act | gag | atc | atg | aag | 2259 |
| Phe | Glu | Ser | Gly | Arg | Ile | Lys | Lys | Glu | Glu | Phe | Thr | Glu | Ile | Met | Lys | |
| 730 | | | | | 735 | | | | | 740 | | | | | 745 | |
| atc | tgt | tcc | acc | att | gaa | gag | ctc | aga | cgg | caa | aaa | tag | tgaatttagc | | | 2308 |
| Ile | Cys | Ser | Thr | Ile | Glu | Glu | Leu | Arg | Arg | Gln | Lys | | | | | |
| | | | 750 | | | | | 755 | | | | | | | | | ttgtccttca tgaaaaaatg ccttgtttct act        2341

<210> SEQ ID NO 44
<211> LENGTH: 757
<212> TYPE: PRT
<213> ORGANISM: unknown
<220> FEATURE:
<223> OTHER INFORMATION: Synthetic Construct

<400> SEQUENCE: 44

Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
                20                  25                  30

Gly Thr Gly Thr Gly Tyr Thr Met Asp Thr Val Asn Arg Thr His Gln
            35                  40                  45

Tyr Ser Glu Lys Gly Arg Trp Thr Thr Asn Thr Glu Thr Gly Ala Pro
        50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Ile Glu Thr Met Glu
            100                 105                 110

Val Val Gln Gln Thr Arg Val Asp Lys Leu Thr Gln Gly Arg Gln Thr
        115                 120                 125

Tyr Asp Trp Thr Leu Asn Arg Asn Gln Pro Ala Ala Thr Ala Leu Ala
    130                 135                 140

Asn Thr Ile Glu Val Phe Arg Ser Asn Gly Leu Thr Ala Asn Glu Ser
145                 150                 155                 160

Gly Arg Leu Ile Asp Phe Leu Lys Asp Val Met Glu Ser Met Lys Lys
                165                 170                 175

Glu Glu Met Gly Ile Thr Thr His Phe Gln Arg Lys Arg Arg Val Arg
            180                 185                 190

Asp Asn Met Thr Lys Lys Met Ile Thr Gln Arg Thr Ile Gly Lys Lys
            195                 200                 205

Lys Gln Arg Leu Asn Lys Arg Ser Tyr Leu Ile Arg Ala Leu Thr Leu
        210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Ser Ile Cys Glu Lys Leu Glu Gln Ser Gly Leu Pro
                260                 265                 270

Val Gly Gly Asn Glu Lys Lys Ala Lys Leu Ala Asn Val Val Arg Lys
            275                 280                 285

Met Met Thr Asn Ser Gln Asp Thr Glu Leu Ser Phe Thr Ile Thr Gly
        290                 295                 300

Asp Asn Thr Lys Trp Asn Glu Asn Gln Asn Pro Arg Met Phe Leu Ala
305                 310                 315                 320

Met Ile Thr Tyr Met Thr Arg Asn Gln Pro Glu Trp Phe Arg Asn Val
                325                 330                 335

Leu Ser Ile Ala Pro Ile Met Phe Ser Asn Lys Met Ala Arg Leu Gly
                340                 345                 350

Lys Gly Tyr Met Phe Glu Ser Lys Ser Met Lys Leu Arg Thr Gln Ile
            355                 360                 365

Pro Ala Glu Met Leu Ala Ser Ile Asp Leu Lys Tyr Phe Asn Asp Ser
        370                 375                 380

Thr Arg Lys Lys Ile Glu Lys Ile Arg Pro Leu Leu Ile Glu Gly Thr
385                 390                 395                 400

Ala Ser Leu Ser Pro Gly Met Met Met Gly Met Phe Asn Met Leu Ser
                405                 410                 415

Thr Val Leu Gly Val Ser Ile Leu Asn Leu Gly Gln Lys Arg Tyr Thr
                420                 425                 430

Lys Thr Thr Tyr Trp Trp Asp Gly Leu Gln Ser Ser Asp Asp Phe Ala
            435                 440                 445

Leu Ile Val Asn Ala Pro Asn His Glu Gly Ile Gln Ala Gly Val Asp
        450                 455                 460

Arg Phe Tyr Arg Thr Cys Lys Leu Leu Gly Ile Asn Met Ser Lys Lys
465                 470                 475                 480

Lys Ser Tyr Ile Asn Arg Thr Gly Thr Phe Glu Phe Thr Ser Phe Phe
                485                 490                 495

Tyr Arg Tyr Gly Phe Val Ala Asn Phe Ser Met Glu Leu Pro Ser Phe
                500                 505                 510

Gly Val Ser Gly Ile Asn Glu Ser Ala Asp Met Ser Ile Gly Val Thr
            515                 520                 525

Val Ile Lys Asn Asn Met Ile Asn Asn Asp Leu Gly Pro Ala Thr Ala
        530                 535                 540

Gln Met Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Ile
                565                 570                 575

Lys Lys Leu Trp Glu Gln Thr Arg Ser Lys Ala Gly Leu Leu Val Ser
                580                 585                 590

Asp Gly Gly Pro Asn Leu Tyr Asn Ile Arg Asn Leu His Ile Pro Glu
            595                 600                 605

Val Cys Leu Lys Trp Glu Leu Met Asp Glu Asp Tyr Gln Gly Arg Leu

```
                610              615               620
    Cys Asn Pro Leu Asn Pro Phe Val Ser His Lys Glu Ile Glu Ser Met
    625                 630                 635                 640

Asn Asn Ala Val Met Met Pro Ala His Gly Pro Ala Lys Asn Met Glu
                        645                 650                 655

Tyr Asp Ala Val Ala Thr Thr His Ser Trp Ile Pro Lys Arg Asn Arg
                        660                 665                 670

Ser Ile Leu Asn Thr Ser Gln Arg Gly Val Leu Glu Asp Glu Gln Met
                675                 680                 685

Tyr Gln Arg Cys Cys Asn Leu Phe Glu Lys Phe Phe Pro Ser Ser Ser
            690                 695                 700

Tyr Arg Arg Pro Val Gly Ile Ser Ser Met Val Glu Ala Met Val Ser
    705                 710                 715                 720

Arg Ala Arg Ile Asp Ala Arg Ile Asp Phe Glu Ser Gly Arg Ile Lys
                        725                 730                 735

Lys Glu Glu Phe Thr Glu Ile Met Lys Ile Cys Ser Thr Ile Glu Glu
                    740                 745                 750

Leu Arg Arg Gln Lys
            755

<210> SEQ ID NO 45
<211> LENGTH: 2341
<212> TYPE: DNA
<213> ORGANISM: unknown
<220> FEATURE:
<223> OTHER INFORMATION: synthetic
<220> FEATURE:
<221> NAME/KEY: CDS
<222> LOCATION: (25)..(2298)
<220> FEATURE:
<221> NAME/KEY: misc_difference
<222> LOCATION: (531)..(1488)

<400> SEQUENCE: 45
agcgaaagca ggcaaaccat ttga atg gat gtc aat ccg acc tta ctt ttc         51
                          Met Asp Val Asn Pro Thr Leu Leu Phe
                          1               5 tta aaa gtg cca gca caa aat gct ata agc aca act ttc cct tat act        99
Leu Lys Val Pro Ala Gln Asn Ala Ile Ser Thr Thr Phe Pro Tyr Thr
 10                  15                  20                  25 gga gac cct cct tac agc cat ggg aca gga aca gga tac acc atg gat       147
Gly Asp Pro Pro Tyr Ser His Gly Thr Gly Thr Gly Tyr Thr Met Asp
                 30                  35                  40 act gtc aac agg aca cat cag tac tca gaa aag gga aga tgg aca aca       195
Thr Val Asn Arg Thr His Gln Tyr Ser Glu Lys Gly Arg Trp Thr Thr
             45                  50                  55 aac acc gaa act gga gca ccg caa ctc aac ccg att gat ggg cca ctg       243
Asn Thr Glu Thr Gly Ala Pro Gln Leu Asn Pro Ile Asp Gly Pro Leu
         60                  65                  70 cca gaa gac aat gaa cca agt ggt tat gcc caa aca gat tgt gta ttg       291
Pro Glu Asp Asn Glu Pro Ser Gly Tyr Ala Gln Thr Asp Cys Val Leu
     75                  80                  85 gaa gca atg gct ttc ctt gag gaa tcc cat cct ggt att ttt gaa aac       339
Glu Ala Met Ala Phe Leu Glu Glu Ser His Pro Gly Ile Phe Glu Asn
 90                  95                 100                 105 tcg tgt att gaa acg atg gag gtt gtt cag caa aca cga gta gac aag       387
Ser Cys Ile Glu Thr Met Glu Val Val Gln Gln Thr Arg Val Asp Lys
                110                 115                 120 ctg aca caa ggc cga cag acc tat gac tgg act cta aat aga aac caa       435
Leu Thr Gln Gly Arg Gln Thr Tyr Asp Trp Thr Leu Asn Arg Asn Gln
```

```
                125                  130                  135
cct gct gca aca gca ttg gcc aac aca ata gaa gtg ttc aga tca aat       483
Pro Ala Ala Thr Ala Leu Ala Asn Thr Ile Glu Val Phe Arg Ser Asn
        140                  145                  150 ggc ctc acg gcc aat gag tct gga agg ctc ata gac ttc ctt aag gac       531
Gly Leu Thr Ala Asn Glu Ser Gly Arg Leu Ile Asp Phe Leu Lys Asp
155                  160                  165 gtt atg gag tct atg aaa aaa gag gaa atg ggg att acg aca cat ttt       579
Val Met Glu Ser Met Lys Lys Glu Glu Met Gly Ile Thr Thr His Phe
170                  175                  180                  185 caa cga aaa aga cgg gtt agg gat aat atg aca aaa aaa atg att acg       627
Gln Arg Lys Arg Arg Val Arg Asp Asn Met Thr Lys Lys Met Ile Thr
                190                  195                  200 caa cga aca atc gga aag aaa aaa cag aga ctg aat aag cga tca tac       675
Gln Arg Thr Ile Gly Lys Lys Lys Gln Arg Leu Asn Lys Arg Ser Tyr
            205                  210                  215 ttg att agg gca ctt aca ctt aac act atg act aag gac gcc gaa agg       723
Leu Ile Arg Ala Leu Thr Leu Asn Thr Met Thr Lys Asp Ala Glu Arg
        220                  225                  230 gga aag cta aag cgt aga gca att gca aca ccc gga atg caa att agg       771
Gly Lys Leu Lys Arg Arg Ala Ile Ala Thr Pro Gly Met Gln Ile Arg
235                  240                  245 ggg ttc gta tac ttc gtc gag aca ctc gct aga tcc ata tgc gaa aag       819
Gly Phe Val Tyr Phe Val Glu Thr Leu Ala Arg Ser Ile Cys Glu Lys
250                  255                  260                  265 tta gag caa tcc gga ctg cca gtc ggg ggg aac gaa aaa aaa gcg aaa       867
Leu Glu Gln Ser Gly Leu Pro Val Gly Gly Asn Glu Lys Lys Ala Lys
                270                  275                  280 ctc gct aac gtc gtt aga aaa atg atg act aat agt cag gat acc gaa       915
Leu Ala Asn Val Val Arg Lys Met Met Thr Asn Ser Gln Asp Thr Glu
            285                  290                  295 ctg tca ttt acg att acc ggc gat aat act aag tgg aac gag aat cag       963
Leu Ser Phe Thr Ile Thr Gly Asp Asn Thr Lys Trp Asn Glu Asn Gln
        300                  305                  310 aat cct aga atg ttt ctc gca atg atc aca tat atg aca cgt aac caa      1011
Asn Pro Arg Met Phe Leu Ala Met Ile Thr Tyr Met Thr Arg Asn Gln
315                  320                  325 ccc gaa tgg ttt aga aac gta ctg tca atc gca cca att atg ttt agc      1059
Pro Glu Trp Phe Arg Asn Val Leu Ser Ile Ala Pro Ile Met Phe Ser
330                  335                  340                  345 aat aag atg gct aga ttg ggc aag ggg tat atg ttt gaa tct aag agt      1107
Asn Lys Met Ala Arg Leu Gly Lys Gly Tyr Met Phe Glu Ser Lys Ser
                350                  355                  360 atg aaa ttg cga aca cag ata cct gcc gaa atg cta gca tca atc gat      1155
Met Lys Leu Arg Thr Gln Ile Pro Ala Glu Met Leu Ala Ser Ile Asp
            365                  370                  375 cta aag tac ttt aac gat agt aca cga aaa aaa atc gaa aag att aga      1203
Leu Lys Tyr Phe Asn Asp Ser Thr Arg Lys Lys Ile Glu Lys Ile Arg
        380                  385                  390 ccg tta ctg ata gag gga acc gcc agc cta tcc ccc gga atg atg atg      1251
Pro Leu Leu Ile Glu Gly Thr Ala Ser Leu Ser Pro Gly Met Met Met
395                  400                  405 ggg atg ttt aat atg ctt agt acc gtt tta ggc gtt agc ata ctt aac      1299
Gly Met Phe Asn Met Leu Ser Thr Val Leu Gly Val Ser Ile Leu Asn
410                  415                  420                  425 tta ggg caa aaa cgt tat act aag act aca tat tgg tgg gac gga ctg      1347
Leu Gly Gln Lys Arg Tyr Thr Lys Thr Thr Tyr Trp Trp Asp Gly Leu
                430                  435                  440 caa tct agc gac gat ttc gca cta atc gtt aac gca cct aac cat gag      1395
Gln Ser Ser Asp Asp Phe Ala Leu Ile Val Asn Ala Pro Asn His Glu
```

```
Gln Ser Ser Asp Asp Phe Ala Leu Ile Val Asn Ala Pro Asn His Glu
            445                 450                 455 ggg ata caa gcc gga gtc gat aga ttc tat aga aca tgc aaa ctg tta      1443
Gly Ile Gln Ala Gly Val Asp Arg Phe Tyr Arg Thr Cys Lys Leu Leu
        460                 465                 470 ggg att aat atg tct aaa aaa aag tca tac ata aat aga acc gga aca      1491
Gly Ile Asn Met Ser Lys Lys Lys Ser Tyr Ile Asn Arg Thr Gly Thr
475                 480                 485 ttt gaa ttc aca agt ttt ttc tat cgt tat ggg ttt gtt gcc aat ttc      1539
Phe Glu Phe Thr Ser Phe Phe Tyr Arg Tyr Gly Phe Val Ala Asn Phe
490                 495                 500                 505 agc atg gag ctc ccc agt ttt ggg gtg tct ggg atc aac gag tca gcg      1587
Ser Met Glu Leu Pro Ser Phe Gly Val Ser Gly Ile Asn Glu Ser Ala
                510                 515                 520 gac atg agt att gga gtt act gtc atc aaa aac aat atg ata aac aat      1635
Asp Met Ser Ile Gly Val Thr Val Ile Lys Asn Asn Met Ile Asn Asn
            525                 530                 535 gat ctt ggt cca gca aca gct caa atg gcc ctt cag ttg ttc atc aaa      1683
Asp Leu Gly Pro Ala Thr Ala Gln Met Ala Leu Gln Leu Phe Ile Lys
        540                 545                 550 gat tac agg tac acg tac cga tgc cat aga ggt gac aca caa ata caa      1731
Asp Tyr Arg Tyr Thr Tyr Arg Cys His Arg Gly Asp Thr Gln Ile Gln
    555                 560                 565 acc cga aga tca ttt gaa ata aag aaa ctg tgg gag caa acc cgt tcc      1779
Thr Arg Arg Ser Phe Glu Ile Lys Lys Leu Trp Glu Gln Thr Arg Ser
570                 575                 580                 585 aaa gct gga ctg ctg gtc tcc gac gga ggc cca aat tta tac aac att      1827
Lys Ala Gly Leu Leu Val Ser Asp Gly Gly Pro Asn Leu Tyr Asn Ile
                590                 595                 600 aga aat ctc cac att cct gaa gtc tgc cta aaa tgg gaa ttg atg gat      1875
Arg Asn Leu His Ile Pro Glu Val Cys Leu Lys Trp Glu Leu Met Asp
            605                 610                 615 gag gat tac cag ggg cgt tta tgc aac cca ctg aac cca ttt gtc agc      1923
Glu Asp Tyr Gln Gly Arg Leu Cys Asn Pro Leu Asn Pro Phe Val Ser
        620                 625                 630 cat aaa gaa att gaa tca atg aac aat gca gtg atg atg cca gca cat      1971
His Lys Glu Ile Glu Ser Met Asn Asn Ala Val Met Met Pro Ala His
    635                 640                 645 ggt cca gcc aaa aac atg gag tat gat gct gtt gca aca aca cac tcc      2019
Gly Pro Ala Lys Asn Met Glu Tyr Asp Ala Val Ala Thr Thr His Ser
650                 655                 660                 665 tgg atc ccc aaa aga aat cga tcc atc ttg aat aca agt caa aga gga      2067
Trp Ile Pro Lys Arg Asn Arg Ser Ile Leu Asn Thr Ser Gln Arg Gly
                670                 675                 680 gta ctt gaa gat gaa caa atg tac caa agg tgc tgc aat tta ttt gaa      2115
Val Leu Glu Asp Glu Gln Met Tyr Gln Arg Cys Cys Asn Leu Phe Glu
            685                 690                 695 aaa ttc ttc ccc agc agt tca tac aga aga cca gtc ggg ata tcc agt      2163
Lys Phe Phe Pro Ser Ser Ser Tyr Arg Arg Pro Val Gly Ile Ser Ser
        700                 705                 710 atg gtg gag gct atg gtt tcc aga gcc cga att gat gca cgg att gat      2211
Met Val Glu Ala Met Val Ser Arg Ala Arg Ile Asp Ala Arg Ile Asp
    715                 720                 725 ttc gaa tct gga agg ata aag aaa gaa gag ttc act gag atc atg aag      2259
Phe Glu Ser Gly Arg Ile Lys Lys Glu Glu Phe Thr Glu Ile Met Lys
730                 735                 740                 745 atc tgt tcc acc att gaa gag ctc aga cgg caa aaa tag tgaatttagc       2308
Ile Cys Ser Thr Ile Glu Glu Leu Arg Arg Gln Lys
                750                 755
```
ttgtccttca tgaaaaaatg ccttgtttct act 2341

<210> SEQ ID NO 46
<211> LENGTH: 757
<212> TYPE: PRT
<213> ORGANISM: unknown
<220> FEATURE:
<223> OTHER INFORMATION: Synthetic Construct

<400> SEQUENCE: 46

```
Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
            20                  25                  30

Gly Thr Gly Thr Gly Tyr Thr Met Asp Thr Val Asn Arg Thr His Gln
        35                  40                  45

Tyr Ser Glu Lys Gly Arg Trp Thr Thr Asn Thr Glu Thr Gly Ala Pro
    50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Ile Glu Thr Met Glu
            100                 105                 110

Val Val Gln Gln Thr Arg Val Asp Lys Leu Thr Gln Gly Arg Gln Thr
        115                 120                 125

Tyr Asp Trp Thr Leu Asn Arg Asn Gln Pro Ala Ala Thr Ala Leu Ala
    130                 135                 140

Asn Thr Ile Glu Val Phe Arg Ser Asn Gly Leu Thr Ala Asn Glu Ser
145                 150                 155                 160

Gly Arg Leu Ile Asp Phe Leu Lys Asp Val Met Glu Ser Met Lys Lys
                165                 170                 175

Glu Glu Met Gly Ile Thr Thr His Phe Gln Arg Lys Arg Arg Val Arg
            180                 185                 190

Asp Asn Met Thr Lys Lys Met Ile Thr Gln Arg Thr Ile Gly Lys Lys
        195                 200                 205

Lys Gln Arg Leu Asn Lys Arg Ser Tyr Leu Ile Arg Ala Leu Thr Leu
    210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Ser Ile Cys Glu Lys Leu Glu Gln Ser Gly Leu Pro
            260                 265                 270

Val Gly Gly Asn Glu Lys Lys Ala Lys Leu Ala Asn Val Val Arg Lys
        275                 280                 285

Met Met Thr Asn Ser Gln Asp Thr Glu Leu Ser Phe Thr Ile Thr Gly
    290                 295                 300

Asp Asn Thr Lys Trp Asn Glu Asn Gln Asn Pro Arg Met Phe Leu Ala
305                 310                 315                 320

Met Ile Thr Tyr Met Thr Arg Asn Gln Pro Glu Trp Phe Arg Asn Val
                325                 330                 335

Leu Ser Ile Ala Pro Ile Met Phe Ser Asn Lys Met Ala Arg Leu Gly
            340                 345                 350

Lys Gly Tyr Met Phe Glu Ser Lys Ser Met Lys Leu Arg Thr Gln Ile
        355                 360                 365
```

```
Pro Ala Glu Met Leu Ala Ser Ile Asp Leu Lys Tyr Phe Asn Asp Ser
    370                 375                 380

Thr Arg Lys Lys Ile Glu Lys Ile Arg Pro Leu Leu Ile Glu Gly Thr
385                 390                 395                 400

Ala Ser Leu Ser Pro Gly Met Met Met Gly Met Phe Asn Met Leu Ser
                405                 410                 415

Thr Val Leu Gly Val Ser Ile Leu Asn Leu Gly Gln Lys Arg Tyr Thr
                420                 425                 430

Lys Thr Thr Tyr Trp Trp Asp Gly Leu Gln Ser Ser Asp Asp Phe Ala
                435                 440                 445

Leu Ile Val Asn Ala Pro Asn His Glu Gly Ile Gln Ala Gly Val Asp
                450                 455                 460

Arg Phe Tyr Arg Thr Cys Lys Leu Leu Gly Ile Asn Met Ser Lys Lys
465                 470                 475                 480

Lys Ser Tyr Ile Asn Arg Thr Gly Thr Phe Glu Phe Thr Ser Phe Phe
                485                 490                 495

Tyr Arg Tyr Gly Phe Val Ala Asn Phe Ser Met Glu Leu Pro Ser Phe
                500                 505                 510

Gly Val Ser Gly Ile Asn Glu Ser Ala Asp Met Ser Ile Gly Val Thr
                515                 520                 525

Val Ile Lys Asn Asn Met Ile Asn Asn Asp Leu Gly Pro Ala Thr Ala
                530                 535                 540

Gln Met Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Ile
                565                 570                 575

Lys Lys Leu Trp Glu Gln Thr Arg Ser Lys Ala Gly Leu Leu Val Ser
                580                 585                 590

Asp Gly Gly Pro Asn Leu Tyr Asn Ile Arg Asn Leu His Ile Pro Glu
                595                 600                 605

Val Cys Leu Lys Trp Glu Leu Met Asp Glu Asp Tyr Gln Gly Arg Leu
                610                 615                 620

Cys Asn Pro Leu Asn Pro Phe Val Ser His Lys Glu Ile Glu Ser Met
625                 630                 635                 640

Asn Asn Ala Val Met Met Pro Ala His Gly Pro Ala Lys Asn Met Glu
                645                 650                 655

Tyr Asp Ala Val Ala Thr Thr His Ser Trp Ile Pro Lys Arg Asn Arg
                660                 665                 670

Ser Ile Leu Asn Thr Ser Gln Arg Gly Val Leu Glu Asp Glu Gln Met
                675                 680                 685

Tyr Gln Arg Cys Cys Asn Leu Phe Glu Lys Phe Phe Pro Ser Ser Ser
                690                 695                 700

Tyr Arg Arg Pro Val Gly Ile Ser Ser Met Val Glu Ala Met Val Ser
705                 710                 715                 720

Arg Ala Arg Ile Asp Ala Arg Ile Asp Phe Glu Ser Gly Arg Ile Lys
                725                 730                 735

Lys Glu Glu Phe Thr Glu Ile Met Lys Ile Cys Ser Thr Ile Glu Glu
                740                 745                 750

Leu Arg Arg Gln Lys
                755

<210> SEQ ID NO 47
<211> LENGTH: 2341
```

<212> TYPE: DNA
<213> ORGANISM: Influenza virus

<400> SEQUENCE: 47

```
agcgaaagca ggtcaattat attcaatatg gaaagaataa aagaactaag aaatctaatg      60
tcgcagtctc gcacccgcga gatactcaca aaaccaccg tggaccatat ggccataatc     120
aagaagtaca catcaggaag acaggagaag aacccagcac ttaggatgaa atggatgatg     180
gcaatgaaat atccaattac agcagacaag aggataacgg aaatgattcc tgagagaaat     240
gagcaaggac aaactttatg gagtaaaatg aatgatgcag atcagaccg agtgatggta     300
tcacctctgg ctgtgacatg gtggaatagg aatggaccaa taacaaatac agttcattat     360
ccaaaaatct acaaaactta ttttgaaaga gtcgaaaggc taaagcatgg aaccttggc      420
cctgtccatt ttagaaacca agtcaaaata cgtcggagag ttgacataaa tcctggtcat     480
gcagatctca gtgccaagga ggcacaggat gtaatcatgg aagttgtttt ccctaacgaa     540
gtgggagcca ggatactaac atcggaatcg caactaacga taaccaaaga gaagaaagaa     600
gaactccagg attgcaaaat ttctcctttg atggttgcat acatgttgga gagagaactg     660
gtccgcaaaa cgagattcct cccagtggct ggtggaacaa gcagtgtgta cattgaagtg     720
ttgcatttga ctcaaggaac atgctgggaa cagatgtata ctccaggagg ggaagtgagg     780
aatgatgatg ttgatcaaag cttgattatt gctgctagga acatagtgag aagagctgca     840
gtatcagcag atccactagc atctttattg gagatgtgcc acagcacaca gattggtgga     900
attaggatgg tagacatcct taggcagaac ccaacagaag agcaagccgt ggatatatgc     960
aaggctgcaa tgggactgag aattagctca tccttcagtt ttggtggatt cacatttaag    1020
agaacaagcg gatcatcagt caagagagag gaagaggtgc ttacgggcaa tcttcaaaca    1080
ttgaagataa gagtgcatga gggatatgaa gagttcacaa tggttgggag aagagcaaca    1140
gccatactca gaaaagcaac caggagattg attcagctga tagtgagtgg gagagacgaa    1200
cagtcgattg ccgaagcaat aattgtggcc atggtatttt cacaagagga ttgtatgata    1260
aaagcagtca gaggtgatct gaatttcgtc aataggcgga atcagcgatt gaatcctatg    1320
catcaacttt taagacattt tcagaaggat gcgaaagtgc ttttttcaaa ttggggagtt    1380
gaacctatcg acaatgtgat gggaatgatt gggatattgc cagacatgac tccaagcatc    1440
gagatgtcaa tgagaggagt gagaatcagc aaaatgggtg tagatgagta ctccagcacg    1500
gagagggtag tggtgagcat tgaccgtttt ttgagaatcc gggaccaacg aggaaatgta    1560
ctactgtctc ccgaggaggt cagtgaaaca caggaacag agaaactgac aataacttac    1620
tcatcgtcaa tgatgtggga gattaatggt cctgaatcag tgttggtcaa tacctatcaa    1680
tggatcatca gaaactggga aactgttaaa attcagtggt cccagaaccc tacaatgcta    1740
tacaataaaa tggaatttga accatttcag tctttagtac ctaaggccat tagaggccaa    1800
tacagtgggt ttgtaagaac tctgttccaa caaatgaggg atgtgcttgg acatttgat     1860
accgcacaga taataaaact tcttcccttc gcagccgctc caccaaagca agtagaatg      1920
cagttctcct catttactgt gaatgtgagg ggatcaggaa tgagaatact tgtaaggggc    1980
aattctcctg tattcaacta taacaaggcc acgaagagac tcacagttct cggaaaggat    2040
gctggcactt taactgaaga cccagatgaa ggcacagctg gagtggagtc cgctgttctg    2100
agggattcc tcattctggg caagaagac aagagatatg gccagcact aagcatcaat      2160
gaactgagca accttgcgaa aggagagaag gctaatgtgc taattgggca aggagacgtg    2220
```

| | |
|---|---|
| gtgttggtaa tgaaacggaa acgggactct agcatactta ctgacagcca gacagcgacc | 2280 |
| aaaagaattc ggatggccat caattagtgt cgaatagttt aaaaacgacc ttgtttctac | 2340 |
| t | 2341 |

<210> SEQ ID NO 48
<211> LENGTH: 2341
<212> TYPE: DNA
<213> ORGANISM: unknown
<220> FEATURE:
<223> OTHER INFORMATION: synthetic

<400> SEQUENCE: 48

| | |
|---|---|
| agcgaaagca ggtcaattat attcaatatg gagagaatca aagagcttag gaatcttatg | 60 |
| tcacaatcta gaactagaga gatactgact aagactacag tcgatcatat ggctataatc | 120 |
| aaaaaatata ctagcggaag acaggaaaaa atcccgcac ttagaatgaa atggatgatg | 180 |
| gctatgaaat accctattac agccgataag cgaattaccg aaatgatacc agagagaaac | 240 |
| gaacagggac agacattgtg gtctaaaatg aacgacgccg gatccgatag agtgatggtt | 300 |
| tcgccactag ccgtaacatg gtggaataga acggaccta ttacgaatac agtgcattac | 360 |
| cctaagatat acaaaacata tttcgaaaga gtcgagagac tgaaacacgg aacattcgga | 420 |
| ccagtgcatt ttcggaatca ggttaagatt agacgtagag tcgatattaa tccagggcat | 480 |
| gcagatctct ccgctaaaga ggcacaagac gttattatgg aggtcgtgtt tcctaacgag | 540 |
| gtcggcgcta ggatactgac tagcgaatcg caattgacaa ttacgaaaga gaaaaaagag | 600 |
| gaactccagg attgcaaaat tagcccactt atggtcgcat atatgctcga acgcgaattg | 660 |
| gttagaaaga ctagattcct accagtcgca ggcggaacgt ctagcgtgta tatcgaagtg | 720 |
| ttgcatctaa cacagggaac atgttgggag caaatgtata ctccaggagg cgaagtgaga | 780 |
| aacgacgacg ttgatcaatc gctaatcata gccgctagga atatagtgag aagggcagcc | 840 |
| gttagcgcag acccacttgc gtcactactc gaaatgtgcc atagtacgca aatcggaggg | 900 |
| attagaatgg tcgatatcct taggcagaat cctacagagg aacaggccgt agacatatgc | 960 |
| aaagccgcaa tgggattgcg aattagctca tcattctcat tcggagggtt tacgtttaaa | 1020 |
| cggactagcg gatctagcgt aaaacgcgaa gaggaagtgc ttactggcaa tctgcaaaca | 1080 |
| ctaaagatta gggtgcatga gggatacgaa gagtttacaa tggtcggacg tagagcaacc | 1140 |
| gctatactta gaaaagcgac taggagactg atacaattga tcgttagcgg aagggacgaa | 1200 |
| cagtcaatcg ccgaagcgat aatagtcgca atggtgtttt cgcaagagga ttgcatgatt | 1260 |
| aaggccgtta gggggggatct gaatttcgtt aatagggcta atcagagact gaatcctatg | 1320 |
| catcaattgc ttagacattt tcagaaagac gctaaagtgt tgtttcagaa ttggggagtc | 1380 |
| gaacctatcg ataacgttat gggtatgata gggatactgc cagatatgac accatcaatc | 1440 |
| gaaatgtcaa tgagaggcgt taggattagt aagatgggcg tagacgaata ctccagcact | 1500 |
| gagagagtgg tagtgtcaat cgatagattt cttaggatta gggatcagag aggcaacgta | 1560 |
| ctgctatcac ccgaagaagt tagcgaaaca cagggaaccg aaaaattgac aattacgtat | 1620 |
| agtagtagta tgatgtggga gattaacgga ccagagtcag tgttagtgaa tacatatcaa | 1680 |
| tggataatac ggaattggga gacagtgaaa atacaatggt cacagaatcc tacaatgcta | 1740 |
| tacaataaga tggagttcga acctttcaa tcgttagtgc ctaaggccat aagaggccaa | 1800 |
| tatagtgggt tcgttagaac attgtttcag caaatgagag acgtactcgg aacattcgat | 1860 |
| accgcacaga taattaagct attgccattc gcagccgcac cacctaagca atctagaatg | 1920 |

```
caattttcta gctttaccgt taacgttagg ggatccggaa tgcgaatact cgttagggggg    1980 aatagtccag tgtttaatta caataaggca actaagagat tgacagtgtt aggcaaggac    2040
gcaggaacat tgaccgaaga cccagacgag ggaaccgctg gagtggaatc cgcagtgctt    2100 aggggggtttc tgatactcgg aaaggaggat aagagatacg gacctgcact atcgattaac    2160
gaactatcta atctcgctaa aggcgaaaaa gcgaatgtgt aatcggaca gggagacgta    2220 gtgttagtga tgaaacggaa acgcgatagc tcaatactga cagactcaca aaccgctact    2280
aagagaattc ggatggcaat taattagtgt cgaatagttt aaaaacgacc ttgtttctac    2340
t                                                                   2341

<210> SEQ ID NO 49
<211> LENGTH: 2233
<212> TYPE: DNA
<213> ORGANISM: Influenza virus

<400> SEQUENCE: 49
agcgaaagca ggtactgatc caaaatggaa gattttgtgc gacaatgctt caatccgatg      60
attgtcgagc ttgcggaaaa acaatgaaa gagtatgggg aggacctgaa atcgaaaca      120 aacaaatttg cagcaatatg cactcacttg gaagtatgct tcatgtattc agattttcac     180
ttcatcaatg agcaaggcga gtcaataatc gtagaacttg gtgatccaaa tgcacttttg     240
aagcacagat ttgaaataat cgagggaaga gatcgcacaa tggcctggac agtagtaaac     300
agtatttgca acactacagg ggctgagaaa ccaaagtttc taccagattt gtatgattac     360
aaggagaata gattcatcga aattggagta acaaggagag aagttcacat atactatctg     420
gaaaaggcca ataaaattaa atctgagaaa acacacatcc acattttctc gttcactggg     480
gaagaaatgg ccacaaaggc agactacact ctcgatgaag aaagcagggc taggatcaaa     540
accagactat tcaccataag acaagaaatg gccagcagag gcctctggga ttccttttcgt     600 cagtccgaga gaggagaaga gacaattgaa gaaaggtttg aaatcacagg aacaatgcgc     660
aagcttgccg accaaagtct cccgccgaac ttctccagcc ttgaaaattt tagagcctat     720
gtggatggat tcgaaccgaa cggctacatt gagggcaagc tgtctcaaat gtccaaagaa     780
gtaaatgcta gaattgaacc ttttttgaaa acaacaccac gaccacttag acttccgaat     840
gggcctccct gttctcagcg gtccaaattc ctgctgatgg atgccttaaa attaagcatt     900
gaggacccaa gtcatgaagg agagggaata ccgctatatg atgcaatcaa atgcatgaga     960
acattctttg gatggaagga acccaatgtt gttaaaccac acgaaaaggg aataaatcca    1020
aattatcttc tgtcatggaa gcaagtactg gcagaactgc aggacattga gaatgaggag    1080
aaaattccaa agactaaaaa tatgaagaaa acaagtcagc taaagtgggc acttggtgag    1140
aacatggcac cagaaaaggt agactttgac gactgtaaag atgtaggtga tttgaagcaa    1200
tatgatagtg atgaaccaga attgaggtcg ctagcaagtt ggattcagaa tgagtttaac    1260
aaggcatgcg aactgacaga ttcaagctgg atagagctcg atgagattgg agaagatgtg    1320
gctccaattg aacacattgc aagcatgaga aggaattatt tcacatcaga ggtgtctcac    1380
tgcagagcca cagaatacat aatgaagggg gtgtacatca atactgcctt gcttaatgca    1440
tcttgtgcag caatggatga tttccaatta attccaatga taagcaagtg tagaactaag    1500
gagggaaggc gaaagaccaa cttgtatggt tcatcataa aaggaagatc ccacttaagg    1560
aatgacaccg acgtggtaaa ctttgtgagc atggagtttt ctctcactga cccaagactt    1620
```

| | | |
|---|---|---|
| gaaccacata aatgggagaa gtactgtgtt cttgagatag gagatatgct tataagaagt | 1680 | |
| gccataggcc aggtttcaag gcccatgttc ttgtatgtga gaacaaatgg aacctcaaaa | 1740 | |
| attaaaatga aatggggaat ggagatgagg cgttgcctcc tccagtcact tcaacaaatt | 1800 | |
| gagagtatga ttgaagctga gtcctctgtc aaagagaaag acatgaccaa agagttcttt | 1860 | |
| gagaacaaat cagaaacatg gcccattgga gagtccccca aaggagtgga ggaaagttcc | 1920 | |
| attgggaagg tctgcaggac tttattagca aagtcggtat tcaacagctt gtatgcatct | 1980 | |
| ccacaactag aaggattttc agctgaatca agaaaactgc ttcttatcgt tcaggctctt | 2040 | |
| agggacaacc ttgaacctgg gacctttgat cttgggggc tatatgaagc aattgaggag | 2100 | |
| tgcctgatta atgatccctg ggttttgctt aatgcttctt ggttcaactc cttccttaca | 2160 | |
| catgcattga gttagttgtg gcagtgctac tatttgctat ccatactgtc caaaaagta | 2220 | |
| ccttgtttct act | 2233 | |

<210> SEQ ID NO 50
<211> LENGTH: 2233
<212> TYPE: DNA
<213> ORGANISM: unknown
<220> FEATURE:
<223> OTHER INFORMATION: synthetic

<400> SEQUENCE: 50

| | | |
|---|---|---|
| agcgaaagca ggtactgatc caaaatggag gatttcgtta ggcaatgctt taatccaatg | 60 | |
| atagtcgagt tagccgaaaa gactatgaaa gagtatggcg aagacctaaa gattgagact | 120 | |
| aataaattcg ccgcaatttg cacacacctt gaggtttgct ttatgtattc cgattttcac | 180 | |
| tttattaacg aacagggaga gtcaattata gtcgagttag gcgatccgaa cgcattgcta | 240 | |
| aagcatagat ttgaaattat agagggacgc gataggacaa tggcatggac cgtagttaat | 300 | |
| tcgatttgca atacaaccgg agccgaaaaa ccgaaattct acccgatct atacgattat | 360 | |
| aaagagaata ggtttatcga aatcggagtg actagacgcg aagtgcatat ttattatctc | 420 | |
| gaaaaagcga ataagattaa gtccgaaaag acacacatac acatttttag ctttaccgga | 480 | |
| gaggaaatgg caacaaaagc cgattataca cttgacgaag agtctagggc taggattaag | 540 | |
| actagactgt ttacaattag acaggaaatg gctagtaggg ggttgtggga tagctttaga | 600 | |
| caatccgaaa gaggcgaaga gacaatcgaa gagagatttg aaattaccgg aacaatgcga | 660 | |
| aagcttgccg atcaatccct accccccaat ttctctagcc ttgagaattt tagggcatac | 720 | |
| gttgacggat cgaacctaa cggatatata gagggaaagc tatcgcaaat gtctaaagag | 780 | |
| gttaacgcta gaatcgaacc attcctaaag acaacaccta gaccacttag actgccaaac | 840 | |
| ggaccaccat gctcacagcg atctaagttt ctgcttatgg acgcactaaa gttgtcaatc | 900 | |
| gaagacccat cacacgaggg agaggggata ccattgtacg acgcaattaa gtgtatgcga | 960 | |
| acatttttcg gatggaaaga gcctaacgta gtgaaaccac acgaaaaagg gattaatccg | 1020 | |
| aattatctgc ttagttggaa acaggtgtta gccgaattgc aggatatcga aaacgaagag | 1080 | |
| aaaattccga aaactaagaa tatgaaaaaa actagccaac tgaaatgggc acttggcgag | 1140 | |
| aatatggcac ccgaaaaagt cgatttcgac gattgcaaag acgtcggcga tctaaagcaa | 1200 | |
| tacgatagcg acgaacccga acttagatca ctcgctagtt ggatacagaa cgagttcaat | 1260 | |
| aaggcatgcg aattgaccga tagctcatgg atagagcttg acgagatagg cgaagacgta | 1320 | |
| gcaccaatcg aacacatagc ctctatgaga cggaattatt ttcatccga agtgtcacat | 1380 | |
| tgtagggcaa cagagtatat tatgaagggg gtgtatatta ataccgcatt gcttaacgct | 1440 | |

```
agttgcgccg caatggacga tttccaactg ataccgatga tctcgaagtg tagaacaaaa    1500
gagggacgta gaaagactaa tctgtatggg ttcattatta agggaaggtc tcatttaagg    1560
aacgatacag acgtagtgaa tttcgttagt atggagttta gccttaccga tccgagactc    1620
gaaccacaca aatgggaaaa gtattgcgta ctagagatag gggatatgtt gattagatcc    1680
gcaatcggac aggtttcgag accaatgttt ttgtacgtta ggactaacgg aacctcgaag    1740
attaaaatga aatgggaat ggagatgcgt agatgcctat tgcaatccct tcagcaaatc    1800
gaatctatga tagaggccga atctagcgtt aaagagaaag atatgacaaa agagttttt    1860 gaaaataagt ccgaaacatg gccaatcgga gagtcaccaa aaggggttga ggaatcctca    1920
atcggaaaag tttgtagaac attgctcgca aaatccgtat tcaatagtct atacgccagc    1980
ccacaactag agggattctc tgctgagtca cgaaaactgt tactgatagt gcaagccctt    2040
agggataatc tcgaacccgg aacattcgat ctaggggggt tgtacgaagc aatcgaagag    2100
tgtctgatta acgatccatg ggtactgctt aacgctagtt ggtttaattc gttccttaca    2160
cacgcactat cttagttgtg gcagtgctac tatttgctat ccatactgtc caaaaaagta    2220
ccttgtttct act                                                       2233

<210> SEQ ID NO 51
<211> LENGTH: 1775
<212> TYPE: DNA
<213> ORGANISM: Influenza virus
<220> FEATURE:
<221> NAME/KEY: CDS
<222> LOCATION: (33)..(1730)

<400> SEQUENCE: 51
agcaaaagca ggggaaaata aaacaaccaa a atg aag gca aac cta ctg gtc         53
                                  Met Lys Ala Asn Leu Leu Val
                                  1               5 ctg tta agt gca ctt gca gct gca gat gca gac aca ata tgt ata ggc       101
Leu Leu Ser Ala Leu Ala Ala Ala Asp Ala Asp Thr Ile Cys Ile Gly
            10                  15                  20 tac cat gcg aac aat tca acc gac act gtt gac aca gta ctc gag aag       149
Tyr His Ala Asn Asn Ser Thr Asp Thr Val Asp Thr Val Leu Glu Lys
        25                  30                  35 aat gtg aca gtg aca cac tct gtt aac ctg ctc gaa gac agc cac aac       197
Asn Val Thr Val Thr His Ser Val Asn Leu Leu Glu Asp Ser His Asn
40                  45                  50                  55 gga aaa cta tgt aga tta aaa gga ata gcc cca cta caa ttg ggg aaa       245
Gly Lys Leu Cys Arg Leu Lys Gly Ile Ala Pro Leu Gln Leu Gly Lys
                60                  65                  70 tgt aac atc gcc gga tgg ctc ttg gga aac cca gaa tgc gac cca ctg       293
Cys Asn Ile Ala Gly Trp Leu Leu Gly Asn Pro Glu Cys Asp Pro Leu
            75                  80                  85 ctt cca gtg aga tca tgg tcc tac att gta gaa aca cca aac tct gag       341
Leu Pro Val Arg Ser Trp Ser Tyr Ile Val Glu Thr Pro Asn Ser Glu
        90                  95                  100 aat gga ata tgt tat cca gga gat ttc atc gac tat gag gag ctg agg       389
Asn Gly Ile Cys Tyr Pro Gly Asp Phe Ile Asp Tyr Glu Glu Leu Arg
    105                 110                 115 gag caa ttg agc tca gtg tca tca ttc gaa aga ttc gaa ata ttt ccc       437
Glu Gln Leu Ser Ser Val Ser Ser Phe Glu Arg Phe Glu Ile Phe Pro
120                 125                 130                 135 aaa gaa agc tca tgg ccc aac cac aac aca aac gga gta acg gca gca       485
Lys Glu Ser Ser Trp Pro Asn His Asn Thr Asn Gly Val Thr Ala Ala
                140                 145                 150
```

```
tgc tcc cat gag ggg aaa agc agt ttt tac aga aat ttg cta tgg ctg    533
Cys Ser His Glu Gly Lys Ser Ser Phe Tyr Arg Asn Leu Leu Trp Leu
            155                 160                 165 acg gag aag gag ggc tca tac cca aag ctg aaa aat tct tat gtg aac    581
Thr Glu Lys Glu Gly Ser Tyr Pro Lys Leu Lys Asn Ser Tyr Val Asn
        170                 175                 180 aaa aaa ggg aaa gaa gtc ctt gta ctg tgg ggt att cat cac ccg cct    629
Lys Lys Gly Lys Glu Val Leu Val Leu Trp Gly Ile His His Pro Pro
    185                 190                 195 aac agt aag gaa caa cag aat atc tat cag aat gaa aat gct tat gtc    677
Asn Ser Lys Glu Gln Gln Asn Ile Tyr Gln Asn Glu Asn Ala Tyr Val
200                 205                 210                 215 tct gta gtg act tca aat tat aac agg aga ttt acc ccg gaa ata gca    725
Ser Val Val Thr Ser Asn Tyr Asn Arg Arg Phe Thr Pro Glu Ile Ala
                220                 225                 230 gaa aga ccc aaa gta aga gat caa gct ggg agg atg aac tat tac tgg    773
Glu Arg Pro Lys Val Arg Asp Gln Ala Gly Arg Met Asn Tyr Tyr Trp
            235                 240                 245 acc ttg cta aaa ccc gga gac aca ata ata ttt gag gca aat gga aat    821
Thr Leu Leu Lys Pro Gly Asp Thr Ile Ile Phe Glu Ala Asn Gly Asn
        250                 255                 260 cta ata gca cca atg tat gct ttc gca ctg agt aga ggc ttt ggg tcc    869
Leu Ile Ala Pro Met Tyr Ala Phe Ala Leu Ser Arg Gly Phe Gly Ser
    265                 270                 275 ggc atc atc acc tca aac gca tca atg cat gag tgt aac acg aag tgt    917
Gly Ile Ile Thr Ser Asn Ala Ser Met His Glu Cys Asn Thr Lys Cys
280                 285                 290                 295 caa aca ccc ctg gga gct ata aac agc agt ctc cct tac cag aat ata    965
Gln Thr Pro Leu Gly Ala Ile Asn Ser Ser Leu Pro Tyr Gln Asn Ile
                300                 305                 310 cac cca gtc aca ata gga gag tgc cca aaa tac gtc agg agt gcc aaa   1013
His Pro Val Thr Ile Gly Glu Cys Pro Lys Tyr Val Arg Ser Ala Lys
            315                 320                 325 ttg agg atg gtt aca gga cta agg aac act ccg tcc att caa tcc aga   1061
Leu Arg Met Val Thr Gly Leu Arg Asn Thr Pro Ser Ile Gln Ser Arg
        330                 335                 340 ggt cta ttt gga gcc att gcc ggt ttt att gaa ggg gga tgg act gga   1109
Gly Leu Phe Gly Ala Ile Ala Gly Phe Ile Glu Gly Gly Trp Thr Gly
    345                 350                 355 atg ata gat gga tgg tat ggt tat cat cat cag aat gaa cag gga tca   1157
Met Ile Asp Gly Trp Tyr Gly Tyr His His Gln Asn Glu Gln Gly Ser
360                 365                 370                 375 ggc tat gca gcg gat caa aaa agc aca caa aat gcc att aac ggg att   1205
Gly Tyr Ala Ala Asp Gln Lys Ser Thr Gln Asn Ala Ile Asn Gly Ile
                380                 385                 390 aca aac aag gtg aac act gtt atc gag aaa atg aac att caa ttc aca   1253
Thr Asn Lys Val Asn Thr Val Ile Glu Lys Met Asn Ile Gln Phe Thr
            395                 400                 405 gct gtg ggt aaa gaa ttc aac aaa tta gaa aaa agg atg gaa aat tta   1301
Ala Val Gly Lys Glu Phe Asn Lys Leu Glu Lys Arg Met Glu Asn Leu
        410                 415                 420 aat aaa aaa gtt gat gat gga ttt ctg gac att tgg aca tat aat gca   1349
Asn Lys Lys Val Asp Asp Gly Phe Leu Asp Ile Trp Thr Tyr Asn Ala
    425                 430                 435 gaa ttg tta gtt cta ctg gaa aat gaa agg act ctg gat ttc cat gac   1397
Glu Leu Leu Val Leu Leu Glu Asn Glu Arg Thr Leu Asp Phe His Asp
440                 445                 450                 455 tca aat gtg aag aat ctg tat gag aaa gta aaa agc caa tta aag aat   1445
Ser Asn Val Lys Asn Leu Tyr Glu Lys Val Lys Ser Gln Leu Lys Asn
```

```
                        460                 465                  470
aat gcc aaa gaa atc gga aat gga tgt ttt gag ttc tac cac aag tgt        1493
Asn Ala Lys Glu Ile Gly Asn Gly Cys Phe Glu Phe Tyr His Lys Cys
            475                 480                 485 gac aat gaa tgc atg gaa agt gta aga aat ggg act tat gat tat ccc        1541
Asp Asn Glu Cys Met Glu Ser Val Arg Asn Gly Thr Tyr Asp Tyr Pro
            490                 495                 500 aaa tat tca gaa gag tca aag ttg aac agg gaa aag gta gat gga gtg        1589
Lys Tyr Ser Glu Glu Ser Lys Leu Asn Arg Glu Lys Val Asp Gly Val
            505                 510                 515 aaa ttg gaa tca atg ggg atc tat cag att ctg gcg atc tac tca act        1637
Lys Leu Glu Ser Met Gly Ile Tyr Gln Ile Leu Ala Ile Tyr Ser Thr
520                 525                 530                 535 gtc gcc agt tca ctg gtg ctt ttg gtc tcc ctg ggg gca atc agt ttc        1685
Val Ala Ser Ser Leu Val Leu Leu Val Ser Leu Gly Ala Ile Ser Phe
                540                 545                 550 tgg atg tgt tct aat gga tct ttg cag tgc aga ata tgc atc tga            1730
Trp Met Cys Ser Asn Gly Ser Leu Gln Cys Arg Ile Cys Ile
                555                 560                 565 gattagaatt tcagaaatat gaggaaaaac acccttgttt ctact                      1775

<210> SEQ ID NO 52
<211> LENGTH: 565
<212> TYPE: PRT
<213> ORGANISM: Influenza virus

<400> SEQUENCE: 52

Met Lys Ala Asn Leu Leu Val Leu Leu Ser Ala Leu Ala Ala Ala Asp
1               5                   10                  15

Ala Asp Thr Ile Cys Ile Gly Tyr His Ala Asn Asn Ser Thr Asp Thr
                20                  25                  30

Val Asp Thr Val Leu Glu Lys Asn Val Thr Val Thr His Ser Val Asn
            35                  40                  45

Leu Leu Glu Asp Ser His Asn Gly Lys Leu Cys Arg Leu Lys Gly Ile
        50                  55                  60

Ala Pro Leu Gln Leu Gly Lys Cys Asn Ile Ala Gly Trp Leu Leu Gly
65                  70                  75                  80

Asn Pro Glu Cys Asp Pro Leu Leu Pro Val Arg Ser Trp Ser Tyr Ile
                85                  90                  95

Val Glu Thr Pro Asn Ser Glu Asn Gly Ile Cys Tyr Pro Gly Asp Phe
                100                 105                 110

Ile Asp Tyr Glu Glu Leu Arg Glu Gln Leu Ser Ser Val Ser Ser Phe
            115                 120                 125

Glu Arg Phe Glu Ile Phe Pro Lys Glu Ser Ser Trp Pro Asn His Asn
        130                 135                 140

Thr Asn Gly Val Thr Ala Ala Cys Ser His Glu Gly Lys Ser Ser Phe
145                 150                 155                 160

Tyr Arg Asn Leu Leu Trp Leu Thr Glu Lys Glu Gly Ser Tyr Pro Lys
                165                 170                 175

Leu Lys Asn Ser Tyr Val Asn Lys Lys Gly Lys Glu Val Leu Val Leu
            180                 185                 190

Trp Gly Ile His His Pro Pro Asn Ser Lys Glu Gln Gln Asn Ile Tyr
        195                 200                 205

Gln Asn Glu Asn Ala Tyr Val Ser Val Val Thr Ser Asn Tyr Asn Arg
    210                 215                 220

Arg Phe Thr Pro Glu Ile Ala Glu Arg Pro Lys Val Arg Asp Gln Ala
225                 230                 235                 240
```

Gly Arg Met Asn Tyr Tyr Trp Thr Leu Leu Lys Pro Gly Asp Thr Ile
            245                 250                 255

Ile Phe Glu Ala Asn Gly Asn Leu Ile Ala Pro Met Tyr Ala Phe Ala
            260                 265                 270

Leu Ser Arg Gly Phe Gly Ser Gly Ile Ile Thr Ser Asn Ala Ser Met
        275                 280                 285

His Glu Cys Asn Thr Lys Cys Gln Thr Pro Leu Gly Ala Ile Asn Ser
    290                 295                 300

Ser Leu Pro Tyr Gln Asn Ile His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Thr Pro Ser Ile Gln Ser Arg Gly Leu Phe Gly Ala Ile Ala Gly Phe
            340                 345                 350

Ile Glu Gly Gly Trp Thr Gly Met Ile Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Thr Val Ile Glu
385                 390                 395                 400

Lys Met Asn Ile Gln Phe Thr Ala Val Gly Lys Glu Phe Asn Lys Leu
                405                 410                 415

Glu Lys Arg Met Glu Asn Leu Asn Lys Lys Val Asp Asp Gly Phe Leu
            420                 425                 430

Asp Ile Trp Thr Tyr Asn Ala Glu Leu Leu Val Leu Leu Glu Asn Glu
        435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asp Asn Glu Cys Met Glu Ser Val Arg
                485                 490                 495

Asn Gly Thr Tyr Asp Tyr Pro Lys Tyr Ser Glu Glu Ser Lys Leu Asn
            500                 505                 510

Arg Glu Lys Val Asp Gly Val Lys Leu Glu Ser Met Gly Ile Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
            565

<210> SEQ ID NO 53
<211> LENGTH: 1775
<212> TYPE: DNA
<213> ORGANISM: unknown
<220> FEATURE:
<223> OTHER INFORMATION: synthetic
<220> FEATURE:
<221> NAME/KEY: CDS
<222> LOCATION: (33)..(1730)
<220> FEATURE:
<221> NAME/KEY: misc_difference
<222> LOCATION: (180)..(1655)

<400> SEQUENCE: 53

```
agcaaaagca ggggaaaata aaaacaacca aa atg aag gca aac cta ctg gtc      53
                                   Met Lys Ala Asn Leu Leu Val
                                   1               5 ctg tta agt gca ctt gca gct gca gat gca gac aca ata tgt ata ggc     101
Leu Leu Ser Ala Leu Ala Ala Ala Asp Ala Asp Thr Ile Cys Ile Gly
            10              15                  20 tac cat gcg aac aat tca acc gac act gtt gac aca gta ctc gag aag     149
Tyr His Ala Asn Asn Ser Thr Asp Thr Val Asp Thr Val Leu Glu Lys
        25              30                  35 aat gtg aca gtg aca cac tct gtt aac ctg tta gag gac tca cat aac     197
Asn Val Thr Val Thr His Ser Val Asn Leu Leu Glu Asp Ser His Asn
40              45                  50                  55 gga aag cta tgt agg ctt aag gga atc gca cca ctg caa ttg ggc aag     245
Gly Lys Leu Cys Arg Leu Lys Gly Ile Ala Pro Leu Gln Leu Gly Lys
                60                  65                  70 tgt aat ata gcc gga tgg ttg ttg ggg aat ccc gaa tgc gat cca ctg     293
Cys Asn Ile Ala Gly Trp Leu Leu Gly Asn Pro Glu Cys Asp Pro Leu
            75                  80                  85 tta ccc gtt agg tca tgg tca tat ata gtc gag aca cct aat agc gaa     341
Leu Pro Val Arg Ser Trp Ser Tyr Ile Val Glu Thr Pro Asn Ser Glu
        90                  95                  100 aac gga att tgt tat ccc ggc gat ttt atc gat tac gaa gag ctt aga     389
Asn Gly Ile Cys Tyr Pro Gly Asp Phe Ile Asp Tyr Glu Glu Leu Arg
    105                 110                 115 gag caa ttg tct agc gtt agt tca ttc gaa aga ttc gaa att ttt ccg     437
Glu Gln Leu Ser Ser Val Ser Ser Phe Glu Arg Phe Glu Ile Phe Pro
120                 125                 130                 135 aaa gag tct agt tgg cca aat cat aat act aac gga gtg act gcc gca     485
Lys Glu Ser Ser Trp Pro Asn His Asn Thr Asn Gly Val Thr Ala Ala
                140                 145                 150 tgc tca cac gaa ggc aag tct agc ttt tat agg aat ctg ttg tgg ttg     533
Cys Ser His Glu Gly Lys Ser Ser Phe Tyr Arg Asn Leu Leu Trp Leu
            155                 160                 165 act gag aaa gag gga tca tat ccg aaa ctg aaa aac tca tac gtg aac     581
Thr Glu Lys Glu Gly Ser Tyr Pro Lys Leu Lys Asn Ser Tyr Val Asn
        170                 175                 180 aaa aag gga aag gaa gtg tta gtg ttg tgg ggg ata cac cat cca cca     629
Lys Lys Gly Lys Glu Val Leu Val Leu Trp Gly Ile His His Pro Pro
    185                 190                 195 aat agt aaa gag caa cag aat ata tat cag aac gaa aac gca tac gtt     677
Asn Ser Lys Glu Gln Gln Asn Ile Tyr Gln Asn Glu Asn Ala Tyr Val
200                 205                 210                 215 agc gtc gta act agt aat tat aat aga agg ttt aca ccc gaa atc gca     725
Ser Val Val Thr Ser Asn Tyr Asn Arg Arg Phe Thr Pro Glu Ile Ala
                220                 225                 230 gag aga ccg aaa gtt aga gac caa gcc gga aga atg aat tat tat tgg     773
Glu Arg Pro Lys Val Arg Asp Gln Ala Gly Arg Met Asn Tyr Tyr Trp
            235                 240                 245 aca cta ctg aaa ccc ggc gat aca att ata ttc gaa gcg aac gga aat     821
Thr Leu Leu Lys Pro Gly Asp Thr Ile Ile Phe Glu Ala Asn Gly Asn
        250                 255                 260 ctg atc gca ccg atg tat gca ttc gca cta tct agg ggg ttc gga tcc     869
Leu Ile Ala Pro Met Tyr Ala Phe Ala Leu Ser Arg Gly Phe Gly Ser
    265                 270                 275 gga att att act agt aac gct agt atg cac gaa tgt aac acg aag tgt     917
Gly Ile Ile Thr Ser Asn Ala Ser Met His Glu Cys Asn Thr Lys Cys
280                 285                 290                 295 cag act cca cta ggc gca att aac tct agt ctg cca tat cag aat ata     965
Gln Thr Pro Leu Gly Ala Ile Asn Ser Ser Leu Pro Tyr Gln Asn Ile
```

```
                    300              305              310
cat ccc gta aca atc ggc gaa tgc cca aaa tac gtt aga tcc gct aag       1013
His Pro Val Thr Ile Gly Glu Cys Pro Lys Tyr Val Arg Ser Ala Lys
            315                  320                  325 ctt aga atg gtt acc gga ctg aga aat aca cca tca atc caa tct agg       1061
Leu Arg Met Val Thr Gly Leu Arg Asn Thr Pro Ser Ile Gln Ser Arg
            330                  335                  340 ggg ttg ttc gga gcg ata gcc gga ttt atc gaa ggg ggg tgg aca ggg       1109
Gly Leu Phe Gly Ala Ile Ala Gly Phe Ile Glu Gly Gly Trp Thr Gly
    345                  350                  355 atg ata gac ggt tgg tac gga tat cat cac caa aac gaa cag gga tcc       1157
Met Ile Asp Gly Trp Tyr Gly Tyr His His Gln Asn Glu Gln Gly Ser
360                  365                  370                  375 gga tac gca gcc gat cag aaa tcg acg caa aac gct att aac gga att       1205
Gly Tyr Ala Ala Asp Gln Lys Ser Thr Gln Asn Ala Ile Asn Gly Ile
                380                  385                  390 act aat aaa gtg aat acc gta atc gaa aaa atg aat atc caa ttt acc       1253
Thr Asn Lys Val Asn Thr Val Ile Glu Lys Met Asn Ile Gln Phe Thr
            395                  400                  405 gca gtc gga aag gaa ttc aat aag ctt gag aaa aga atg gag aat ctg       1301
Ala Val Gly Lys Glu Phe Asn Lys Leu Glu Lys Arg Met Glu Asn Leu
            410                  415                  420 aat aaa aaa gtc gac gac gga ttt cta gac ata tgg act tat aac gcc       1349
Asn Lys Lys Val Asp Asp Gly Phe Leu Asp Ile Trp Thr Tyr Asn Ala
    425                  430                  435 gaa ctg tta gtg ttg ctc gaa aac gaa aga aca cta gac ttt cac gac       1397
Glu Leu Leu Val Leu Leu Glu Asn Glu Arg Thr Leu Asp Phe His Asp
440                  445                  450                  455 tca aac gtt aag aat cta tac gaa aaa gtg aaa tcc caa ttg aaa aat       1445
Ser Asn Val Lys Asn Leu Tyr Glu Lys Val Lys Ser Gln Leu Lys Asn
                460                  465                  470 aac gct aaa gag ata ggg aac gga tgt ttc gag ttc tat cat aaa tgc       1493
Asn Ala Lys Glu Ile Gly Asn Gly Cys Phe Glu Phe Tyr His Lys Cys
            475                  480                  485 gat aac gaa tgt atg gaa tcc gtt agg aac gga aca tac gat tat cct       1541
Asp Asn Glu Cys Met Glu Ser Val Arg Asn Gly Thr Tyr Asp Tyr Pro
            490                  495                  500 aag tat agc gaa gag tca aaa ctg aat agg gag aaa gtc gac gga gtg       1589
Lys Tyr Ser Glu Glu Ser Lys Leu Asn Arg Glu Lys Val Asp Gly Val
    505                  510                  515 aaa ctc gaa tca atg ggg ata tat cag ata ctg gca atc tat agt aca       1637
Lys Leu Glu Ser Met Gly Ile Tyr Gln Ile Leu Ala Ile Tyr Ser Thr
520                  525                  530                  535 gtc gcc agc tca ctg gtt ctt ttg gtc tcc ctg ggg gca atc agt ttc       1685
Val Ala Ser Ser Leu Val Leu Leu Val Ser Leu Gly Ala Ile Ser Phe
                540                  545                  550 tgg atg tgt tct aat gga tct ttg cag tgc aga ata tgc atc tga           1730
Trp Met Cys Ser Asn Gly Ser Leu Gln Cys Arg Ile Cys Ile
            555                  560                  565 gattagaatt tcagaaatat gaggaaaaac acccttgttt ctact                     1775

<210> SEQ ID NO 54
<211> LENGTH: 565
<212> TYPE: PRT
<213> ORGANISM: unknown
<220> FEATURE:
<223> OTHER INFORMATION: Synthetic Construct

<400> SEQUENCE: 54

Met Lys Ala Asn Leu Leu Val Leu Leu Ser Ala Leu Ala Ala Ala Asp
1               5                   10                  15
```

```
Ala Asp Thr Ile Cys Ile Gly Tyr His Ala Asn Asn Ser Thr Asp Thr
             20                  25                  30

Val Asp Thr Val Leu Glu Lys Asn Val Thr Val Thr His Ser Val Asn
         35                  40                  45

Leu Leu Glu Asp Ser His Asn Gly Lys Leu Cys Arg Leu Lys Gly Ile
 50                  55                  60

Ala Pro Leu Gln Leu Gly Lys Cys Asn Ile Ala Gly Trp Leu Leu Gly
65                   70                  75                  80

Asn Pro Glu Cys Asp Pro Leu Leu Pro Val Arg Ser Trp Ser Tyr Ile
             85                  90                  95

Val Glu Thr Pro Asn Ser Glu Asn Gly Ile Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Glu Ser Ser Trp Pro Asn His Asn
    130                 135                 140

Thr Asn Gly Val Thr Ala Ala Cys Ser His Glu Gly Lys Ser Ser Phe
145                 150                 155                 160

Tyr Arg Asn Leu Leu Trp Leu Thr Glu Lys Glu Gly Ser Tyr Pro Lys
                165                 170                 175

Leu Lys Asn Ser Tyr Val Asn Lys Lys Gly Lys Glu Val Leu Val Leu
            180                 185                 190

Trp Gly Ile His His Pro Pro Asn Ser Lys Glu Gln Gln Asn Ile Tyr
        195                 200                 205

Gln Asn Glu Asn Ala Tyr Val Ser Val Val Thr Ser Asn Tyr Asn Arg
    210                 215                 220

Arg Phe Thr Pro Glu Ile Ala Glu Arg Pro Lys Val Arg Asp Gln Ala
225                 230                 235                 240

Gly Arg Met Asn Tyr Tyr Trp Thr Leu Leu Lys Pro Gly Asp Thr Ile
                245                 250                 255

Ile Phe Glu Ala Asn Gly Asn Leu Ile Ala Pro Met Tyr Ala Phe Ala
            260                 265                 270

Leu Ser Arg Gly Phe Gly Ser Gly Ile Ile Thr Ser Asn Ala Ser Met
        275                 280                 285

His Glu Cys Asn Thr Lys Cys Gln Thr Pro Leu Gly Ala Ile Asn Ser
    290                 295                 300

Ser Leu Pro Tyr Gln Asn Ile His Pro Val Thr Ile Gly Glu Cys Pro
305                 310                 315                 320

Lys Tyr Val Arg Ser Ala Lys Leu Arg Met Val Thr Gly Leu Arg Asn
                325                 330                 335

Thr Pro Ser Ile Gln Ser Arg Gly Leu Phe Gly Ala Ile Ala Gly Phe
            340                 345                 350

Ile Glu Gly Gly Trp Thr Gly Met Ile Asp Gly Trp Tyr Gly Tyr His
        355                 360                 365

His Gln Asn Glu Gln Gly Ser Gly Tyr Ala Ala Asp Gln Lys Ser Thr
    370                 375                 380

Gln Asn Ala Ile Asn Gly Ile Thr Asn Lys Val Asn Thr Val Ile Glu
385                 390                 395                 400

Lys Met Asn Ile Gln Phe Thr Ala Val Gly Lys Glu Phe Asn Lys Leu
                405                 410                 415

Glu Lys Arg Met Glu Asn Leu Asn Lys Lys Val Asp Asp Gly Phe Leu
            420                 425                 430
```

```
Asp Ile Trp Thr Tyr Asn Ala Glu Leu Leu Val Leu Leu Glu Asn Glu
            435                 440                 445

Arg Thr Leu Asp Phe His Asp Ser Asn Val Lys Asn Leu Tyr Glu Lys
    450                 455                 460

Val Lys Ser Gln Leu Lys Asn Asn Ala Lys Glu Ile Gly Asn Gly Cys
465                 470                 475                 480

Phe Glu Phe Tyr His Lys Cys Asp Asn Glu Cys Met Glu Ser Val Arg
                485                 490                 495

Asn Gly Thr Tyr Asp Tyr Pro Lys Tyr Ser Glu Glu Ser Lys Leu Asn
            500                 505                 510

Arg Glu Lys Val Asp Gly Val Lys Leu Glu Ser Met Gly Ile Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565

<210> SEQ ID NO 55
<211> LENGTH: 1565
<212> TYPE: DNA
<213> ORGANISM: Influenza virus
<220> FEATURE:
<221> NAME/KEY: CDS
<222> LOCATION: (46)..(1542)

<400> SEQUENCE: 55
agcaaaagca gggtagataa tcactcactg agtgacatca aaatc atg gcg tcc caa      57
                                                 Met Ala Ser Gln
                                                 1 ggc acc aaa cgg tct tac gaa cag atg gag act gat gga gaa cgc cag        105
Gly Thr Lys Arg Ser Tyr Glu Gln Met Glu Thr Asp Gly Glu Arg Gln
5                   10                  15                  20 aat gcc act gaa atc aga gca tcc gtc gga aaa atg att ggt gga att        153
Asn Ala Thr Glu Ile Arg Ala Ser Val Gly Lys Met Ile Gly Gly Ile
                25                  30                  35 gga cga ttc tac atc caa atg tgc acc gaa ctc aaa ctc agt gat tat        201
Gly Arg Phe Tyr Ile Gln Met Cys Thr Glu Leu Lys Leu Ser Asp Tyr
            40                  45                  50 gag gga cgg ttg atc caa aac agc tta aca ata gag aga atg gtg ctc        249
Glu Gly Arg Leu Ile Gln Asn Ser Leu Thr Ile Glu Arg Met Val Leu
        55                  60                  65 tct gct ttt gac gaa agg aga aat aaa tac ctg gaa gaa cat ccc agt        297
Ser Ala Phe Asp Glu Arg Arg Asn Lys Tyr Leu Glu Glu His Pro Ser
70                  75                  80 gcg ggg aaa gat cct aag aaa act gga gga cct ata tac agg aga gta        345
Ala Gly Lys Asp Pro Lys Lys Thr Gly Gly Pro Ile Tyr Arg Arg Val
85                  90                  95                  100 aac gga aag tgg atg aga gaa ctc atc ctt tat gac aaa gaa gaa ata        393
Asn Gly Lys Trp Met Arg Glu Leu Ile Leu Tyr Asp Lys Glu Glu Ile
                105                 110                 115 agg cga atc tgg cgc caa gct aat aat ggt gac gat gca acg gct ggt        441
Arg Arg Ile Trp Arg Gln Ala Asn Asn Gly Asp Asp Ala Thr Ala Gly
            120                 125                 130 ctg act cac atg atg atc tgg cat tcc aat ttg aat gat gca act tat        489
Leu Thr His Met Met Ile Trp His Ser Asn Leu Asn Asp Ala Thr Tyr
        135                 140                 145 cag agg aca aga gct ctt gtt cgc acc gga atg gat ccc agg atg tgc        537
```

```
                    Gln Arg Thr Arg Ala Leu Val Arg Thr Gly Met Asp Pro Arg Met Cys
                        150                 155                 160 tct ctg atg caa ggt tca act ctc cct agg agg tct gga gcc gca ggt        585
Ser Leu Met Gln Gly Ser Thr Leu Pro Arg Arg Ser Gly Ala Ala Gly
165                 170                 175                 180 gct gca gtc aaa gga gtt gga aca atg gtg atg gaa ttg gtc agg atg        633
Ala Ala Val Lys Gly Val Gly Thr Met Val Met Glu Leu Val Arg Met
                185                 190                 195 atc aaa cgt ggg atc aat gat cgg aac ttc tgg agg ggt gag aat gga        681
Ile Lys Arg Gly Ile Asn Asp Arg Asn Phe Trp Arg Gly Glu Asn Gly
            200                 205                 210 cga aaa aca aga att gct tat gaa aga atg tgc aac att ctc aaa ggg        729
Arg Lys Thr Arg Ile Ala Tyr Glu Arg Met Cys Asn Ile Leu Lys Gly
        215                 220                 225 aaa ttt caa act gct gca caa aaa gca atg atg gat caa gtg aga gag        777
Lys Phe Gln Thr Ala Ala Gln Lys Ala Met Met Asp Gln Val Arg Glu
    230                 235                 240 agc cgg aac cca ggg aat gct gag ttc gaa gat ctc act ttt cta gca        825
Ser Arg Asn Pro Gly Asn Ala Glu Phe Glu Asp Leu Thr Phe Leu Ala
245                 250                 255                 260 cgg tct gca ctc ata ttg aga ggg tcg gtt gct cac aag tcc tgc ctg        873
Arg Ser Ala Leu Ile Leu Arg Gly Ser Val Ala His Lys Ser Cys Leu
                265                 270                 275 cct gcc tgt gtg tat gga cct gcc gta gcc agt ggg tac gac ttt gaa        921
Pro Ala Cys Val Tyr Gly Pro Ala Val Ala Ser Gly Tyr Asp Phe Glu
            280                 285                 290 aga gag gga tac tct cta gtc gga ata gac cct ttc aga ctg ctt caa        969
Arg Glu Gly Tyr Ser Leu Val Gly Ile Asp Pro Phe Arg Leu Leu Gln
        295                 300                 305 aac agc caa gtg tac agc cta atc aga cca aat gag aat cca gca cac       1017
Asn Ser Gln Val Tyr Ser Leu Ile Arg Pro Asn Glu Asn Pro Ala His
    310                 315                 320 aag agt caa ctg gtg tgg atg gca tgc cat tct gcc gca ttt gaa gat       1065
Lys Ser Gln Leu Val Trp Met Ala Cys His Ser Ala Ala Phe Glu Asp
325                 330                 335                 340 cta aga gta tta agc ttc atc aaa ggg acg aag gtg ctc cca aga ggg       1113
Leu Arg Val Leu Ser Phe Ile Lys Gly Thr Lys Val Leu Pro Arg Gly
                345                 350                 355 aag ctt tcc act aga gga gtt caa att gct tcc aat gaa aat atg gag       1161
Lys Leu Ser Thr Arg Gly Val Gln Ile Ala Ser Asn Glu Asn Met Glu
            360                 365                 370 act atg gaa tca agt aca ctt gaa ctg aga agc agg tac tgg gcc ata       1209
Thr Met Glu Ser Ser Thr Leu Glu Leu Arg Ser Arg Tyr Trp Ala Ile
        375                 380                 385 agg acc aga agt gga gga aac acc aat caa cag agg gca tct gcg ggc       1257
Arg Thr Arg Ser Gly Gly Asn Thr Asn Gln Gln Arg Ala Ser Ala Gly
    390                 395                 400 caa atc agc ata caa cct acg ttc tca gta cag aga aat ctc cct ttt       1305
Gln Ile Ser Ile Gln Pro Thr Phe Ser Val Gln Arg Asn Leu Pro Phe
405                 410                 415                 420 gac aga aca acc att atg gca gca ttc aat ggg aat aca gag gga aga       1353
Asp Arg Thr Thr Ile Met Ala Ala Phe Asn Gly Asn Thr Glu Gly Arg
                425                 430                 435 aca tct gac atg agg acc gaa atc ata agg atg atg gaa agt gca aga       1401
Thr Ser Asp Met Arg Thr Glu Ile Ile Arg Met Met Glu Ser Ala Arg
            440                 445                 450 cca gaa gat gtg tct ttc cag ggg cgg gga gtc ttc gag ctc tcg gac       1449
Pro Glu Asp Val Ser Phe Gln Gly Arg Gly Val Phe Glu Leu Ser Asp
        455                 460                 465
```

| | | |
|---|---|---|
| gaa aag gca gcg agc ccg atc gtg cct tcc ttt gac atg agt aat gaa<br>Glu Lys Ala Ala Ser Pro Ile Val Pro Ser Phe Asp Met Ser Asn Glu<br>470                               475                        480 | | 1497 |
| gga tct tat ttc ttc gga gac aat gca gag gag tac gac aat taa<br>Gly Ser Tyr Phe Phe Gly Asp Asn Ala Glu Glu Tyr Asp Asn<br>485                       490                       495 | | 1542 |
| agaaaaatac ccttgtttct act | | 1565 |

<210> SEQ ID NO 56
<211> LENGTH: 498
<212> TYPE: PRT
<213> ORGANISM: Influenza virus

<400> SEQUENCE: 56

Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Lys Met
            20                  25                  30

Ile Gly Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Leu Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Val Asn Gly Lys Trp Met Arg Glu Leu Ile Leu Tyr Asp
            100                 105                 110

Lys Glu Glu Ile Arg Arg Ile Trp Arg Gln Ala Asn Asn Gly Asp Asp
        115                 120                 125

Ala Thr Ala Gly Leu Thr His Met Met Ile Trp His Ser Asn Leu Asn
130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190

Leu Val Arg Met Ile Lys Arg Gly Ile Asn Asp Arg Asn Phe Trp Arg
        195                 200                 205

Gly Glu Asn Gly Arg Lys Thr Arg Ile Ala Tyr Glu Arg Met Cys Asn
210                 215                 220

Ile Leu Lys Gly Lys Phe Gln Thr Ala Ala Gln Lys Ala Met Met Asp
225                 230                 235                 240

Gln Val Arg Glu Ser Arg Asn Pro Gly Asn Ala Glu Phe Glu Asp Leu
                245                 250                 255

Thr Phe Leu Ala Arg Ser Ala Leu Ile Leu Arg Gly Ser Val Ala His
            260                 265                 270

Lys Ser Cys Leu Pro Ala Cys Val Tyr Gly Pro Ala Val Ala Ser Gly
        275                 280                 285

Tyr Asp Phe Glu Arg Glu Gly Tyr Ser Leu Val Gly Ile Asp Pro Phe
290                 295                 300

Arg Leu Leu Gln Asn Ser Gln Val Tyr Ser Leu Ile Arg Pro Asn Glu
305                 310                 315                 320

Asn Pro Ala His Lys Ser Gln Leu Val Trp Met Ala Cys His Ser Ala
                325                 330                 335

```
Ala Phe Glu Asp Leu Arg Val Leu Ser Phe Ile Lys Gly Thr Lys Val
                340                 345                 350

Leu Pro Arg Gly Lys Leu Ser Thr Arg Gly Val Gln Ile Ala Ser Asn
            355                 360                 365

Glu Asn Met Glu Thr Met Glu Ser Ser Thr Leu Glu Leu Arg Ser Arg
        370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Ile Gln Pro Thr Phe Ser Val Gln Arg
                405                 410                 415

Asn Leu Pro Phe Asp Arg Thr Thr Ile Met Ala Ala Phe Asn Gly Asn
            420                 425                 430

Thr Glu Gly Arg Thr Ser Asp Met Arg Thr Glu Ile Ile Arg Met Met
        435                 440                 445

Glu Ser Ala Arg Pro Glu Asp Val Ser Phe Gln Gly Arg Gly Val Phe
    450                 455                 460

Glu Leu Ser Asp Glu Lys Ala Ala Ser Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn

<210> SEQ ID NO 57
<211> LENGTH: 1565
<212> TYPE: DNA
<213> ORGANISM: unknown
<220> FEATURE:
<223> OTHER INFORMATION: synthetic
<220> FEATURE:
<221> NAME/KEY: CDS
<222> LOCATION: (46)..(1542)
<220> FEATURE:
<221> NAME/KEY: misc_difference
<222> LOCATION: (126)..(1425)

<400> SEQUENCE: 57
agcaaaagca gggtagataa tcactcactg agtgacatca aaatc atg gcg tcc caa      57
                                              Met Ala Ser Gln
                                              1 ggc acc aaa cgg tct tac gaa cag atg gag act gat gga gaa cgc cag     105
Gly Thr Lys Arg Ser Tyr Glu Gln Met Glu Thr Asp Gly Glu Arg Gln
5                   10                  15                  20 aat gcc act gaa atc aga gct agc gtc gga aaa atg ata ggg gga atc     153
Asn Ala Thr Glu Ile Arg Ala Ser Val Gly Lys Met Ile Gly Gly Ile
                25                  30                  35 gga agg ttt tac ata caa atg tgt acc gaa ctc aaa ttg tcc gat tac     201
Gly Arg Phe Tyr Ile Gln Met Cys Thr Glu Leu Lys Leu Ser Asp Tyr
            40                  45                  50 gaa ggg aga ttg atc caa aat agt ctg aca atc gaa aga atg gtg tta     249
Glu Gly Arg Leu Ile Gln Asn Ser Leu Thr Ile Glu Arg Met Val Leu
        55                  60                  65 agc gca ttc gac gaa aga cgg aat aag tat ctc gaa gag cat cct agc     297
Ser Ala Phe Asp Glu Arg Arg Asn Lys Tyr Leu Glu Glu His Pro Ser
    70                  75                  80 gca ggc aag gat cca aaa aaa acc gga ggg cca atc tat agg aga gtg     345
Ala Gly Lys Asp Pro Lys Lys Thr Gly Gly Pro Ile Tyr Arg Arg Val
85                  90                  95                  100 aac gga aag tgg atg cgc gaa ctg ata ctg tac gat aaa gag gag att     393
Asn Gly Lys Trp Met Arg Glu Leu Ile Leu Tyr Asp Lys Glu Glu Ile
```

```
                      105                 110                 115
aga cgg ata tgg cga caa gcg aat aac gga gac gac gct act gcc gga    441
Arg Arg Ile Trp Arg Gln Ala Asn Asn Gly Asp Asp Ala Thr Ala Gly
        120                 125                 130 ctg aca cat atg atg ata tgg cac tct aat ctt aac gac gct aca tac    489
Leu Thr His Met Met Ile Trp His Ser Asn Leu Asn Asp Ala Thr Tyr
            135                 140                 145 caa cgg act agg gca ctc gtt aga acc gga atg gat cct aga atg tgc    537
Gln Arg Thr Arg Ala Leu Val Arg Thr Gly Met Asp Pro Arg Met Cys
150                 155                 160 tca ctt atg cag gga tct aca ctc cct aga cga tcc gga gcc gca gga    585
Ser Leu Met Gln Gly Ser Thr Leu Pro Arg Arg Ser Gly Ala Ala Gly
165                 170                 175                 180 gca gcc gtt aag gga gtc gga act atg gtt atg gaa ctc gtt aga atg    633
Ala Ala Val Lys Gly Val Gly Thr Met Val Met Glu Leu Val Arg Met
                185                 190                 195 ata aaa agg ggg att aac gat agg aat ttt tgg aga ggc gaa aac gga    681
Ile Lys Arg Gly Ile Asn Asp Arg Asn Phe Trp Arg Gly Glu Asn Gly
            200                 205                 210 cgt aaa act aga atc gca tac gaa aga atg tgc aat ata ctc aaa ggg    729
Arg Lys Thr Arg Ile Ala Tyr Glu Arg Met Cys Asn Ile Leu Lys Gly
        215                 220                 225 aaa ttc caa acc gca gcg caa aaa gct atg atg gat caa gtt agg gag    777
Lys Phe Gln Thr Ala Ala Gln Lys Ala Met Met Asp Gln Val Arg Glu
230                 235                 240 tct agg aat cca gga aat gcc gaa ttc gaa gac ctt aca ttt ctc gct    825
Ser Arg Asn Pro Gly Asn Ala Glu Phe Glu Asp Leu Thr Phe Leu Ala
245                 250                 255                 260 cgg tcc gca cta atc ctt cgc gga tca gtc gca cac aaa tct tgc tta    873
Arg Ser Ala Leu Ile Leu Arg Gly Ser Val Ala His Lys Ser Cys Leu
                265                 270                 275 ccc gca tgc gta tac gga cct gca gtc gct agc gga tac gat ttc gaa    921
Pro Ala Cys Val Tyr Gly Pro Ala Val Ala Ser Gly Tyr Asp Phe Glu
            280                 285                 290 cgc gaa ggg tat agt cta gta gga att gat cca ttt aga ttg ctc caa    969
Arg Glu Gly Tyr Ser Leu Val Gly Ile Asp Pro Phe Arg Leu Leu Gln
        295                 300                 305 aat tcg caa gtg tat agt ctg att aga cct aac gag aat cct gca cac    1017
Asn Ser Gln Val Tyr Ser Leu Ile Arg Pro Asn Glu Asn Pro Ala His
310                 315                 320 aaa tct caa ctc gta tgg atg gca tgc cat agt gcc gca ttc gaa gac    1065
Lys Ser Gln Leu Val Trp Met Ala Cys His Ser Ala Ala Phe Glu Asp
325                 330                 335                 340 ctt aga gtg cta tct ttc ata aag gga acg aaa gtg ttg cct agg gga    1113
Leu Arg Val Leu Ser Phe Ile Lys Gly Thr Lys Val Leu Pro Arg Gly
                345                 350                 355 aag cta tct act agg gga gtg caa atc gct agt aac gag aat atg gag    1161
Lys Leu Ser Thr Arg Gly Val Gln Ile Ala Ser Asn Glu Asn Met Glu
            360                 365                 370 act atg gag tct agt aca ctc gaa ctg aga tct aga tat tgg gct att    1209
Thr Met Glu Ser Ser Thr Leu Glu Leu Arg Ser Arg Tyr Trp Ala Ile
        375                 380                 385 agg act aga tcc gga ggg aat acg aat cag caa cga gct agc gcc ggg    1257
Arg Thr Arg Ser Gly Gly Asn Thr Asn Gln Gln Arg Ala Ser Ala Gly
390                 395                 400 caa atc tca atc caa cct aca ttt tcc gtg caa cgg aat ctg cca ttc    1305
Gln Ile Ser Ile Gln Pro Thr Phe Ser Val Gln Arg Asn Leu Pro Phe
405                 410                 415                 420 gat cgg aca acg att atg gcc gca ttc aat ggg aat acc gag gga cgg    1353
```

```
                Asp Arg Thr Thr Ile Met Ala Ala Phe Asn Gly Asn Thr Glu Gly Arg
                                425                 430                 435 act agc gat atg aga acc gaa att atc aga atg atg gaa tcc gct aga               1401
Thr Ser Asp Met Arg Thr Glu Ile Ile Arg Met Met Glu Ser Ala Arg
            440                 445                 450 cca gag gac gtt tcg ttt caa gga cgg gga gtc ttc gag ctc tcg gac               1449
Pro Glu Asp Val Ser Phe Gln Gly Arg Gly Val Phe Glu Leu Ser Asp
            455                 460                 465 gaa aag gca gcg agc ccg atc gtg cct tcc ttt gac atg agt aat gaa               1497
Glu Lys Ala Ala Ser Pro Ile Val Pro Ser Phe Asp Met Ser Asn Glu
            470                 475                 480 gga tct tat ttc ttc gga gac aat gca gag gag tac gac aat taa                   1542
Gly Ser Tyr Phe Phe Gly Asp Asn Ala Glu Glu Tyr Asp Asn
485                 490                 495 agaaaaatac ccttgtttct act                                                     1565

<210> SEQ ID NO 58
<211> LENGTH: 498
<212> TYPE: PRT
<213> ORGANISM: unknown
<220> FEATURE:
<223> OTHER INFORMATION: Synthetic Construct

<400> SEQUENCE: 58

Met Ala Ser Gln Gly Thr Lys Arg Ser Tyr Glu Gln Met Glu Thr Asp
1               5                   10                  15

Gly Glu Arg Gln Asn Ala Thr Glu Ile Arg Ala Ser Val Gly Lys Met
            20                  25                  30

Ile Gly Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Leu Thr Ile Glu
    50                  55                  60

Arg Met Val Leu Ser Ala Phe Asp Glu Arg Arg Asn Lys Tyr Leu Glu
65                  70                  75                  80

Glu His Pro Ser Ala Gly Lys Asp Pro Lys Lys Thr Gly Gly Pro Ile
                85                  90                  95

Tyr Arg Arg Val Asn Gly Lys Trp Met Arg Glu Leu Ile Leu Tyr Asp
            100                 105                 110

Lys Glu Glu Ile Arg Arg Ile Trp Arg Gln Ala Asn Asn Gly Asp Asp
        115                 120                 125

Ala Thr Ala Gly Leu Thr His Met Met Ile Trp His Ser Asn Leu Asn
    130                 135                 140

Asp Ala Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190

Leu Val Arg Met Ile Lys Arg Gly Ile Asn Asp Arg Asn Phe Trp Arg
        195                 200                 205

Gly Glu Asn Gly Arg Lys Thr Arg Ile Ala Tyr Glu Arg Met Cys Asn
    210                 215                 220

Ile Leu Lys Gly Lys Phe Gln Thr Ala Ala Gln Lys Ala Met Met Asp
225                 230                 235                 240

Gln Val Arg Glu Ser Arg Asn Pro Gly Asn Ala Glu Phe Glu Asp Leu
                245                 250                 255

Thr Phe Leu Ala Arg Ser Ala Leu Ile Leu Arg Gly Ser Val Ala His
```

```
            260                 265                 270
Lys Ser Cys Leu Pro Ala Cys Val Tyr Gly Pro Ala Val Ala Ser Gly
            275                 280                 285

Tyr Asp Phe Glu Arg Glu Gly Tyr Ser Leu Val Gly Ile Asp Pro Phe
            290                 295                 300

Arg Leu Leu Gln Asn Ser Gln Val Tyr Ser Leu Ile Arg Pro Asn Glu
305                 310                 315                 320

Asn Pro Ala His Lys Ser Gln Leu Val Trp Met Ala Cys His Ser Ala
                325                 330                 335

Ala Phe Glu Asp Leu Arg Val Leu Ser Phe Ile Lys Gly Thr Lys Val
            340                 345                 350

Leu Pro Arg Gly Lys Leu Ser Thr Arg Gly Val Gln Ile Ala Ser Asn
            355                 360                 365

Glu Asn Met Glu Thr Met Glu Ser Ser Thr Leu Glu Leu Arg Ser Arg
            370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Ile Gln Pro Thr Phe Ser Val Gln Arg
                405                 410                 415

Asn Leu Pro Phe Asp Arg Thr Thr Ile Met Ala Ala Phe Asn Gly Asn
                420                 425                 430

Thr Glu Gly Arg Thr Ser Asp Met Arg Thr Glu Ile Ile Arg Met Met
            435                 440                 445

Glu Ser Ala Arg Pro Glu Asp Val Ser Phe Gln Gly Arg Gly Val Phe
450                 455                 460

Glu Leu Ser Asp Glu Lys Ala Ala Ser Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn

<210> SEQ ID NO 59
<211> LENGTH: 1413
<212> TYPE: DNA
<213> ORGANISM: Influenza virus

<400> SEQUENCE: 59
agcgaaagca ggggtttaaa atgaatccaa atcagaaaat aacaaccatt ggatcaatct      60
gtctggtagt cggactaatt agcctaatat tgcaaatagg aatataatc tcaatatgga     120 ttagccattc aattcaaact ggaagtcaaa accatactgg aatatgcaac caaacatca      180 ttacctataa aaatagcacc tgggtaaagg acacaacttc agtgatatta accggcaatt     240
catctctttg tcccatccgt gggtgggcta tatacagcaa agacaatagc ataagaattg     300
gttccaaagg agacgttttt gtcataagag agccctttat ttcatgttct cacttggaat     360
gcaggacctt ttttctgacc caaggtgcct tactgaatga caagcattca aatgggactg     420
ttaaggacag aagcccttat agggccttaa tgagctgccc tgtcggtgaa gctccgtccc     480
cgtacaattc aagatttgaa tcggttgctt ggtcagcaag tgcatgtcat gatggcatgg     540
gctggctaac aatcggaatt tcaggtccag ataatggagc agtggctgta ttaaaataca     600
acggcataat aactgaaacc ataaaaagtt ggaggaagaa atattgagg acacaagagt     660 ctgaatgtgc ctgtgtaaat ggttcatgtt ttactataat gactgatggc ccgagtgatg     720
ggctggcctc gtacaaaatt ttcaagatcg aaaagggaa ggttactaaa tcaatagagt     780
```

```
tgaatgcacc taattctcac tatgaggaat gttcctgtta ccctgatacc ggcaaagtga      840
tgtgtgtgtg cagagacaac tggcatggtt cgaaccggcc atgggtgtct ttcgatcaaa      900
acctggatta tcaaatagga tacatctgca gtggggtttt cggtgacaac ccgcgtcccg      960
aagatggaac aggcagctgt ggtccagtgt atgttgatgg agcaaacgga gtaaagggat     1020
tttcatatag gtatggtaat ggtgtttgga taggaaggac caaaagtcac agttccagac     1080
atgggtttga gatgatttgg gatcctaatg gatggacaga gactgatagt aagttctctg     1140
ttaggcaaga tgttgtggca atgactgatt ggtcaggggta tagcggaagt ttcgttcaac    1200
atcctgagct aacagggcta gactgtatga ggccgtgctt ctgggttgaa ttaatcaggg     1260
gacgacctaa agaaaaaaca atctggacta gtgcgagcag catttctttt tgtggcgtga     1320
atagtgatac tgtagattgg tcttggccag acggtgctga gttgccattc agcattgaca     1380
agtagtctgt tcaaaaaact ccttgtttct act                                  1413

<210> SEQ ID NO 60
<211> LENGTH: 1413
<212> TYPE: DNA
<213> ORGANISM: unknown
<220> FEATURE:
<223> OTHER INFORMATION: synthetic

<400> SEQUENCE: 60
agcgaaagca ggggtttaaa atgaatccaa atcagaaaat aacaaccatt ggatcaatct       60
gtctggtagt cggactaatt agcctaatat tgcaaatagg gaatataatc tcaatatgga      120
tttcgcattc aatccaaacc ggatcacaaa atcatacagg catatgcaat cagaatataa      180
ttacttataa aaatagtaca tggggtgaaag atactactag cgtgatacta accggcaatt      240
ctagtctatg tccgattagg gggtgggcta tatactctaa agacaatagt atacggatag      300
ggtctaaggg agacgttttc gtaattaggg aaccgtttat aagttgttca catctagagt      360
gtaggaccct ttttctgaca caaggcgcac tattaaacga taagcattct aacggtacag      420
ttaaggatag gtcaccttat agggcactta tgtcatgtcc cgtaggcgaa gcccctagtc      480
catacaatag tagatttgaa tccgttgcat ggtccgctag cgcatgtcac gacggaatgg      540
ggtggttgac tatagggatt agcggacccg ataacggagc cgttgccgta ctgaaatata      600
acggtataat taccgaaaact attaagagtt ggcgtaaaaa aatattgcgt acacaagagt     660
ccgaatgcgc atgcgttaac ggatcatgtt ttacaattat gactgacgga cctagcgacg      720
ggttagcgtc atacaaaatt tttaaaatcg aaaaaggcaa ggttactaag tcaatcgagt      780
taaacgcacc taattcgcat tacgaagagt gttcatgtta tcccgatacc ggaaaggtta     840
tgtgcgtttg tagggataat tggcacggtt cgaacagacc ttgggtgtca ttcgatcaaa      900
atctagacta tcaaatcgga tatatatgta gcggagtgtt cggcgataat cctagaccag      960
aggacggtac aggcagctgt ggaccggttt acgttgacgg cgctaacggc gttaagggggt    1020 ttagttatag atacggcaat ggcgtatgga tcggtaggac taagtcacat agttctagac     1080
acggatttga aatgatatgg gatcctaacg gatggaccga aaccgactcg aagtttagcg     1140
ttaggcaaga cgtagtcgct atgaccgatt ggtccgggta tagcggatca ttcgtgcaac     1200
atccagagtt aaccggattg gattgtatgc gaccatgttt tgggttgagt tgattaggg     1260 ggagaccgaa agagaaaact atatggacta gcgcgagcag catttctttt tgtggcgtga    1320
atagtgatac tgtagattgg tcttggccag acggtgctga gttgccattc agcattgaca    1380
```

| | |
|---|---:|
| agtagtctgt tcaaaaaact ccttgtttct act | 1413 |

<210> SEQ ID NO 61
<211> LENGTH: 1026
<212> TYPE: DNA
<213> ORGANISM: Influenza virus

<400> SEQUENCE: 61

| | |
|---|---:|
| agcgaaagca ggtagatatt gaaagatgag tcttctaacc gaggtcgaaa cgtacgtact | 60 |
| ctctatcatc ccgtcaggcc ccctcaaagc cgagatcgca cagagacttg aagatgtctt | 120 |
| tgcagggaag aacactgatc ttgaggttct catggaatgg ctaaagacaa gaccaatcct | 180 |
| gtcacctctg actaagggga ttttaggatt tgtgttcacg ctcaccgtgc ccagtgagcg | 240 |
| aggactgcag cgtagacgct ttgtccaaaa tgcccttaat gggacgggga tccaaataa | 300 |
| catggacaaa gcagttaaac tgtataggaa gctcaagagg gagataacat ccatggggc | 360 |
| caaagaaatc tcactcagtt attctgctgg tgcacttgcc agttgtatgg ccctcatata | 420 |
| caacaggatg ggggctgtga ccactgaagt ggcatttggc ctggtatgtg caacctgtga | 480 |
| acagattgct gactcccagc atcggtctca taggcaaatg gtgacaacaa ccaatccact | 540 |
| aatcagacat gagaacagaa tggttttagc cagcactaca gctaaggcta tggagcaaat | 600 |
| ggctggatcg agtgagcaag cagcagaggc catggaggtt gctagtcagg ctagacaaat | 660 |
| ggtgcaagcg atgagaacca ttgggactca tcctagctcc agtgctggtc tgaaaaatga | 720 |
| tcttcttgaa aatttgcagg cctatcagaa acgaatgggg gtgcagatgc aacggttcaa | 780 |
| gtgatcctct cgctattgcc gcaaatatca ttgggatctt gcacttgaca ttgtggattc | 840 |
| ttgatcgtct ttttttcaaa tgcatttacc gtcgctttaa atacggactg aaaggagggc | 900 |
| cttctacgga aggagtgcca aagtctatga gggaagaata tcgaaaggaa cagcagagtg | 960 |
| ctgtggatgc tgacgatggt cattttgtca gcatagagct ggagtaaaaa actaccttgt | 1020 |
| ttctac | 1026 |

<210> SEQ ID NO 62
<211> LENGTH: 890
<212> TYPE: DNA
<213> ORGANISM: Influenza virus

<400> SEQUENCE: 62

| | |
|---|---:|
| agcaaaagca gggtgacaaa gacataatgg atccaaacac tgtgtcaagc tttcaggtag | 60 |
| attgctttct ttggcatgtc cgcaaacgag ttgcagacca agaactaggt gatgccccat | 120 |
| tccttgatcg gcttcgccga gatcagaaat ccctaagagg aaggggcagc accctcggtc | 180 |
| tggacatcga gacagccaca cgtgctggaa agcagatagt ggagcggatt ctgaaagaag | 240 |
| aatccgatga ggcacttaaa atgaccatgg cctctgtacc tgcgtcgcgt tacctaactg | 300 |
| acatgactct tgaggaaatg tcaagggact ggtccatgct catacccaag cagaaagtgg | 360 |
| caggccctct ttgtatcaga atggaccagg cgatcatgga taagaacatc atactgaaag | 420 |
| cgaacttcag tgtgattttt gaccggctgg agactctaat attgctaagg ctttcaccg | 480 |
| aagagggagc aattgttggc gaaatttcac cattgccttc tcttccagga catactgctg | 540 |
| aggatgtcaa aaatgcagtt ggagtcctca tcgggggact tgaatggaat gataacacag | 600 |
| ttcgagtctc tgaaactcta cagagattcg cttggagaag cagtaatgag atgggagac | 660 |
| ctccactcac tccaaaacag aaacgagaaa tggcgggaac aattaggtca gaagtttgaa | 720 |
| gaaataagat ggttgattga agaagtgaga cacaaactga agataacaga gaatagtttt | 780 |

```
gagcaaataa catttatgca agccttacat ctattgcttg aagtggagca agagataaga      840
actttctcgt ttcagcttat ttaataataa aaaacaccct tgtttctact                890

<210> SEQ ID NO 63
<211> LENGTH: 890
<212> TYPE: DNA
<213> ORGANISM: unknown
<220> FEATURE:
<223> OTHER INFORMATION: synthetic

<400> SEQUENCE: 63
agcaaaagca gggtgacaaa gacataatgg atccaaacac tgtgtcaagc tttcaggtag       60
attgctttct ttggcatgtc cgcaaacgag ttgcagacca agaactaggt gatgcccat       120 tccttgaccg actgagacgg gatcagaaat cccttagggg caggggatcg accctaggcc     180
tagacatcga aaccgcaact agggccggaa agcagatcgt ggagcgtata ctgaaagagg     240
agtccgacga agcgcttaag atgactatgg ccagcgtacc cgctagtcgg taccttaccg     300
atatgacact cgaagagatg tcacgcgatt ggtctatgct aatccctaag cagaaagtgg     360
ccggacctct atgtatacgg atggaccagg cgattatgga caaaaacatt atccttaaag     420
cgaacttttc cgtgatattc gatcgcctag agactctgat actgttgcgt gcattcacag     480
aagagggagc aattgttggc gaaatttcac cattgccttc tcttccagga catactgctg     540
aggatgtcaa aaatgcagtt ggagtcctca tcgggggact tgaatggaat gataacacag     600
ttcgagtctc tgaaactcta cagagattcg cttggagaag cagtaatgag aatgggagac     660
ctccactcac tccaaaacag aaacgagaaa tggcgggaac aattaggtca gaagtttgaa     720 gaataagat ggttgattga agaagtgaga cacaaactga agataacaga gaatagtttt     780
gagcaaataa catttatgca agccttacat ctattgcttg aagtggagca agagataaga    840
actttctcgt ttcagcttat ttaataataa aaaacaccct tgtttctact               890
```